(12) United States Patent
Mullins et al.

(10) Patent No.: US 7,655,774 B2
(45) Date of Patent: Feb. 2, 2010

(54) ANCESTRAL AND COT VIRAL SEQUENCES, PROTEINS AND IMMUNOGENIC COMPOSITIONS

(75) Inventors: James I. Mullins, Seattle, WA (US); Allen G. Rodrigo, Auckland (NZ); Gerald H. Learn, Kingston, WA (US); Fusheng Li, Seattle, WA (US); David C. Nickle, Seattle, WA (US); Mark A. Jensen, Snohomish, WA (US)

(73) Assignee: University of Washington, Seattle, WA (US)

( * ) Notice: Subject to any disclaimer, the term of this patent is extended or adjusted under 35 U.S.C. 154(b) by 677 days.

(21) Appl. No.: 10/780,507

(22) Filed: Feb. 17, 2004

(65) Prior Publication Data
US 2005/0137387 A1 Jun. 23, 2005

Related U.S. Application Data

(63) Continuation-in-part of application No. 10/204,204, filed as application No. PCT/US01/05288 on Feb. 16, 2001, now abandoned.

(60) Provisional application No. 60/183,659, filed on Feb. 18, 2000, provisional application No. 60/447,586, filed on Feb. 14, 2003.

(51) Int. Cl.
C07H 21/02 (2006.01)
C12N 15/00 (2006.01)
C12N 1/20 (2006.01)
(52) U.S. Cl. ............... 536/23.1; 435/320.1; 435/252.3
(58) Field of Classification Search ............ None
See application file for complete search history.

(56) References Cited

U.S. PATENT DOCUMENTS 6,958,226 B1 * 10/2005 Gray et al. ............... 435/91.4

FOREIGN PATENT DOCUMENTS

| WO | WO 98/34640 | * | 8/1998 |
| WO | WO 00/29561 | | 5/2000 |
| WO | WO 01/60838 | | 8/2001 |

OTHER PUBLICATIONS

Draenert RD et al. "Immune selection for altered antigen processing leads to cytotoxic T lymphocyte escape in chronic HIV-1 infection". J Exp Med. Apr 5,2004;199(7):905-15.*
Kuiken et al., "HIV Sequence Compendium, Part II. HIV-1/SIV cpz Complete Genomes" 279-466 (2001).
Ahlers et al., "Enhanced immunogenicity of HIV-1 vaccine construct by modification of the native peptide sequence," *Proc. Natl. Acad. Sci. USA* 94:10856-10861 (1997).
Akaike, "A New Look at the Statistical Model Identification," *IEEE Trans. Atom. Contr.* 19:716-723 (1974).

Altschul et al., "Basic local alignment search tool," *J. Mol. Biol.* 215:403-410 (1990).
Anderson, "Human gene therapy," *Nature*392(Suppl):25-30 (1998).
Anderson, "Testing the Hypothesis of a Recombinant Origin of Human Immunodeficiency Virus Type 1 Subtype E," *J. Virol.* 74(22):10752-10765 (2000).
Andre et al., "Increased Immune Response Elicited by DNA Vaccination with a Synthetic gp 120 Sequence with Optimized Codon Usage," *J. Virol.* 74(2):1497-1503 (1990).
Avise et al., "Phylogenetics and the origin of species," *Proc. Natl. Acad. Sci. USA* 94(15):7748-7755 (1997).
Barnett at al., "Vaccination with HIV-1 gp120 DNA induces immune responses that are boosted by a recombinant gp120 protein subunit," *Vaccine* 15:869-873 (1997).
Barouch et al., "Control of viremia and prevention of clinical AIDS in rhesus monkeys by cytokine-augmented DNA vaccination," *Science* 290:486-492 (2000).
Beaumont, "Detecting Population Expansion and Decline Using Micro satellites," *Genetics*153(4):2013-2029 (1999).
Beddows et al., "Comparison of the Antibody Repertoire Generated in Healthy Volunteers following Immunizations with a Monomeric Recombinant gp 120 Construct Derived from a CCR5/CXCR4-Using Human Immunodeficiency Virus Type 1 Isolate with Sera from Naturally Infected Individuals," *J. Virol.*73(2):1740-1745 (1999).
Beerli et al., "Maximum-Likelihood Estimation of Migration Rates and Effective Population Numbers. in Two Populations Using a Coalescent Approach," *Genetics* 152(2):763-773 (1999).
Brandt et al., "Association of chemokine-mediated block to HIV entry with coreceptor internalization," *J. Biol. Chem.* 277:17291-17299 (2002).
Buonaguro el al., "Heteroduplex Mobility Assay and Phylogenetic Analysis of V3 Region Sequences of Human Immunodeficiency Virus Type 1 Isolates from Gulu, Northern Uganda," *J. Virol.* 69(12):7971-7981 (1995).
Burton et al., "Why do we not have an HIV vaccine and how can we make one?," *Nat Med Vaccine Suppl.* 4(5):495-498 (1998).
Cecilia et al., "Neutralization Profiles of Primary Human Immunodeficiency Virus Type 1 Isolates in the Context of the Coreceptor Usage," *J. Virol.* 72(9):6988-6996 (1998).
Chackerian et al., "Human Immunodeficiency Virus Type 1 Coreceptors Participate in Postentry Stages in the Virus Replication Cycle and Function in Simian Immunodeficiency Virus Infection," *J. Virol.* 71:3932-3939 (1997).
Cornelissen et al., "*pol* Gene Diversity of Five Human Immunodeficiency Virus Type 1 Subtypes: Evidence for Naturally Occurring Mutations that Contribute to Drug Resistance, Limited Recombination Patterns, and Common Ancestry for Subtypes B and D," *J. Virol.* 71(9):6348-6358 (1997).
Crandall et al., "Empirical Tests of Some Predictions from Coalescent Theory With Applications to Intraspecific Phylogeny Reconstruction," *Genetics* 134(3):959-969 (1993).
Database Accession No. AX028621, Sequence 71 from Wo 00/29561(May 25, 2000).

(Continued)

*Primary Examiner*—Bo Peng

(57) ABSTRACT

The present invention is directed to ancestral and COT nucleic acid and amino acid sequences, methods for producing such sequences and uses thereof, including prophylactic and diagnostic uses.

11 Claims, 61 Drawing Sheets

OTHER PUBLICATIONS

Doria-Rose et al., "Human Immunodeficiency Type 1 Subtype B Ancestral Envelope Protein Is Functional and Elicits Neutralizing Antibodies in Rabbits Similar to Those Elicited by a Circulating Subtype B Envelope," *J. Virol.* 77:11563-11577 (2003).

Edmonson et al., "Evolution of a Simian Immunodeficiency Virus Pathogen," *J. Virol.* 72:405-414 (1998).

Edwards et al., "Phylogenetically Informative Length Polymorphism and Sequence Variability in Mitochondrial DNA of Australian Songbirds (*Pomatostomus*)," *Genetics* 126(3):695-711 (1990).

Feng et al., "Progressive sequence alignment as a prerequisite to correct phylogenetic trees," *J. Mol. Evol.* 35:351-360 (1987).

Fu, "Estimating Effective Population Size or Mutation Rate Using the Frequencies of Mutations of Various Classes in a Sample of DNA Sequences," *Genetics* 138(4):1375-1386 (1994).

Gao et al., "A Comprehensive Panel of Near-Full Length Clones and Reference Sequences for Non-subtype B Isolates of Human Immunodeficiency Virus Type 1," *J. Virol.* 72(7):5690-5698 (1998).

Gao et al., "HIV-1 clone 92us657.1 from Chicago (USA), tat protein, rev protein, envelope glycoprotein (env) genes, complete cds and vpr protein and nef protein genes, partial cds," retrieved from EBI Database Accession No. U04908 (Jul. 19, 1996).

Gao et al., "HIV-1 isolate 714 clone 1 from Baltimore, MD, USA, envelope glycoprotein (env) gene, partial cds," retrieved from EBI Database Accession No. U08450 (May 9, 1994).

Gao et al., "HIV-1 isolate 959 clone 18 from Malawi, envelope glycoprotein (env) gene, partial cds," retrieved from EBI Database Accession No. U08453 (May 9, 1994).

Gao et al., "Molecular Cloning and Analysis of Functional Envelope Genes from Human Immunodeficiency Virus Type 1 Sequence Subtypes A through G. The Who and NIAD Networks for HIV Isolation and Characterization," *J. Virol.* 70(3):1651-1667 (1996).

Gao et al., "Envelope glycoprotein, human immunodeficiency virus 1," retrieved from EBI Database Accession No. Q74749 (Nov. 1, 1996).

Gao et al., "Envelope glycoprotein, human immunodeficiency virus," retrieved from EBI Database Accession No. Q70010 (Nov. 1, 1996).

Gao et al., "Origin of HIV-1 in the chimpanzee *Pan troglodytes troglodytes*," *Nature* 397(6718):436-441 (1999).

Gao et al., "The Heterosexual Human Immunodeficiency Virus Type 1 Epidemic in Thailand is Caused by an Intersubtype (A/E) Recombinant of African Origin," *J. Virol.* 70(10):7013-7029 (1996).

Gillespie, "Genetic Drift in an Infinite Population: The Pseudo hitchhiking Model," *Genetics* 155(2):909-919 (2000).

Goddard et al., "Recurrent invasion and extinction of a selfish gene," *Proc. Natl. Acad. Sci. USA* 96(24)13880-13885 (1999).

Graham et al., "A Coalescent Model of Ancestry for a Rare Allele," *Genetics* 156(1):375-384 (2000).

Gupta et al., "Adjuvants—a balance between toxicity and adjuvanticity," *Vaccine* 11:293-306 (1993).

Henikoff et al., "Amino acid substitution matrices from protein blocks," *Proc. Natl. Acad. Sci. USA* 89:10915-10919 (1992).

Higgins et al., "Clustal: a package for performing multiple sequence alignment on a microcomputer," *Gene* 73:237-244 (1988).

Higgins et al., "Fast and sensitive multiple sequence alignments on a microcomputer," *Comput. Appl . Biosci.* 5:151-153 (1989).

Itescu et al., "Human immunodeficiency virus type 1 strains in the lungs of infected individuals evolve independently from those in peripheral blood and are highly conserved in the C-terminal region of the envelope V3 loop," *Proc. Natl. Acad. Sci. USA* 91(24)11378-11382 (1994).

Karlin et al., "Applications and statistics for multiple high-scoring segments in molecular sequence," *Proc. Natl. Acad. Sci. USA* 90:5873-5887 (1993).

Kelly, "An application of population genetic theory to synonymous gene sequence evolution in the human immunodeficiency virus (HIV)," *Gen. Res.* 64:1-9 (1994).

Kimpton et al., "Detection of Replication-Competent and Pseudotyped Human Immunodeficiency Virus with a Sensitive Cell Line on the Basis of Activation of an Integrated β-Galactosidase Gene," *J. Virol.* 66: 2232-2239 (1992).

Korber et al., "Limitations of a Molecular Clock Applied to Considerations of the Origin of HIV-1," *Science* 280(5371):1868-1871 (1998).

Kornfeld et al., "Cloning of HTLV-4 and its relation to simian and human immunodeficiency viruses" *Nature* 326:610-613 (1987).

Kuiken et al., "Increasing antigenic and genetic diversity of the V3 variable domain of the human immunodeficiency virus envelope protein in the course of the AIDS epidemic," *Proc. Natl. Acad. Sci. USA* 90(19):9061-9065 (1993).

Kuiken et al., "HIV Sequence Compendium, Part II. HIV-1/SIVcpz Complete Genomes" 279-466 (2001).

Learn et al, "Maintaining the Integrity of Human Immunodeficiency Virus Sequence Database," *J. Virol.* 70:5720-5730 (1996).

Leitner et al., "Tempo and Mode of Nucleotide Substitutions in gag and env Gene Fragments in Human Immunodeficiency Virus Type 1 Populations with a Known Transmission History," *J. Viol.* 71(6):4761-4770 (1997).

Letvin, "Progress in the Development of an HIV-1 Vaccine," *Science* 280(5371):1875-1880 (1998).

Lole et at, "Full-Length Human Immunodeficiency Virus Type 1 Genomes from Subtype C-Infected Seroconverters in India, with Evidence of Intersubtype Recombination," *J. Virol.* 73(1):152-160 (1999).

Long et al., "HIV Type 1 Variants Transmitted to Women in Kenya Require the CCR5 Coreceptor for Entry, Regardless of the Genetic Complexity of the Infecting Virus," *AIDS Res. Hum. Retroviruses* 18:567-576(2002).

Louwagie et al., "Genetic Diversity of the Envelope Glycoprotein from Human Immunodeficiency Virus Type 1 isolates of African Origin," *J. Virol* 69(1):263-271 (1995).

McCutchan et al., "Envelope protein human immunodeficiency virus 1," retrieved from EBI Database Accession No. 092763 (Nov. 1, 1998).

McCutchan et al., "Diversity of the Human Immunodeficiency Virus Type 1 Envelope Glycoprotein in San Francisco Men's Health Study Participants," *AID Research and Human Retroviruses* 14(4):329-337 (1998).

Needleman et al., "A General Method Applicable to the Search for Similarities in the Amino Acid Sequence of Two Proteins," *J. Mol. Biol.* 48:443-453 (1970).

Pearson et al., "Improved tools for biological sequence comparison," *Proc. Natl. Acad. Sci.* USA 85:2444-2448 (1988).

Penny et al., "Envelope glycoprotein, human Immunodeficiency virus 1," retrieved from EBI Database Accession No. Q73343 (Nov. 1, 1996).

Penny et al., "env Gene Sequences of Primary HIV Type 1 isolates of Subtypes B, C, D, E, and F Obtained from the World Health Organization Network for HIV isolation and Characterization," *AIDS Research and Human Retroviruses*, U.S. 12(8):741-747 (1996).

Posada et al., "Bioinformatics Applications Note — Model test: testing the model of DNA substitution," *Bioinformatics* 14:817-818 (1998).

Rambaut et al., "Seq-Gen: an application for the Monte Carlo simulation of DNA sequence evolution along phylogenetic trees," *Comput. Appl. Biosci* 13:235-238 (1997).

Richman et al., "Self-incompatibility alleles from *Physalis:* Implications fro historical inference from balanced genetic polymorphisms," *Proc. Natl. Acad. Sci* USA 96(1):168-172 (1999).

Robertson et al., "Recombination in HIV-1," *Nature* 374(6518):124-126 (1995).

Robinson et al., "Simian Immunodeficiency Virus DNA Vaccine Trial in Macaques," *Ann. New York Acad. Sci* 27:209-211 (1995).

Robinson, "DNA vaccines for immunodeficiency viruses," AIDS 11(A):S109-S119 (1997).

Rodrigo et at, "Coalescent estimates of HIV-1 generation time in vivo," *Proc. Natl. Acad. Sci* USA 96(5):2187-2191 (1999).

Schaal et al., "Gene genealogies and population variation in plants," *Proc. Natl. Acad. Sci.* USA 97(13):7024-7029 (2000).

Schadt et al., "Computational Advances in Maximum Likelihood Methods for Molecular Phylogeny," *Genome Research* 8(3):222-233 (1998).

Shankarappa et al., "Consistent Viral Evolutionary Changes Associated with the Progression of Human Immunodeficiency Virus Type 1 Infection," *J. Virol.* 73(12):10489-10502 (1999).

Sherry et al., "Alu, Evolution in Human Populations: Using the Coalescent to Estimate Effective Population Size," *Genetics* 147(4):1977-1982 (1997).

Slatkin, "Gene Genealogies Within Mutant Allelic Classes," *Genetics* 143(1):579-587 (1996).

Smith et al., "Human Rhinovirus Type 14:Human Immunodeficiency Virus Type 1 (HIV-1) V3 Loop Chimeras from a Combinatorial Library Induce Potent Neutralizing Antibody Responses Against HIV-1," *J. Virol.* 72(1):651-659 (1998).

Smith et al., "Comparison of Biosequences," *Adv. Appl. Math.* 2:482-489 (1981).

Smith et al., "The genetic data environment an expandable GUI for multiple sequence analysis," *CABIOS* 10:671-675 (1994).

Takehisa et al., "Human Immunodeficiency Virus Type 1 Intergroup(M/0) Recombination in Cameroon," *J. Virol.* 73(8):6810-6820 (1999).

Theodore et al., "Short Communication—Construction and Characterization of a Stable Full-Length Macrophage-Tropic HIV Type 1 Molecular Clone That Directs the Production of High Titers and Progeny Virions," *AIDS Res. Human Retrovir.* 12:191-194 (1996).

Thompson et al., "Clustal W: improving the sensitivity of progressive multiple sequence alignment through sequence weighting, position-specific gap penalties and weight matrix choice," *Nucleic Acids Res.* 22:4673-4680 (1994).

Upchurch et at., "Position and degree of mismatches and the mobility of DNA heteroduplexes," *Nucleic Acids Res.* 28(12):E69 (2000).

Verma et al., "Gene Therapy —promises, problems and prospects," *Nature* 389:239-242 (1997).

Yasutomi et al., "Simian Immunodeficiency Virus-Specific Cytotoxic T-Lymphocyte Induction through DNA Vaccination of Rhesus Monkeys," *J. Virol.* 70:678-681 (1996).

Yu et al., "Phenotypic and Genotypic Characteristics of Human Immunodeficiency Virus Type 1 from Patients with AIDS in Northern Thailand," *J. Viol.* 69(8):4649-4655 (1995).

Zhu et al., "An African HIV-1 sequence from 1959 and implications for the origin of the epidemic," *Nature* 391(6667):594-597 (1998).

The AIDS Knowledge Bases —AIDS Vaccines —Internet website: www.hivinsite.ucsf.edu (printed Aug. 17, 1999).

The NIAID Division of AIDS, Science, Vaccine Concepts/Designs, Recombinant Viral Surface Protein Vaccines—Internet website: www.niaid.nih.gov (printed Aug. 16, 1999).

The NIAID Division of AIDS, General Info, Basic Information About AIDS and HIV Internet website: www.niaid.nih.gov (printed Aug. 16, 1999).

The NIAID Division of AIDS, Science, Vaccine Concepts/Designs, Naked DNA Vaccines —Internet website:: www.niaid.nih.gov (printed Aug. 16, 1999).

The NIAID Division of AIDS, Science, Vaccine Designs/Concepts—Internet website: www.niaid.nih.gov (printed Aug. 16, 1999).

International AIDS Vaccine Initiative, IAVI Report —Jul. —Sep. 1998, HIV DNA Vaccines Move Slowly Into Human Trials —Internet website: www. iavi.org Vaccine Initiative, IAVI Report—Jul.-Aug. 1999, A Newsletter on International Aids Vaccine Research—Internet website: www.iavi.org (printed Aug. 16, 1999).

International AIDS Vaccine Initiative —Scientific Areas of Emphasis — Internet website: www.iavi.org (printed Aug. 16, 1999).

* cited by examiner

Phylogenetic Classification of HIV-1

Figure 4

```
┌─────────────────────────────────────┐
│ Collect HIV-1 subtype gag or        │
│ env sequence from databases         │
└─────────────────────────────────────┘
                 ↓
┌─────────────────────────────────────┐
│        Phylogenetic analysis        │
└─────────────────────────────────────┘
                 ↓
┌─────────────────────────────────────┐
│     Determine ancestor sequence     │
└─────────────────────────────────────┘
                 ↓
┌─────────────────────────────────────┐
│      Synthesis of env/gag           │
│      ancestors from long oligos     │
└─────────────────────────────────────┘
                 ↓
┌─────────────────────────────────────┐
│    Construction of transient        │
│    expression system                │
│    (SFV+CMV promoter)               │
└─────────────────────────────────────┘
                 ↓
┌─────────────────────────────────────┐
│      In vitro expression analysis   │
└─────────────────────────────────────┘
                 ↓
┌─────────────────────────────────────┐
│     Ancestor immunity analysis      │
│              in vivo                │
└─────────────────────────────────────┘
                 ↓
┌─────────────────────────────────────┐
│    Protection analysis in large     │
│          animal model               │
└─────────────────────────────────────┘
```

Figure 5

MP
Reconstruction

ML
Reconstruction

Figure 9
Comparison of Clade B *gag* Gene Sequence Reconstructions

```
[              10         20         30         40         50         60         70         80]
[                .          .          .          .          .          .          .          .]
Bgag.mrca    ATGGGTGCGA GAGCGTCAGT ATTAAGCGGG GGAGAATTAG ATAAATGGGA AAAAATTCGG TTACGGCCAG GGGGAAAGAA  [80]
Bgag.LScot   .......... .......... .......... .......... ...G...... .......... ...A...... ..........  [80]
Bgag.MMcot   .........G .......G.. .......... ...A...... ...GG..... .......... ...A...... ..........  [80]

[              90        100        110        120        130        140        150        160]
[                .          .          .          .          .          .          .          .]
Bgag.mrca    AAAATATAAA TTAAAACATA TAGTATGGGC AAGCAGGGAG CTAGAACGAT TCGCAGTTAA TCCTGGCCTT TTAGAAACAT  [160]
Bgag.LScot   ........G. .......... .......... .......... .......... .......... .........G ..........  [160]
Bgag.MMcot   .......... .......... .......... .......... .......... .T.....C.. .........G ..........  [160]

[             170        180        190        200        210        220        230        240]
[                .          .          .          .          .          .          .          .]
Bgag.mrca    CAGAAGGCTG TAGACAAATA CTGGGACAGC TACAACCATC CCTTCAGACA GGATCAGAAG AACTTAGATC ATTATATAAT  [240]
Bgag.LScot   .......... .......... .......... .......... .......... .......... .......... ..........  [240]
Bgag.MMcot   .......... C....G.... ....A..... ....T..... .......... .......... .......A... ..........  [240]

[             250        260        270        280        290        300        310        320]
[                .          .          .          .          .          .          .          .]
Bgag.mrca    ACAGTAGCAG TCCTCTATTG TGTGCATCAA AAGATAGAGG TAAAAGACAC CAAGGAAGCT TTAGATAAGA TAGAGGAAGA  [320]
Bgag.LScot   ........A C .......... .......... .G........ .......... .......... .....G.... ..........  [320]
Bgag.MMcot   ..G.....A C .......... .......... ..T....... ...G...... ......T... .....A..A. ..........  [320]

[             330        340        350        360        370        380        390        400]
[                .          .          .          .          .          .          .          .]
Bgag.mrca    GCAAAACAAA AGTAAGAAAA AGGCACAGCA AGCAGCAGCT GACACAGGAA ACAGCAGCCA GGTCAGCCAA AATTACCCTA  [400]
Bgag.LScot   .......... .......... .......... .......... .......... .......... .......... ..........  [400]
Bgag.MMcot   A......... .T........ G......... .......... .......... ......A..C .......... ..........  [400]

[             410        420        430        440        450        460        470        480]
[                .          .          .          .          .          .          .          .]
Bgag.mrca    TAGTGCAGAA CCTACAGGGG CAAATGGTAC ATCAGGCCCT ATCACCTAGA ACTTTAAATG CATGGGTAAA AGTAATAGAA  [480]
Bgag.LScot   .......... ...C...... .......... .......A.. .......... .......... .......... ....G....G  [480]
Bgag.MMcot   .......... TA.G...... .......... .......A.. .......... .......... .......... ....G.....  [480]

[             490        500        510        520        530        540        550        560]
[                .          .          .          .          .          .          .          .]
Bgag.mrca    GAGAAGGCTT TCAGCCCAGA AGTAATACCC ATGTTTTCAG CATTATCAGA AGGAGCCACC CCACAAGATT TAAACACCAT  [560]
Bgag.LScot   .......... .......... .......... .......... .......... .......... .......... ..........  [560]
Bgag.MMcot   .......... .......C.. .......... .......... .......... .......... .......... ..........  [560]

[             570        580        590        600        610        620        630        640]
[                .          .          .          .          .          .          .          .]
Bgag.mrca    GCTAAACACA GTGGGGGGAC ATCAAGCAGC CATGCAAATG TTAAAAGAGA CCATCAATGA GGAAGCTGCA GAATGGGATA  [640]
Bgag.LScot   .......... .......... .......... .......... .......... .......... .......... ..........  [640]
Bgag.MMcot   .......... .......... .......... .......... .......... .......A.. .......... ..........  [640]

[             650        660        670        680        690        700        710        720]
[                .          .          .          .          .          .          .          .]
Bgag.mrca    GATTGCATCC AGTGCATGCA GGGCCTATTG CACCAGGCCA GATGAGAGAA CCAAGGGGAA GTGACATAGC AGGAACTACT  [720]
Bgag.LScot   .......... .......... .......... .......... .......... .......... .......... ..........  [720]
Bgag.MMcot   .......C.. .......... .......... .......... .......... .......... .......... ..........  [720]

[             730        740        750        760        770        780        790        800]
[                .          .          .          .          .          .          .          .]
Bgag.mrca    AGTACCCTTC AGGAACAAAT AGCATGGATG ACAAATAATC CACCTATCCC AGTAGGAGAA ATCTATAAAA GATGGATAAT  [800]
Bgag.LScot   .......... ......G... .......... .......... .......... .......... .......... ..........  [800]
Bgag.MMcot   .......... ......G... .......C.. .......... .......... .......... .......... ..........  [800]

[             810        820        830        840        850        860        870        880]
[                .          .          .          .          .          .          .          .]
Bgag.mrca    CCTGGGATTA AATAAAATAG TAAGAATGTA TAGCCCTGTC AGCATTCTGG ACATAAGACA AGGACCAAAG GAACCCTTTA  [880]
Bgag.LScot   .......... .......... .......... .......AC. .......... .......... .......... ..........  [880]
Bgag.MMcot   .A........ .......... .......... .......AC. .......... .......... .......... ..........  [880]
```

```
[               890        900        910        920        930        940        950       960]
[                 .          .          .          .          .          .          .         .]
Bgag.mrca     GAGACTATGT AGACCGGTTC TATAAAACTC TAAGAGCCGA GCAAGCTTCA CAGGAGGTAA AAAATTGGAT GACAGAAACC  [960]
Bgag.LScot    .......... .......... .......... .......... .......... .......... .......... ..........  [960]
Bgag.MMcot    ....T..... T......... .......... .......... .......... .......... .......... ..........  [960]

[               970        980        990       1000       1010       1020       1030      1040]
[                 .          .          .          .          .          .          .         .]
Bgag.mrca     TTGTTGGTCC AAAATGCGAA CCCAGATTGT AAGACTATCT TAAAAGCATT GGGACCAGGA GCTACACTAG AAGAAATGAT  [1040]
Bgag.LScot    .......... .......... .......... ........T. .......... ........C. .......... ..........  [1040]
Bgag.MMcot    .......... .......... .......... .....C..T. .......... A.......C. .......... ..........  [1040]

[              1050       1060       1070       1080       1090       1100       1110      1120]
[                 .          .          .          .          .          .          .         .]
Bgag.mrca     GACAGCATGT CAGGGAGTGG GGGGACCCGG CCATAAAGCA AGAGTTTTGG CTGAAGCAAT GAGCCAAGTA ACAAATTCAG  [1120]
Bgag.LScot    .......... .......... .......... .......... .......... .......... .......... ..........  [1120]
Bgag.MMcot    .......... .......... .A..G...A. .......... .......... .A........ ........C. ..........  [1120]

[              1130       1140       1150       1160       1170       1180       1190      1200]
[                 .          .          .          .          .          .          .         .]
Bgag.mrca     CTACCATAAT GATGCAGAGA GGCAATTTTA GGAACCCAAG AAAGACTGTT AAGTGTTTCA ATTGTGGCAA AGAAGGGCAC  [1200]
Bgag.LScot    .......... .......... .......... ......A... .......... .......... .......... ..........  [1200]
Bgag.MMcot    .......... ........G. .......... A.GG..A... .......... ..A....... .......... ..........  [1200]

[              1210       1220       1230       1240       1250       1260       1270      1280]
[                 .          .          .          .          .          .          .         .]
Bgag.mrca     ATAGCCAGAA ATTGCAGGGC CCCTAGGAAA AAGGGCTGTT GGAAATGTGG AAAGGAAGGA CACCAAATGA AAGATTGTAC  [1280]
Bgag.LScot    .......A.. .......... .......... .......... .......... .......... .......... ..........  [1280]
Bgag.MMcot    .......... .......... ......A... .......... .......... .......... .......... ..........  [1280]

[              1290       1300       1310       1320       1330       1340       1350      1360]
[                 .          .          .          .          .          .          .         .]
Bgag.mrca     TGAGAGACAG GCTAATTTTT TAGGGAAAAT CTGGCCTTCC CACAAGGGAA GGCCAGGGAA TTTTCTTCAG AGCAGACCAG  [1360]
Bgag.LScot    .......... .......... .......G.. .......... .......... .......... .......... ..........  [1360]
Bgag.MMcot    .......... .......... .......G.. .......... .......... .......... ......C..A .....G....  [1360]

[              1370       1380       1390       1400       1410       1420       1430      1440]
[                 .          .          .          .          .          .          .         .]
Bgag.mrca     AGCCAACAGC CCCACCAGAA GAGAGCTTCA GGTTTGGGGA AGAGACAACA ACTCCCTCTC AGAAGCAGGA GCAAAAGAC  [1440]
Bgag.LScot    .......... .......... .......... .......... .......... .......... .......... ..C..T....  [1440]
Bgag.MMcot    .......... .......... .......... .......... G......... .......C.. .......... ..C..GG...  [1440]

[              1450       1460       1470       1480       1490       1500 ]
[                 .          .          .          .          .          . ]
Bgag.mrca     AAGGAACTGT ATCCTTTAGC TTCCCTCAAA TCACTCTTTG GCAACGACCC CTCGTCACAA TAA     [1503]
Bgag.LScot    .......... .......... ........G. .......... .......... .......... ...     [1503]
Bgag.MMcot    .......A.. ....C..GA. ........G. .......... .......... A......... ...     [1503]
```

Figure 10
Comparison of Clade B env Gene Sequence Reconstructions

```
[                10        20        30        40        50        60        70        80]
[                 .         .         .         .         .         .         .         .]
Bgp160.mrca   ATGAGAGTGA AGGGGATCAG GAAGAATTGT CAGCACTTGT GGAAATGGGG CACCATGCTC CTTGGGATGT TGATGATCTG   [80]
Bgp160.LScot  .......... .......... ........A. .......... ...G...... .......... .......... ..........   [80]
Bgp160.MMcot  .......... .......... ........A. .......... ...G...... .......... .......... ..........   [80]

[                90       100       110       120       130       140       150       160]
[                 .         .         .         .         .         .         .         .]
Bgp160.mrca   TAGTGCTGCA GAAAACTTGT GGGTCACAGT CTATTATGGG GTACCTGTGT GGAAAGAAGC AACCACCACT CTATTTTGTG   [160]
Bgp160.LScot  .......... .....A.... .......... .......... .......... .......... .......... ..........   [160]
Bgp160.MMcot  .......... .....A.... .......... .......... .......... .......... .......... ..........   [160]

[               170       180       190       200       210       220       230       240]
[                 .         .         .         .         .         .         .         .]
Bgp160.mrca   CATCAGATGC TAAAGCATAT AAAACAGAGG TACATAATGT CTGGGCCACA CATGCCTGTG TACCCACAGA CCCCAACCCA   [240]
Bgp160.LScot  .......... .......... ...... G.T. .......... T......... .......... .......... ..........   [240]
Bgp160.MMcot  .......... .......... ...... G.T. .......... T......... .......... .......... ..........   [240]

[               250       260       270       280       290       300       310       320]
[                 .         .         .         .         .         .         .         .]
Bgp160.mrca   CAAGAAGTAG TATTGGAAAA TGTGACAGAA AATTTTAACA TGTGGAAAAA TAACATGGTA GAACAGATGC ATGAGGATAT   [320]
Bgp160.LScot  .......... .......... .......... .......... .......... .......... .......... ..........   [320]
Bgp160.MMcot  .......... .......... .......... .......... .......... .......... .......... ..........   [320]

[               330       340       350       360       370       380       390       400]
[                 .         .         .         .         .         .         .         .]
Bgp160.mrca   AATCAGTTTA TGGGATCAAA GCCTAAAGCC ATGTGTAAAA TTAACCCCAC TCTGTGTTAC TTTAAATTGC ACTGATGCGA   [400]
Bgp160.LScot  .......... .......... .......... .......... .......... .......... .......... ......TT..   [400]
Bgp160.MMcot  .......... .......... .......... .......... .......... .......... .......... ......TT..   [400]

[               410       420       430       440       450       460       470       480]
[                 .         .         .         .         .         .         .         .]
Bgp160.mrca   ACAAGAATGC TACTAATACC AATAGTAGTA GTGGGGGAAC AATGGAGAAA GGAGAAATGA AAAACTGCTC TTTCAATATC   [480]
Bgp160.LScot  .T........ .......... .......... .C....A..T G......... ........A. .......... ..........   [480]
Bgp160.MMcot  .T........ .......... .......... .C....A..T G......... ........A. .......... ..........   [480]

[               490       500       510       520       530       540       550       560]
[                 .         .         .         .         .         .         .         .]
Bgp160.mrca   ACCACAAGCA TAAGAGATAA GATGCAGAAA GAATATGCAC TTTTTTATAA ACTTGATGTA GTACCAATAG ATAATGATAA   [560]
Bgp160.LScot  .......... ....... .G. .......... .......... .......... .......... .......... ..........   [560]
Bgp160.MMcot  .......... ....... .G. .......... .......... .......... .......... .......... ..........   [560]

[               570       580       590       600       610       620       630       640]
[                 .         .         .         .         .         .         .         .]
Bgp160.mrca   TAATAGTAAT AATAATACCA ACTATAGGTT GATAAATTGT AATACCTCAG TCATTACACA GGCCTGTCCA AAGGTATCCT   [640]
Bgp160.LScot  .....C.... ....C..... G......... .....G.... ..C....... .......... .......... ..........   [640]
Bgp160.MMcot  .....C.... ....C..... G......... .....G.... ..C....... .......... .......... ..........   [640]

[               650       660       670       680       690       700       710       720]
[                 .         .         .         .         .         .         .         .]
Bgp160.mrca   TTGAGCCAAT TCCCATACAT TATTGTACCC CGGCTGGTTT TGCGATTCTA AAGTGTAATG ATAAGAAGTT CAATGGAACA   [720]
Bgp160.LScot  .......... .......... ......G... .......... .......... .......... .......... ..........   [720]
Bgp160.MMcot  .......... .......... ......G... .......... .......... .......... .......... ..........   [720]

[               730       740       750       760       770       780       790       800]
[                 .         .         .         .         .         .         .         .]
Bgp160.mrca   GGACCATGTA AAAATGTCAG CACAGTACAA TGTACACATG GAATTAGGCC AGTAGTGTCA ACTCAACTGC TGTTAAATGG   [800]
Bgp160.LScot  .......... C......... .......... .......... .......... ......A... .......... ..........   [800]
Bgp160.MMcot  .......... C......... .......... .......... .......... ......A... .......... ..........   [800]

[               810       820       830       840       850       860       870       880]
[                 .         .         .         .         .         .         .         .]
Bgp160.mrca   CAGTCTAGCA GAAGAAGAGG TAGTAATTAG ATCTGAAAAT TTCACGGACA ATGCTAAAAC CATAATAGTA CAGCTGAATG   [880]
Bgp160.LScot  .......... .......... .......... ......C... .......... .......... .......... ..........   [880]
Bgp160.MMcot  .......... .......... .......... ......C... .......... .......... .......... ..........   [880]
```

```
[              890        900        910        920        930        940        950       960]
[                .          .          .          .          .          .          .         .]
Bgp160.mrca    AATCTGTAGA AATTAATTGT ACAAGACCCA ACAACAATAC AAGAAAAAGT ATACCTATAG GACCAGGGAG AGCACTTTAT  [960]
Bgp160.LScot   .......... .......... .......... .......... .......... ....A..... .......... ....T.....  [960]
Bgp160.MMcot   .......... .......... .......... .......... .......... ....A..... .......... ....T.....  [960]

[              970        980        990       1000       1010       1020       1030      1040]
[                .          .          .          .          .          .          .         .]
Bgp160.mrca    ACAACAGGAG AAATAATAGG AGATATAAGA CAAGCACATT GTAACATTAG TAGAGCAAAA TGGAATAACA CTTTAAAACA [1040]
Bgp160.LScot   .......... .......... .......... .......... .......... .......... .......... .......... [1040]
Bgp160.MMcot   .......... .......... .......... .......... .......... .......... .......... .......... [1040]

[             1050       1060       1070       1080       1090       1100       1110      1120]
[                .          .          .          .          .          .          .         .]
Bgp160.mrca    GGTAGTTACA AAATTAAGAG AACAATTTGG GAATAATAAA ACAATAGTCT TTAATCCATC CTCAGGAGGG GACCCAGAAA [1120]
Bgp160.LScot   .A......A. .......... .......... .......... .......... ......A... .......... .......... [1120]
Bgp160.MMcot   .A......A. .......... .......... .......... .......... ......A... .......... .......... [1120]

[             1130       1140       1150       1160       1170       1180       1190      1200]
[                .          .          .          .          .          .          .         .]
Bgp160.mrca    TTGTAATGCA CAGTTTTAAT TGTGGAGGGG AATTTTTCTA CTGTAATACA ACACAACTGT TTAATAGTAC TTGGAATAGT [1200]
Bgp160.LScot   .......... .......... .......... .......... .......T.. .......... .......... .......G.. [1200]
Bgp160.MMcot   .......... .......... .......... .......... .......T.. .......... .......... .......G.. [1200]

[             1210       1220       1230       1240       1250       1260       1270      1280]
[                .          .          .          .          .          .          .         .]
Bgp160.mrca    ACTGAAGGGT CAAATAAAAC TACAGGGTCA AATAACACTG GAGGAGAAAC TATCACACTC CCATGCAGAA TAAAACAAAT [1280]
Bgp160.LScot   ...TGGACT. GG....CT.. .GA....... ...G...... A......C.. .......... .......... .......... [1280]
Bgp160.MMcot   ...TGGACT. GG....CT.. .GA....... ...G...... A......C.. .......... .......... .......... [1280]

[             1290       1300       1310       1320       1330       1340       1350      1360]
[                .          .          .          .          .          .          .         .]
Bgp160.mrca    TATAAACATG TGGCAGGAAG TAGGAAAAGC AATGTATGCC CCTCCCATCA GAGGACAAAT TAAATGTTCA TCAAATATTA [1360]
Bgp160.LScot   .......... .......... .......... .......... .......... ..G....... .......... .......... [1360]
Bgp160.MMcot   .......... .......... .......... .......... .......... ..G....... .......... .......... [1360]

[             1370       1380       1390       1400       1410       1420       1430      1440]
[                .          .          .          .          .          .          .         .]
Bgp160.mrca    CAGGGCTACT ATTAACAAGA GATGGTGGTG AAAATAGTAC CAATGACACC GAGATCTTCA GACCTGGAGG AGGAGATATG [1440]
Bgp160.LScot   .......G.. .......... .........A .T....AC.. ...C...... .......... .......... .......... [1440]
Bgp160.MMcot   .......G.. .......... .........A .T....AC.. ...C...... .......... .......... .......... [1440]

[             1450       1460       1470       1480       1490       1500       1510      1520]
[                .          .          .          .          .          .          .         .]
Bgp160.mrca    AGGGACAATT GGAGAAGTGA ATTATATAAA TATAAAGTAG TAAAAATTGA ACCATTAGGA GTAGCACCCA CCAAGGCAAA [1520]
Bgp160.LScot   .......... .......... .......... .......... .......... .......... .......... .......... [1520]
Bgp160.MMcot   .......... .......... .......... .......... .......... .......... .......... .......... [1520]

[             1530       1540       1550       1560       1570       1580       1590      1600]
[                .          .          .          .          .          .          .         .]
Bgp160.mrca    GAGAAGAGTG GTGCAAAGAG AAAAAAGAGC AGTGGGAATA ATAGGAGCTA TGTTCCTTGG GTTCTTGGGA GCAGCAGGAA [1600]
Bgp160.LScot   .......... .....G.... .......... .......... .........G .......... .......... .......... [1600]
Bgp160.MMcot   .......... .....G.... .......... .......... .........G .......... .......... .......... [1600]

[             1610       1620       1630       1640       1650       1660       1670      1680]
[                .          .          .          .          .          .          .         .]
Bgp160.mrca    GCACTATGGG CGCAGCGTCA ATGACGCTGA CGGTACAGGC CAGACAATTA TTGTCTGGTA TAGTGCAACA GCAAAACAAT [1680]
Bgp160.LScot   .......... .......... .......... .......... .......... .......... .......... ...G...... [1680]
Bgp160.MMcot   .......... .......... .......... .......... .......... .......... .......... ...G...... [1680]

[             1690       1700       1710       1720       1730       1740       1750      1760]
[                .          .          .          .          .          .          .         .]
Bgp160.mrca    TTGCTGAGGG CTATTGAGGC GCAACAGCAT CTGTTGCAAC TCACGGTCTG GGGCATCAAA CAGCTCCAGG CAAGAGTCCT [1760]
Bgp160.LScot   .......... .......... .......... .......... ....A..... .......G.. .......... .......... [1760]
Bgp160.MMcot   .......... .......... .......... .......... ....A..... .......G.. .......... .......... [1760]
```

```
[            1770       1780       1790       1800       1810       1820       1830       1840]
[                .          .          .          .          .          .          .          .]
Bgp160.mrca  GGCTGTGGAA AGATACCTAA GGGATCAACA GCTCCTAGGA ATTTGGGGTT GCTCTGGAAA ACTCATTTGC ACCACTACTG  [1840]
Bgp160.LScot ........... .......... .......... ......G..G .......... .......... .......... ......G...  [1840]
Bgp160.MMcot ........... .......... .......... ......G..G .......... .......... .......... ......G...  [1840]

[            1850       1860       1870       1880       1890       1900       1910       1920]
[                .          .          .          .          .          .          .          .]
Bgp160.mrca  TGCCTTGGAA TGCTAGTTGG AGTAATAAAT CTCTGGATAA GATTTGGAAT AACATGACCT GGATGGAGTG GGAAAGAGAA  [1920]
Bgp160.LScot ........... .......... .......... ........G. .......... .......... .......... ..........  [1920]
Bgp160.MMcot ........... .......... .......... ........G. .......... .......... .......... ..........  [1920]

[            1930       1940       1950       1960       1970       1980       1990       2000]
[                .          .          .          .          .          .          .          .]
Bgp160.mrca  ATTGACAATT ACACAGGCTT AATATACAAC TTAATTGAAG AATCGCAGAA CCAGCAAGAA AAGAATGAAC AAGAATTATT  [2000]
Bgp160.LScot ........... .....A.... ........C. .......... ......A... ...A...... .......... ..........  [2000]
Bgp160.MMcot ........... .....A.... ........C. .......... ......A... ...A...... .......... ..........  [2000]

[            2010       2020       2030       2040       2050       2060       2070       2080]
[                .          .          .          .          .          .          .          .]
Bgp160.mrca  GGAATTGGAT AAGTGGGCAA GTTTGTGGAA TTGGTTTGAC ATAACACAAT GGCTGTGGTA TATAAAAATA TTCATAATGA  [2080]
Bgp160.LScot ......A... ..A....... .......... .......... ......A.C. .......... .......... ..........  [2080]
Bgp160.MMcot ......A... ..A....... .......... .......... ......A.C. .......... .......... ..........  [2080]

[            2090       2100       2110       2120       2130       2140       2150       2160]
[                .          .          .          .          .          .          .          .]
Bgp160.mrca  TAGTAGGAGG CTTGGTAGGT TTAAGAATAG TTTTTGCTGT GCTTTCTATA GTGAATAGAG TTAGGCAGGG ATACTCACCA  [2160]
Bgp160.LScot ........... .......... .......... .......... A......... .......... .......... ..........  [2160]
Bgp160.MMcot ........... .......... .......... .......... A......... .......... .......... ..........  [2160]

[            2170       2180       2190       2200       2210       2220       2230       2240]
[                .          .          .          .          .          .          .          .]
Bgp160.mrca  TTATCATTTC AGACCCGCCT CCCAGCCCCG AGGGGACCCG ACAGGCCCGA AGGAATCGAA GAAGAAGGTG GAGAGAGAGA  [2240]
Bgp160.LScot .....G.... .......... .......... .......... .......... .......... .......... ..........  [2240]
Bgp160.MMcot .....G.... .......... .......... .......... .......... .......... .......... ..........  [2240]

[            2250       2260       2270       2280       2290       2300       2310       2320]
[                .          .          .          .          .          .          .          .]
Bgp160.mrca  CAGAGACAGA TCCGGTCGAT TAGTGAATGG ATTCTTAGCA CTTATCTGGG ACGATCTGCG GAGCCTGTGC CTCTTCAGCT  [2320]
Bgp160.LScot ........... .......C.. .......... .......... ....C..... .......... .......... ..........  [2320]
Bgp160.MMcot ........... .......C.. .......... .......... ....C..... .......... .......... ..........  [2320]

[            2330       2340       2350       2360       2370       2380       2390       2400]
[                .          .          .          .          .          .          .          .]
Bgp160.mrca  ACCACCGCTT GAGAGACTTA CTCTTGATTG TAGCGAGGAT TGTGGAACTT CTGGGACGCA GGGGGTGGGA AGCCCTCAAA  [2400]
Bgp160.LScot ........... .......... ..A....... .......... .......... .......... .......... ..........  [2400]
Bgp160.MMcot ........... .......... ..A....... .......... .......... .......... .......... ..........  [2400]

[            2410       2420       2430       2440       2450       2460       2470       2480]
[                .          .          .          .          .          .          .          .]
Bgp160.mrca  TATTGGTGGA ATCTCCTGCA GTATTGGAGT CAGGAACTAA AGAATAGTGC TGTTAGCTTG CTTAATGCCA CAGCAATAGC  [2480]
Bgp160.LScot ........... ......A... .......... .......... .......... ..C....... ....C..... ..........  [2480]
Bgp160.MMcot ........... ......A... .......... .......... .......... ..C....... ....C..... ..........  [2480]

[            2490       2500       2510       2520       2530       2540       2550       2560]
[                .          .          .          .          .          .          .          .]
Bgp160.mrca  AGTAGCTGAG GGGACAGATA GGGTTATAGA AGTAGTACAA AGAGCTTGTA GAGCTATTCT TCACATACCT AGAAGAATAA  [2560]
Bgp160.LScot ........... .......... .......... .......... .......... C......... .C........ ..........  [2560]
Bgp160.MMcot ........... .......... .......... .......... .......... C......... .C........ ..........  [2560]

[            2570       2580       ]
[                .          .       ]
Bgp160.mrca  GACAGGGCTT AGAAAGGGCT TTGCTATAA   [2589]
Bgp160.LScot .......... G......... .........   [2589]
Bgp160.MMcot .......... G......... .........   [2589]
```

Figure 11
Comparison of Clade B nef Gene Sequence Reconstructions

```
[                  10         20         30         40         50         60         70         80]
[                   .          .          .          .          .          .          .          .]
Bnef.mrca   ATGGGTGGCA AGTGGTCAAA ACGTAGTGTG GTTGGATGGC CTGCTGTAAG GGAAAGAATG AGACGAGCTG AGCCAGCAGC  [80]
Bnef.MMcot  .......... .......... .......... .......... .......... .......... .......... ..........  [80]
Bnef.LScot  .......... .......... .......... .......... .......... .......... .......... ..........  [80]

[                  90        100        110        120        130        140        150        160]
[                   .          .          .          .          .          .          .          .]
Bnef.mrca   AGATGGGGTG GGAGCAGTAT CTCGAGACCT GGAAAAACAT GGAGCAATCA CAAGTAGCAA TACAGCAGCT ACTAATGCTG  [160]
Bnef.MMcot  .......... .......... .......... .......... .......... .......... .......... ..........  [160]
Bnef.LScot  .......... .......... .......... .......... .......... .......... .......... ..........  [160]

[                 170        180        190        200        210        220        230        240]
[                   .          .          .          .          .          .          .          .]
Bnef.mrca   CTTGTGCCTG GCTAGAAGCA CAAGAGGAGG AGGAGGTGGG TTTTCCAGTC AGACCTCAGG TACCTTTAAG ACCAATGACT  [240]
Bnef.MMcot  A......... .......... .......... .......... .......... .......... .......... ..........  [240]
Bnef.LScot  A......... .......... .......... .......... .......... .......... .......... ..........  [240]

[                 250        260        270        280        290        300        310        320]
[                   .          .          .          .          .          .          .          .]
Bnef.mrca   TACAAGGCAG CTGTAGATCT TAGCCACTTT TTAAAAGAAA AGGGGGGACT GGAAGGGCTA GTTTACTCCC AAAAAAGACA  [320]
Bnef.MMcot  .......... ..T....... .......... .......... .......... .......... A......... ..........  [320]
Bnef.LScot  ...Y...... ..T....... .......... .......... .......... .......... A......... ..........  [320]

[                 330        340        350        360        370        380        390        400]
[                   .          .          .          .          .          .          .          .]
Bnef.mrca   AGATATCCTT GATCTGTGGG TCTACCACAC ACAAGGCTAC TTCCCTGATT GGCAGAACTA CACACCAGGG CCAGGGACCA  [400]
Bnef.MMcot  .......... .......... .......... .......... .......... .......... .......... .......T..  [400]
Bnef.LScot  .......... .......... .......... .......... .......... .......... .......... .......T..  [400]

[                 410        420        430        440        450        460        470        480]
[                   .          .          .          .          .          .          .          .]
Bnef.mrca   GATATCCACT GACCTTTGGA TGGTGCTTCA AGCTAGTACC AGTTGAGCCA GAGAAGGTAG AAGAGGCCAC TGAAGGAGAG  [480]
Bnef.MMcot  .......... .......... .......... .......... .......... .......... ........A. ..........  [480]
Bnef.LScot  .......... .......... .......... .......... .......... .......... ........A. ..........  [480]

[                 490        500        510        520        530        540        550        560]
[                   .          .          .          .          .          .          .          .]
Bnef.mrca   AACAACAGCT TGTTACACCC TATGAGCCTG CATGGAATGG ATGACCCGGA GAGAGAAGTG TTAGTGTGGA GGTTTGACAG  [560]
Bnef.MMcot  ......T... .......... ........A. .....G.... .......... ..A....... .......... A.........  [560]
Bnef.LScot  .......... .......... .......... .....G.... .......... ..A....... .......... A.........  [560]

[                 570        580        590        600        610        620]
[                   .          .          .          .          .          .]
Bnef.mrca   CCGCCTAGCA TTTCATCACA TGGCCCGAGA GAAGCATCCG GAGTACTACA AGGACTGCTG A    [621]
Bnef.MMcot  .......... .......... .........CT...... .......... .......... .    [621]
Bnef.LScot  .......... .......... .........CT...... .......... .......... .    [621]
```

Figure 12
**Comparison of Clade B *pol* Gene Sequence Reconstructions**

```
[           10         20         30         40         50         60         70         80]
[                                                                                         .]
Bpol.mrca   TTTTTTAGGG AAAATCTGGC CTTCCCACAA GGGAAGGCCA GGGAACTTTC TTCAGAGCAG ACCAGAGCCA ACAGCCCCAC  [80]
Bpol.LScot  ..........G..... .......... .......... .....T.... .......... .......... ..........  [80]
Bpol.MMcot  ..........G..... .......... .......... .....T.... .......... .......... ..........  [80]

[           90        100        110        120        130        140        150        160]
[                                                                                         .]
Bpol.mrca   CAGAAGAGAG CTTCAGGTTT GGGGAAGAGA CAACAACTCC CTCTCAGAAG CAGGAGCAGA TAGACAAGGA ACTGTATCCT  [160]
Bpol.LScot  .......... .......... .......... .......... .......... .......C.. .......... ..........  [160]
Bpol.MMcot  .......... .......... .......... .......... .......... .......C.. .......... ..........  [160]

[          170        180        190        200        210        220        230        240]
[                                                                                         .]
Bpol.mrca   TTAGCTTCCC TCAAATCACT CTTTGGCAAC GACCCCTCGT CACAATAAAG ATAGGGGGGC AACTAAAGGA AGCTCTATTA  [240]
Bpol.LScot  ..........G..... .......... .......... .......... .......... .......... ..........  [240]
Bpol.MMcot  ..........G..... .......... .......... .......... .......... .......... ..........  [240]

[          250        260        270        280        290        300        310        320]
[                                                                                         .]
Bpol.mrca   GATACAGGAG CAGATGATAC AGTATTAGAA GAAATGAATT TGCCAGGAAA ATGGAAACCA AAAATGATAG GGGGAATTGG  [320]
Bpol.LScot  .......... .......... .......... .......... .........G .......... .......... ..........  [320]
Bpol.MMcot  .......... .......... .......... .......... .........G .......... .......... ..........  [320]

[          330        340        350        360        370        380        390        400]
[                                                                                         .]
Bpol.mrca   AGGTTTTATC AAAGTAAGAC AGTATGATCA AATACCCATA GAAATCTGTG GACATAAAGC TATAGGTACA GTATTAGTAG  [400]
Bpol.LScot  .......... .......... .......... G......... .......... .......... .......... ..........  [400]
Bpol.MMcot  .......... .......... .......... G....T.... .......... .......... .......... ..........  [400]

[          410        420        430        440        450        460        470        480]
[                                                                                         .]
Bpol.mrca   GACCTACACC TGTCAACATA ATTGGAAGAA ATCTGTTGAC TCAGATTGGT TGCACTTTAA ATTTTCCCAT TAGTCCTATT  [480]
Bpol.LScot  .......... .......... .......... .......... .......... .......... .......... ..........  [480]
Bpol.MMcot  .......... .......... .......... .......... .......... .......... .......... ..........  [480]

[          490        500        510        520        530        540        550        560]
[                                                                                         .]
Bpol.mrca   GAAACTGTAC CAGTAAAATT AAAGCCAGGA ATGGATGGCC CAAAAGTTAA ACAATGGCCA TTGACAGAAG AAAAAATAAA  [560]
Bpol.LScot  .......... .......... .......... .......... .......... .......... .......... ..........  [560]
Bpol.MMcot  .......... .......... .......... .......... .......... .......... .......... ..........  [560]

[          570        580        590        600        610        620        630        640]
[                                                                                         .]
Bpol.mrca   AGCATTAGTA GAAATTTGTA CAGAAATGGA AAAGGAAGGA AAAATTTCAA AAATTGGGCC TGAAAATCCA TACAATACTC  [640]
Bpol.LScot  .......... .......... .......... .........C .......... .......... .......... ..........  [640]
Bpol.MMcot  .......... .......... .......... .........G .......... .......... .......... ..........  [640]

[          650        660        670        680        690        700        710        720]
[                                                                                         .]
Bpol.mrca   CAGTATTTGC CATAAAGAAA AAAGACAGTA CTAAATGGAG AAAATTAGTA GATTTCAGAG AACTTAATAA GAGAACTCAA  [720]
Bpol.LScot  .......... .......... .......... .......... .......... .......... .......... ..........  [720]
Bpol.MMcot  .......... .......... .......... .......... .......... .......... .......... ..........  [720]

[          730        740        750        760        770        780        790        800]
[                                                                                         .]
Bpol.mrca   GACTTCTGGG AAGTTCAATT AGGAATACCA CATCCTGCAG GGTTAAAAAA GAAAAAATCA GTAACAGTAC TGGATGTGGG  [800]
Bpol.LScot  .......... .......... .......... .....C.... .......... .......... .......... ..........  [800]
Bpol.MMcot  .......... .......... .......... .....C.... .......... .......... .......... ..........  [800]

[          810        820        830        840        850        860        870        880]
[                                                                                         .]
Bpol.mrca   TGATGCATAT TTTTCAGTTC CCTTAGATGA AGACTTCAGG AAGTATACTG CATTTACCAT ACCTAGTATA AACAATGAGA  [880]
Bpol.LScot  .......... .......... .......... .......... .......... .......... .......... ..........  [880]
Bpol.MMcot  .......... .......... .......... .......... .......... .......... .......... ..........  [880]
```

```
[                890        900        910        920        930        940        950        960]
[                  .          .          .          .          .          .          .         .]
Bpol.mrca    CACCAGGGAT TAGATATCAG TACAATGTGC TTCCACAGGG ATGGAAAGGA TCACCAGCAA TATTCCAAAG TAGCATGACA  [960]
Bpol.LScot   .......... .......... .......... .......... .......... .......... .......... ..........  [960]
Bpol.MMcot   .......... .......... .......... .......... .......... .......... .......... ..........  [960]

[                970        980        990       1000       1010       1020       1030       1040]
[                  .          .          .          .          .          .          .         .]
Bpol.mrca    AAAATCTTAG AGCCTTTTAG AAAACAAAAT CCAGAAATAG TTATCTATCA ATACATGGAT GATTTGTATG TAGGATCTGA  [1040]
Bpol.LScot   .......... .......... .......... .....C.... .......... .......... .......... ..........  [1040]
Bpol.MMcot   .......... .......... .......... .....C.... .......... .......... .......... ..........  [1040]

[               1050       1060       1070       1080       1090       1100       1110       1120]
[                  .          .          .          .          .          .          .         .]
Bpol.mrca    CTTAGAAATA GGGCAGCATA GAACAAAAAT AGAGGAACTG AGAGAACATC TGTTGAGGTG GGGATTTACC ACACCAGACA  [1120]
Bpol.LScot   .......... .......... .......... ...C...... .......... .......... .......... ..........  [1120]
Bpol.MMcot   .......... .......... .......... ...C...... .......... .......... .......... ..........  [1120]

[               1130       1140       1150       1160       1170       1180       1190       1200]
[                  .          .          .          .          .          .          .         .]
Bpol.mrca    AAAAACATCA GAAAGAACCT CCATTTCTTT GGATGGGTTA TGAACTCCAT CCTGATAAAT GGACAGTACA GCCTATAGTG  [1200]
Bpol.LScot   .......... .......... .....C.... .......... .......... .......... .......... ..........  [1200]
Bpol.MMcot   .......... .......... .....C.... .......... .......... .......... .......... ..........  [1200]

[               1210       1220       1230       1240       1250       1260       1270       1280]
[                  .          .          .          .          .          .          .         .]
Bpol.mrca    CTGCCAGAAA AAGACAGCTG GACTGTCAAT GACATACAGA AGTTAGTGGG AAAATTGAAT TGGGCAAGTC AGATTTATGC  [1280]
Bpol.LScot   .......... .......... .......... .......... .......... .......... .......... ..........  [1280]
Bpol.MMcot   .......... .......... .......... .......... .......... .......... .......... .....CC.  [1280]

[               1290       1300       1310       1320       1330       1340       1350       1360]
[                  .          .          .          .          .          .          .         .]
Bpol.mrca    AGGGATTAAA GTAAAGCAAT TATGTAAACT CCTTAGGGGA ACCAAAGCAC TAACAGAAGT AGTACCACTA ACAGAAGAAG  [1360]
Bpol.LScot   .......... .......... .......... .......... .......... .......... .A........ ..........  [1360]
Bpol.MMcot   .......... .......... .......... .......... .......... .......... .A........ ..........  [1360]

[               1370       1380       1390       1400       1410       1420       1430       1440]
[                  .          .          .          .          .          .          .         .]
Bpol.mrca    CAGAGCTAGA ACTGGCAGAA AACAGGGAGA TTCTAAAAGA ACCAGTACAT GGAGTGTATT ATGACCCATC AAAAGACTTA  [1440]
Bpol.LScot   .......... .......... .......... .......... .......... .......... .......... ..........  [1440]
Bpol.MMcot   .......... .......... ........A. .......... .......... .......... .......... ..........  [1440]

[               1450       1460       1470       1480       1490       1500       1510       1520]
[                  .          .          .          .          .          .          .         .]
Bpol.mrca    ATAGCAGAAA TACAGAAGCA GGGGCAAGGC CAATGGACAT ATCAAATTTA TCAAGAGCCA TTTAAAAATC TGAAAACAGG  [1520]
Bpol.LScot   .......... .......... .......... .......... .......... .......... .......... ..........  [1520]
Bpol.MMcot   .......... .......... .......... .......... .......... .......... .......... ..........  [1520]

[               1530       1540       1550       1560       1570       1580       1590       1600]
[                  .          .          .          .          .          .          .         .]
Bpol.mrca    AAAGTATGCA AGAATGAGGG GTGCCCACAC TAATGATGTA AAACAATTAA CAGAGGCAGT GCAAAAAATA GCCACAGAAA  [1600]
Bpol.LScot   .......... .......... .......... .......... .......... .......... .......... ..........  [1600]
Bpol.MMcot   ...A...... .......... .......... .......... .......... .......... .......... ..........  [1600]

[               1610       1620       1630       1640       1650       1660       1670       1680]
[                  .          .          .          .          .          .          .         .]
Bpol.mrca    GCATAGTAAT ATGGGGAAAG ACTCCTAAAT TTAAACTACC CATACAAAAG GAAACATGGG AAGCATGGTG GACAGAGTAT  [1680]
Bpol.LScot   .......... .......... .......... .........A .......... .......... .......... ..........  [1680]
Bpol.MMcot   .......... .......... .......... .........A .......... ..A....... .......... ..........  [1680]

[               1690       1700       1710       1720       1730       1740       1750       1760]
[                  .          .          .          .          .          .          .         .]
Bpol.mrca    TGGCAAGCCA CCTGGATTCC TGAGTGGGAG TTTGTCAATA CCCCTCCCTT AGTAAAATTA TGGTACCAGT TAGAGAAAGA  [1760]
Bpol.LScot   .......... .......... .......... .......... ...G...... .......... .......... ..........  [1760]
Bpol.MMcot   .......... .......... .......... .......... ...G...... .......... .......... ..........  [1760]

[               1770       1780       1790       1800       1810       1820       1830       1840]
[                  .          .          .          .          .          .          .         .]
Bpol.mrca    ACCCATAGTA GGAGCAGAAA CTTTCTATGT AGATGGGGCA GCTAATAGAG AGACTAAATT AGGAAAAGCA GGATATGTTA  [1840]
Bpol.LScot   .......... .......... .......... ........G. .......... .......... .......... ..........  [1840]
Bpol.MMcot   .......... .......... .......... .....C..G. .......... .......... .......... ..........  [1840]
```

```
[              1850       1860       1870       1880       1890       1900       1910       1920]
[                 .          .          .          .          .          .          .          .]
Bpol.mrca    CTGACAGAGG AAGACAAAAA GTTGTCTCCC TAACTGACAC AACAAATCAG AAGACTGAGT TACAAGCAAT TCATCTAGCT  [1920]
Bpol.LScot   .......... .......... .......... .......... .......... .......... .......... ..........  [1920]
Bpol.MMcot   ..A....... .......... .......... .......... .......... .......... .......... ..........  [1920]

[              1930       1940       1950       1960       1970       1980       1990       2000]
[                 .          .          .          .          .          .          .          .]
Bpol.mrca    TTGCAGGATT CGGGATTAGA AGTAAACATA GTAACAGACT CACAATATGC ATTAGGAATC ATTCAAGCAC AACCAGATAA  [2000]
Bpol.LScot   .......... .......... .......... .......... .......... .......... .......... ..........  [2000]
Bpol.MMcot   .......... .......... .......... .......... .......... .......... .......... ..........  [2000]

[              2010       2020       2030       2040       2050       2060       2070       2080]
[                 .          .          .          .          .          .          .          .]
Bpol.mrca    GAGTGAATCA GAGTTAGTCA GTCAAATAAT AGAGCAGTTA ATAAAAAAGG AAAAGGTCTA CCTGGCATGG GTACCAGCAC  [2080]
Bpol.LScot   .......... .......... .......... .......... .......... .......... .......... ..........  [2080]
Bpol.MMcot   A......... .......... .......... .......... .......... .......... .......... ..........  [2080]

[              2090       2100       2110       2120       2130       2140       2150       2160]
[                 .          .          .          .          .          .          .          .]
Bpol.mrca    ACAAAGGAAT TGGAGGAAAT GAACAAGTAG ATAAATTAGT CAGTACTGGA ATCAGGAAAG TACTATTTTT GGATGGAATA  [2160]
Bpol.LScot   .......... .......... .......... .......... ....G..... .......... .......... ..........  [2160]
Bpol.MMcot   .......... .......... .......... .......... ....G..... .......... .......... A.........  [2160]

[              2170       2180       2190       2200       2210       2220       2230       2240]
[                 .          .          .          .          .          .          .          .]
Bpol.mrca    GATAAGGCCC AAGAAGAACA TGAGAAATAT CACAGTAATT GGAGAGCAAT GGCTAGTGAT TTTAACCTGC CACCTGTAGT  [2240]
Bpol.LScot   .......... .......... .......... .......... .......... .......... .......... ..........  [2240]
Bpol.MMcot   .......... .......... .......... .......... .......... .......... .......... ..........  [2240]

[              2250       2260       2270       2280       2290       2300       2310       2320]
[                 .          .          .          .          .          .          .          .]
Bpol.mrca    AGCAAAAGAA ATAGTAGCCA GCTGTGATAA ATGTCAGCTA AAAGGAGAAG CCATGCATGG ACAAGTAGAC TGTAGTCCAG  [2320]
Bpol.LScot   .......... .......... .......... .......... .......... .......... .......... ..........  [2320]
Bpol.MMcot   .......... .......... .......... .......... .......... .......... .......... ..........  [2320]

[              2330       2340       2350       2360       2370       2380       2390       2400]
[                 .          .          .          .          .          .          .          .]
Bpol.mrca    GAATATGGCA ACTAGATTGT ACACATTTAG AAGGAAAAGT TATCCTGGTA GCAGTTCATG TAGCCAGTGG CTATATAGAA  [2400]
Bpol.LScot   .......... .......... .......... .......... .......... .......... .......A.. ..........  [2400]
Bpol.MMcot   .......... .......... .......... .......... .......... .......... .......A.. ..........  [2400]

[              2410       2420       2430       2440       2450       2460       2470       2480]
[                 .          .          .          .          .          .          .          .]
Bpol.mrca    GCAGAAGTTA TTCCAGCAGA AACAGGGCAG GAAACAGCAT ACTTTCTCTT AAAATTAGCA GGAAGATGGC CAGTAAAAGT  [2480]
Bpol.LScot   .......... .......... G......... .......... .......... .......... .............. ......AC  [2480]
Bpol.MMcot   .......... .......... G......... .......... .......... .......... ............. .......AC  [2480]

[              2490       2500       2510       2520       2530       2540       2550       2560]
[                 .          .          .          .          .          .          .          .]
Bpol.mrca    AATACATACA GACAATGGCA GCAATTTCAC CAGTACTACA GTTAAGGCCG CCTGTTGGTG GGCAGGGATC AAGCAGGAAT  [2560]
Bpol.LScot   .......... .......... .........: ........G. .......... .......... .......... ..........  [2560]
Bpol.MMcot   .......... .......... .......... ........G. .......... .......... ...G...... ..........  [2560]

[              2570       2580       2590       2600       2610       2620       2630       2640]
[                 .          .          .          .          .          .          .          .]
Bpol.mrca    TTGGCATTCC CTACAATCCC CAAAGTCAAG GAGTAGTAGA ATCTATGAAT AAAGAATTAA AGAAAATTAT AGGACAGGTA  [2640]
Bpol.LScot   .......... .......... .......... .......... .......... .......... .......... ..........  [2640]
Bpol.MMcot   .......... .......... .......... .......... .......... .......... .......... ..........  [2640]

[              2650       2660       2670       2680       2690       2700       2710       2720]
[                 .          .          .          .          .          .          .          .]
Bpol.mrca    AGAGATCAGG CTGAACATCT TAAGACAGCA GTACAAATGG CAGTATTCAT CCACAATTTT AAAAGAAAAG GGGGGATTGG  [2720]
Bpol.LScot   .......... .......... .......... .......... .......... .......... .......... ..........  [2720]
Bpol.MMcot   .......... .......... .......... .......... .......... .......... .......... ..........  [2720]
```

```
[                2730       2740       2750       2760       2770       2780       2790      2800]
[                  .          .          .          .          .          .          .         .]
Bpol.mrca   GGGGTACAGT GCAGGGGAAA GAATAGTAGA CATAATAGCA ACAGACATAC AAACTAAAGA ACTACAAAAA CAAATTACAA  [2800]
Bpol.LScot  .......... .......... .......... .......... .......... .T........ .......... ..........  [2800]
Bpol.MMcot  .......... .......... .......... .......... .......... .T........ .......... ..........  [2800]

[                2810       2820       2830       2840       2850       2860       2870      2880]
[                  .          .          .          .          .          .          .         .]
Bpol.mrca   AAATTCAAAA TTTTCGGGTT TATTACAGGG ACAGCAGAGA TCCACTTTGG AAAGGACCAG CAAAGCTTCT CTGGAAAGGT  [2880]
Bpol.LScot  .......... .......... .......... .......... .......... .......... .......... ..........  [2880]
Bpol.MMcot  .......... .......... .......... .......... .......... .......... .......... ..........  [2880]

[                2890       2900       2910       2920       2930       2940       2950      2960]
[                  .          .          .          .          .          .          .         .]
Bpol.mrca   GAAGGGGCAG TAGTAATACA AGATAATAGT GACATAAAAG TAGTGCCAAG AAGAAAAGCA AAGATCATTA GGGATTATGG  [2960]
Bpol.LScot  .......... .......... .......... .......... .......... .......... .......... ..........  [2960]
Bpol.MMcot  .......... .......... .......... .......... .......... .......... .......... ..........  [2960]

[                2970       2980       2990       3000       3010]
[                  .          .          .          .         .  ]
Bpol.mrca   AAAACAGATG GCAGGTGATG ATTGTGTGGC AAGTAGACAG GATGAGGATT AG    [3012]
Bpol.LScot  .......... .......... .......... .......... ..........      [3012]
Bpol.MMcot  .......... .......... .......... .......... ..........      [3012]
```

Figure 13
Comparison of Clade B rev Gene Sequence Reconstructions

```
[              10         20         30         40         50         60         70         80]
[               .          .          .          .          .          .          .          .]
Brev.mrca   ATGGCAGGAA GAAGCGGAGA CAGCGACGAA GAGCTCCTCA AGACAGTCAG ACTCATCAAG TTTCTCTATC AAAGCAACCC   [80]
Brev.LScot  .......... .......... .......... .......... .......... .......... .......... ..........   [80]
Brev.MMcot  .......... .......... .......... .......... .......... .......... .......... ..........   [80]

[              90        100        110        120        130        140        150        160]
[               .          .          .          .          .          .          .          .]
Brev.mrca   GCCTCCCAGC CCCGAGGGGA CCCGACAGGC CCGAAGGAAT AGAAGAAGAA GGTGGAGAGA GAGACAGAGA CAGATCCGTT  [160]
Brev.LScot  .......... .......... .......... .......... C......... .......... .......... ........G.  [160]
Brev.MMcot  .......... .......... .......... .......... C......... .......... .......... ........G.  [160]

[             170        180        190        200        210        220        230        240]
[               .          .          .          .          .          .          .          .]
Brev.mrca   CGATTAGTGA ACGGATTCTT AGCACTTATC TGGGACGATC TGCGGAGCCT GTGCCTCTTC AGCTACCACC GCTTGAGAGA  [240]
Brev.LScot  .......... .T........ .......... ....T...C. .......... .......... .......... ..........  [240]
Brev.MMcot  .......... .T........ .......... ........C. .......... .......... .......... ..........  [240]

[             250        260        270        280        290        300        310        320]
[               .          .          .          .          .          .          .          .]
Brev.mrca   CTTACTCTTG ATTGTAGCGA GGATTGTGGA ACTTCTGGGA CGCAGGGGGT GGGAAGTCCT CAAATATTGG TGGAATCTCC  [320]
Brev.LScot  .......... ......A... .......... .......... .......... .......... .......... ..........  [320]
Brev.MMcot  .......... .......... .......... .......... .......... .......... .......... ..........  [320]

[             330        340        350        360]
[               .          .          .          .]
Brev.mrca   TGCAGTATTG GAGTCAGGAA CTAAAGAATA GTGCTGTTAG  [360]
Brev.LScot  .A........ .......... .......... ..........  [360]
Brev.MMcot  .......... .......... .......... ..........  [360]
```

Figure 14
Comparison of Clade B tat Gene Sequence Reconstructions

```
[                    10         20         30         40         50         60         70         80]
[            .         .         .         .         .         .         .         .]
Btat.mrca   ATGGAGCCAG TAGATCCTAG ACTAGAGCCC TGGAAGCATC CAGGAAGTCA GCCTAAGACT GCTTGTACCA ATTGCTATTG   [80]
Btat.LScot  .......... .......... .......... .......... .......... .......... .......... ..........   [80]
Btat.MMcot  .......... .......... .......... .......... .......... .......... .......... ..........   [80]

[                    90        100        110        120        130        140        150        160]
[            .         .         .         .         .         .         .         .]
Btat.mrca   TAAAAAGTGT TGCTATCATT GCCAAGTTTG CTTCATAACA AAAGGCTTAG GCATCTCCTA TGGCAGGAAG AAGCGGAGAC   [160]
Btat.LScot  .......... ....T..... .......... T......... .......... .......... .......... ..........   [160]
Btat.MMcot  .......... ....T..... .......... T......... .......... .......... .......... ..........   [160]

[                   170        180        190        200        210        220        230        240]
[            .         .         .         .         .         .         .         .]
Btat.mrca   AGCGACGAAG ACCTCCTCAA GGCAGTCAGA CTCATCAAGT TTCTCTATCA AAGCAACCCG CCTCCCAGCC CGAGGGGAC    [240]
Btat.LScot  .......... .G........ .A........ .......... .......... .......... .......... ..........   [240]
Btat.MMcot  .......... .G........ .A........ .......... .......... .......... .......... ..........   [240]

[                   250        260        270        280        290        300        310        320]
[            .         .         .         .         .         .         .         .]
Btat.mrca   CCGACAGGCC CGAAGGAATC GAAGAAGAAG GTGGAGAGAG AGACAGAGAC AGATCCGGTC GATTAGTGAA TGGATTCTTA   [320]
Btat.LScot  .......... .......... .......... .......... .......... .......... .......... ..........   [320]
Btat.MMcot  .......... .......... .......... .......... .......... .......... .......... ........G.   [320]

[           ]
[           ]
Btat.mrca   G   [321]
Btat.LScot  .   [321]
Btat.MMcot  T   [321]
```

Figure 15
**Comparison of Clade B *vif* Gene Sequence Reconstructions**

```
[                        10         20         30         40         50         60         70         80]
[                         .          .          .          .          .          .          .         .]
Bvif.mrca        ATGGAAAACA GATGGCAGGT GATGATTGTG TGGCAAGTAG ACAGGATGAG GATTAGAACA TGGAAAAGTT TAGTAAAACA   [80]
Bvif.LScot       .......... .......... .......... .......... .......... .......... .......... ..........   [80]
Bvif.MMcot       .......... .......... .......... .......... .......... .......... .......... ..........   [80]

[                        90        100        110        120        130        140        150        160]
[                         .          .          .          .          .          .          .         .]
Bvif.mrca        CCATATGTAT ATTTCAAAGA AAGCTAAGGG ATGGTTTTAT AGACATCACT ATGAAAGCAC TCATCCAAGA ATAAGTTCAG   [160]
Bvif.LScot       .......... .......G.. .......... .......... .......... .......... .......... ..........   [160]
Bvif.MMcot       .......... .......G.. .......... .......... .......... .......... .......... ..........   [160]

[                       170        180        190        200        210        220        230        240]
[                         .          .          .          .          .          .          .         .]
Bvif.mrca        AAGTACACAT CCCACTAGGA GATGCTAGAT TGGTAATAAA AACATATTGG GGTCTGCATA CAGGAGAAAG AGAATGGCAT   [240]
Bvif.LScot       .......... .........G .......... .........C .......... .......... .......... ...C......   [240]
Bvif.MMcot       .......... .........G .......... .........C .......... .......... .......... ...C......   [240]

[                       250        260        270        280        290        300        310        320]
[                         .          .          .          .          .          .          .         .]
Bvif.mrca        TTGGGTCAGG GAGTCTCCAT AGAATGGAGG AAAAGGAGAT ATAGCACACA AGTAGACCCT GGCCTAGCAG ACCAACTAAT   [320]
Bvif.LScot       .......... .......... .......... ....A..... .......... .......... .A........ ..........   [320]
Bvif.MMcot       .......... .......... .......... ....A..... .......... .......... .A........ ..........   [320]

[                       330        340        350        360        370        380        390        400]
[                         .          .          .          .          .          .          .         .]
Bvif.mrca        TCATCTGTAT TATTTTGATT GTTTTTCAGA ATCTGCTATA AGAAATGCCA TATTAGGACA TATAGTTAGT CCTAGGTGTG   [400]
Bvif.LScot       .......... ..C....... .......... .......... .......... .......... .......... ..........   [400]
Bvif.MMcot       .......... ..C....... .......... .......... .......... .......... .......... ..........   [400]

[                       410        420        430        440        450        460        470        480]
[                         .          .          .          .          .          .          .         .]
Bvif.mrca        AATATCAAGC AGGACATAAC AAGGTAGGAT CTCTACAGTA CTTGGCACTA ACAGCATTAA TAACACCAAA AAAGATAAAG   [480]
Bvif.LScot       .......... .......... .......... .......... .......... G......... .......... ..........   [480]
Bvif.MMcot       .......... .......... .......... .......... .......... G......... .......... ..........   [480]

[                       490        500        510        520        530        540        550        560]
[                         .          .          .          .          .          .          .         .]
Bvif.mrca        CCACCTTTGC CTAGTGTTAG GAAACTGACA GAGGATAGAT GGAACAAGCC CCAGAAGACC AAGGGCCACA GAGGGAGCCA   [560]
Bvif.LScot       .......... .........C .......... .......... .......... .......... .......... ..........   [560]
Bvif.MMcot       .......... .........C .......... .......... .......... .......... .......... ..........   [560]

[                       570          ]
[                         .          ]
Bvif.mrca        TACAATGAAT GGACACTAG   [579]
Bvif.LScot       .......... .........   [579]
Bvif.MMcot       .......... .........   [579]
```

Figure 16
Comparison of Clade B vpr Gene Sequence Reconstructions

```
[              10         20         30         40         50         60         70         80]
[                .          .          .          .          .          .          .          .]
Bvpr.mrca   ATGGAACAAG CCCCAGAAGA CCAAGGGCCA CAGAGGGAGC CATACAATGA ATGGACACTA GAGCTTTTAG AGGAGCTTAA    [80]
Bvpr.LScot  .......... .......... .......... .......... .......... .......... .......... ..........   [80]
Bvpr.MMcot  .......... .......... .......... .......... .......... .......... .......... ..........   [80]

[              90        100        110        120        130        140        150        160]
[                .          .          .          .          .          .          .          .]
Bvpr.mrca   GAGTGAAGCT GTTAGACATT TTCCTAGGCT ATGGCTCCAT AGCTTAGGAC AACATATCTA TGAAACTTAT GGGGATACCT    [160]
Bvpr.LScot  .......... .......... ........A. .......... .......... .......... .......... ........T.   [160]
Bvpr.MMcot  .......... .......... ........A. .......... .......... .......... .......... ........T.   [160]

[             170        180        190        200        210        220        230        240]
[                .          .          .          .          .          .          .          .]
Bvpr.mrca   GGGCAGGAGT GGAAGCTATA ATAAGAATTC TGCAACAACT GCTGTTTATT CATTTCAGAA TTGGGTGTCA ACATAGCAGA    [240]
Bvpr.LScot  .......... ......C... .......... .......... .......... .......... .........G ..........   [240]
Bvpr.MMcot  .......... ......C... .......... .......... .......... .......... .......... ..........   [240]

[             250        260        270        280        290]
[                .          .          .          .          .]
Bvpr.mrca   ATAGGCATTA CTCGACAGAG AAGAGCAAGA AATGGAGCCA GTAGATCCTA G    [291]
Bvpr.LScot  .......... .........G .......... .......... ..........      [291]
Bvpr.MMcot  .......... .........G .......... .......... ..........      [291]
```

Figure 17
Comparison of Clade B vpu Gene Sequence Reconstructions

```
[                 10         20         30         40         50         60         70         80]
[                  .          .          .          .          .          .          .          .]
Bvpu.mrca    ATGCAACCTT TAGAAATATT AGCAATAGTA GCATTAGTAG TAGCAGCAAT ACTAGCAATA GTTGTGTGGA CCATAGTATT    [80]
Bvpu.LScot   .......... ..C....... .......... .......... .A........ .......... .......... ..........    [80]
Bvpu.MMcot   .......... ..C....... .......... .......... .A........ .......... .......... ..........    [80]

[                 90        100        110        120        130        140        150        160]
[                  .          .          .          .          .          .          .          .]
Bvpu.mrca    CATAGAATAT AGGAAAATAT TAAGGCAAAG AAAAATAGAC AGGTTAATTG ATAGAATAAG AGAAAGAGCA GAAGACAGTG    [160]
Bvpu.LScot   .......... .......... ....A..... .......... .......... .......... .......... ..........    [160]
Bvpu.MMcot   .......... .......... ....A..... .......... .......... .......... .......... ..........    [160]

[                170        180        190        200        210        220        230        240]
[                  .          .          .          .          .          .          .          .]
Bvpu.mrca    GCAATGAGAG TGAAGGGGAT CAGGAAGAAT TATCAGCACT TGTGGAAATG GGGCACCATG CTCCTTGGGA TGTTGATGAT    [240]
Bvpu.LScot   .......... .......... .......... .......... ......G... .......... .......... ..........    [240]
Bvpu.MMcot   .......... .......... .......... .......... ......G... .......... .......... ..........    [240]

[            ]
[            ]
Bvpu.mrca    CTGTAG    [246]
Bvpu.LScot   ......    [246]
Bvpu.MMcot   ......    [246]
```

Figure 18
Comparison of Clade B gag Protein Sequence Reconstructions

```
[                 10         20         30         40         50         60         70         80]
[                  .          .          .          .          .          .          .          .]
Bgag.mrca   MGARASVLSG GELDKWEKIR LRPGGKKKYK LKHIVWASRE LERFAVNPGL LETSEGCRQI LGQLQPSLQT GSEELRSLYN  [80]
Bgag.LScot  .......... ....R..... ........R. .......... .......... .......... .......... ..........  [80]
Bgag.MMcot  ...G...... .K..R..... .......... .......... .......... .......R.. .E..H..... .....K....  [80]

[                 90        100        110        120        130        140        150        160]
[                  .          .          .          .          .          .          .          .]
Bgag.mrca   TVAVLYCVHQ KIEVKDTKEA LDKIEEEQNK SKKKAQQAAA DTGNSSQVSQ NYPIVQNLQG QMVHQALSPR TLNAWVKVIE  [160]
Bgag.LScot  ...T...... R......... .E........ .......... .......... .......... ......I... ........V.  [160]
Bgag.MMcot  ...T...... N...R...D. .E........ I..R...... .....NP... .......M.. ......I... ........V.  [160]

[                170        180        190        200        210        220        230        240]
[                  .          .          .          .          .          .          .          .]
Bgag.mrca   EKAFSPEVIP MFSALSEGAT PQDLNTMLNT VGGHQAAMQM LKETINEEAA EWDRLHPVHA GPIAPGQMRE PRGSDIAGTT  [240]
Bgag.LScot  .......... .......... .......... .......... .......... .......... .......... ..........  [240]
Bgag.MMcot  .......... .......... .......... .......... .......... .......... .......... ..........  [240]

[                250        260        270        280        290        300        310        320]
[                  .          .          .          .          .          .          .          .]
Bgag.mrca   STLQEQIAWM TNNPPIPVGE IYKRWIILGL NKIVRMYSPV SILDIRQGPK EPFRDYVDRF YKTLRAEQAS QEVKNWMTET  [320]
Bgag.LScot  .......G.. .......... .......... .......T.. .......... .......... .......... ..........  [320]
Bgag.MMcot  .......G.. .H........ .......M.. .......T.. .......... .......... .......... ..........  [320]

[                330        340        350        360        370        380        390        400]
[                  .          .          .          .          .          .          .          .]
Bgag.mrca   LLVQNANPDC KTILKALGPG ATLEEMMTAC QGVGGPGHKA RVLAEAMSQV TNSATIMMQR GNFRNPRKTV KCFNCGKEGH  [400]
Bgag.LScot  .......... .......A.. .......... .......... .......... .......... ......Q... ..........  [400]
Bgag.MMcot  .......... .......A.. .......... ......S... .......A.. .......... ...KGQ.... ..........  [400]

[                410        420        430        440        450        460        470        480]
[                  .          .          .          .          .          .          .          .]
Bgag.mrca   IARNCRAPRK KGCWKCGKEG HQMKDCTERQ ANFLGKIWPS HKGRPGNFLQ SRPEPTAPPE ESFRFGEETT TPSQKQEQKD  [480]
Bgag.LScot  ..K....... .......... .......... .......... .......... .......... .......... ......PI.  [480]
Bgag.MMcot  .......... .......... .......... .......... .......... .......... .......... ..P....PR.  [480]

[                490        500]
[                  .          .]
Bgag.mrca   KELYPLASLK SLFGNDPSSQ  [500]
Bgag.LScot  ........R  ..........  [500]
Bgag.MMcot  ..Q...T..R ..........  [500]
```

Figure 19
Comparison of Clade B gp160 Protein Sequence Reconstructions

```
[                  10         20         30         40         50         60         70         80]
[                   .          .          .          .          .          .          .          .]
Bgp160.mrca    MRVKGIRKNC QHLWKWGTML LGMLMICSAA ENLWVTVYYG VPVWKEATTT LFCASDAKAY KTEVHNVWAT HACVPTDPNP  [80]
Bgp160.LScot   .........Y ....R..... .......... .K........ .......... .......... D......... ..........  [80]
Bgp160.MMcot   .........Y ....R..... .......... .K........ .......... .......... D......... ..........  [80]

[                  90        100        110        120        130        140        150        160]
[                   .          .          .          .          .          .          .          .]
Bgp160.mrca    QEVVLENVTE NFNMWKNNMV EQMHEDIISL WDQSLKPCVK LTPLCVTLNC TDANKNATNT NSSSGGTMEK GEMKNCSFNI  [160]
Bgp160.LScot   .......... .......... .......... .......... .......... ..L....... .....EM... ..I.......  [160]
Bgp160.MMcot   .......... .......... .......... .......... .......... ..L....... .....EM... ..I.......  [160]

[                 170        180        190        200        210        220        230        240]
[                   .          .          .          .          .          .          .          .]
Bgp160.mrca    TTSIRDKMQK EYALFYKLDV VPIDNDNNSN NNTNYRLINC NTSVITQACP KVSFEPIPIH YCTPAGFAIL KCNDKKFNGT  [240]
Bgp160.LScot   .......V.. .......... ........T. .T.S....S. .......... .......... ..A....... ..........  [240]
Bgp160.MMcot   .......V.. .......... ........T. .T.S....S. .......... .......... ..A....... ..........  [240]

[                 250        260        270        280        290        300        310        320]
[                   .          .          .          .          .          .          .          .]
Bgp160.mrca    GPCKNVSTVQ CTHGIRPVVS TQLLLNGSLA EEEVVIRSEN FTDNAKTIIV QLNESVEINC TRPNNNTRKS IPIGPGRALY  [320]
Bgp160.LScot   ...T...... .......... .......... .....D.... .......... .......... .H......F.  [320]
Bgp160.MMcot   ...T...... .......... .......... .....D.... .......... .......... .H......F.  [320]

[                 330        340        350        360        370        380        390        400]
[                   .          .          .          .          .          .          .          .]
Bgp160.mrca    TTGEIIGDIR QAHCNISRAK WNNTLKQVV- -TKLREQFGN NKTIVFNPSS GGDPEIVMHS FNCGGEFFYC NTTQLFNSTW  [398]
Bgp160.LScot   .......... .......... ......I.- -K........ ......Q... .......... .S........  [398]
Bgp160.MMcot   .......... .......... ......I.- -K........ ......Q... .......... .S........  [398]

[                 410        420        430        440        450        460        470        480]
[                   .          .          .          .          .          .          .          .]
Bgp160.mrca    NSTEGSNKTT GSNNTGGETI TLPCRIKQII NMWQEVGKAM YAPPIRGQIK CSSNITGLLL TRDGGENSTN ETEIFRPGGG  [478]
Bgp160.LScot   .G.WTW.T.E ...D.E.D.. .......... .......... .........R .......... ......N.N. ..........  [478]
Bgp160.MMcot   .G.WTW.T.E ...D.E.D.. .......... .......... .........R .......... ......N.N. ..........  [478]

[                 490        500        510        520        530        540        550        560]
[                   .          .          .          .          .          .          .          .]
Bgp160.mrca    DMRDNWRSEL YKYKVVKIEP LGVAPTKAKR RVVQREKRAV GIIGAMFLGF LGAAGSTMGA ASMTLTVQAR QLLSGIVQQQ  [558]
Bgp160.LScot   .......... .......... .......... ......V... .......... .......... .......... ..........  [558]
Bgp160.MMcot   .......... .......... .......... ......V... .......... .......... .......... ..........  [558]

[                 570        580        590        600        610        620        630        640]
[                   .          .          .          .          .          .          .          .]
Bgp160.mrca    NNLLRAIEAQ QHLLQLTVWG IKQLQARVLA VERYLRDQQL LGIWGCSGKL ICTTTVPWNA SWSNKSLDKI WNNMTWMEWE  [638]
Bgp160.LScot   .......... .......... .......... .......... .......... ....A..... ........E. ..........  [638]
Bgp160.MMcot   .......... .......... .......... .......... .......... ....A..... ........E. ..........  [638]

[                 650        660        670        680        690        700        710        720]
[                   .          .          .          .          .          .          .          .]
Bgp160.mrca    REIDNYTGLI YNLIEESQNQ QEKNEQELLE LDKWASLWNW FDITQWLWYI KIFIMIVGGL VGLRIVFAVL SIVNRVRQGY  [718]
Bgp160.LScot   .......S.. .T........ .......... .......... ....N..... .......... .......... ..........  [718]
Bgp160.MMcot   .......S.. .T........ .......... .......... ....N..... .......... .......... ..........  [718]

[                 730        740        750        760        770        780        790        800]
[                   .          .          .          .          .          .          .          .]
Bgp160.mrca    SPLSFQTRLP APRGPDRPEG IEEEGGERDR DRSGRLVNGF LALIWDDLRS LCLFSYHRLR DLLLIVARIV ELLGRRGWEA  [798]
Bgp160.LScot   .......... .......... .......... .......... .......... .......... .....T... ..........  [798]
Bgp160.MMcot   .......... .......... .......... .......... .......... .......... .....T... ..........  [798]

[                 810        820        830        840        850        860  ]
[                   .          .          .          .          .          .   ]
Bgp160.mrca    LKYWWNLLQY WSQELKNSAV SLLNATAIAV AEGTDRVIEV VQRACRAILH IPRRIRQGLE RALL  [862]
Bgp160.LScot   .......... .......... .......... .......... .......... ..T....... ....  [862]
Bgp160.MMcot   .......... .......... .......... .......... .......... ..T....... ....  [862]
```

Figure 20
Comparison of Clade B nef Protein Sequence Reconstructions

```
[                    10         20         30         40         50         60         70         80]
[                     .          .          .          .          .          .          .          .]
Bnef.mrca    MGGKWSKRSV VGWPAVRERM RRAEPAADGV GAVSRDLEKH GAITSSNTAA TNAACAWLEA QEEEEVGFPV RPQVPLRPMT    [80]
Bnef.MMcot   .......... .......... .......... .......... .......... ...D...... .......... ..........    [80]
Bnef.LScot   .......... .......... .......... .......... .......... ...D...... .......... ..........    [80]

[                    90        100        110        120        130        140        150        160]
[                     .          .          .          .          .          .          .          .]
Bnef.mrca    YKAAVDLSHF LKEKGGLEGL VYSQKRQDIL DLWVYHTQGY FPDWQNYTPG PGTRYPLTFG WCFKLVPVEP EKVEEATEGE    [160]
Bnef.MMcot   ....L..... .......... I......... .......... .......... ..I....... .......... ......N...    [160]
Bnef.LScot   ....L..... .......... I......... .......... .......... ..I....... .......... ......N...    [160]

[                   170        180        190        200   ]
[                     .          .          .          .   ]
Bnef.mrca    NNSLLHPMSL HGMDDPEREV LVWRFDSRLA FHHMAREKHP EYYKDC    [206]
Bnef.MMcot   ..C.....Q. .......K.. ...K...... .......L.. ......    [206]
Bnef.LScot   .......... .......K.. ...K...... .......L.. ......    [206]
```

Figure 21
Comparison of Clade B pol Protein Sequence Reconstructions

```
[                   10         20         30         40         50         60         70        80]
[                    .          .          .          .          .          .          .         .]
Bpol.mrca   FFRENLAFPQ GKARELSSEQ TRANSPTRRE LQVWGRDNNS LSEAGADRQG TVSFSFPQIT LWQRPLVTIK IGGQLKEALL   [80]
Bpol.LScot  ....D..... ......F...  .......... .......... .......... .......... .......... ..........   [80]
Bpol.MMcot  ....D..... ......F...  .......... .......... .......... .......... .......... ..........   [80]

[                   90        100        110        120        130        140        150       160]
[                    .          .          .          .          .          .          .         .]
Bpol.mrca   DTGADDTVLE EMNLPGKWKP KMIGGIGGFI KVRQYDQIPI EICGHKAIGT VLVGPTPVNI IGRNLLTQIG CTLNFPISPI  [160]
Bpol.LScot  .......... ......R... .......... .......... .......... .......... .......... ..........  [160]
Bpol.MMcot  .......... ......R... .......... .......... ......L... .......... .......... ..........  [160]

[                  170        180        190        200        210        220        230       240]
[                    .          .          .          .          .          .          .         .]
Bpol.mrca   ETVPVKLKPG MDGPKVKQWP LTEEKIKALV EICTEMEKEG KISKIGPENP YNTPVFAIKK KDSTKWRKLV DFRELNKRTQ  [240]
Bpol.LScot  .......... .......... .......... .......... .......... .......... .......... ..........  [240]
Bpol.MMcot  .......... .......... .......... .......... .......... .......... .......... ..........  [240]

[                  250        260        270        280        290        300        310       320]
[                    .          .          .          .          .          .          .         .]
Bpol.mrca   DFWEVQLGIP HPAGLKKKKS VTVLDVGDAY FSVPLDEDFR KYTAFTIPSI NNETPGIRYQ YNVLPQGWKG SPAIFQSSMT  [320]
Bpol.LScot  .......... .......... .......... .......... .......... .......... .......... ..........  [320]
Bpol.MMcot  .......... .......... .......... .......... .......... .......... .......... ..........  [320]

[                  330        340        350        360        370        380        390       400]
[                    .          .          .          .          .          .          .         .]
Bpol.mrca   KILEPFRKQN PEIVIYQYMD DLYVGSDLEI GQHRTKIEEL REHLLRWGFT TPDKKHQKEP PFLWMGYELH PDKWTVQPIV  [400]
Bpol.LScot  .......... .D........ .......... .Q........ .......... .......... .......... ..........  [400]
Bpol.MMcot  .......... .D........ .......... .Q........ .......... .......... .......... ..........  [400]

[                  410        420        430        440        450        460        470       480]
[                    .          .          .          .          .          .          .         .]
Bpol.mrca   LPEKDSWTVN DIQKLVGKLN WASQIYAGIK VKQLCKLLRG TKALTEVVPL TEEAELELAE NREILKEPVH GVYYDPSKDL  [480]
Bpol.LScot  .......... .......... .......... .......... .......I.. .......... .......... ..........  [480]
Bpol.MMcot  .......... .......... ......P... .......... .......I.. .......... .......... ..........  [480]

[                  490        500        510        520        530        540        550       560]
[                    .          .          .          .          .          .          .         .]
Bpol.mrca   IAEIQKQGQG QWTYQIYQEP FKNLKTGKYA RMRGAHTNDV KQLTEAVQKI ATESIVIWGK TPKFKLPIQK ETWEAWWTEY  [560]
Bpol.LScot  .......... .......... .......... .......... .......... .......... .......... ..........  [560]
Bpol.MMcot  .......... .......... .......... .......... .......... .......... .......... ....T.....  [560]

[                  570        580        590        600        610        620        630       640]
[                    .          .          .          .          .          .          .         .]
Bpol.mrca   WQATWIPEWE FVNTPPLVKL WYQLEKEPIV GAETFYVDGA ANRETKLGKA GYVTDRGRQK VVSLTDTTNQ KTELQAIHLA  [640]
Bpol.LScot  .......... .......... .......... .......... .......... .......... .......... ..........  [640]
Bpol.MMcot  .......... .......... .......... .......... .......... ....N..... .......... ..........  [640]

[                  650        660        670        680        690        700        710       720]
[                    .          .          .          .          .          .          .         .]
Bpol.mrca   LQDSGLEVNI VTDSQYALGI IQAQPDKSES ELVSQIIEQL IKKEKVYLAW VPAHKGIGGN EQVDKLVSTG IRKVLFLDGI  [720]
Bpol.LScot  .......... .......... .......... .......... .......... .......... .......A.. ..........  [720]
Bpol.MMcot  .......... .......... .......... .......... .......... .......... .......A.. ..........  [720]

[                  730        740        750        760        770        780        790       800]
[                    .          .          .          .          .          .          .         .]
Bpol.mrca   DKAQEEHEKY HSNWRAMASD FNLPPVVAKE IVASCDKCQL KGEAMHGQVD CSPGIWQLDC THLEGKVILV AVHVASGYIE  [800]
Bpol.LScot  .......... .......... .......... .......... .......... .......... .......... ..........  [800]
Bpol.MMcot  .......... .......... .......... .......... .......... .......... .......... ..........  [800]

[                  810        820        830        840        850        860        870       880]
[                    .          .          .          .          .          .          .         .]
Bpol.mrca   AEVIPAETGQ ETAYFLLKLA GRWPVKVIHT DNGSNFTSTT VKAACWWAGI KQEFGIPYNP QSQGVVESMN KELKKIIGQV  [880]
Bpol.LScot  .......... ......T... .......... .......... .......... .......... .......... ..........  [880]
Bpol.MMcot  .......... ......T... .......... .......... .......... .......... .......... ..........  [880]
```

```
[                 890        900        910        920        930        940        950        960]
[                   .          .          .          .          .          .          .          .]
Bpol.mrca    RDQAEHLKTA VQMAVFIHNF KRKGGIGGYS AGERIVDIIA TDIQTKELQK QITKIQNFRV YYRDSRDPLW KGPAKLLWKG    [960]
Bpol.LScot   .......... .......... .......... .......... .......... .......... .......... ..........   [960]
Bpol.MMcot   .......... .......... .......... .......... .......... .......... .......... ..........   [960]

[                 970        980        990       1000 ]
[                   .          .          .          . ]
Bpol.mrca    EGAVVIQDNS DIKVVPRRKA KIIRDYGKQM AGDDCVASRQ DED    [1003]
Bpol.LScot   .......... .......... .......... .......... ...    [1003]
Bpol.MMcot   .......... .......... .......... .......... ...    [1003]
```

Figure 22
Comparison of Clade B rev Protein Sequence Reconstructions

```
[                    10         20         30         40         50         60         70         80]
[                     .          .          .          .          .          .          .          .]
Brev.mrca    MAGRSGDSDE ELLKTVRLIK FLYQSNPPPS PEGTRQARRN RRRRWRERQR QIRSISERIL STYLGRSAEP VPLQLPPLER    [80]
Brev.LScot   .......... .......... .......... .......... .......... .......W.. ......P... ..........    [80]
Brev.MMcot   .......... .......... .......... .......... .......... .......W.. ......P... ..........    [80]

[                    90        100        110    ]
[                     .          .          .    ]
Brev.mrca    LTLDCSEDCG TSGTQGVGSP QILVESPAVL ESGTKE    [116]
Brev.LScot   .....N.... .......... .......T.. ......    [116]
Brev.MMcot   .......... .......... .......... ......    [116]
```

Figure 23
Comparison of Clade B tat Protein Sequence Reconstructions

```
[                   10         20         30         40         50         60         70         80]
[          .         .         .         .         .         .         .         .]
Btat.mrca  MEPVDPRLEP WKHPGSQPKT ACTNCYCKKC CYHCQVCFIT KGLGISYGRK KRRQRRRPPQ GSQTHQVSLS KQPASQPRGD    [80]
Btat.LScot ..........  ..........  ..........  .F........  ..........  .......A..  D.........  ..........    [80]
Btat.MMcot ..........  ..........  ..........  .F........  ..........  .......A..  D.........  ..........    [80]

[                   90        100]
[          .         . ]
Btat.mrca  PTGPKESKKK VERETETDPV D    [101]
Btat.LScot ..........  ..........  .    [101]
Btat.MMcot ..........  ..........  .    [101]
```

Figure 24
Comparison of Clade B vif Protein Sequence Reconstructions

```
[                    10         20         30         40         50         60         70         80]
[                     .          .          .          .          .          .          .          .]
Bvif.mrca    MENRWQVMIV WQVDRMRIRT WKSLVKHHMY ISKKAKGWFY RHHYESTHPR ISSEVHIPLG DARLVIKTYW GLHTGEREWH    [80]
Bvif.LScot   .......... .......... .......... ..R....... .......... .......... ......T... .......D..   [80]
Bvif.MMcot   .......... .......... .......... ..R....... .......... .......... ......T... .......D..   [80]

[                    90        100        110        120        130        140        150        160]
[                     .          .          .          .          .          .          .          .]
Bvif.mrca    LGQGVSIEWR KRRYSTQVDP GLADQLIHLY YFDCFSESAI RNAILGHIVS PRCEYQAGHN KVGSLQYLAL TALITPKKIK    [160]
Bvif.LScot   .......... .K........ D......... .......... .......... .......... .......... A.........   [160]
Bvif.MMcot   .......... .K........ D......... .......... .......... .......... .......... A.........   [160]

[                   170        180        190 ]
[                     .          .          . ]
Bvif.mrca    PPLPSVRKLT EDRWNKPQKT KGHRGSHTMN GH      [192]
Bvif.LScot   ......T... .......... .......... ..      [192]
Bvif.MMcot   ......T... .......... .......... ..      [192]
```

Figure 25
Comparison of Clade B vpr Protein Sequence Reconstructions

```
[                     10         20         30         40         50         60         70        80]
[                      .          .          .          .          .          .          .         .]
Bvpr.mrca    MEQAPEDQGP QREPYNEWTL ELLEELKSEA VRHFPRLWLH SLGQHIYETY GDTWAGVEAI IRILQQLLFI HFRIGCQHSR    [80]
Bvpr.LScot   .......... .......... .......... ......I... .......... .......... .......... ......R...    [80]
Bvpr.MMcot   .......... .......... .......... ......I... .......... .......... .......... ..........    [80]

[                     90        ]
[                      .        ]
Bvpr.mrca    IGITRQRRAR NGASRS    [96]
Bvpr.LScot   .......... ......    [96]
Bvpr.MMcot   .......... ......    [96]
```

Figure 26
Comparison of Clade B vpu Protein Sequence Reconstructions

```
[                    10        20        30        40        50        60        70        80]
[                     .         .         .         .         .         .         .         .]
Bvpu.mrca    MQPLEILAIV ALVVAAILAI VVWTIVFIEY RKILRQRKID RLIDRIRERA EDSGNESEGD QEELSALVEM GHHAPWDVDD  [80]
Bvpu.LScot   ....Q..... .......I.. .......... .......... .......... .......... .......... ..........  [80]
Bvpu.MMcot   ....Q..... .......I.. .......... .......... .......... .......... .......... ..........  [80]

[            ]
[            ]
Bvpu.mrca    L  [81]
Bvpu.LScot   .  [81]
Bvpu.MMcot   .  [81]
```

Figure 27
Comparison of Clade C *gag* Gene Sequence Reconstructions

```
[            10         20         30         40         50         60         70         80]
[             .          .          .          .          .          .          .          .]
Cgag.mrca  ATGGGTGCGA GAGCGTCAAT ATTAAGAGGG GGAAAATTAG ATACATGGGA AAAAATTAGG TTAAGGCCAG GGGGAAAGAA  [80]
Cgag.LScot ..........  .......... .........C .......... .......... .......... .......... ..........  [80]
Cgag.MMcot ..........  .......... .........C .......... .......... .......... .......... ..........  [80]

[            90        100        110        120        130        140        150        160]
[             .          .          .          .          .          .          .          .]
Cgag.mrca  ACATTATATG ATAAAACACC TAGTATGGGC AAGCAGGGAG CTGGAAAGAT TTGCACTTAA CCCTGGCCTT TTAGAGACAT  [160]
Cgag.LScot ..........C  .......... .......... .......... .......... .......... .......... ..........  [160]
Cgag.MMcot ..........C  .......... .......... .......... .......... .......... .......... ..........  [160]

[           170        180        190        200        210        220        230        240]
[             .          .          .          .          .          .          .          .]
Cgag.mrca  CAGAAGGCTG TAAACAAATA ATAAAACAGC TACAACCAGC TCTTCAGACA GGAACAGAGG AACTTAAATC ATTATATAAC  [240]
Cgag.LScot ..........  .......... ..G....... .......... .......... .......... ......G... ..........  [240]
Cgag.MMcot ..........  .......... ..G....... .......... .......... .......... ......G... ..........  [240]

[           250        260        270        280        290        300        310        320]
[             .          .          .          .          .          .          .          .]
Cgag.mrca  ACAGTAGCAA CTCTCTATTG TGTACATCAA AGGATAGAGG TACGAGACAC CAAGGAAGCC TTAGACAAGA TAGAGGAAGA  [320]
Cgag.LScot ..........  .......... .......G.. .A........ .......... .......... .......... ..........  [320]
Cgag.MMcot ..........  .......... .......G.. .A........ .......... .......... .......... ..........  [320]

[           330        340        350        360        370        380        390        400]
[             .          .          .          .          .          .          .          .]
Cgag.mrca  ACAAAACAAA AGTCAGCAAA AAACACAGCA GGCAGAAGCG ---GCTGACG GAAAGGTCAG TCAAAATTAT CCTATAGTGC  [397]
Cgag.LScot ..........  .......... .......... .......... ---....... .......... .......... ..........  [397]
Cgag.MMcot ..........  .......... .......... .......... GCT....... .......... .......... ..........  [400]

[           410        420        430        440        450        460        470        480]
[             .          .          .          .          .          .          .          .]
Cgag.mrca  AGAATCTCCA AGGGCAAATG GTACACCAGG CCATATCACC TAGAACTTTG AATGCATGGG TAAAAGTAAT AGAGGAGAAG  [477]
Cgag.LScot ..........  .......... .......... .......... .......... .......... .......... ..........  [477]
Cgag.MMcot ..........  .......... .......... .......... .......... .......... .......... ..........  [480]

[           490        500        510        520        530        540        550        560]
[             .          .          .          .          .          .          .          .]
Cgag.mrca  GCTTTCAGCC CAGAGGTAAT ACCCATGTTT ACAGCATTAT CAGAAGGAGC CACCCCACAA GATTTAAACA CCATGTTAAA  [557]
Cgag.LScot ..........  .......... .......... .......... .......... .......... .......... ..........  [557]
Cgag.MMcot ..........  .......... .......... .......... .......... .......... .......... ..........  [560]

[           570        580        590        600        610        620        630        640]
[             .          .          .          .          .          .          .          .]
Cgag.mrca  TACAGTGGGG GGACATCAAG CAGCCATGCA AATGTTAAAA GATACCATCA ATGAGGAGGC TGCAGAATGG GATAGGTTAC  [637]
Cgag.LScot ..........  .......... .......... .......... .......... .......... .......... ..........  [637]
Cgag.MMcot ..........  .......... .......... .......... .......... .......... .......... ..........  [640]

[           650        660        670        680        690        700        710        720]
[             .          .          .          .          .          .          .          .]
Cgag.mrca  ATCCAGTGCA TGCAGGGCCT GTTGCACCAG GCCAAATGAG AGAACCAAGG GGAAGTGACA TAGCAGGAAC TACTAGTACC  [717]
Cgag.LScot .......A..  .......... .......... .......... .......... .......... .......... ..........  [717]
Cgag.MMcot .......A..  .......... .......... .......... .......... .......... .......... ..........  [720]

[           730        740        750        760        770        780        790        800]
[             .          .          .          .          .          .          .          .]
Cgag.mrca  CTTCAGGAAC AAATAGCATG GATGACAAGT AACCCACCTA TCCCAGTGGG AGACATCTAT AAAAGATGGA TAATTCTGGG  [797]
Cgag.LScot ..........  .......... .......... .........G .T........ .......... .......... ..........  [797]
Cgag.MMcot ..........  .......... .......... .........G .T........ .......... .......... ..........  [800]

[           810        820        830        840        850        860        870        880]
[             .          .          .          .          .          .          .          .]
Cgag.mrca  GTTAAATAAA ATAGTAAGAA TGTATAGCCC TGTCAGCATT TTGGACATAA AACAAGGGCC AAAGGAACCC TTTAGAGACT  [877]
Cgag.LScot ..........  .......... .......... .......... .......... .......... .......... ..........  [877]
Cgag.MMcot ..........  .......... .......... .......... .......... .......... .......... ..........  [880]
```

```
               890        900        910        920        930        940        950        960]
                 .          .          .          .          .          .          .          .]
Cgag.mrca    ATGTAGACCG GTTCTTTAAA ACTTTAAGAG CTGAACAAGC TACACAAGAT GTAAAAAATT GGATGACAGA CACCTTGTTG   [957]
Cgag.LScot   .......... .......... .......... .......... .......... .......... .......... ..........   [957]
Cgag.MMcot   .......... .......... .......... .......... .......... .......... .......... ..........   [960]

970        980        990       1000       1010       1020       1030       1040]
                 .          .          .          .          .          .          .          .]
Cgag.mrca    GTCCAAAATG CGAACCCAGA TTGTAAGACC ATTTTAAGAG CATTAGGACC AGGGGCTACA CTAGAAGAAA TGATGACAGC  [1037]
Cgag.LScot   .......... .......... .......... .......... .......... .......... T......... ..........  [1037]
Cgag.MMcot   .......... .......... .......... .......... .......... .......... T......... ..........  [1040]

1050       1060       1070       1080       1090       1100       1110       1120]
                 .          .          .          .          .          .          .          .]
Cgag.mrca    ATGTCAGGGA GTGGGAGGAC CTAGCCATAA AGCAAGAGTT TTGGCTGAGG CAATGAGCCA AGCAAACAAT ACAAACATAA  [1117]
Cgag.LScot   .......... .......... ..G....C.. .........G .......... .......... .......... ..........  [1117]
Cgag.MMcot   .......... .......... ..G....C.. .........G .......... .......... .......... ..........  [1120]

1130       1140       1150       1160       1170       1180       1190       1200]
                 .          .          .          .          .          .          .          .]
Cgag.mrca    TGATGCAGAG AGGCAATTTT AAGGGCCCTA GAAGAATTGT TAAATGTTTC AACTGTGGCA AGGAAGGACA CATAGCCAGA  [1197]
Cgag.LScot   .......... .A........ ..A....... A......... .......... .......... .......G.. ..........  [1197]
Cgag.MMcot   .......... .A........ ..A....... A......... .......... .......... .......G.. ..........  [1200]

1210       1220       1230       1240       1250       1260       1270       1280]
                 .          .          .          .          .          .          .          .]
Cgag.mrca    AATTGCAGGG CCCCTAGGAA AAAGGGCTGT TGGAAATGTG GAAAGGAAGG ACACCAAATG AAAGACTGTA CTGAGAGGCA  [1277]
Cgag.LScot   .......... .......... ...A...... .......... .......... .......... .......... ..........  [1277]
Cgag.MMcot   .......... .......... ...A...... .......... .......... .......... .......... ..........  [1280]

1290       1300       1310       1320       1330       1340       1350       1360]
                 .          .          .          .          .          .          .          .]
Cgag.mrca    GGCTAATTTT TTAGGGAAAA TTTGGCCTTC CCACAAGGGG AGGCCAGGGA ATTTCCTTCA GAGCAGACCA GAGCCAACAG  [1357]
Cgag.LScot   .......... .......... .......... .......... .......... .......... .......... ..........  [1357]
Cgag.MMcot   .......... .......... .......... .......... .......... .......... .......... ..........  [1360]

1370       1380       1390       1400       1410       1420       1430       1440]
                 .          .          .          .          .          .          .          .]
Cgag.mrca    CCCCACCAGC AGAGAGCTTC AGGTTCGAGG AGACAACCCC CGCTCCGAAG CAGGAGCCGA AAGACAGGGA ACCCTTAACT  [1437]
Cgag.LScot   .......... .......... .......... .......... .......... .......... .......... ..........  [1437]
Cgag.MMcot   .......... .......... .......... .......... .......... .......... .......... ..........  [1440]

1450       1460       1470       1480]
                 .          .          .          .]
Cgag.mrca    TCCCTCAAAT CACTCTTTGG CAGCGACCCC TTGTCTCAAT AA  [1479]
Cgag.LScot   .......... .......... .......... .......... ..  [1479]
Cgag.MMcot   .......... .......... .......... .......... ..  [1482]
```

Figure 28
Comparison of Clade C env Gene Sequence Reconstructions

```
[               10         20         30         40         50         60         70         80]
[                .          .          .          .          .          .          .          .]
Cgp160.mrca    ATGAGAGTGA TGGGGATACA GAGGAATTGT CAACAATGGT GGATATGGGG CATCTTAGGC TTTTGGATGT TAATGATTTG  [80]
Cgp160.LScot   .......... G........T .......... .......... .......... .......... .......... ..........  [80]
Cgp160.MMcot   .......... G........T .......... .......... .......... .......... .......... ..........  [80]

[               90        100        110        120        130        140        150        160]
[                .          .          .          .          .          .          .          .]
Cgp160.mrca    TAGTGTGGTG GGGAACTTGT GGGTCACAGT CTATTATGGG GTACCTGTGT GGAAAGAAGC AAAAACTACT CTATTTTGTG  [160]
Cgp160.LScot   ..A....... .......... .......... .......... .......... .......... .....C.... ..........  [160]
Cgp160.MMcot   ..A....... .......... .......... .......... .......... .......... .....C.... ..........  [160]

[              170        180        190        200        210        220        230        240]
[                .          .          .          .          .          .          .          .]
Cgp160.mrca    CATCAGATGC TAAAGCATAT GAGAGAGAAG TGCATAATGT CTGGGCTACA CATGCCTGTG TACCCACAGA CCCCAACCCA  [240]
Cgp160.LScot   .......... .......... ....A..... .......... .......... .......... .......... ..........  [240]
Cgp160.MMcot   .......... .......... ....A..... .......... .......... .......... .......... ..........  [240]

[              250        260        270        280        290        300        310        320]
[                .          .          .          .          .          .          .          .]
Cgp160.mrca    CAAGAAATGG TTTTGGAAAA TGTAACAGAA AATTTTAACA TGTGGAAAAA TGACATGGTG GATCAGATGC ATGAGGATAT  [320]
Cgp160.LScot   .......... .......... .......... .......... .......... .......... .......... ..........  [320]
Cgp160.MMcot   .......... .......... .......... .......... .......... .......... .......... ..........  [320]

[              330        340        350        360        370        380        390        400]
[                .          .          .          .          .          .          .          .]
Cgp160.mrca    AATCAGTTTA TGGGATCAAA GCCTAAAGCC ATGTGTAAAG TTGACCCCAC TCTGTGTCAC TTTAAACTGT ACTAATGTTA  [400]
Cgp160.LScot   .......... .......... .......... .......... .......... .......... ......T.... .G........  [400]
Cgp160.MMcot   .......... .......... .......... .......... .......... .......... ......T.... .G........  [400]

[              410        420        430        440        450        460        470        480]
[                .          .          .          .          .          .          .          .]
Cgp160.mrca    ATAATACTAA TAATACCAAT AGTACCATGA ATGGAGAAAT GAAAAATTGC TCTTTCAATA TAACCACAGA AATAAGAGAT  [480]
Cgp160.LScot   ..GC...C.. ..C....... .A........ .G........ A......... .......G C.......... ..........  [480]
Cgp160.MMcot   ...C...C.. ..C....... .A........ .A........ A......... .........G .......... .C........  [480]

[              490        500        510        520        530        540        550        560]
[                .          .          .          .          .          .          .          .]
Cgp160.mrca    AAGAAGAAGA AAGAATATGC ACTTTTTTAT AGACTTGATA TAGTACCACT TAATGAAAAT AATAACAATA CTAGTGAATA  [560]
Cgp160.LScot   .....AC... ...TG..... .......... .......... .......... .......G... .....G....T ........G..  [560]
Cgp160.MMcot   .....A.... ....G..... .......... .......... .......... .......G... ...........T ........G..  [560]

[              570        580        590        600        610        620        630        640]
[                .          .          .          .          .          .          .          .]
Cgp160.mrca    TAGATTAATA AATTGTAATA CCTCAGCCAT AACACAAGCC TGTCCAAAGG TCTCTTTTGA CCCAATTCCT ATACATTATT  [640]
Cgp160.LScot   .......... .......... .......... .......... .......... .......... .......... ..........  [640]
Cgp160.MMcot   .......... .......... .......... .......... .......... .......... .......... ..........  [640]

[              650        660        670        680        690        700        710        720]
[                .          .          .          .          .          .          .          .]
Cgp160.mrca    GTGCTCCAGC TGGTTATGCG ATTCTAAAGT GTAATAATAA GACATTCAAT GGAACAGGAC CATGCAAAAA TGTCAGCACA  [720]
Cgp160.LScot   .......... .......... .......... .......... .......... .......... ........T. ..........  [720]
Cgp160.MMcot   .......... .......... .......... .......... .......... .......... ........T. ..........  [720]

[              730        740        750        760        770        780        790        800]
[                .          .          .          .          .          .          .          .]
Cgp160.mrca    GTACAATGTA CACATGGAAT TAAGCCAGTG GTATCAACTC AACTACTGTT AAATGGTAGT CTAGCAGAAG AAGAGATAAT  [800]
Cgp160.LScot   .......... .......... .......... .......... .........C .......... .......... ..........  [800]
Cgp160.MMcot   .......... .......... .......... .......... .........C .......... .......... ..........  [800]

[              810        820        830        840        850        860        870        880]
[                .          .          .          .          .          .          .          .]
Cgp160.mrca    AATTAGATCT GAAAATCTGA CAAACAATGC CAAAACAATA ATAGTACAGC TTAATGAATC TGTAGAAATT GTGTGTACAA  [880]
Cgp160.LScot   .......... .......... .......T.. .......... ........T. .......... .......... ..........  [880]
Cgp160.MMcot   .......... .......... .......... .......... ........T. .......... .......... ..........  [880]
```

```
[              890        900        910        920        930        940        950       960]
[                .          .          .          .          .          .          .         .]
Cgp160.mrca    GACCCAACAA TAATACAAGA AAAAGTATGA GGATAGGACC AGGACAAACA TTCTATGCAA CAGGAGACAT AATAGGAGAT  [960]
Cgp160.LScot   .......... .......... .......A.. .......... .......... .......... .......... ........C  [960]
Cgp160.MMcot   .......... .......... .......A.. .......... .......... .......... .......... ........C  [960]

[              970        980        990       1000       1010       1020       1030      1040]
[                .          .          .          .          .          .          .         .]
Cgp160.mrca    ATAAGACAAG CACATTGTAA CATTAGTGGA AGGGAATGGA ATAACACTTT ACAACAGGTA GCTGAAAAAT TAAGAAAACA  [1040]
Cgp160.LScot   .......... .......... .......A.. GA........ ....A..... ....AG.... .G.A...... ..GA.G....  [1040]
Cgp160.MMcot   .......... .......... .......A.. GA........ ....A..... ....AG.... .G.A...... ..GA.G....  [1040]

[             1050       1060       1070       1080       1090       1100       1110      1120]
[                .          .          .          .          .          .          .         .]
Cgp160.mrca    CTTCCCTAAT AAAACAATAA AATTTGCACC ATCCTCAGGA GGGGACCTAG AAATTACAAC ACATAGCTTT AATTGTAGAG  [1120]
Cgp160.LScot   .......... .......... .....A.... .......... .......... .......... .......... ..........  [1120]
Cgp160.MMcot   .......... .......... .....A.... .......... .......... .......... .......... ..........  [1120]

[             1130       1140       1150       1160       1170       1180       1190      1200]
[                .          .          .          .          .          .          .         .]
Cgp160.mrca    GAGAATTTTT CTATTGCAAT ACATCAAAAC TGTTTAATAG TACATACAAT AGTACAAATA GTACAAATTC AACCATCACA  [1200]
Cgp160.LScot   .......... .......... .......... .......... .......... G......... ........A. ..........  [1200]
Cgp160.MMcot   .......... .......... .......... .......... .......... G......... .......... ..........  [1200]

[             1210       1220       1230       1240       1250       1260       1270      1280]
[                .          .          .          .          .          .          .         .]
Cgp160.mrca    CTCCCATGCA GAATAAAACA AATTATAAAC ATGTGGCAGG GGGTAGGACA AGCAATGTAT GCCCCTCCCA TTGCAGGAAA  [1280]
Cgp160.LScot   .......... .......... .......... .......... A........G .......... .......... ..........  [1280]
Cgp160.MMcot   ....A..... .......... .......... .......... A........G .......... .......... ..........  [1280]

[             1290       1300       1310       1320       1330       1340       1350      1360]
[                .          .          .          .          .          .          .         .]
Cgp160.mrca    CATAACATGT AAATCAAATA TCACAGGACT ACTATTGACA CGTGATGGAG GAAAAAATGA AACTAATGAA ACTGAGACAT  [1360]
Cgp160.LScot   .......... .......... .......... .......GT. .......... .........A C..A...A.C ..A....T..  [1360]
Cgp160.MMcot   .......... .......... .......... .......GT. .......... .......... C..A.....C ..A....T..  [1360]

[             1370       1380       1390       1400       1410       1420       1430      1440]
[                .          .          .          .          .          .          .         .]
Cgp160.mrca    TCAGACCTGG AGGAGGAGAT ATGAGGGACA ATTGGAGAAG TGAATTATAT AAATATAAAG TAGTAGAAAT TAAACCATTA  [1440]
Cgp160.LScot   .......... .......... .......... .......... .......... .G........ ...G.....G  [1440]
Cgp160.MMcot   .......... .......... .......... .......... .......... .G........ ...G.....G  [1440]

[             1450       1460       1470       1480       1490       1500       1510      1520]
[                .          .          .          .          .          .          .         .]
Cgp160.mrca    GGAGTAGCAC CCACTAAGGC AAAAAGGAGA GTGGTGGAGA GAGAAAAAAG AGCAGTGGGA CTAGGAGCTG TGTTCCTTGG  [1520]
Cgp160.LScot   ...A...... .......... .......... .......... .......... .......... A......... ..........  [1520]
Cgp160.MMcot   ...A...... .......... .......... .......... .......... .......... A......... ..........  [1520]

[             1530       1540       1550       1560       1570       1580       1590      1600]
[                .          .          .          .          .          .          .         .]
Cgp160.mrca    GTTCTTGGGA GCAGCAGGAA GCACTATGGG CGCAGCGTCA ATAACGCTGA CGGTACAGGC CAGACAATTA TTGTCTGGTA  [1600]
Cgp160.LScot   .......... .......... ......G... .......... .......... .......... .........G ..........  [1600]
Cgp160.MMcot   .......... .......... .......... .......... .......... .......... .........G ..........  [1600]

[             1610       1620       1630       1640       1650       1660       1670      1680]
[                .          .          .          .          .          .          .         .]
Cgp160.mrca    TAGTGCAACA GCAAAGCAAT TTGCTGAGGG CTATAGAGGC GCAACAGCAT ATGTTCAAC TCACAGTCTG GGGCATTAAG  [1680]
Cgp160.LScot   .......... .......... .......... .......... .......... ....G..... ..........  [1680]
Cgp160.MMcot   .......... .......... .......... .......... .......... ....G..... ..........  [1680]

[             1690       1700       1710       1720       1730       1740       1750      1760]
[                .          .          .          .          .          .          .         .]
Cgp160.mrca    CAGCTCCAGG CAAGAGTCCT GGCTATGAA AGATACCTAA AGGATCAACA GCTCCTAGGG ATTTGGGGCT GCTCTGGAAA  [1760]
Cgp160.LScot   ........A. .......... .....A.... .......... .......... .......... .......... ..........  [1760]
Cgp160.MMcot   ........A. .......... .....A.... .......... .......... .......... .......... ..........  [1760]
```

```
[                    1770       1780       1790       1800       1810       1820       1830      1840]
[                      .          .          .          .          .          .          .         .]
Cgp160.mrca     ACTCATCTGC ACCACTGCTG TGCCTTGGAA CTCTAGTTGG AGTAATAAAT CTCAAGATGA TATTTGGGAT AACATGACCT  [1840]
Cgp160.LScot    .......... .......... .......... .......... .......... ........A. .......... ..........  [1840]
Cgp160.MMcot    .......... .......... .......... .......... .......... ........G. .......... ..........  [1840]

[                    1850       1860       1870       1880       1890       1900       1910      1920]
[                      .          .          .          .          .          .          .         .]
Cgp160.mrca     GGATGGAGTG GGATAGAGAA ATTAACAATT ACACAGACAC AATATACAGG TTGCTTGAAG AATCGCAAAA CCAGCAGGAA  [1920]
Cgp160.LScot    .....C.... .......... ....GT.... .......... .......... .........C .......... ..........  [1920]
Cgp160.MMcot    .....C.... .......... ....GT.... .......... .......... .........C .......... ..........  [1920]

[                    1930       1940       1950       1960       1970       1980       1990      2000]
[                      .          .          .          .          .          .          .         .]
Cgp160.mrca     AAAAATGAAC AAGATTTATT GGCATTGGAC AGTTGGGAAA ATCTGTGGAA TTGGTTTGAC ATATCAAATT GGCTGTGGTA  [2000]
Cgp160.LScot    C.......A ........C. A......... ......A... .......... .......A.. .......... ..........  [2000]
Cgp160.MMcot    C.......A ........C. A......... ......A... .......... .......A.. .......... ..........  [2000]

[                    2010       2020       2030       2040       2050       2060       2070      2080]
[                      .          .          .          .          .          .          .         .]
Cgp160.mrca     TATAAAAATA TTCATAATGA TAGTAGGAGG CTTGATAGGT TTAAGAATAA TTTTTGCTGT GCTTTCTATA GTAAATAGAG  [2080]
Cgp160.LScot    .......... .......... .......... .......... .......... .......... ..G....... ..........  [2080]
Cgp160.MMcot    .......... .......... .......... .......... .......... .......... ..G....... ..........  [2080]

[                    2090       2100       2110       2120       2130       2140       2150      2160]
[                      .          .          .          .          .          .          .         .]
Cgp160.mrca     TTAGGCAGGG ATACTCACCT TTGTCGTTTC AGACCCTTAC CCCAAACCCG AGGGGACCCG ACAGGCTCGA AGAATCGAA  [2160]
Cgp160.LScot    .......... .......... .......... .......... .......... .......... .........G ..........  [2160]
Cgp160.MMcot    .......... .......... .......... .......... .......... .......... .........G ..........  [2160]

[                    2170       2180       2190       2200       2210       2220       2230      2240]
[                      .          .          .          .          .          .          .         .]
Cgp160.mrca     GAAGAAGGTG GAGAGCAAGA CAGAGACAGA TCCATTCGAT TAGTGAGCGG ATTCTTAGCA CTTGCCTGGG ACGACCTGCG  [2240]
Cgp160.LScot    .......... .......... .......... .......... .......... .......... .......... ..........  [2240]
Cgp160.MMcot    .......... .......... .......... .......... .......... .......... .......... ..........  [2240]

[                    2250       2260       2270       2280       2290       2300       2310      2320]
[                      .          .          .          .          .          .          .         .]
Cgp160.mrca     GAGCCTGTGC CTCTTCAGCT ACCACCGCTT GAGAGACTTC ATCTTGATTG CAGCGAGGAC TGTGGAACTT CTGGGACGCA  [2320]
Cgp160.LScot    .......... .......... .......A.. .......... ..A...G.G. ........AG. G......... ..........  [2320]
Cgp160.MMcot    .......... .......... .......A.. .......... ..A...G.G. ........AG. G......... ..........  [2320]

[                    2330       2340       2350       2360       2370       2380       2390      2400]
[                      .          .          .          .          .          .          .         .]
Cgp160.mrca     GCAGTCTCAG GGGACTACAG AGGGGGTGGG AAGCCCTTAA ATATCTGGGA AGTCTTGTGC AGTATTGGGG TCAGGAGCTA  [2400]
Cgp160.LScot    .......... .......... .......... .......... G......... .......... .......... ..T.......  [2400]
Cgp160.MMcot    .......... .......... .......... .......... G......... .......... .......... ..T.......  [2400]

[                    2410       2420       2430       2440       2450       2460       2470      2480]
[                      .          .          .          .          .          .          .         .]
Cgp160.mrca     AAAAAGAGTG CTATTAGTCT GCTTGATACC ATAGCAATAG CAGTAGCTGA AGGGACAGAT AGGATTATAG AAGTAGTACA  [2480]
Cgp160.LScot    .......... .......... .......... .......... .......A.. .......... ..T..A.... ..........  [2480]
Cgp160.MMcot    .......... .......... .......... .......... .......A.. .......... ..T..A.... ..........  [2480]

[                    2490       2500       2510       2520       2530       2540      2550]
[                      .          .          .          .          .          .         .]
Cgp160.mrca     AAGAGCTTGT AGAGCTATCC TCAACATACC TAGAAGAATA AGACAGGGCT TTGAAGCAGC TTTGCAATAA  [2550]
Cgp160.LScot    ....AT.... .......... G......... .......... .......... .......... ..........  [2550]
Cgp160.MMcot    ....AT.... .......... G......... .......... .......... .......... ..........  [2550]
```

Figure 29
Comparison of Clade C nef Gene Sequence Reconstructions

```
[                10        20        30        40        50        60        70        80]
[                 .         .         .         .         .         .         .         .]
Cnef.mrca   ATGGGGGGCA AGTGGTCAAA AAGCAGTATA GTTGGATGGC CTGCTGTAAG AGAAAGAATA AGACGAACTG CTCCAGCAGC  [80]
Cnef.LScot  .......... .......... .......... .......... .......... .......... ........AG ........    [80]
Cnef.MMcot  .......... .......... .......... .......... .......... .......... ........AG ........    [80]

[                90       100       110       120       130       140       150       160]
[                 .         .         .         .         .         .         .         .]
Cnef.mrca   AGAAGGAGTA GGAGCAGCGT CTCAAGACTT AGATAAACAT GGAGCACTTA CAAGCAGCAA CACAGCCGCC ACTAATGCTG  [160]
Cnef.LScot  ...G...... .......... .......... .......... .......... .......... .A........ ........    [160]
Cnef.MMcot  ...G...... .......... .......... .......... .......... .......... .A........ ........    [160]

[               170       180       190       200       210       220       230       240]
[                 .         .         .         .         .         .         .         .]
Cnef.mrca   ATTGTGCCTG GCTGGAAGCA CAAGAGGAGG AAGAAG---T AGGCTTTCCA GTCAGACCTC AGGTGCCTTT AAGACCAATG  [237]
Cnef.LScot  .......... .......... .......... .....AAG.. .......... .......... .......... ........    [240]
Cnef.MMcot  .......... .......... .......... .....AAG.. .......... .......... .......... ........    [240]

[               250       260       270       280       290       300       310       320]
[                 .         .         .         .         .         .         .         .]
Cnef.mrca   ACTTATAAGG GAGCAGTCGA TCTCAGCTTC TTTTTAAAAG AAAAGGGGGG ACTGGAAGGG TTAATTTACT CTAAGAAAAG  [317]
Cnef.LScot  .......... .....T.... .......... .......... .......... .......... .......... ........    [320]
Cnef.MMcot  .......... .....T.... .......... .......... .......... .......... .......... ........    [320]

[               330       340       350       360       370       380       390       400]
[                 .         .         .         .         .         .         .         .]
Cnef.mrca   GCAAGAGATC CTTGATTTGT GGGTCTATCA CACACAAGGC TACTTCCCTG ATTGGCAAAA CTACACACCG GGACCAGGGA  [397]
Cnef.LScot  .......... .......... .......... .......... .......... .......... .......... .......G    [400]
Cnef.MMcot  .......... .......... .......... .......... .......... .......... .......... .......G    [400]

[               410       420       430       440       450       460       470       480]
[                 .         .         .         .         .         .         .         .]
Cnef.mrca   TCAGATTTCC ACTGACCTTT GGATGGTGCT TCAAGCTAGT GCCAGTTGAC CCAAGGGAAG TAGAAGAGGC CAATGAAGGA  [477]
Cnef.LScot  ......A... .......... .......... .......... .......... .......... ...C...... ........    [480]
Cnef.MMcot  ......A... .......... .......... .......... .......... .......... ...C...... ........    [480]

[               490       500       510       520       530       540       550       560]
[                 .         .         .         .         .         .         .         .]
Cnef.mrca   GAGAACAACT GCTTGCTACA CCCTATGAGC CAGCATGGAA TGGAGGATGA AGACAGAGAA GTATTAAAGT GGAAGTTTGA  [557]
Cnef.LScot  ...........T........ .......... .......... .......... .......... .......... ........    [560]
Cnef.MMcot  ...........T........ .......... .......... .......... .......... .......... ........    [560]

[               570       580       590       600       610       620  ]
[                 .         .         .         .         .         .  ]
Cnef.mrca   CAGTCACCTA GCACGCAGAC ACATGGCCCG CGAGCTACAT CCGGAGTATT ACAAAGACTG CTGA  [621]
Cnef.LScot  .......... .......... .......... .......... .......... ....           [624]
Cnef.MMcot  .......... .......... .......... .......... .......... ....           [624]
```

Figure 30
Comparison of Clade C pol Gene Sequence Reconstructions

```
[              10         20         30         40         50         60         70         80]
[          .         .         .         .         .         .         .         .]
Cpol.mrca  TTTTTTAGGG AAAATTTGGC CTTCCCACAA GGGGAGGCCA GGGAATTTCC TTCAGAGCAG ACCAGAGCCA ACAGCCCCAC  [80]
Cpol.LScot ..........  ..........  ..........  ..........  ..........  ..........  ..........  ..........  [80]
Cpol.MMcot ..........  ..........  ..........  ..........  ..........  ..........  ..........  ..........  [80]

[              90        100        110        120        130        140        150        160]
[          .         .         .         .         .         .         .         .]
Cpol.mrca  CAGCAGAGAG CTTCAGGTTC GAGGAGACAA CCCCCGCTCC GAAGCAGGAG CCGAAAGACA GGGAACCCTT AACTTCCCTC  [160]
Cpol.LScot ..........  ..........  ..........  ..........  ..........  ..........  ..........  ..........  [160]
Cpol.MMcot ..........  ..........  ..........  .....T....  ..........  ..........  ..........  ..........  [160]

[             170        180        190        200        210        220        230        240]
[          .         .         .         .         .         .         .         .]
Cpol.mrca  AAATCACTCT TTGGCAGCGA CCCCTTGTCT CAATAAAAGT AGGGGGCCAG ATAAAGGAAG CTCTATTAGA TACAGGAGCA  [240]
Cpol.LScot ..........  ..........  ..........  ..........  ..........  .........G.  ....C.....  C.........  [240]
Cpol.MMcot ..........  ..........  ..........  ........A.  ......A...  C.......G.  ....C.....  C.........  [240]

[             250        260        270        280        290        300        310        320]
[          .         .         .         .         .         .         .         .]
Cpol.mrca  GATGATACAG TATTAGAAGA CATAAATTTG CCAGGAAAAT GGAAACCAAA AATGATAGGG GGAATTGGAG GTTTTATCAA  [320]
Cpol.LScot ..........  ..........  A.........  ..........  ..........  ..........  ..A.......  ..........  [320]
Cpol.MMcot ..........  ..........  A.........  ..........  ..........  ..........  ..A.......  ..........  [320]

[             330        340        350        360        370        380        390        400]
[          .         .         .         .         .         .         .         .]
Cpol.mrca  AGTAAGACAG TATGATCAAA TACTTATAGA AATTTGTGGA AAAAAGGCTA TAGGTACAGT ATTAGTAGGA CCTACACCTG  [400]
Cpol.LScot ..........  ..........  ..........  ..........  ..........  ..........  ..........  ..........  [400]
Cpol.MMcot ..........  ..........  ..........  ..........  ..........  ..........  .C........  ..........  [400]

[             410        420        430        440        450        460        470        480]
[          .         .         .         .         .         .         .         .]
Cpol.mrca  TCAACATAAT TGGAAGAAAT ATGTTGACTC AGCTTGGTTG CACTCTAAAT TTTCCAATTA GTCCTATTGA AACTGTACCA  [480]
Cpol.LScot ..........  ..........  ..........  ......A..  ...A......  ..........  ....C.....  ..........  [480]
Cpol.MMcot ..........  ..........  ..........  ......A..  ...A......  ..........  ....C.....  ..........  [480]

[             490        500        510        520        530        540        550        560]
[          .         .         .         .         .         .         .         .]
Cpol.mrca  GTAAAATTAA AGCCAGGAAT GGATGGCCCA AAGGTTAAAC AATGGCCATT GACAGAAGAG AAAATAAAAG CATTAACAGC  [560]
Cpol.LScot ..........  ..........  ..........  ..........  ..........  ..........  ..........  ..........  [560]
Cpol.MMcot ..........  ..........  ..........  .....C....  ..........  ..........  ..........  ..........  [560]

[             570        580        590        600        610        620        630        640]
[          .         .         .         .         .         .         .         .]
Cpol.mrca  AATTTGTGAA GAAATGGAAA AGGAAGGAAA AATTACAAAA ATTGGGCCTG AAAATCCATA TAACACTCCA GTATTTGCCA  [640]
Cpol.LScot ..........  ........G.  ..........  ..........  ..........  ..........  ..........  ..........  [640]
Cpol.MMcot ..........  ........G.  ..........  ..........  ..........  ..........  ..........  ..........  [640]

[             650        660        670        680        690        700        710        720]
[          .         .         .         .         .         .         .         .]
Cpol.mrca  TAAAAAAGAA GGACAGTACT AAGTGGAGAA AATTAGTAGA TTTCAGAGAA CTCAATAAAA GAACTCAAGA CTTCTGGGAA  [720]
Cpol.LScot ..........  ..........  ..........  ..........  ......G...  ..........  ..........  ...T......  [720]
Cpol.MMcot ..........  ..........  ..........  ..........  ......G...  ..........  ..........  ...T......  [720]

[             730        740        750        760        770        780        790        800]
[          .         .         .         .         .         .         .         .]
Cpol.mrca  GTTCAATTAG GAATACCACA CCCAGCAGGG TTAAAAAAGA AAAAATCAGT AACAGTACTG GATGTGGGGG ATGCATATTT  [800]
Cpol.LScot ..........  ..........  ..........  ..........  ..........  ......G...  ..........  ..........  [800]
Cpol.MMcot ..........  .G........  ..........  ..........  ..........  ......G...  ..........  ..........  [800]

[             810        820        830        840        850        860        870        880]
[          .         .         .         .         .         .         .         .]
Cpol.mrca  TTCAGTTCCT TTAGATGAAG ACTTCAGGAA ATATACTGCA TTCACCATAC CTAGTATAAA CAATGAAACA CCAGGGATTA  [880]
Cpol.LScot ..........  ......G...  ..........  ..........  ..........  ..........  ..........  ..........  [880]
Cpol.MMcot ..........  ......G...  ..........  ..........  ..........  ..........  ..........  ..........  [880]
```

```
[              890        900        910        920        930        940        950       960]
[                .          .          .          .          .          .          .         .]
Cpol.mrca     GATATCAATA TAATGTGCTT CCACAGGGAT GGAAAGGATC ACCAGCAATA TTCCAGAGTA GCATGACAAA AATCTTAGAG   [960]
Cpol.LScot    .......... .......... .......... .......... .......... .......... .......... ..........   [960]
Cpol.MMcot    .......... .......... .......... .......... .......... .......... .......... ..........   [960]

[              970        980        990       1000       1010       1020       1030      1040]
[                .          .          .          .          .          .          .         .]
Cpol.mrca     CCCTTTAGGG CACAAAACCC AGAAATAGTT ATCTATCAAT ACATGGATGA CTTGTATGTA GGATCTGACT TAGAAATAGG  [1040]
Cpol.LScot    .......... .......T.. .........C .......... .T........ .......... .......... ..........  [1040]
Cpol.MMcot    .......... .......T.. .......... .......... .T........ .......... .......... ..........  [1040]

[             1050       1060       1070       1080       1090       1100       1110      1120]
[                .          .          .          .          .          .          .         .]
Cpol.mrca     GCAACATAGA GCAAAAATAG AGGAGTTAAG AGAACATCTA TTGAAATGGG GATTTACCAC ACCAGACAAG AAACATCAGA  [1120]
Cpol.LScot    .......... .......... .......... .......... ..A..G.... .......... .......... ..........  [1120]
Cpol.MMcot    .......... .......... .......... .......... .....G.... .......... .......... ..........  [1120]

[             1130       1140       1150       1160       1170       1180       1190      1200]
[                .          .          .          .          .          .          .         .]
Cpol.mrca     AAGAACCCCC ATTTCTTTGG ATGGGGTATG AACTCCATCC TGACAAATGG ACAGTACAGC CTATACAGCT GCCAGAAAAG  [1200]
Cpol.LScot    .......... .......... .......... .......... .......... .......... .......... ..........  [1200]
Cpol.MMcot    .......... .......... .......... .......... .......... .......... .......... ..........  [1200]

[             1210       1220       1230       1240       1250       1260       1270      1280]
[                .          .          .          .          .          .          .         .]
Cpol.mrca     GATAGCTGGA CTGTCAATGA TATACAGAAG TTAGTGGGAA AATTAAACTG GGCAAGTCAG ATTTACCCAG GGATTAAAGT  [1280]
Cpol.LScot    .......... .......... .......... .......... .......... .......... .......... ..........  [1280]
Cpol.MMcot    .......... .......... .......... .......... .......... .......... .......... ..........  [1280]

[             1290       1300       1310       1320       1330       1340       1350      1360]
[                .          .          .          .          .          .          .         .]
Cpol.mrca     AAGGCAACTG TGTAAACTCC TTAGGGGAGC CAAAGCACTA ACAGACATAG TACCACTGAC TGAAGAAGCA GAATTAGAAT  [1360]
Cpol.LScot    .........T .......... ......G... .......... .......... .......A.. .......... ..........  [1360]
Cpol.MMcot    .......... .......... .......... .......... .......... .......A.. .......... ..........  [1360]

[             1370       1380       1390       1400       1410       1420       1430      1440]
[                .          .          .          .          .          .          .         .]
Cpol.mrca     TGGCAGAGAA CAGGGAAATT CTAAAAGAAC CAGTACATGG AGTATATTAT GACCCATCAA AAGACTTAAT AGCTGAAATA  [1440]
Cpol.LScot    .......... .......... .......... .......... .......... .......... .......G.. ..........  [1440]
Cpol.MMcot    .......... .......... .......... .......... .......... .......... .......... ..........  [1440]

[             1450       1460       1470       1480       1490       1500       1510      1520]
[                .          .          .          .          .          .          .         .]
Cpol.mrca     CAGAAACAGG GGCATGACCA ATGGACATAT CAAATTTACC AAGAACCATT CAAAAATCTG AAAACAGGAA AGTATGCAAA  [1520]
Cpol.LScot    .......... .......... .......... .......... .......... .......... ........G. ..........  [1520]
Cpol.MMcot    .......... .......... .......... .......... .......... .......... ........G. ..........  [1520]

[             1530       1540       1550       1560       1570       1580       1590      1600]
[                .          .          .          .          .          .          .         .]
Cpol.mrca     AATGAGGTCT GCCCACACTA ATGATGTAAA ACAATTAACA GAAGCAGTGC AAAAAATAGC CATGGAAAGC ATAGTAATAT  [1600]
Cpol.LScot    .......A.. .......... ...G...... ..G....... .......... .......... .......... ..........  [1600]
Cpol.MMcot    .......A.. .......... ...G...... ..G....... .......... .......... .......... ..........  [1600]

[             1610       1620       1630       1640       1650       1660       1670      1680]
[                .          .          .          .          .          .          .         .]
Cpol.mrca     GGGGAAAGAC TCCTAAATTT AGACTACCCA TCCAAAAAGA AACATGGGAG ACATGGTGGA CAGACTATTG GCAAGCCACC  [1680]
Cpol.LScot    .......... .......... .......... .......... .......... .......... .......... ..........  [1680]
Cpol.MMcot    .......... .......... ...T...... ....G..... .......... G......... .......... ..........  [1680]

[             1690       1700       1710       1720       1730       1740       1750      1760]
[                .          .          .          .          .          .          .         .]
Cpol.mrca     TGGATTCCTG AGTGGGAGTT TGTTAATACC CCTCCCCTAG TAAAATTATG GTACCAGCTA GAAAAAGAAC CCATAGCAGG  [1760]
Cpol.LScot    .......... .......... .......... .......... .......... .........G ..G....... ..........  [1760]
Cpol.MMcot    .......... .......... .......... .......... .......... .........G ..G....... ..........  [1760]
```

```
[                 1770       1780       1790       1800       1810       1820       1830       1840]
[                   .          .          .          .          .          .          .         .]
Cpol.mrca     AGCAGAAACT TTCTATGTAG ATGGGGCAGC TAATAGGGAA ACTAAACTAG GAAAAGCAGG GTATGTTACT GACAAAGGAA   [1840]
Cpol.LScot    .......... .......... ....A..... .......... ......A... .......... .......... ....G.....   [1840]
Cpol.MMcot    .......... .......... ....A..... .......... ......A... .......... .......... ....G.....   [1840]

[                 1850       1860       1870       1880       1890       1900       1910       1920]
[                   .          .          .          .          .          .          .         .]
Cpol.mrca     GACAGAAAGT TGTTTCTCTA ACTGAAACAA CAAATCAGAA GACTGAATTA CAAGCAATTC AGCTAGCTTT GCAGGATTCA   [1920]
Cpol.LScot    .G......A. .......... .......... .......... .......... .......... .........A ......       [1920]
Cpol.MMcot    .G......A. .......... .......... .......... .......... .......... .......... ..........   [1920]

[                 1930       1940       1950       1960       1970       1980       1990       2000]
[                   .          .          .          .          .          .          .         .]
Cpol.mrca     GGATCAGAAG TAAACATAGT AACAGACTCA CAATATGCAT TAGGAATCAT TCAAGCACAA CCAGATAAGA GTGAATCAGA   [2000]
Cpol.LScot    .......... .......... .......... ..G....... .......... .......... .......... ..........   [2000]
Cpol.MMcot    .......... .......... .......... ..G....... .......... .......... .......... ..........   [2000]

[                 2010       2020       2030       2040       2050       2060       2070       2080]
[                   .          .          .          .          .          .          .         .]
Cpol.mrca     GTTAGTCAAT CAAATAATAG AGCAGTTAAT AAAAAAGGAA AAGGTCTACC TGTCATGGGT ACCAGCACAT AAAGGAATTG   [2080]
Cpol.LScot    ........C. .......... .A..A..... .......... .G........ .......... .......... ..........   [2080]
Cpol.MMcot    .......... .......... .A........ .......... .G........ .......... .......... ..........   [2080]

[                 2090       2100       2110       2120       2130       2140       2150       2160]
[                   .          .          .          .          .          .          .         .]
Cpol.mrca     GAGGAAATGA ACAAGTAGAT AAATTAGTAA GTTCTGGAAT CAGGAAAGTG CTGTTTCTAG ATGGAATAGA TAAAGCTCAA   [2160]
Cpol.LScot    .......... .......... .......... ..AG...... .......... .......... .......... ...G......   [2160]
Cpol.MMcot    .......... .......... .......... ..AG...... .......... .......... .......... ...G......   [2160]

[                 2170       2180       2190       2200       2210       2220       2230       2240]
[                   .          .          .          .          .          .          .         .]
Cpol.mrca     GAAGAACATG AAAAATATCA CAGCAATTGG AGAGCAATGG CTAGTGAGTT TAATCTGCCA CCCATAGTAG CAAAAGAAAT   [2240]
Cpol.LScot    .....G.... ....G..... .......... .......... .......... .......... .......... ..........   [2240]
Cpol.MMcot    .....G.... .......... .......... .......... .......... .......... .......... ..........   [2240]

[                 2250       2260       2270       2280       2290       2300       2310       2320]
[                   .          .          .          .          .          .          .         .]
Cpol.mrca     AGTAGCTAGC TGTGATAAAT GTCAGCTAAA AGGGGAAGCC ATGCATGGAC AAGTAGACTG TAGTCCAGGG ATATGGCAAT   [2320]
Cpol.LScot    .......... .......... .......... .......... ..A....... .......... .......... ..........   [2320]
Cpol.MMcot    .......... .......... .......... .......... ..A....... .......... .......... ..........   [2320]

[                 2330       2340       2350       2360       2370       2380       2390       2400]
[                   .          .          .          .          .          .          .         .]
Cpol.mrca     TAGATTGTAC ACATTTAGAA GGAAAAGTTA TCCTGGTAGC AGTCCATGTA GCCAGTGGCT ACATAGAAGC AGAAGTTATC   [2400]
Cpol.LScot    .......... .......... ......A.C. .......... .......... .......... .......... ...G......   [2400]
Cpol.MMcot    .......... .......... ......A.C. .......... .......... .......... .......... ...G......   [2400]

[                 2410       2420       2430       2440       2450       2460       2470       2480]
[                   .          .          .          .          .          .          .         .]
Cpol.mrca     CCAGCAGAAA CAGGACAGGA AACAGCATAC TTTATATTAA AATTAGCAGG AAGATGGCCA GTAAAAGTAA TACATACAGA   [2480]
Cpol.LScot    .......... ........A. .......... ......C... .......... .......... ..C....... ..........   [2480]
Cpol.MMcot    .......... ........A. .......... ......C... .......... .......... ..C....... ..........   [2480]

[                 2490       2500       2510       2520       2530       2540       2550       2560]
[                   .          .          .          .          .          .          .         .]
Cpol.mrca     CAATGGCAGC AATTTCACCA GTGCTGCAGT TAAGGCAGCC TGTTGGTGGG CAGGTATCCA ACAGGAATTT GGAATTCCCT   [2560]
Cpol.LScot    ........T. .......... .......... .......... .......... .......... .......... ..........   [2560]
Cpol.MMcot    ........T. .......... ...A...... .......... .......... .......... .......... ..........   [2560]

[                 2570       2580       2590       2600       2610       2620       2630       2640]
[                   .          .          .          .          .          .          .         .]
Cpol.mrca     ACAATCCCCA AAGTCAGGGA GTAGTAGAAT CCATGAATAA AGAATTAAAG AAAATCATAG GCAGGTAAG AGATCAAGCT   [2640]
Cpol.LScot    .......... .......... .......... .......... .......... .......... .......... ..........   [2640]
Cpol.MMcot    .......... .......... .......... .......... .......... .......... .......... ..........   [2640]

[                 2650       2660       2670       2680       2690       2700       2710       2720]
[                   .          .          .          .          .          .          .         .]
Cpol.mrca     GAGCACCTTA AGACAGCAGT ACAAATGGCA GTATTCATTC ACAATTTTAA AAGAAAAGGG GGGATTGGGG GGTACAGTGC   [2720]
Cpol.LScot    .......... .......... .......... .......... .......... .......... .......... ..........   [2720]
Cpol.MMcot    .......... .......... .......... .......... .......... .......... .......... ..........   [2720]
```

```
[                2730       2740       2750       2760       2770       2780       2790       2800]
[                  .          .          .          .          .          .          .         .]
Cpol.mrca    AGGGGAAAGA ATAATAGACA TAATAGCAAC AGACATACAA ACTAAAGAAT TACAAAAACA AATTATAAAA ATTCAAAATT   [2800]
Cpol.LScot   .......... .......... .......... .......... .......... .......... .......... ..........   [2800]
Cpol.MMcot   .......... .......... .......... .......... .......... .......... .......... ..........   [2800]

[                2810       2820       2830       2840       2850       2860       2870       2880]
[                  .          .          .          .          .          .          .         .]
Cpol.mrca    TTCGGGTTTA TTACAGAGAC AGCAGAGACC CTGTTTGGAA AGGACCAGCC AAACTACTCT GGAAAGGTGA AGGGGCAGTA   [2880]
Cpol.LScot   .......... .......... ...A...... .......... .......... .......... .......... ..........   [2880]
Cpol.MMcot   .......... .......... ...A...... .......... .......... .......... .......... ..........   [2880]

[                2890       2900       2910       2920       2930       2940       2950       2960]
[                  .          .          .          .          .          .          .         .]
Cpol.mrca    GTAATACAAG ACAATAGTGA CATAAAGGTA GTACCAAGGA GGAAAGCAAA GATCATTAGG GATTATGGAA AACAGATGGC   [2960]
Cpol.LScot   ..........T....... .......... .......... .......... A........A. ..C....... ..........   [2960]
Cpol.MMcot   ..........T..C..... .......... .......... .......... A........A. ..C....... ..........   [2960]

[                2970       2980       2990       3000]
[                  .          .          .         .]
Cpol.mrca    AGGTGCTGAT TGTGTGGCAG GTAGACAGGA TGAAGATTAG    [3000]
Cpol.LScot   .......... .......... .......... ..........    [3000]
Cpol.MMcot   .......... .......... .......... ..........    [3000]
```

Figure 31
Comparison of Clade C rev Gene Sequence Reconstructions

```
[                10         20         30         40         50         60         70         80]
[                 .          .          .          .          .          .          .          .]
Crev.mcra    ATGGCAGGAA GAAGCGGAGA CAGCGACGAA GCGCTCCTCC AAGCAGTGAG GATCATCAAA ATCCTATATC AAAGCAACCC    [80]
Crev.LScot   .......... .......... .......... .......... .......... .......... ...T...... ..........    [80]
Crev.MMcot   .......... .......... .......... .......... .......... .......... .......... ..........    [80]

[                90        100        110        120        130        140        150        160]
[                 .          .          .          .          .          .          .          .]
Crev.mcra    TTACCCCAAA CCCGAGGGGA CCCGACAGGC TCGAAGGAAT CGAAGAAGAA GGTGGAGAGC AAGACAGAGA CAGATCCATT    [160]
Crev.LScot   .......... .......... .......... ...G.A.... .......... .......... .......... ..........    [160]
Crev.MMcot   .......... .......... .......... ...G.A.... .......... .......... .......... ..........    [160]

[               170        180        190        200        210        220        230        240]
[                 .          .          .          .          .          .          .          .]
Crev.mcra    CGATTAGTGA GCGGATTCTT AGCACTTGCC TGGGACGACC TGCGGAGCCT GTGCCTCTTC AGCTACCACC GCTTGAGAGA    [240]
Crev.LScot   .......... .......... .......... .......... .......... .......... .......... .A........    [240]
Crev.MMcot   .......... .......... .......... .......... .......... ......T... .......... .A........    [240]

[               250        260        270        280        290        300        310        320]
[                 .          .          .          .          .          .          .          .]
Crev.mcra    CTTCATCTTG ATTGCAGCGA GGACTGTGGA ACTTCTGGGA CGCAGCAGTC TCAGGGGACT ACAGAGGGGG TGGGAAGCCC    [320]
Crev.LScot   ......A... G.GA...... .AG.A..... .......... .......... .......... .......... ..........    [320]
Crev.MMcot   ......A... G.GA...... .AG.A..... .......... .......... .......... .......... ..........    [320]

[               330        340        350        360        370        380]
[                 .          .          .          .          .          .]
Crev.mcra    TTAAATATCT GGGAAGCCTT GTGCAGTATT GGGGTCAGGA GCTAAAAAAG AGTGCTATTA G    [381]
Crev.LScot   ....G..... ......T... .......... ......T... A......... .......... .    [381]
Crev.MMcot   ....G..... ......T... .......... ......T... A......... .......... .    [381]
```

Figure 32
Comparison of Clade C tat Gene Sequence Reconstructions

```
[                 10         20         30         40         50         60         70         80]
[                  .          .          .          .          .          .          .           .]
Ctat.mrca    ATGGAGCCAG TAGATCCTAA CCTAGAGCCC TGGAACCATC CAGGAAGTCA GCCTAAAACT GCTTGTAATA AATGTTATTG    [80]
Ctat.LScot   .......... .......... .......... .......... .......... C......... .G........             [80]
Ctat.MMcot   .......... .......... .......... .......... .......... C......... .G........             [80]

[                 90        100        110        120        130        140        150       160]
[                  .          .          .          .          .          .          .           .]
Ctat.mrca    TAAAAAATGT AGCTATCATT GTCTAGTTTG CTTTCTGACA AAAGGCTTAG GCATTTCCTA TGGCAGGAAG AAGCGGAGAC   [160]
Ctat.LScot   ....C.C... .......... .......... .....A.... .......... .......... .......... ..........  [160]
Ctat.MMcot   ....C.C... .......... .......... .....A.... .......... .......... .......... ..........  [160]

[                170        180        190        200        210        220        230       240]
[                  .          .          .          .          .          .          .           .]
Ctat.mrca    AGCGACGAAG AGCTCCTCCA AGCAGTGAGG ATCATCAAAA TCCTATATCA AAGCAACCCT TATCCCAAAC CCGAGGGGAC   [240]
Ctat.LScot   .......... C......... .......... .......... .......... .......... ..C....... ..........  [240]
Ctat.MMcot   .......... C......... .......... .......... .......... .......... ..C....... ..........  [240]

[                250        260        270        280        290        300    ]
[                  .          .          .          .          .          .     ]
Ctat.mrca    CCGACAGGCT CGGAGGAATC GAAGAAGAAG GTGGAGAGCA AGACAGAGAC AGATCCGTGC GATTAG   [306]
Ctat.LScot   .......... ....A..... .......... .......... .......... ......A.T. ......   [306]
Ctat.MMcot   .......... .......... .......... .......... .......... ......A.T. ......   [306]
```

Figure 33
Comparison of Clade C vif Gene Sequence Reconstructions

```
[                    10         20         30         40         50         60         70         80]
[                     .          .          .          .          .          .          .          .]
Cvif.mrca   ATGGAAAACA GATGGCAGGT GCTGATTGTG TGGCAGGTAG ACAGGATGAA GATTAGAACA TGGAATAGTT TAGTAAAACA   [80]
Cvif.LScot  .......... .......... .......... .......... .......... .......... .......... .......G..   [80]
Cvif.MMcot  .......... .......... .......... .......... .......... .......... .......... .......G..   [80]

[                    90        100        110        120        130        140        150        160]
[                     .          .          .          .          .          .          .          .]
Cvif.mrca   CCATATGTAT GTTTCAAGGA GAGCTAAAGG ATGGTTTTAT AGACATCACT ATGAAAGCAG ACATCCAAAA ATAAGTTCAG   [160]
Cvif.LScot  .......... .......... .......T.. ..........C ........T. .......... .......... G.........   [160]
Cvif.MMcot  .......... .......... .......T.. ..........C ........T. .......... .......... G.........   [160]

[                   170        180        190        200        210        220        230        240]
[                     .          .          .          .          .          .          .          .]
Cvif.mrca   AAGTACACAT CCCATTAGGG GATGCTAGAT TAGTAATAAA AACATATTGG GGTTTGCATA CAGGAGAAAG AGATTGGCAT   [240]
Cvif.LScot  .......... .......... .......... .......... .......... .......A.. .......... ..........   [240]
Cvif.MMcot  .......... .......... .......... .......... .......... .......... .......... ..........   [240]

[                   250        260        270        280        290        300        310        320]
[                     .          .          .          .          .          .          .          .]
Cvif.mrca   TTGGGTCATG GAGTCTCCAT AGAATGGAGA CTGAGAAGAT ATAGCACACA AGTAGACCCT GGCCTGGCAG ACCAACTAAT   [320]
Cvif.LScot  .......... .......... .......... T......... .......... .......... .......... ....G.....   [320]
Cvif.MMcot  .......... .......... .......... T......... .......... .......... .......... ....G.....   [320]

[                   330        340        350        360        370        380        390        400]
[                     .          .          .          .          .          .          .          .]
Cvif.mrca   TCATATGCAT TATTTTGATT GTTTTGCAGA CTCTGCCATA AGGAAAGCCA TATTAGGACA TATAGTTAGC CCTAGGTGTG   [400]
Cvif.LScot  .......... .......... .......... .......... ..A....... .......... C.......TT ..........   [400]
Cvif.MMcot  .......... .......... .......... .......... ..A....... .......... C.......TT ..........   [400]

[                   410        420        430        440        450        460        470        480]
[                     .          .          .          .          .          .          .          .]
Cvif.mrca   ACTATCAAGC AGGACATAAC AAGGTAGGAT CTCTACAATA CTTGGCACTG ACAGCATTAA TAAAACCAAA AAAGATAAAG   [480]
Cvif.LScot  .......... .........T .......... .......... .......... .......G.. .......... ..........   [480]
Cvif.MMcot  .......... .........T .......... .......... .......... .......G.. .......... ..........   [480]

[                   490        500        510        520        530        540        550        560]
[                     .          .          .          .          .          .          .          .]
Cvif.mrca   CCACCTCTGC CTAGTGTTAA GAAATTAGTA GAGGATAGAT GGAACAAGCC CCAGAAGACC AGGGGCCACA GAGGGAGCCA   [560]
Cvif.LScot  .......... ........G. .......... .......... .......... .......... .......G.. .......A...   [560]
Cvif.MMcot  .......... ........G. .......... .......... .......... .......... .......G.. .......A...   [560]

[                   570         ]
[                     .          ]
Cvif.mrca   TACAATGAAT GGACACTAG   [579]
Cvif.LScot  .......... .........  [579]
Cvif.MMcot  .......... .........  [579]
```

Figure 34
Comparison of Clade C vpr Gene Sequence Reconstructions

```
[                  10         20         30         40         50         60         70         80]
[                   .          .          .          .          .          .          .          .]
Cvpr.mrca    ATGGAACAAG CCCCAGAAGA CCAGGGGCCA CAGAGGGAGC CATACAATGA ATGGACACTA GAGCTTTTAG AGGAACTTAA  [80]
Cvpr.LScot   .......... .......... .........G ........A. .......... .......... ...A...... ......C..  [80]
Cvpr.MMcot   .......... .......... .........G ........A. .......... .......... .......... ......C..  [80]

[                  90        100        110        120        130        140        150        160]
[                   .          .          .          .          .          .          .          .]
Cvpr.mrca    GCAGGAAGCT GTCAGACATT TTCCTAGACC ATGGCTCCAT AGCTTAGGAC AACATATCTA TGAAACCTAT GGGGATACTT  [160]
Cvpr.LScot   .......... ........C. .......... .......... .......... ...T...... .......... ..........  [160]
Cvpr.MMcot   .......... ........C. .......... .......... .......... .......... .......... ..........  [160]

[                 170        180        190        200        210        220        230        240]
[                   .          .          .          .          .          .          .          .]
Cvpr.mrca    GGGCGGGAGT TGAAGCTATA ATAAGAATTC TGCAACAACT ACTGTTTATT CATTTCAGAA TTGGGTGCCA ACATAGCAGA  [240]
Cvpr.LScot   ..A.A..... C......C.. ........A. .......... .......... .......... .......G.. ..........  [240]
Cvpr.MMcot   ..A....... .......C.. .......... .......... .......... .......... .......G.. ..........  [240]

[                 250        260        270        280        290]
[                   .          .          .          .          .]
Cvpr.mrca    ATAGGCATTA TTCGACAGAG AAGAGCAAGA AATGGAGCCA GTAGATCCTA A   [291]
Cvpr.LScot   .......T .G........ .......... .......... .......... .   [291]
Cvpr.MMcot   .......... .G........ .......... .......... .......... .   [291]
```

Figure 35
Comparison of Clade C vpu Gene Sequence Reconstructions

```
[              10         20         30         40         50         60         70         80]
[                .          .          .          .          .          .          .          .]
Cvpu.mrca   ATGTTAGATT TAATAGCAAG AGTAGATTAT AGATTAGGAG TAGGAGCATT GATAGTAGCA CTAATCATAG CAATAGTTGT  [80]
Cvpu.LScot  .......... ..C....... .......... .......... .......... .......... .......... ..........  [80]
Cvpu.MMcot  .......... ..C....... .......... .......... .......... .......... .......... ..........  [80]

[              90        100        110        120        130        140        150        160]
[                .          .          .          .          .          .          .          .]
Cvpu.mrca   GTGGACCATA GTATATATAG AATATAGGAA ATTGGTAAGA CAAAGAAAAA TAGACTGGTT AATTAAAAGA ATTAGGGAAA  [160]
Cvpu.LScot  .......... .......... .......... ....T..... .......... .......... .......... ..........  [160]
Cvpu.MMcot  .......... .......... .......... ....T..... .......... .......... .......... ..........  [160]

[             170        180        190        200        210        220        230        240]
[                .          .          .          .          .          .          .          .]
Cvpu.mrca   GAGCAGAAGA CAGTGGCAAT GAGAGTGATG GGGATACAGA GGAATTGTCA ACACTGGTGG ATATGGGCA TCTTAGGCTT    [240]
Cvpu.LScot  .......... .......... ........G. ........T.. .......... ...A...... .......... ..........  [240]
Cvpu.MMcot  .......... .......... ........G. ........T.. .......A... ...A...... .......... ..........  [240]

[             250        260]
[                .          .]
Cvpu.mrca   TTGGATGTTA ATGATTTGTA A  [261]
Cvpu.LScot  .......... .......... .  [261]
Cvpu.MMcot  .......... .......... .  [261]
```

Figure 36
Comparison of Clade C gag Protein Sequence Reconstructions

```
[                  10         20         30         40         50         60         70         80]
[                   .          .          .          .          .          .          .          .]
Cgag.mrca    MGARASILRG GKLDTWEKIR LRPGGKKHYM IKHLVWASRE LERFALNPGL LETSEGCKQI IKQLQPALQT GTEELKSLYN    [80]
Cgag.LScot   .......... .......... .......... L......... .......... .......... M......... .....R....   [80]
Cgag.MMcot   .......... .......... .......... L......... .......... .......... M......... .....R....   [80]

[                  90        100        110        120        130        140        150        160]
[                   .          .          .          .          .          .          .          .]
Cgag.mrca    TVATLYCVHQ RIEVRDTKEA LDKIEEEQNK SQQKTQQAEA -ADGKVSQNY PIVQNLQGQM VHQAISPRTL NAWVKVIEEK   [159]
Cgag.LScot   ........E K......... .......... .......... -......... .......... .......... ..........   [159]
Cgag.MMcot   ........E K......... .......... .......... A......... .......... .......... ..........   [160]

[                 170        180        190        200        210        220        230        240]
[                   .          .          .          .          .          .          .          .]
Cgag.mrca    AFSPEVIPMF TALSEGATPQ DLNTMLNTVG GHQAAMQMLK DTINEEAAEW DRLHPVHAGP VAPGQMREPR GSDIAGTTST   [239]
Cgag.LScot   .......... .......... .......... .......... .......... .......... .......... ..........   [239]
Cgag.MMcot   .......... .......... .......... .......... .......... .......... .......... ..........   [240]

[                 250        260        270        280        290        300        310        320]
[                   .          .          .          .          .          .          .          .]
Cgag.mrca    LQEQIAWMTS NPPIPVGDIY KRWIILGLNK IVRMYSPVSI LDIKQGPKEP FRDYVDRFFK TLRAEQATQD VKNWMTDTLL   [319]
Cgag.LScot   .......... ...V...... .......... .......... .......... .......... .......... ..........   [319]
Cgag.MMcot   .......... ...V...... .......... .......... .......... .......... .......... ..........   [320]

[                 330        340        350        360        370        380        390        400]
[                   .          .          .          .          .          .          .          .]
Cgag.mrca    VQNANPDCKT ILRALGPGAT LEEMMTACQG VGGPSHKARV LAEAMSQANN TNIMMQRGNF KGPRRIVKCF NCGKEGHIAR   [399]
Cgag.LScot   .......... .......... .......... ....G..... .......... .......S.. ...K...... ..........   [399]
Cgag.MMcot   .......... .......... .......... ....G..... .......... .......S.. ...K...... ..........   [400]

[                 410        420        430        440        450        460        470        480]
[                   .          .          .          .          .          .          .          .]
Cgag.mrca    NCRAPRKKGC WKCGKEGHQM KDCTERQANF LGKIWPSHKG RPGNFLQSRP EPTAPPAESF RFEETTPAPK QEPKDREPLT   [479]
Cgag.LScot   .......... .......... .......... .......... .......... .......... .......... ..........   [479]
Cgag.MMcot   .......... .......... .......... .......... .......... .......... .......... ..........   [480]

[                 490 ]
[                   . ]
Cgag.mrca    SLKSLFGSDP LSQ    [492]
Cgag.LScot   .......... ...    [492]
Cgag.MMcot   .......... ...    [493]
```

Figure 37
Comparison of Clade C gp160 Protein Sequence Reconstructions

```
[               10         20         30         40         50         60         70         80]
[                .          .          .          .          .          .          .          .]
Cgp160.mrca    MRVMGIQRNC QQWWIWGILG FWMLMICSVV GNLWVTVYYG VPVWKEAKTT LFCASDAKAY EREVHNVWAT HACVPTDPNP    [80]
Cgp160.LScot   ...R..L... .......... .......N.. .......... .......... .......... .K........ ..........    [80]
Cgp160.MMcot   ...R..L... .......... .......N.. .......... .......... .......... .K........ ..........    [80]

[               90        100        110        120        130        140        150        160]
[                .          .          .          .          .          .          .          .]
Cgp160.mrca    QEMVLENVTE NFNMWKNDMV DQMHEDIISL WDQSLKPCVK LTPLCVTLNC TNVNNTNNTN STMNGEMKNC SFNITTEIRD    [160]
Cgp160.LScot   .......... .......... .......... .......... .......... S...A..T.. N..K..I... ...A......    [160]
Cgp160.MMcot   .......... .......... .......... .......... .......... S...T..T.. N..K..I... ...V...L..    [160]

[              170        180        190        200        210        220        230        240]
[                .          .          .          .          .          .          .          .]
Cgp160.mrca    KKKKEYALFY RLDIVPLNEN NNNTSEYRLI NCNTSAITQA CPKVSFDPIP IHYCAPAGYA ILKCNNKTFN GTGPCKNVST    [240]
Cgp160.LScot   ..Q.V..... .......... ...S.S.... .......... .......... .......... .......... .....N....    [240]
Cgp160.MMcot   .......... .......... ......S... .......... .......... .......... .......... .....N....    [240]

[              250        260        270        280        290        300        310        320]
[                .          .          .          .          .          .          .          .]
Cgp160.mrca    VQCTHGIKPV VSTQLLLNGS LAEEEIIIRS ENLTNNAKTI IVQLNESVEI VCTRPNNNTR KSMRIGPGQT FYATGDIIGD    [320]
Cgp160.LScot   .......... .......... ......V... ..H....... .......... ..I....... .......... ..........    [320]
Cgp160.MMcot   .......... .......... .......... ..H....... .......... ..I....... .......... ..........    [320]

[              330        340        350        360        370        380        390        400]
[                .          .          .          .          .          .          .          .]
Cgp160.mrca    IRQAHCNISG REWNNTLQQV AEKLRKHFPN KTIKFAPSSG GDLEITTHSF NCRGEFFYCN TSKLFNSTYN STNSTNSTIT    [400]
Cgp160.LScot   .........E E...K...R. GK..EE.... .....E.... .......... .......... ......G... ..T....    [400]
Cgp160.MMcot   .........E E...K...R. GK..EE.... .....E.... .......... .......... ......G... ..........    [400]

[              410        420        430        440        450        460        470        480]
[                .          .          .          .          .          .          .          .]
Cgp160.mrca    LPCRIKQIIN MWQGVGQAMY APPIAGNITC KSNITGLLLT RDGGKNETNE TETFRPGGGD MRDNWRSELY KYKVVEIKPL    [480]
Cgp160.LScot   .......... ...E..R... .......... .........V .......N..N ..I....... .......... ..........    [480]
Cgp160.MMcot   .Q........ ...E..R... .......... .........V .......D..D ..I....... .......... ..........    [480]

[              490        500        510        520        530        540        550        560]
[                .          .          .          .          .          .          .          .]
Cgp160.mrca    GVAPTKAKRR VVEREKRAVG LGAVFLGFLG AAGSTMGAAS ITLTVQARQL LSGIVQQQSN LLRAIEAQQH MLQLTVWGIK    [560]
Cgp160.LScot   .I........ .......... .I........ .......... .......... .......... .......... ..........    [560]
Cgp160.MMcot   .I........ .......... .I........ .......... .......... .......... .......... ..........    [560]

[              570        580        590        600        610        620        630        640]
[                .          .          .          .          .          .          .          .]
Cgp160.mrca    QLQARVLAME RYLKDQQLLG IWGCSGKLIC TTAVPWNSSW SNKSQDDIWD NMTWMEWDRE INNYTDTIYR LLEESQNQQE    [640]
Cgp160.LScot   ...T....I. .......... .......... .......... .....E.... .....Q.... ...S...... ...D......    [640]
Cgp160.MMcot   ...T....I. .......... .......... .......... .....E.... .....Q.... .S........ ...D......    [640]

[              650        660        670        680        690        700        710        720]
[                .          .          .          .          .          .          .          .]
Cgp160.mrca    KNEQDLLALD SWENLWNWFD ISNWLWYIKI FIMIVGGLIG LRIIFAVLSI VNRVRQGYSP LSFQTLTPNP RGPDRLERIE    [720]
Cgp160.LScot   Q..K...... ..K....... .T........ .......... .......... .......... .......... ......G...    [720]
Cgp160.MMcot   Q..K...... ..K....... .T........ .......... .......... .......... .......... ......G...    [720]

[              730        740        750        760        770        780        790        800]
[                .          .          .          .          .          .          .          .]
Cgp160.mrca    EEGGEQDRDR SIRLVSGFLA LAWDDLRSLC LFSYHRLRDF ILIAARTVEL LGRSSLRGLQ RGWEALKYLG SLVQYWGQEL    [800]
Cgp160.LScot   .......... .......... .......... .......... ..V...A... .......... .......... .......L..    [800]
Cgp160.MMcot   .......... .......... .......... .......... ..V...A... .......... .......... .......L..    [800]

[              810        820        830        840         ]
[                .          .          .          .         ]
Cgp160.mrca    KKSAISLLDT IAIAVAEGTD RIIEVVQRAC RAILNIPRRI RQGFEAALQ    [849]
Cgp160.LScot   .......... .......... ....LI..I. ....R..... .........    [849]
Cgp160.MMcot   .......... .......... ....LI..I. ....R..... .........    [849]
```

Figure 38
Comparison of Clade C nef Protein Sequence Reconstructions

```
[                10        20        30        40        50        60        70        80)
[                 .         .         .         .         .         .         .         .]
Cnef.mrca    MGGKWSKSSI VGWPAVRERI RRTAPAAEGV GAASQDLDKH GALTSSNTAA TNADCAWLEA QEEE-EVGFP VRPQVPLRPM   [79]
Cnef.LScot   .......... .......... ...E...... .......... .......... N......... ....E..... ..........   [80]
Cnef.MMcot   .......... .......... ...E...... .......... .......... N......... ....E..... ..........   [80]

[                90       100       110       120       130       140       150       160]
[                 .         .         .         .         .         .         .         .]
Cnef.mrca    TYKGAVDLSF FLKEKGGLEG LIYSKKRQEI LDLWVYHTQG YFPDWQNYTP GPGIRFPLTF GWCFKLVPVD PREVEEANEG   [159]
Cnef.LScot   .....F.... .......... .......... .......... .......... ...V.Y.... .......... ..........   [160]
Cnef.MMcot   .....F.... .......... .......... .......... .......... ...V.Y.... .......... ..........   [160]

[               170       180       190       200      ]
[                 .         .         .         .      ]
Cnef.mrca    ENNCLLHPMS QHGMEDEDRE VLKWKFDSHL ARRHMARELH PEYYKDC    [206]
Cnef.LScot   .......... .......... .......... .......... .......    [207]
Cnef.MMcot   .......... .......... .......... .......... .......    [207]
```

Figure 39
Comparison of Clade C pol Protein Sequence Reconstructions

```
                       10         20         30         40         50         60         70         80]
[                       .          .          .          .          .          .          .         .]
Cpol.mrca     FFRENLAFPQ GEAREFPSEQ TRANSPTSRE LQVRGDNPRS EAGAERQGTL NFPQITLWQR PLVSIKVGGQ IKEALLDTGA  [80]
Cpol.LScot    .......... .......... .......... .......... .......... .......... .......... ..........  [80]
Cpol.MMcot    .......... .......... .......... .......L.. .......... .......... ...T...... L.........  [80]

90        100        110        120        130        140        150        160]
[                       .          .          .          .          .          .          .         .]
Cpol.mrca     DDTVLEDINL PGKWKPKMIG GIGGFIKVRQ YDQILIEICG KKAIGTVLVG PTPVNIIGRN MLTQLGCTLN FPISPIETVP  [160]
Cpol.LScot    ......E... .......... .......... .......... .......... .......... .......... ..........  [160]
Cpol.MMcot    ......E... .......... .......... .......... .......... .......... .......... ..........  [160]

170        180        190        200        210        220        230        240]
[                       .          .          .          .          .          .          .         .]
Cpol.mrca     VKLKPGMDGP KVKQWPLTEE KIKALTAICE EMEKEGKITK IGPENPYNTP VFAIKKKDST KWRKLVDFRE LNKRTQDFWE  [240]
Cpol.LScot    .......... .......... .......... .......... .......... .......... .......... ..........  [240]
Cpol.MMcot    .......... .......... .......... .......... .......... .......... .......... ..........  [240]

250        260        270        280        290        300        310        320]
[                       .          .          .          .          .          .          .         .]
Cpol.mrca     VQLGIPHPAG LKKKKSVTVL DVGDAYFSVP LDEDFRKYTA FTIPSINNET PGIRYQYNVL PQGWKGSPAI FQSSMTKILE  [320]
Cpol.LScot    .......... .......... ......G... .......... .......... .......... .......... ..........  [320]
Cpol.MMcot    .......... .......... ......G... .......... .......... .......... .......... ..........  [320]

330        340        350        360        370        380        390        400]
[                       .          .          .          .          .          .          .         .]
Cpol.mrca     PFRAQNPEIV IYQYMDDLYV GSDLEIGQHR AKIEELREHL LKWGFTTPDK KHQKEPPFLW MGYELHPDKW TVQPIQLPEK  [400]
Cpol.LScot    .......... .......... .......... .......... .......... .......... .......... ..........  [400]
Cpol.MMcot    .......... .......... .......... .......... .......... .......... .......... ..........  [400]

410        420        430        440        450        460        470        480]
[                       .          .          .          .          .          .          .         .]
Cpol.mrca     DSWTVNDIQK LVGKLNWASQ IYPGIKVRQL CKLLRGAKAL TDIVPLTEEA ELELAENREI LKEPVHGVYY DPSKDLIAEI  [480]
Cpol.LScot    .......... .......... .......... .......... .......... .......... .......... ..........  [480]
Cpol.MMcot    .......... .......... .......... .......... .......... .......... .......... ..........  [480]

490        500        510        520        530        540        550        560]
[                       .          .          .          .          .          .          .         .]
Cpol.mrca     QKQGHDQWTY QIYQEPFKNL KTGKYAKMRS AHTNDVKQLT EAVQKIAMES IVIWGKTPKF RLPIQKETWE TWWTDYWQAT  [560]
Cpol.LScot    .......... ........T. .......... .......... .......... .......... .......... ..........  [560]
Cpol.MMcot    .......... ........T. .......... .......... .......... .......... .......... A.........  [560]

570        580        590        600        610        620        630        640]
[                       .          .          .          .          .          .          .         .]
Cpol.mrca     WIPEWEFVNT PPLVKLWYQL EKEPIAGAET FYVDGAANRE TKLGKAGYVT DKGRQKVVSL TETTNQKTEL QAIQLALQDS  [640]
Cpol.LScot    .......... .......... .......... ..I....... .R....I... .......... .......... ..........  [640]
Cpol.MMcot    .......... .......... .......... ..I....... .R....I... .......... .......... ..........  [640]

650        660        670        680        690        700        710        720]
[                       .          .          .          .          .          .          .         .]
Cpol.mrca     GSEVNIVTDS QYALGIIQAQ PDKSESELVN QIIEQLIKKE KVYLSWVPAH KGIGGNEQVD KLVSSGIRKV LFLDGIDKAQ  [720]
Cpol.LScot    .......... .......... .......... R......... .......... .......... .......... ..........  [720]
Cpol.MMcot    .......... .......... .......... R......... .......... .......... .......... ..........  [720]

730        740        750        760        770        780        790        800]
[                       .          .          .          .          .          .          .         .]
Cpol.mrca     EEHEKYHSNW RAMASEFNLP PIVAKEIVAS CDKCQLKGEA MHGQVDCSPG IWQLDCTHLE GKVILVAVHV ASGYIEAEVI  [800]
Cpol.LScot    .......... .......... .......... I......... .......... ..I....... .I........ ..........  [800]
Cpol.MMcot    .......... .......... .......... I......... .......... ..I....... .I........ ..........  [800]

810        820        830        840        850        860        870        880]
[                       .          .          .          .          .          .          .         .]
Cpol.mrca     PAETGQETAY FILKLAGRWP VKVIHTDNGS NFTSAAVKAA CWWAGIQQEF GIPYNPQSQG VVESMNKELK KIIGQVRDQA  [880]
Cpol.LScot    .......... .......... .......... .......... .......... .......... .......... ..........  [880]
Cpol.MMcot    .......... .......... .......... .......... .......... .......... .......... ..........  [880]
```

```
[              890        900        910        920        930        940        950        960]
[                .          .          .          .          .          .          .          .]
Cpol.mrca     EHLKTAVQMA VFIHNFKRKG GIGGYSAGER IIDIIATDIQ TKELQKQIIK IQNFRVYYRD SRDPVWKGPA KLLWKGEGAV  [960]
Cpol.LScot    .......... .......... .......... .......... .......... .......... ....I..... ..........  [960]
Cpol.MMcot    .......... .......... .......... .......... .......... .......... ....I..... ..........  [960]

[              970        980        990        ]
[                .          .          .        ]
Cpol.mrca     VIQDNSDIKV VPRRKAKIIR DYGKQMAGAD CVAGRQDED  [999]
Cpol.LScot    .......... .........K .......... .........  [999]
Cpol.MMcot    .......... .........K .......... .........  [999]
```

Figure 40
Comparison of Clade C rev Protein Sequence Reconstructions

```
[                    10         20         30         40         50         60         70        80]
[                     .          .          .          .          .          .          .         .]
Crev.mcra    MAGRSGDSDE ALLQAVRIIK ILYQSNPYPK PEGTRQARRN RRRRWRARQR QIHSISERIL STCLGRPAEP VPLQLPPLER    [80]
Crev.LScot   .......... .......... .......... ........K. .......... .......... .......... .......I..   [80]
Crev1.MMcot  .......... .......... .......... ........K. .......... .......... .......... ..F....I..   [80]

[                    90        100    ]
[                     .          .     ]
Crev.mcra    LHLDCSEDCG TSGTQQSQGT TEGVGSP      [107]
Crev.LScot   ..IGD..SS. .......... .......      [107]
Crev1.MMcot  ..IGD..SS. .......... .......      [107]
```

Figure 41
Comparison of Clade C tat Protein Sequence Reconstructions

```
[                    10         20         30         40         50         60         70         80]
[                     .          .          .          .          .          .          .          .]
Ctat.mrca    MEPVDPNLEP WNHPGSQPKT ACNKCYCKKC SYHCLVCFLT KGLGISYGRK KRRQRRRAPP SSEDHQNPIS KQPLSQTRGD    [80]
Ctat.LScot   .......... .......... P.......H. ........Q. .......... ......S... .......... ....P.....   [80]
Ctat.MMcot   .......... .......... P.......H. ........Q. .......... ......S... .......... ....P.....   [80]

[                    90        100]
[                     .          .]
Ctat.mrca    PTGSEESKKK VESKTETDPC D    [101]
Ctat.LScot   .......... ........F .    [101]
Ctat.MMcot   .......... ........F .    [101]
```

Figure 42
Comparison of Clade C vif Protein Sequence Reconstructions

```
[              10         20         30         40         50         60         70         80]
[                .          .          .          .          .          .          .          .]
Cvif.mrca      MENRWQVLIV WQVDRMKIRT WNSLVKHHMY VSRRAKGWFY RHHYESRHPK ISSEVHIPLG DARLVIKTYW GLHTGERDWH    [80]
Cvif.LScot     .......... .......... .......... .....N.... .......... V......... .......... ..Q.......   [80]
Cvif.MMcot     .......... .......... .......... .....N.... .......... V......... .......... ..........   [80]

[              90        100        110        120        130        140        150       160]
[                .          .          .          .          .          .          .          .]
Cvif.mrca      LGHGVSIEWR LRRYSTQVDP GLADQLIHMH YFDCFADSAI RKAILGHIVS PRCDYQAGHN KVGSLQYLAL TALIKPKKIK   [160]
Cvif.LScot     .......... .......... .......... .......... .........I .......... .......... ..........  [160]
Cvif.MMcot     .......... .......... .......... .......... .........I .......... .......... ..........  [160]

[             170        180        190 ]
[                .          .          . ]
Cvif.mrca      PPLPSVKKLV EDRWNKPQKT RGHRGSHTMN GH    [192]
Cvif.LScot     ......R... .......... ..R..N.... ..    [192]
Cvif.MMcot     ......R... .......... ..R..N.... ..    [192]
```

Figure 43
Comparison of Clade C vpr Protein Sequence Reconstructions

```
[            10         20         30         40         50         60         70         80]
[             .          .          .          .          .          .          .          .]
Cvpr.mrca   MEQAPEDQGP QREPYNEWTL ELLEELKQEA VRHFPRPWLH SLGQHIYETY GDTWAGVEAI IRILQQLLFI HFRIGCQHSR   [80]
Cvpr.LScot  .......... .......... .I........ .......... .....Y.... ....T....L .......... ..........   [80]
Cvpr.MMcot  .......... .......... .......... .......... .......... ....T....L .......... ..........   [80]

[            90     ]
[             .     ]
Cvpr.mrca   IGIIRQRRAR NGASRS  [96]
Cvpr.LScot  ...L...... ......  [96]
Cvpr.MMcot  ...M...... ......  [96]
```

Figure 44
Comparison of Clade C vpu Protein Sequence Reconstructions

```
[                  10         20         30         40         50         60         70         80]
[                   .          .          .          .          .          .          .          .]
Cvpu.mrca   MLDLIARVDY RLGVGALIVA LIIAIVVWTI VYIEYRKLVR QRKIDWLIKR IRERAEDSGN ESDGDTEELS TLVDMGHLRL   [80]
Cvpu.LScot  ....L..... .......... .......... ........L. .......... .......... ..E....... .M........  [80]
Cvpu.MMcot  ....L..... .......... .......... ........L. .......... .......... ..E....... .M........  [80]

[            ]
[            ]
Cvpu.mrca   LDVNDL  [86]
Cvpu.LScot  ......  [86]
Cvpu.MMcot  ......  [86]
```

Figure 46. Deduced ancestor protein sequences

A.
SIVBK28 ancestor (Env segment)
NKSETDRWGLTKSNETSSCIAQNNCTGLEQEQMISCKFNMTGLKRDKTKEYNETW
YSTDLVCEQGNSTDNESRCYMNHCNTSVIQESCDKHYWDTIRFRYCAPPGYALLRC
NDTNYSGFMPKCSKVVVSSCTRMMETQTSTWFGFNGTRAENRTYIYWHGRDNRTII
SLNKYYNLTMKCRRPGNKTVLPVTIMSGLVFHSQPINDRPKQAWCWFGGKWKDAI
KEVKQTIVKHPRYTGTNNTDKINLTAPGGGDPEVTFMWTNCRGEFLYCKMNWFLN
WVEDRDVTTQRPKERHRRNYVPCHIRQIINTWHKVGKNVYLPPREGDLTCNSTVTS
LIANIDWTDGNQTNITMSAEVA B.
AN1-EnvB
MRVKGIRKNYQHLWRWGTMLLGMLMICSAAEKLWVTVYYGVPVWKEATTTLFC
ASDAKAYDTEVHNVWATHACVPTDPNPQEVVLENVTENFNMWKNNMVEQMHED
IISLWDQSLKPCVKLTPLCVTLNCTDDLRTNATNTTNSSATTNTTSSGGGTMEGEKG
EIKNCSFNVTTSIRDKMQKEYALFYKLDVVPIDNDNNNTNNNTSYRLINCNTSVITQ
ACPKVSFEPIPIHYCTPAGFAILKCNDKKFNGTGPCTNVSTVQCTHGIRPVVSTQLLL
NGSLAEEEVVIRSENFTDNAKTIIVQLNESVEINCTRPNNNTRKSIPIGPGRALYATGK
IIGDIRQAHCNLSRAKWNNTLKQIVTKLREQFGNNKTTIVFNQSSGGDPEIVMHSFN
CGGEFFYCNSTQLFNSTWHFNGTWGNNNTERSNNAADDNDTITLPCRIKQIINMWQ
EVGKAMYAPPISGQIRCSSNITGLLLTRDGGNNENTNNTDTEIFRPGGGDMRDNWRS
ELYKYKVVKIEPLGVAPTKAKRRVVQREKSAVGMLGAMFLGFLGAAGSTMGAAS
MTLTVQARQLLSGIVQQQNNLLRAIEAQQHLLQLTVWGIKQLQARVLAVERYLKD
QQLLGIWGCSGKLICTTAVPWNASWSNKSLDKIWNNMTWMEWEREIDNYTGLIYT
LIEESQNQQEKNEQELLELDKWASLWNWFDITNWLWYIKIFIMIVGGLVGLRIVFAV
LSIVNRVRQGYSPLSFQTHLPAPRGPDRPEGIEEEGGERDRDRSGRLVNGFLALIWD
DLRSLCLFSYHRLSDLLLIVARIVELLGRRGWEALKYWWNLLQYWSQELKNSAVSL
LNATAIAVAEGTDRVIEVVQRACRAILHIPRRIRQGLERALL

SEQUENCE LISTING

```
<160> NUMBER OF SEQ ID NOS: 125

<210> SEQ ID NO 1
<211> LENGTH: 2652
<212> TYPE: DNA
<213> ORGANISM: Artificial Sequence
<220> FEATURE:
<223> OTHER INFORMATION: Ancestral HIV-1 group M, subtype B, env
      sequence

<400> SEQUENCE: 1
atgcgcgtga agggcatccg caagaactac cagcacctgt ggcgctgggg caccatgctg      60
ctggggatgc tgatgatctg ctccgcggcc gagaagctgt gggtgaccgt gtactacggc     120
gtgcccgtgt ggaaggaggc caccaccacc ctgttctgcg ccagcgacgc caaggcttac     180
gacaccgagg tccacaacgt gtgggccacc cacgcctgcg tgcccaccga ccccaacccc     240
caggaggtgg tgctggagaa cgtgaccgag aacttcaaca tgtggaagaa caacatggtg     300
gagcagatgc acgaggacat catcagcctg tgggaccaga gcctgaagcc ctgcgtgaag     360 ttaaccccccc tgtgcgtgac cctgaactgc accgacgacc tgcgcaccaa cgccaccaac     420
accaccaaca gcagcgccac caccaacacc accagcagcg gcggcggcac gatggagggc     480
gagaagggcg agatcaagaa ctgcagcttc aacgtgacca ccagcatccg cgacaagatg     540
cagaaggagt acgccctgtt ctacaagctg gacgtggtgc ccatcgacaa cgacaacaac     600
aacaccaaca acaacaccag ctaccgcctc atcaactgca caccagcgt gatcacccag     660 gcctgcccca aggtgagctt cgagcccatc cccatccact actgcacccc cgccggcttc     720
```

```
gccatcctga agtgcaacga caagaagttc aacggcaccg cccctgcac caacgtgagc        780 accgtgcagt gcacccacgg catccgcccc gtggtgagca cccagctgct gctgaacggc        840
agcctggccg aggaggaggt ggtgatccgc agcgagaact tcaccgacaa cgccaagacc        900
atcatcgtgc agctgaacga gagcgtggag atcaactgca cgcgtcccaa caacaacacc        960
cgcaagagca tccccatcgg ccctggccgc gccctgtacg ccaccggcaa gatcatcggc       1020
gacatccgcc aggcccactg caacctgtcg cgagccaagt ggaacaacac cctgaagcag       1080
atcgtgacca gctgcgcga gcagttcggc aacaacaaga ccaccatcgt gttcaaccag       1140
agcagcggcg gcgaccccga gatcgtgatg cacagcttca actgcggcgg cgaattcttc       1200
tactgcaaca gcacccagct gttcaacagc acctggcact tcaacggcac ctggggcaac       1260
aacaacaccg agcgcagcaa caacgccgcc gacgacaacg acaccatcac cctgccctgc       1320
cgcatcaagc agatcatcaa catgtggcag gaggtgggca aggccatgta cgcccccccc       1380
atcagcggcc agatccgctg cagcagcaac atcaccggcc tgctgctgac tcgagacggc       1440
ggcaacaacg agaacaccaa caacaccgac accgagatct ccgcccccgg ggcggcgac       1500 atgcgcgaca actggcgcag cgagctgtac aagtacaagg tggtgaagat cgagcccctg       1560
ggcgtggccc ccaccaaggc caagcgccgc gtggtgcagc gcgagaagcg cgccgtgggc       1620
atgctgggcg ccatgttcct gggcttcctg ggcgccgccg cagcaccat gggcgccgcc       1680 agcatgaccc tgaccgtgca ggcccgccag ctgctgagcg catcgtgca gcagcagaac       1740 aacctgctgc gcgccatcga ggcccagcag cacctgctgc agctgaccgt gtggggcatc       1800
aagcagctgc aggcccgcgt gctggccgtg agcggtacc tgaaggacca gcagctgctg       1860
ggcatctggg gctgcagcgg caagctgatc tgcaccaccg cggtgccctg aacgccagc        1920 tggagcaaca gagcctgga caagatctgg aacaacatga cctggatgga gtgggagcgc       1980
gagatcgaca actacaccgg cctgatctac accctgatcg aggagagcca gaaccagcag       2040
gagaagaacg agcaggagct gctggagctg gacaagtggg ccagcctgtg gaactggttc       2100 gatatccacca actggctgtg gtacatcaag atcttcatca tgatcgtggg cggcctggtg       2160
ggcctgcgca tcgtgttcgc cgtgctgagc atcgtgaacc gcgtgcgcca gggctacagc       2220
cccctgagct tccagacccg cctgcccgcc cccgcggcc ccgaccgccc cgagggcatc       2280
gaggaggagg gcggcgagcg cgaccgcgac cgcagcgggc gcctggtgaa cggcttcctg       2340
gccctgatct gggacgacct cgcagcctg tgcctgttca gctaccaccg cctgcgcgac       2400
ctgctgctga tcgtggcccg catcgtggag ctgctgggcc ggcgcggctg ggaggccctg       2460
aagtattggt ggaaccctgct gcagtactgg agccaggagc tgaagaacag cgccgtgagc       2520
ctgctgaacg ccaccgccat cgccgtggcc gagggcaccg accgcgtgat cgaggtggtg       2580
cagcgcgcct gccgcgccat cctgcacatc ccccgccgca tccgccaggg cctggagcgc       2640
gccctgctgt ga                                                           2652
```

<210> SEQ ID NO 2
<211> LENGTH: 883
<212> TYPE: PRT
<213> ORGANISM: Artificial Sequence
<220> FEATURE:
<223> OTHER INFORMATION: Ancestral HIV-1 group M, subtype B, env
      sequence

<400> SEQUENCE: 2

Met Arg Val Lys Gly Ile Arg Lys Asn Tyr Gln His Leu Trp Arg Trp

-continued

```
1               5                   10                  15

Gly Thr Met Leu Leu Gly Met Leu Met Ile Cys Ser Ala Ala Glu Lys
            20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
            50                  55                  60

His Asn Val Trp Ala Thr His Ala Cys Val Pro Thr Asp Pro Asn Pro
65                      70                  75                  80

Gln Glu Val Val Leu Glu Asn Val Thr Glu Asn Phe Asn Met Trp Lys
            85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
            115                 120                 125

Asn Cys Thr Asp Asp Leu Arg Thr Asn Ala Thr Asn Thr Thr Asn Ser
            130                 135                 140

Ser Ala Thr Thr Asn Thr Thr Ser Ser Gly Gly Gly Thr Met Glu Gly
145                 150                 155                 160

Glu Lys Gly Glu Ile Lys Asn Cys Ser Phe Asn Val Thr Thr Ser Ile
            165                 170                 175

Arg Asp Lys Met Gln Lys Glu Tyr Ala Leu Phe Tyr Lys Leu Asp Val
            180                 185                 190

Val Pro Ile Asp Asn Asp Asn Asn Thr Asn Asn Thr Ser Tyr
            195                 200                 205

Arg Leu Ile Asn Cys Asn Thr Ser Val Ile Thr Gln Ala Cys Pro Lys
            210                 215                 220

Val Ser Phe Glu Pro Ile Pro Ile His Tyr Cys Thr Pro Ala Gly Phe
225                 230                 235                 240

Ala Ile Leu Lys Cys Asn Asp Lys Lys Phe Asn Gly Thr Gly Pro Cys
            245                 250                 255

Thr Asn Val Ser Thr Val Gln Cys Thr His Gly Ile Arg Pro Val Val
            260                 265                 270

Ser Thr Gln Leu Leu Leu Asn Gly Ser Leu Ala Glu Glu Val Val
            275                 280                 285

Ile Arg Ser Glu Asn Phe Thr Asp Asn Ala Lys Thr Ile Ile Val Gln
            290                 295                 300

Leu Asn Glu Ser Val Glu Ile Asn Cys Thr Arg Pro Asn Asn Asn Thr
305                 310                 315                 320

Arg Lys Ser Ile Pro Ile Gly Pro Gly Arg Ala Leu Tyr Ala Thr Gly
            325                 330                 335

Lys Ile Ile Gly Asp Ile Arg Gln Ala His Cys Asn Leu Ser Arg Ala
            340                 345                 350

Lys Trp Asn Asn Thr Leu Lys Gln Ile Val Thr Lys Leu Arg Glu Gln
            355                 360                 365

Phe Gly Asn Asn Lys Thr Thr Ile Val Phe Asn Gln Ser Ser Gly Gly
            370                 375                 380

Asp Pro Glu Ile Val Met His Ser Phe Asn Cys Gly Gly Glu Phe Phe
385                 390                 395                 400

Tyr Cys Asn Ser Thr Gln Leu Phe Asn Ser Thr Trp His Phe Asn Gly
            405                 410                 415

Thr Trp Gly Asn Asn Asn Thr Glu Arg Ser Asn Asn Ala Ala Asp Asp
            420                 425                 430
```

```
Asn Asp Thr Ile Thr Leu Pro Cys Arg Ile Lys Gln Ile Ile Asn Met
        435                 440                 445
Trp Gln Glu Val Gly Lys Ala Met Tyr Ala Pro Pro Ile Ser Gly Gln
    450                 455                 460
Ile Arg Cys Ser Ser Asn Ile Thr Gly Leu Leu Leu Thr Arg Asp Gly
465                 470                 475                 480
Gly Asn Asn Glu Asn Thr Asn Asn Thr Asp Thr Glu Ile Phe Arg Pro
                485                 490                 495
Gly Gly Gly Asp Met Arg Asp Asn Trp Arg Ser Glu Leu Tyr Lys Tyr
                500                 505                 510
Lys Val Val Lys Ile Glu Pro Leu Gly Val Ala Pro Thr Lys Ala Lys
            515                 520                 525
Arg Arg Val Val Gln Arg Glu Lys Arg Ala Val Gly Met Leu Gly Ala
        530                 535                 540
Met Phe Leu Gly Phe Leu Gly Ala Ala Gly Ser Thr Met Gly Ala Ala
545                 550                 555                 560
Ser Met Thr Leu Thr Val Gln Ala Arg Gln Leu Leu Ser Gly Ile Val
                565                 570                 575
Gln Gln Gln Asn Asn Leu Leu Arg Ala Ile Glu Ala Gln Gln His Leu
                580                 585                 590
Leu Gln Leu Thr Val Trp Gly Ile Lys Gln Leu Gln Ala Arg Val Leu
            595                 600                 605
Ala Val Glu Arg Tyr Leu Lys Asp Gln Gln Leu Leu Gly Ile Trp Gly
        610                 615                 620
Cys Ser Gly Lys Leu Ile Cys Thr Thr Ala Val Pro Trp Asn Ala Ser
625                 630                 635                 640
Trp Ser Asn Lys Ser Leu Asp Lys Ile Trp Asn Asn Met Thr Trp Met
                645                 650                 655
Glu Trp Glu Arg Glu Ile Asp Asn Tyr Thr Gly Leu Ile Tyr Thr Leu
                660                 665                 670
Ile Glu Glu Ser Gln Asn Gln Gln Glu Lys Asn Glu Gln Glu Leu Leu
            675                 680                 685
Glu Leu Asp Lys Trp Ala Ser Leu Trp Asn Trp Phe Asp Ile Thr Asn
        690                 695                 700
Trp Leu Trp Tyr Ile Lys Ile Phe Ile Met Ile Val Gly Gly Leu Val
705                 710                 715                 720
Gly Leu Arg Ile Val Phe Ala Val Leu Ser Ile Val Asn Arg Val Arg
                725                 730                 735
Gln Gly Tyr Ser Pro Leu Ser Phe Gln Thr Arg Leu Pro Ala Pro Arg
                740                 745                 750
Gly Pro Asp Arg Pro Glu Gly Ile Glu Glu Glu Gly Gly Glu Arg Asp
            755                 760                 765
Arg Asp Arg Ser Gly Arg Leu Val Asn Gly Phe Leu Ala Leu Ile Trp
        770                 775                 780
Asp Asp Leu Arg Ser Leu Cys Leu Phe Ser Tyr His Arg Leu Arg Asp
785                 790                 795                 800
Leu Leu Leu Ile Val Ala Arg Ile Val Glu Leu Leu Gly Arg Arg Gly
                805                 810                 815
Trp Glu Ala Leu Lys Tyr Trp Trp Asn Leu Leu Gln Tyr Trp Ser Gln
            820                 825                 830
Glu Leu Lys Asn Ser Ala Val Ser Leu Leu Asn Ala Thr Ala Ile Ala
        835                 840                 845
```

```
Val Ala Glu Gly Thr Asp Arg Val Ile Glu Val Val Gln Arg Ala Cys
    850                 855                 860

Arg Ala Ile Leu His Ile Pro Arg Arg Ile Arg Gln Gly Leu Glu Arg
865                 870                 875                 880

Ala Leu Leu

<210> SEQ ID NO 3
<211> LENGTH: 2562
<212> TYPE: DNA
<213> ORGANISM: Artificial sequence
<220> FEATURE:
<223> OTHER INFORMATION: Ancestral HIV-1 group M, subtype C, env
      sequence

<400> SEQUENCE: 3
```

| | | | | | |
|---|---|---|---|---|---|
| atgcgggtga | tgggcatcct | gcggaactgc | cagcagtggt | ggatctgggg | catcctgggc | 60 |
| ttctggatgc | tgatgatctg | cagcgtgatg | ggcaacctgt | gggtgaccgt | gtactacggc | 120 |
| gtgcccgtgt | ggaaggaggc | caagaccacc | ctgttctgcg | ccagcgacgc | caaggcctac | 180 |
| gagcgggagg | tgcacaacgt | gtgggccacc | cacgcctgcg | tgcccaccga | ccccaacccc | 240 |
| caggagatgg | tgctggagaa | cgtgaccgag | aacttcaaca | tgtggaagaa | cgacatggtg | 300 |
| gaccagatgc | acgaggacat | catcagcctg | tgggaccaga | gcctgaagcc | ctgcgtgaag | 360 |
| ctgacccccc | tgtgcgtgac | cctgaactgc | accaacgtga | ccaacaccaa | caacaacaac | 420 |
| aacaccagca | tgggcggcga | gatcaagaac | tgcagcttca | acatcaccac | cgagctgcgg | 480 |
| gacaagaagc | agaaggtgta | cgccctgttc | taccggctgg | acatcgtgcc | cctgaacgag | 540 |
| aacagcaaca | gcaacagcag | cgagtaccgg | ctgatcaact | gcaacaccag | cgccatcacc | 600 |
| caggcctgcc | ccaaggtgag | cttcgacccc | atcccatcc | actactgcgc | ccccgccggc | 660 |
| tacgccatcc | tgaagtgcaa | caacaagacc | ttcaacggca | ccggcccctg | caacaacgtg | 720 |
| agcaccgtgc | agtgcaccca | cggcatcaag | cccgtggtga | gcacccagct | gctgctgaac | 780 |
| ggcagcctgg | ccgaggagga | gatcatcatc | cggagcgaga | acctgaccaa | caacgccaag | 840 |
| accatcatcg | tgcacctgaa | cgagagcgtg | gagatcgtgt | gcacccggcc | caacaacaac | 900 |
| acccggaaga | gcatccggat | cggcccccggc | cagaccttct | acgccaccgg | cgacatcatc | 960 |
| ggcgacatcc | ggcaggccca | ctgcaacatc | agcgagaagg | agtggaacaa | gaccctgcag | 1020 |
| cgggtgggca | agaagctgaa | ggagcacttc | cccaacaaga | ccatcaagtt | cgagcccagc | 1080 |
| agcggcggcg | acctggagat | caccacccac | agcttcaact | gcggggcga | gttcttctac | 1140 |
| tgcaacacca | gcaagctgtt | caacagcacc | tacaacagca | ccaacaacgg | caccaccagc | 1200 |
| aacagcacca | tcaccctgcc | ctgccggatc | aagcagatca | tcaacatgtg | gcagggcgtg | 1260 |
| ggccgggcca | tgtacgcccc | cccatcgcc | ggcaacatca | cctgcaagag | caacatcacc | 1320 |
| ggcctgctgc | tgacccggga | cggcggcaac | accaacaaca | ccaccgagac | cttccggccc | 1380 |
| ggcggcggcg | acatgcggga | caactggcgg | agcgagctgt | acaagtacaa | ggtggtggag | 1440 |
| atcaagcccc | tgggcgtggc | ccccaccgag | gccaagcggc | gggtggtgga | gcggagaag | 1500 |
| cgggccgtgg | gcatcggcgc | cgtgttcctg | ggcttcctgg | gcgccgccgg | cagcaccatg | 1560 |
| ggcgccgcca | gcatcaccct | gaccgtgcag | gcccggcagc | tgctgagcgg | catcgtgcag | 1620 |
| cagcagagca | acctgctgcg | ggccatcgag | gcccagcagc | acatgctgca | gctgaccgtg | 1680 |
| tggggcatca | gcagctgca | gacccgggtg | ctggccatcg | agcggtacct | gaaggaccag | 1740 |
| cagctgctgg | gcatctgggg | ctgcagcggc | aagctgatct | gcaccaccgc | cgtgccctgg | 1800 |

```
aacagcagct ggagcaacaa gagccaggac gacatctggg acaacatgac ctggatgcag    1860
tgggaccggg agatcagcaa ctacaccgac accatctacc ggctgctgga ggacagccag    1920
aaccagcagg agaagaacga gaaggacctg ctggccctgg acagctggaa gaacctgtgg    1980
aactggttcg acatcaccaa ctggctgtgg tacatcaaga tcttcatcat gatcgtgggc    2040
ggcctgatcg gcctgcggat catcttcgcc gtgctgagca tcgtgaaccg ggtgcggcag    2100
ggctacagcc ccctgagctt ccagaccctg acccccaacc cccggggccc cgaccggctg    2160
ggcggcatcg aggaggaggg cggcgagcag gaccgggacc ggagcatccg gctggtgagc    2220
ggcttcctgg ccctggcctg ggacgacctg cggagcctgt gcctgttcag ctaccaccgg    2280
ctgcgggact tcatcctgat cgccgcccgg ggcgtgaacc tgctgggccg gagcagcctg    2340
cggggcctgc agcggggctg ggaggccctg aagtacctgg gcagcctggt gcagtactgg    2400
ggcctggagc tgaagaagag cgccatcagc ctgctggaca ccatcgccat cgccgtggcc    2460
gagggcaccg accggatcat cgagctggtg cagcggatct gccgggccat ccggaacatc    2520
ccccggcgga tccggcaggg cttcgaggcc gccctgcagt ga                       2562
```

<210> SEQ ID NO 4
<211> LENGTH: 853
<212> TYPE: PRT
<213> ORGANISM: Artificial sequence
<220> FEATURE:
<223> OTHER INFORMATION: Ancestral HIV-1 group M, subtype C, env sequence.

<400> SEQUENCE: 4

```
Met Arg Val Met Gly Ile Leu Arg Asn Cys Gln Gln Trp Trp Ile Trp
1               5                   10                  15

Gly Ile Leu Gly Phe Trp Met Leu Met Ile Cys Ser Val Met Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Arg Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Val Thr Asn Thr Asn Asn Asn Asn Thr Ser Met
    130                 135                 140

Gly Gly Glu Ile Lys Asn Cys Ser Phe Asn Ile Thr Thr Glu Leu Arg
145                 150                 155                 160

Asp Lys Lys Gln Lys Val Tyr Ala Leu Phe Tyr Arg Leu Asp Ile Val
                165                 170                 175

Pro Leu Asn Glu Asn Ser Asn Ser Ser Glu Tyr Arg Leu Ile
            180                 185                 190

Asn Cys Asn Thr Ser Ala Ile Thr Gln Ala Cys Pro Lys Val Ser Phe
        195                 200                 205

Asp Pro Ile Pro Ile His Tyr Cys Ala Pro Ala Gly Tyr Ala Ile Leu
    210                 215                 220
```

```
Lys Cys Asn Asn Lys Thr Phe Asn Gly Thr Gly Pro Cys Asn Asn Val
225                 230                 235                 240

Ser Thr Val Gln Cys Thr His Gly Ile Lys Pro Val Val Ser Thr Gln
            245                 250                 255

Leu Leu Leu Asn Gly Ser Leu Ala Glu Glu Ile Ile Ile Arg Ser
            260                 265                 270

Glu Asn Leu Thr Asn Asn Ala Lys Thr Ile Ile Val His Leu Asn Glu
        275                 280                 285

Ser Val Glu Ile Val Cys Thr Arg Pro Asn Asn Thr Arg Lys Ser
        290                 295                 300

Ile Arg Ile Gly Pro Gly Gln Thr Phe Tyr Ala Thr Gly Asp Ile Ile
305                 310                 315                 320

Gly Asp Ile Arg Gln Ala His Cys Asn Ile Ser Glu Lys Glu Trp Asn
                325                 330                 335

Lys Thr Leu Gln Arg Val Gly Lys Lys Leu Lys Glu His Phe Pro Asn
            340                 345                 350

Lys Thr Ile Lys Phe Glu Pro Ser Ser Gly Gly Asp Leu Glu Ile Thr
            355                 360                 365

Thr His Ser Phe Asn Cys Arg Gly Glu Phe Phe Tyr Cys Asn Thr Ser
370                 375                 380

Lys Leu Phe Asn Ser Thr Tyr Asn Ser Thr Asn Asn Gly Thr Thr Ser
385                 390                 395                 400

Asn Ser Thr Ile Thr Leu Pro Cys Arg Ile Lys Gln Ile Ile Asn Met
            405                 410                 415

Trp Gln Gly Val Gly Arg Ala Met Tyr Ala Pro Pro Ile Ala Gly Asn
            420                 425                 430

Ile Thr Cys Lys Ser Asn Ile Thr Gly Leu Leu Leu Thr Arg Asp Gly
            435                 440                 445

Gly Asn Thr Asn Asn Thr Thr Glu Thr Phe Arg Pro Gly Gly Gly Asp
            450                 455                 460

Met Arg Asp Asn Trp Arg Ser Glu Leu Tyr Lys Tyr Lys Val Val Glu
465                 470                 475                 480

Ile Lys Pro Leu Gly Val Ala Pro Thr Glu Ala Lys Arg Arg Val Val
            485                 490                 495

Glu Arg Glu Lys Arg Ala Val Gly Ile Gly Ala Val Phe Leu Gly Phe
            500                 505                 510

Leu Gly Ala Ala Gly Ser Thr Met Gly Ala Ala Ser Ile Thr Leu Thr
            515                 520                 525

Val Gln Ala Arg Gln Leu Leu Ser Gly Ile Val Gln Gln Gln Ser Asn
            530                 535                 540

Leu Leu Arg Ala Ile Glu Ala Gln Gln His Met Leu Gln Leu Thr Val
545                 550                 555                 560

Trp Gly Ile Lys Gln Leu Gln Thr Arg Val Leu Ala Ile Glu Arg Tyr
            565                 570                 575

Leu Lys Asp Gln Gln Leu Leu Gly Ile Trp Gly Cys Ser Gly Lys Leu
            580                 585                 590

Ile Cys Thr Thr Ala Val Pro Trp Asn Ser Ser Trp Ser Asn Lys Ser
            595                 600                 605

Gln Asp Asp Ile Trp Asp Asn Met Thr Trp Met Gln Trp Asp Arg Glu
            610                 615                 620

Ile Ser Asn Tyr Thr Asp Thr Ile Tyr Arg Leu Leu Glu Asp Ser Gln
625                 630                 635                 640

Asn Gln Gln Glu Lys Asn Glu Lys Asp Leu Leu Ala Leu Asp Ser Trp
```

```
                       645                 650                 655
Lys Asn Leu Trp Asn Trp Phe Asp Ile Thr Asn Trp Leu Trp Tyr Ile
                    660                 665                 670

Lys Ile Phe Ile Met Ile Val Gly Gly Leu Ile Gly Leu Arg Ile Ile
                675                 680                 685

Phe Ala Val Leu Ser Ile Val Asn Arg Val Arg Gln Gly Tyr Ser Pro
            690                 695                 700

Leu Ser Phe Gln Thr Leu Thr Pro Asn Pro Arg Gly Pro Asp Arg Leu
705                 710                 715                 720

Gly Gly Ile Glu Glu Glu Gly Gly Glu Gln Asp Arg Asp Arg Ser Ile
                    725                 730                 735

Arg Leu Val Ser Gly Phe Leu Ala Leu Ala Trp Asp Asp Leu Arg Ser
                740                 745                 750

Leu Cys Leu Phe Ser Tyr His Arg Leu Arg Asp Phe Ile Leu Ile Ala
            755                 760                 765

Ala Arg Gly Val Asn Leu Leu Gly Arg Ser Ser Leu Arg Gly Leu Gln
        770                 775                 780

Arg Gly Trp Glu Ala Leu Lys Tyr Leu Gly Ser Leu Val Gln Tyr Trp
785                 790                 795                 800

Gly Leu Glu Leu Lys Lys Ser Ala Ile Ser Leu Leu Asp Thr Ile Ala
                    805                 810                 815

Ile Ala Val Ala Glu Gly Thr Asp Arg Ile Ile Glu Leu Val Gln Arg
                820                 825                 830

Ile Cys Arg Ala Ile Arg Asn Ile Pro Arg Arg Ile Arg Gln Gly Phe
            835                 840                 845

Glu Ala Ala Leu Gln
    850
```

<210> SEQ ID NO 5
<211> LENGTH: 2652
<212> TYPE: DNA
<213> ORGANISM: Artificial sequence
<220> FEATURE:
<223> OTHER INFORMATION: Semi-optimized ancestral viral sequences for
      HIV-1 subtypes B and C

<400> SEQUENCE: 5

```
atgagagtga aggggatcag gaagaactat cagcacttgt ggagatgggg caccatgctc      60
cttgggatgt tgatgatctg tagcgccgcc gagaagctgt gggtgaccgt gtactacggc     120
gtgcccgtgt ggaaggaggc caccaccacc ctgttctgcg ccagcgacgc caaggcttac     180
gacaccgagg tccacaacgt gtgggccacc cacgcctgcg tgcccaccga ccccaacccc     240
caggaggtgg tgctggagaa cgtgaccgag aacttcaaca tgtggaagaa caacatggtg     300
gagcagatgc acgaggacat catcagcctg tgggaccaga gcctgaagcc ctgcgtgaag     360
ttaacccccc tgtgcgtgac cctgaactgc accgacgacc tgcgcaccaa cgccaccaac     420
accaccaaca gcagcgccac caccaacacc accagcagcg gcggcggcac gatggagggc     480
gagaagggcg agatcaagaa ctgcagcttc aacgtgacca ccagcatccg cgacaagatg     540
cagaaggagt acgccctgtt ctacaagctg gacgtggtgc ccatcgacaa cgacaacaac     600
aacaccaaca acaacaccag ctaccgcctc atcaactgca acaccagcgt gatcacccag     660
gcctgcccca aggtgagctt cgagcccatc cccatccact actgcacccc cgccggcttc     720
gccatcctga agtgcaacga caagaagttc aacggcaccg gcccctgcac caacgtgagc     780
accgtgcagt gcacccacgg catccgcccc gtggtgagca cccagctgct gctgaacggc     840
```

-continued

```
agcctggccg aggaggaggt ggtgatccgc agcgagaact tcaccgacaa cgccaagacc    900
atcatcgtgc agctgaacga gagcgtggag atcaactgca cgcgtcccaa caacaacacc    960
cgcaagagca tccccatcgg ccctggccgc gccctgtacg ccaccggcaa gatcatcggc   1020
gacatccgcc aggcccactg caacctgtcg cgagccaagt ggaacaacac cctgaagcag   1080
atcgtgacca gctgcgcga gcagttcggc aacaacaaga ccaccatcgt gttcaaccag   1140
agcagcggcg gcgaccccga gatcgtgatg cacagcttca ctgcggcgg cgaattcttc   1200 tactgcaaca gcacccagct gttcaacagc acctggcact tcaacggcac ctggggcaac   1260
aacaacaccg agcgcagcaa caacgccgcc gacgacaacg acaccatcac cctgccctgc   1320
cgcatcaagc agatcatcaa catgtggcag gaggtgggca aggccatgta cgccccccc    1380 atcagcggcc agatccgctg cagcagcaac atcaccggcc tgctgctgac tcgagacggc   1440
ggcaacaacg agaacaccaa caacaccgac accgagatct ccgcccccgg ggcggcgac   1500 atgcgcgaca actggcgcag cgagctgtac aagtacaagg tggtgaagat cgagcccctg   1560
ggcgtagcac ccaccaaggc aaagagaaga gtggtgcaga gagaaaaaag cgcagtggga   1620
atgctaggag ctatgttcct tgggttcttg ggagcagcag aagcactat gggcgcagcg    1680 tcaatgacgc tgaccgtaca ggccagacaa ttattgtctg gtatagtgca gcagcagaac   1740
aatctgctga gggctattga ggcgcaacag catctgttgc aactcacagt ctggggcatc   1800
aagcagctcc aggcaagagt cctggctgtg gaaagatacc taaaggatca gcagctcctg   1860
gggatttggg gttgctctgg aaaactcatc tgcaccactg ctgtgccttg gaatgctagc   1920
tggagcaaca gagcctggac aagatctgg aacaacatga cctggatgga gtgggagcgc   1980
gagatcgaca actacaccgg cctgatctac accctgatcg aggagagcca gaaccagcag   2040
gagaagaacg agcaggagct gctggagctg acaagtgggg ccagcctgtg aactggttc   2100 gatatccacca actggctgtg gtacatcaag atcttcatca tgatcgtggg cggcctggtg   2160
ggcctgcgca tcgtgttcgc cgtgctgagc atcgtgaacc gcgtgcgcca gggctacagc   2220
cccctgagct tccagaccca cctgccagcc ccgaggggac ccgacaggcc cgaaggaatc   2280
gaagaagaag gtggagagag agacagagac agatccggtc gattagtgaa tggattctta   2340
gcacttatct gggacgacct gcggagcctg tgcctcttca gctaccaccg cttgagcgac   2400
ttactcttga ttgtagcgag gattgtggaa cttctgggac gcaggggtg ggaggccctc   2460 aaatattggt ggaatctcct gcagtactgg agtcaggaac taaagaatag cgccgtgagc   2520
ctgctgaacg ccaccgccat cgccgtggcc gagggcaccg accgcgtgat cgaggtggtg   2580
cagcgcgcct gccgcgccat cctgcacatc ccccgccgca tccgccaggg cctggagcgc   2640
gccctgctgt ga                                                      2652
```

<210> SEQ ID NO 6
<211> LENGTH: 2562
<212> TYPE: DNA
<213> ORGANISM: Artificial sequence
<220> FEATURE:
<223> OTHER INFORMATION: Semi-optimized ancestral viral sequences for HIV-1 subtypes B and C

<400> SEQUENCE: 6

```
atgagagtga tggggatact gaggaattgt caacaatggt ggatatgggg catcctaggc     60
ttttggatgc taatgatttg tgacgtgatg ggcaacctgt gggtgaccgt gtactacggc    120
gtgcccgtgt ggaaggaggc caagaccacc ctgttctgcg ccagcgacgc caaggcctac    180
```

```
gagcgggagg tgcacaacgt gtgggccacc cacgcctgcg tgcccaccga ccccaacccc    240
caggagatgg tgctggagaa cgtgaccgag aacttcaaca tgtggaagaa cgacatggtg    300
gaccagatgc acgaggacat catcagcctg tgggaccaga gcctgaagcc ctgcgtgaag    360
ctgaccccc  tgtgcgtgac cctgaactgc accaacgtga ccaacaccaa caacaacaac    420
aacaccagca tgggcggcga gatcaagaac tgcagcttca acatcaccac cgagctgcgg    480
gacaagaagc agaaggtgta cgccctgttc taccggctgg acatcgtgcc cctgaacgag    540
aacagcaaca gcaacagcag cgagtaccgg ctgatcaact gcaacaccag cgccatcacc    600
caggcctgcc ccaaggtgag cttcgacccc atccccatcc actactgcgc cccgccggc    660
tacgccatcc tgaagtgcaa caacaagacc ttcaacggca ccggcccctg caacaacgtg    720
agcaccgtgc agtgcaccca cggcatcaag cccgtggtga gcacccagct gctgctgaac    780
ggcagcctgg ccgaggagga gatcatcatc cggagcgaga acctgaccaa caacgccaag    840
accatcatcg tgcacctgaa cgagagcgtg gagatcgtgt gcacccggcc caacaacaac    900
acccggaaga gcatccggat cggccccggc cagaccttct acgccaccgg cgacatcatc    960
ggcgacatcc ggcaggccca ctgcaacatc agcgagaagg agtggaacaa gaccctgcag   1020
cgggtgggca gaagctgaa  ggagcacttc cccaacaaga ccatcaagtt cgagcccagc   1080
agcggcggcg acctggagat caccacccac agcttcaact gccggggcga gttcttctac   1140
tgcaacacca gcaagctgtt caacagcacc tacaacagca ccaacaacgg caccaccagc   1200
aacagcacca tcaccctgcc ctgccggatc aagcagatca tcaacatgtg gcagggcgtg   1260
ggccgggcca tgtacgcccc ccccatcgcc ggcaacatca cctgcaagag caacatcacc   1320
ggcctgctgc tgacccggga cggcggcaac accaacaaca ccaccgagac cttccggccc   1380
ggcggcggcg acatgcggga caactggcgg agcgagctgt acaagtacaa ggtggtggag   1440
atcaagcccc tgggcgtagc acccactgag gcaaaaagga gagtggtgga gagagaaaaa   1500
agagcagtgg gaataggagc tgtgttcctt gggttcttgg gagcagcagg aagcactatg   1560
ggcgcggcgt caataacgct gacggtacag gccagacaat tattgtctgg tatagtgcaa   1620
cagcaaagca atttgctgag ggctatagag gcgcaacagc atatgttgca actcacggtc   1680
tggggcatta agcagctcca gacaagagtc ctggctatag aaagatacct aaaggatcag   1740
cagctcctgg gcatttgggg ctgctctgga aaactcatct gcaccactgc tgtgccttgg   1800
aactctagct ggagcaacaa gagccaggac gacatctggg acaacatgac ctggatgcag   1860
tgggaccggg agatcagcaa ctacaccgac accatctacc ggctgctgga ggacagccag   1920
aaccagcagg agaagaacga gaaggacctg ctggccctgg acagctggaa gaacctgtgg   1980
aactggttcg acatcaccaa ctggctgtgg tacatcaaga tcttcatcat gatcgtgggc   2040
ggcctgatcg gcctgcggat catcttcgcc gtgctgagca tcgtgaaccg ggtgcggcag   2100
ggctacagcc ccctgagctt ccagacccct accccaaacc cgaggggacc cgacaggctc   2160
ggaggaatcg aagaagaagg tggagagcaa gacagagaca gatccattcg attagtgagc   2220
ggattcttag cactggcctg ggacgacctg cggagcctgt gcctcttcag ctaccaccga   2280
ttgagagact tcatattgat tgcagccaga gggtgggaac ttctgggacg cagcagtctc   2340
aggggactgc agagggggtg ggaagccctt aagtatctgg gaagtcttgt gcagtattgg   2400
ggtctggagc taaaaagag  tgctattagc ctgctggaca ccatcgccat cgccgtggcc   2460
gagggcacc  accggatcat cgagctggtg cagcggatct gccgggccat ccggaacatc   2520
```

```
ccccggcgga tccggcaggg cttcgaggcc gccctgcagt ga                              2562
```

<210> SEQ ID NO 7
<211> LENGTH: 7
<212> TYPE: DNA
<213> ORGANISM: Artificial sequence
<220> FEATURE:
<223> OTHER INFORMATION: Consensus sequence-maximum likelihood
      reconstruction of determined ancestral node.

<400> SEQUENCE: 7

```
gatcctg                                                                       7
```

<210> SEQ ID NO 8
<211> LENGTH: 7
<212> TYPE: DNA
<213> ORGANISM: Artificial sequence
<220> FEATURE:
<223> OTHER INFORMATION: Consensus sequence, most parsimonious
      reconstruction of determined ancestral node
<220> FEATURE:
<221> NAME/KEY: variation
<222> LOCATION: (3)..(3)
<223> OTHER INFORMATION: W can be an A or T

<400> SEQUENCE: 8

```
gawcctg                                                                       7
```

<210> SEQ ID NO 9
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 9

```
gaacctg                                                                       7
```

<210> SEQ ID NO 10
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 10

```
gaaactc                                                                       7
```

<210> SEQ ID NO 11
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 11

```
gatactc                                                                       7
```

<210> SEQ ID NO 12
<211> LENGTH: 7
<212> TYPE: DNA
<213> ORGANISM: Artificial sequence
<220> FEATURE:
<223> OTHER INFORMATION: Consensus sequence, most parsimonious
      reconstruction of determined ancestral node.

```
<220> FEATURE:
<221> NAME/KEY: variation
<222> LOCATION: (3)..(3)
<223> OTHER INFORMATION: W can be an A or T

<400> SEQUENCE: 12 gawactc                                                                        7

<210> SEQ ID NO 13
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 13 catactc                                                                        7

<210> SEQ ID NO 14
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 14 catactt                                                                        7

<210> SEQ ID NO 15
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 15 catacta                                                                        7

<210> SEQ ID NO 16
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 16 catattg                                                                        7

<210> SEQ ID NO 17
<211> LENGTH: 7
<212> TYPE: DNA
<213> ORGANISM: Artificial sequence
<220> FEATURE:
<223> OTHER INFORMATION: Consensus sequence, most parsimonious
      reconstruction of determined ancestral node.
<220> FEATURE:
<221> NAME/KEY: variation
<222> LOCATION: (7)..(7)
<223> OTHER INFORMATION: V can also be an A, C or G

<400> SEQUENCE: 17 catactv                                                                        7
```

```
<210> SEQ ID NO 18
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 18 catgctg                                                                   7

<210> SEQ ID NO 19
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 19 catactg                                                                   7

<210> SEQ ID NO 20
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 20 caagctg                                                                   7

<210> SEQ ID NO 21
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 21 catgctg                                                                   7

<210> SEQ ID NO 22
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 22 cttgctg                                                                   7

<210> SEQ ID NO 23
<211> LENGTH: 7
<212> TYPE: DNA
<213> ORGANISM: Artificial sequence
<220> FEATURE:
<223> OTHER INFORMATION: Consensus sequence, maximum likelihood
      reconstruction of determined ancestral node.

<400> SEQUENCE: 23 cttgctt                                                                   7

<210> SEQ ID NO 24
```

<211> LENGTH: 1503
<212> TYPE: DNA
<213> ORGANISM: Artificial sequence
<220> FEATURE:
<223> OTHER INFORMATION: Most recent common ancestor of reconstruction
      clade B gag gene sequence

<400> SEQUENCE: 24

| | | | | |
|---|---|---|---|---|
| atgggtgcga | gagcgtcagt | attaagcggg | ggagaattag | ataaatggga aaaaattcgg | 60 |
| ttacggccag | ggggaaagaa | aaaatataaa | ttaaaacata | tagtatgggc aagcagggag | 120 |
| ctagaacgat | tcgcagttaa | tcctggcctt | ttagaaacat | cagaaggctg tagacaaata | 180 |
| ctgggacagc | tacaaccatc | ccttcagaca | ggatcagaag | aacttagatc attatataat | 240 |
| acagtagcag | tcctctattg | tgtgcatcaa | aagatagagg | taaaagacac caaggaagct | 300 |
| ttagataaga | tagaggaaga | gcaaaacaaa | agtaagaaaa | aggcacagca agcagcagct | 360 |
| gacacaggaa | acagcagcca | ggtcagccaa | aattacccta | tagtgcagaa cctacagggg | 420 |
| caaatggtac | atcaggccct | atcacctaga | actttaaatg | catgggtaaa agtaatagaa | 480 |
| gagaaggctt | tcagcccaga | agtaataccc | atgttttcag | cattatcaga aggagccacc | 540 |
| ccacaagatt | taaacaccat | gctaaacaca | gtggggggac | atcaagcagc catgcaaatg | 600 |
| ttaaaagaga | ccatcaatga | ggaagctgca | gaatgggata | gattgcatcc agtgcatgca | 660 |
| gggcctattg | caccaggcca | gatgagagaa | ccaaggggaa | gtgacatagc aggaactact | 720 |
| agtacccttc | aggaacaaat | agcatggatg | acaaataatc | cacctatccc agtaggagaa | 780 |
| atctataaaa | gatggataat | cctgggatta | aataaaatag | taagaatgta tagccctgtc | 840 |
| agcattctgg | acataagaca | aggaccaaag | gaaccctttta | gagactatgt agaccggttc | 900 |
| tataaaactc | taagagccga | gcaagcttca | caggaggtaa | aaaattggat gacagaaacc | 960 |
| ttgttggtcc | aaaatgcgaa | cccagattgt | aagactatct | aaaagcatt gggaccagga | 1020 |
| gctacactag | aagaaatgat | gacagcatgt | cagggagtgg | ggggacccgg ccataaagca | 1080 |
| agagttttgg | ctgaagcaat | gagccaagta | acaaattcag | ctaccataat gatgcagaga | 1140 |
| ggcaattttta | ggaacccaag | aaagactgtt | aagtgtttca | attgtggcaa agaagggcac | 1200 |
| atagccagaa | attgcagggc | ccctaggaaa | aagggctgtt | ggaaatgtgg aaaggaagga | 1260 |
| caccaaatga | aagattgtac | tgagagacag | gctaattttt | tagggaaaat ctggccttcc | 1320 |
| cacaagggaa | ggccagggaa | ttttcttcag | agcagaccag | agccaacagc cccaccagaa | 1380 |
| gagagcttca | ggtttgggga | agagacaaca | actccctctc | agaagcagga gcagaaagac | 1440 |
| aaggaactgt | atcctttagc | ttccctcaaa | tcactctttg | gcaacgaccc ctcgtcacaa | 1500 |
| taa | | | | | 1503 |

<210> SEQ ID NO 25
<211> LENGTH: 1503
<212> TYPE: DNA
<213> ORGANISM: Artificial sequence
<220> FEATURE:
<223> OTHER INFORMATION: Least squares center of tree reconstruction of
      clade B gag gene sequence

<400> SEQUENCE: 25

| | | | | |
|---|---|---|---|---|
| atgggtgcga | gagcgtcagt | attaagcggg | ggagaattag | atagatggga aaaaattcgg | 60 |
| ttaaggccag | ggggaaagaa | aaaatataga | ttaaaacata | tagtatgggc aagcagggag | 120 |
| ctagaacgat | tcgcagttaa | tcctggcctg | ttagaaacat | cagaaggctg tagacaaata | 180 |
| ctgggacagc | tacaaccatc | ccttcagaca | ggatcagaag | aacttagatc attatataat | 240 |

-continued

```
acagtagcaa ccctctattg tgtgcatcaa aggatagagg taaaagacac caaggaagct      300
ttagagaaga tagaggaaga gcaaaacaaa agtaagaaaa aggcacagca agcagcagct      360
gacacaggaa acagcagcca ggtcagccaa aattacccta tagtgcagaa cctccagggg      420
caaatggtac atcaggccat atcacctaga actttaaatg catgggtaaa agtagtagag      480
gagaaggctt tcagcccaga gtaataccc atgttttcag cattatcaga aggagccacc       540
ccacaagatt taaacaccat gctaaacaca gtggggggac atcaagcagc catgcaaatg     600
ttaaaagaga ccatcaatga ggaagctgca gaatgggata gattgcatcc agtgcatgca     660
gggcctattg caccaggcca gatgagagaa ccaaggggaa gtgacatagc aggaactact     720
agtacccttc aggaacaaat aggatggatg acaaataatc cacctatccc agtaggagaa     780
atctataaaa gatggataat cctgggatta aataaaatag taagaatgta tagccctacc     840
agcattctgg acataagaca aggaccaaag gaacccttta gagactatgt agaccggttc     900
tataaaactc taagagccga gcaagcttca caggaggtaa aaaattggat gacagaaacc     960
ttgttggtcc aaaatgcgaa cccagattgt aagactattt taaaagcatt gggaccagca    1020
gctacactag aagaaatgat gacagcatgt cagggagtgg ggggacccgg ccataaagca    1080
agagttttgg ctgaagcaat gagccaagta acaaattcag ctaccataat gatgcagaga    1140
ggcaatttta ggaaccaaag aaagactgtt aagtgtttca attgtggcaa agaagggcac    1200
atagccaaaa attgcagggc ccctaggaaa aagggctgtt ggaaatgtgg aaaggaagga    1260
caccaaatga aagattgtac tgagagacag gctaattttt tagggaagat ctggccttcc    1320
cacaagggaa ggccagggaa ttttcttcag agcagaccag agccaacagc cccaccagaa    1380
gagagcttca ggtttgggga agagacaaca actccctctc agaagcagga gccgatagac    1440
aaggaactgt atcctttagc ttccctcaga tcactctttg gcaacgaccc ctcgtcacaa    1500
taa                                                                   1503
```

<210> SEQ ID NO 26
<211> LENGTH: 1503
<212> TYPE: DNA
<213> ORGANISM: Artificial sequence
<220> FEATURE:
<223> OTHER INFORMATION: Minimum of means center of tree reconstruction
      of clade B gag gene sequence

<400> SEQUENCE: 26

```
atgggtgcgg gagcgtcggt attaagcggg ggaaaattag ataggtggga aaaaattcgg       60
ttaaggccag ggggaaagaa aaaatataaa ttaaaacata tagtatgggc aagcagggag      120
ctagaacgat tgcagtcaa tcctggcctg ttagaaacat cagaaggctg cagacgaata      180
ctggaacagc tacatccatc ccttcagaca ggatcagaag aacttaaatc attatataat     240
acggtagcaa ccctctattg tgtgcatcaa aatatagagg taagagacac caaggatgct     300
ttagaaaaaa tagaggaaga acaaaacaaa attaagaaaa gggcacagca agcagcagct     360
gacacaggaa acagcaaccc ggtcagccaa aattacccta tagtgcagaa tatgcagggg    420
caaatggtac atcaggccat atcacctaga actttaaatg catgggtaaa agtagtagaa    480
gagaaggctt tcagcccgga gtaataccc atgttttcag cattatcaga aggagccacc      540
ccacaagatt taaacaccat gctaaacaca gtggggggac atcaagcagc catgcaaatg     600
ttaaaagaaa ccatcaatga ggaagctgca gaatgggata gattgcaccc agtgcatgca     660
gggcctattg caccaggcca gatgagagaa ccaaggggaa gtgacatagc aggaactact     720
```

| | |
|---|---|
| agtacccttc aggaacaaat aggatggatg acacataatc cacctatccc agtaggagaa | 780 |
| atctataaaa gatggataat catgggatta aataaaatag taagaatgta tagccctacc | 840 |
| agcattctgg acataagaca aggaccaaag gaacccttta gagattatgt tgaccggttc | 900 |
| tataaaactc taagagccga gcaagcttca caggaggtaa aaaattggat gacagaaacc | 960 |
| ttgttggtcc aaaatgcgaa cccagattgt aagaccattt taaaagcatt aggaccagca | 1020 |
| gctacactag aagaaatgat gacagcatgt cagggagtgg gagggcccag ccataaagca | 1080 |
| agagttttgg cagaagcaat gagccaagca acaaattcag ctaccataat gatgcagagg | 1140 |
| ggcaatttta agggccaaag aaagactgtt aaatgtttca attgtggcaa agaagggcac | 1200 |
| atagccagaa attgcagggc ccctagaaaa aagggctgtt ggaaatgtgg aaaggaagga | 1260 |
| caccaaatga aagattgtac tgagagacag gctaattttt tagggaagat ctggccttcc | 1320 |
| cacaagggaa ggccagggaa ttttctccaa agcaggccag agccaacagc cccaccagaa | 1380 |
| gagagcttca ggtttgggga ggagacaaca actccccctc agaagcagga gccgagggac | 1440 |
| aaggaacagt atcccttgac ttccctcaga tcactctttg gcaacgaccc atcgtcacaa | 1500 |
| taa | 1503 |

<210> SEQ ID NO 27
<211> LENGTH: 2589
<212> TYPE: DNA
<213> ORGANISM: Artificial sequence
<220> FEATURE:
<223> OTHER INFORMATION: Most recent common ancestor reconstruction of
      clade B env gene sequence

<400> SEQUENCE: 27

| | |
|---|---|
| atgagagtga aggggatcag gaagaattgt cagcacttgt ggaaatgggg caccatgctc | 60 |
| cttgggatgt tgatgatctg tagtgctgca gaaaacttgt gggtcacagt ctattatggg | 120 |
| gtacctgtgt ggaaagaagc aaccaccact ctattttgtg catcagatgc taaagcatat | 180 |
| aaaacagagg tacataatgt ctgggccaca catgcctgtg tacccacaga ccccaaccca | 240 |
| caagaagtag tattggaaaa tgtgacagaa aatttaaca tgtggaaaaa taacatggta | 300 |
| gaacagatgc atgaggatat aatcagttta tgggatcaaa gcctaaagcc atgtgtaaaa | 360 |
| ttaaccccac tctgtgttac tttaaattgc actgatgcga caagaatgc tactaatacc | 420 |
| aatagtagta gtgggggaac aatggagaaa ggagaaatga aaaactgctc tttcaatatc | 480 |
| accacaagca taagagataa gatgcagaaa gaatatgcac ttttttataa acttgatgta | 540 |
| gtaccaatag ataatgataa taatagtaat aataatacca actataggtt gataaattgt | 600 |
| aatacctcag tcattacaca ggcctgtcca aaggtatcct ttgagccaat tcccatacat | 660 |
| tattgtaccc cggctggttt tgcgattcta aagtgtaatg ataagaagtt caatggaaca | 720 |
| ggaccatgta aaaatgtcag cacagtacaa tgtacacatg gaattaggcc agtagtgtca | 780 |
| actcaactgc tgttaaatgg cagtctagca gaagaagagg tagtaattag atctgaaaat | 840 |
| ttcacggaca atgctaaaac cataatagta cagctgaatg aatctgtaga attaattgt | 900 |
| acaagaccca caacaatac aagaaaaagt atacctatag gaccagggag agcactttat | 960 |
| acaacaggag aaataatagg agatataaga caagcacatt gtaacattag tagagcaaaa | 1020 |
| tggaataaca cttttaaaaca ggtagttaca aaattaagag aacaatttgg gaataataaa | 1080 |
| acaatagtct ttaatccatc ctcaggaggg gacccagaaa ttgtaatgca cagttttaat | 1140 |
| tgtggagggg aattttctac tgtaatacac acaactgt taatagtac ttggaatagt | 1200 |

```
actgaagggt caaataaaac tacagggtca aataacactg gaggagaaac tatcacactc    1260
ccatgcagaa taaacaaat tataaacatg tggcaggaag taggaaaagc aatgtatgcc    1320
cctcccatca gaggacaaat taaatgttca tcaaatatta cagggctact attaacaaga    1380
gatggtggtg aaaatagtac caatgagacc gagatcttca gacctggagg aggagatatg    1440
agggacaatt ggagaagtga attatataaa tataaagtag taaaaattga accattagga    1500
gtagcaccca ccaaggcaaa gagaagagtg gtgcaaagag aaaaaagagc agtgggaata    1560
ataggagcta tgttccttgg gttcttggga gcagcaggaa gcactatggg cgcagcgtca    1620
atgacgctga cggtacaggc cagacaatta ttgtctggta tagtgcaaca gcaaaacaat    1680
ttgctgaggg ctattgaggc gcaacagcat ctgttgcaac tcacggtctg ggcatcaaa    1740 cagctccagg caagagtcct ggctgtggaa agatacctaa gggatcaaca gctcctagga    1800
atttggggtt gctctggaaa actcatttgc accactactg tgccttggaa tgctagttgg    1860
agtaataaat ctctggataa gatttggaat aacatgacct ggatggagtg ggaaagagaa    1920
attgacaatt acacaggctt aatatacaac ttaattgaag aatcgcagaa ccagcaagaa    1980
aagaatgaac aagaattatt ggaattggat aagtgggcaa gtttgtggaa ttggtttgac    2040
ataacacaat ggctgtggta tataaaaata ttcataatga tagtaggagg cttggtaggt    2100
ttaagaatag ttttgctgt gctttctata gtgaatagag ttaggcaggg atactcacca    2160
ttatcatttc agacccgcct cccagccccg aggggacccg acaggcccga aggaatcgaa    2220
gaagaaggtg gagagagaga cagagacaga tccggtcgat tagtgaatgg attcttagca    2280
cttatctggg acgatctgcg gagcctgtgc ctcttcagct accaccgctt gagagactta    2340
ctcttgattg tagcgaggat tgtggaactt ctggacgca ggggtggga agccctcaaa    2400 tattggtgga atctcctgca gtattggagt caggaactaa agaatagtgc tgttagcttg    2460
cttaatgcca cagcaatagc agtagctgag gggacagata gggttataga agtagtacaa    2520
agagcttgta gagctattct tcacatacct agaagaataa gacagggctt agaaagggct    2580
ttgctataa                                                            2589
```

<210> SEQ ID NO 28
<211> LENGTH: 2589
<212> TYPE: DNA
<213> ORGANISM: Artificial sequence
<220> FEATURE:
<223> OTHER INFORMATION: Least square center of tree and minimum of
      means center of tree reconstruction of clade B env gene sequence

<400> SEQUENCE: 28

```
atgagagtga aggggatcag gaagaattat cagcacttgt ggagatgggg caccatgctc      60
cttgggatgt tgatgatctg tagtgctgca gaaaaattgt gggtcacagt ctattatggg     120
gtacctgtgt ggaaagaagc aaccaccact ctattttgtg catcagatgc taaagcatat     180
gatacagagg tacataatgt ttgggccaca catgcctgtg tacccacaga ccccaaccca     240
caagaagtag tattggaaaa tgtgacagaa aatttttaaca tgtggaaaaa taacatggta     300
gaacagatgc atgaggatat aatcagttta tgggatcaaa gcctaaagcc atgtgtaaaa     360
ttaaccccac tctgtgttac tttaaattgc actgatttga ataagaatgc tactaatacc     420
aatagtagta gcggggaaat gatggagaaa ggagaaataa aaaactgctc tttcaatatc     480
accacaagca taagagataa ggtgcagaaa gaatatgcac tttttttataa acttgatgta     540 gtaccaatag ataatgataa taatactaat aatactacca gctataggtt gataagttgt     600
```

```
aacacctcag tcattacaca ggcctgtcca aaggtatcct ttgagccaat tcccatacat      660
tattgtgccc cggctggttt tgcgattcta aagtgtaatg ataagaagtt caatggaaca      720
ggaccatgta caaatgtcag cacagtacaa tgtacacatg gaattaggcc agtagtatca      780
actcaactgc tgttaaatgg cagtctagca gaagaagagg tagtaattag atctgacaat      840
ttcacggaca atgctaaaac cataatagta cagctgaatg aatctgtaga aattaattgt      900
acaagaccca acaacaatac aagaaaaagt atacatatag gaccagggag agcattttat      960
acaacaggag aaataatagg agatataaga caagcacatt gtaacattag tagagcaaaa     1020
tggaataaca ctttaaaaca gatagttaaa aaattaagag aacaatttgg gaataataaa     1080
acaatagtct ttaatcaatc ctcaggaggg gacccagaaa ttgtaatgca cagttttaat     1140
tgtggagggg aattttctcta ctgtaattca acacaactgt ttaatagtac ttggaatggt     1200
acttggactt ggaatactac tgaagggtca aatgacactg aaggagacac tatcacactc     1260
ccatgcagaa taaaacaaat tataaacatg tggcaggaag taggaaaagc aatgtatgcc     1320
cctcccatca gaggacaaat tagatgttca tcaaatatta cagggctgct attaacaaga     1380
gatggtggta ataataacac caacgagacc gagatcttca gacctggagg aggagatatg     1440
agggacaatt ggagaagtga attatataaa tataaagtag taaaaattga accattagga     1500
gtagcaccca ccaaggcaaa gagaagagtg gtgcagagag aaaaaagagc agtgggaata     1560
ataggagctg tgttccttgg gttcttggga gcagcaggaa gcactatggg cgcagcgtca     1620
atgacgctga cggtacaggc cagacaatta ttgtctggta tagtgcaaca gcagaacaat     1680
ttgctgaggg ctattgaggc gcaacagcat ctgttgcaac tcacagtctg gggcatcaag     1740
cagctccagg caagagtcct ggctgtggaa agatacctaa gggatcaaca gctcctgggg     1800
atttggggtt gctctggaaa actcatttgc accactgctg tgccttggaa tgctagttgg     1860
agtaataaat ctctgatga gatttggaat aacatgacct ggatggagtg ggaaagagaa     1920
attgacaatt acacaagctt aatatacacc ttaattgaag aatcgcaaaa ccaacaagaa     1980
aagaatgaac aagaattatt ggaattagat aaatgggcaa gtttgtggaa ttggtttgac     2040
ataacaaact ggctgtggta tataaaaata ttcataatga tagtaggagg cttggtaggt     2100
ttaagaatag ttttttgctgt actttctata gtgaatagag ttaggcaggg atactcacca     2160
ttatcgtttc agacccgcct cccagccccg aggggacccg acaggcccga aggaatcgaa     2220
gaagaaggtg gagagagaga cagagacaga tccggtcgat tagtgaacgg attcttagca     2280
cttatctggg acgacctgcg gagcctgtgc ctcttcagct accaccgctt gagagactta     2340
ctcttgattg taacgaggat tgtggaactt ctgggacgca gggggtggga agccctcaaa     2400
tattggtgga atctcctaca gtattggagt caggaactaa agaatagtgc tgttagcttg     2460
ctcaatgcca cagccatagc agtagctgag gggacagata gggttataga agtagtacaa     2520
agagcttgta gagctattct ccacataccctacaagaataa gacagggctt ggaaagggct     2580
ttgctataa                                                             2589
```

<210> SEQ ID NO 29
<211> LENGTH: 621
<212> TYPE: DNA
<213> ORGANISM: Artificial sequence
<220> FEATURE:
<223> OTHER INFORMATION: Most recent common ancestor reconstruction of
      clade B nef gene sequence

<400> SEQUENCE: 29

```
atgggtggca agtggtcaaa acgtagtgtg gttggatggc ctgctgtaag ggaaagaatg      60
agacgagctg agccagcagc agatgggtg ggagcagtat ctcgagacct ggaaaaacat     120
ggagcaatca caagtagcaa tacagcagct actaatgctg cttgtgcctg gctagaagca    180
caagaggagg aggaggtggg ttttccagtc agacctcagg tacctttaag accaatgact    240
tacaaggcag ctgtagatct tagccacttt ttaaaagaaa aggggggact ggaagggcta    300
gtttactccc aaaaaagaca agatatcctt gatctgtggg tctaccacac acaaggctac    360
ttccctgatt ggcagaacta caccaggg ccagggacca gatatccact gacctttgga     420
tggtgcttca agctagtacc agttgagcca gagaaggtag aagaggccac tgaaggagag    480
aacaacagct tgttacaccc tatgagcctg catggaatgg atgacccgga gagaagtg     540 ttagtgtgga ggttgacag ccgcctagca tttcatcaca tggcccgaga gaagcatccg    600
gagtactaca aggactgctg a                                              621

<210> SEQ ID NO 30
<211> LENGTH: 621
<212> TYPE: DNA
<213> ORGANISM: Artificial sequence
<220> FEATURE:
<223> OTHER INFORMATION: Least squares center of tree reconstruction of
      clade B nef gene sequence

<400> SEQUENCE: 30
atgggtggca agtggtcaaa acgtagtgtg gttggatggc ctgctgtaag ggaaagaatg      60
agacgagctg agccagcagc agatgggtg ggagcagtat ctcgagacct ggaaaaacat     120
ggagcaatca caagtagcaa tacagcagct actaatgctg attgtgcctg gctagaagca    180
caagaggagg aggaggtggg ttttccagtc agacctcagg tacctttaag accaatgact    240
tacaaggcag ctttagatct tagccacttt ttaaaagaaa aggggggact ggaagggcta    300
atttactccc aaaaaagaca agatatcctt gatctgtggg tctaccacac acaaggctac    360
ttccctgatt ggcagaacta caccaggg ccagggatca gatatccact gacctttgga     420
tggtgcttca agctagtacc agttgagcca gagaaggtag aagaggccaa tgaaggagag    480
aacaacagct tgttacaccc tatgagcctg catgggatgg atgacccgga gaagaagtg     540 ttagtgtgga agttgacag ccgcctagca tttcatcaca tggcccgaga gctgcatccg    600
gagtactaca aggactgctg a                                              621

<210> SEQ ID NO 31
<211> LENGTH: 621
<212> TYPE: DNA
<213> ORGANISM: Artificial sequence
<220> FEATURE:
<223> OTHER INFORMATION: Minimum of means center of tree reconstruction
      of clade B nef gene sequence

<400> SEQUENCE: 31
atgggtggca agtggtcaaa acgtagtgtg gttggatggc ctgctgtaag ggaaagaatg      60
agacgagctg agccagcagc agatgggtg ggagcagtat ctcgagacct ggaaaaacat     120
ggagcaatca caagtagcaa tacagcagct actaatgctg attgtgcctg gctagaagca    180
caagaggagg aggaggtggg ttttccagtc agacctcagg tacctttaag accaatgact    240
tacaaggcag ctttagatct tagccacttt ttaaaagaaa aggggggact ggaagggcta    300
atttactccc aaaaaagaca agatatcctt gatctgtggg tctaccacac acaaggctac    360
```

| | |
|---|---|
| ttccctgatt ggcagaacta cacaccaggg ccagggatca gatatccact gacctttgga | 420 |
| tggtgcttca agctagtacc agttgagcca gagaaggtag aagaggccaa tgaaggagag | 480 |
| aacaactgct tgttacaccc tatgagccag catgggatgg atgacccgga gaaagaagtg | 540 |
| ttagtgtgga agtttgacag ccgcctagca tttcatcaca tggcccgaga gctgcatccg | 600 |
| gagtactaca aggactgctg a | 621 |

<210> SEQ ID NO 32
<211> LENGTH: 3012
<212> TYPE: DNA
<213> ORGANISM: Artificial Sequence
<220> FEATURE:
<223> OTHER INFORMATION: Most recent common ancestor reconstruction of clade B pol gene sequence

<400> SEQUENCE: 32

| | |
|---|---|
| tttttagggg aaaatctggc cttcccacaa gggaaggcca gggaactttc ttcagagcag | 60 |
| accagagcca acagccccac cagaagagag cttcaggttt ggggaagaga caacaactcc | 120 |
| ctctcagaag caggagcaga tagacaagga actgtatcct ttagcttccc tcaaatcact | 180 |
| ctttggcaac gacccctcgt cacaataaag ataggggggc aactaaagga agctctatta | 240 |
| gatacaggag cagatgatac agtattagaa gaaatgaatt tgccaggaaa atggaaacca | 300 |
| aaaatgatag ggggaattgg aggttttatc aaagtaagac agtatgatca aatacccata | 360 |
| gaaatctgtg gacataaagc tataggtaca gtattagtag gacctacacc tgtcaacata | 420 |
| attggaagaa atctgttgac tcagattggt tgcactttaa attttcccat tagtcctatt | 480 |
| gaaactgtac cagtaaaatt aaagccagga atggatggcc caaaagttaa acaatggcca | 540 |
| ttgacagaag aaaaaataaa agcattagta gaaatttgta cagaaatgga aaaggaagga | 600 |
| aaaatttcaa aaattgggcc tgaaaatcca tacaatactc cagtatttgc cataaagaaa | 660 |
| aaagacagta ctaaatggag aaaattagta gatttcagag aacttaataa gagaactcaa | 720 |
| gacttctggg aagttcaatt aggaatacca catcctgcag ggttaaaaaa gaaaaaatca | 780 |
| gtaacagtac tggatgtggg tgatgcatat ttttcagttc ccttagatga agacttcagg | 840 |
| aagtatactg catttaccat acctagtata aacaatgaga ccccagggat tagatatcag | 900 |
| tacaatgtgc ttccacaggg atggaaagga tcaccagcaa tattccaaag tagcatgaca | 960 |
| aaaatcttag agccttttag aaaacaaaat ccagaaatag ttatctatca atacatggat | 1020 |
| gatttgtatg taggatctga cttagaaata gggcagcata gaacaaaaat agaggaactg | 1080 |
| agagaacatc tgttgaggtg gggatttacc acaccagaca aaaaacatca gaaagaacct | 1140 |
| ccatttcttt ggatgggtta tgaactccat cctgataaat ggacagtaca gcctatagtg | 1200 |
| ctgccagaaa aagacagctg gactgtcaat gacatacaga agttagtggg aaaattgaat | 1260 |
| tgggcaagtc agatttatgc agggattaaa gtaaagcaat tatgtaaact ccttagggga | 1320 |
| accaaagcac taacagaagt agtaccacta acagaagaag cagagctaga actggcagaa | 1380 |
| aacagggaga ttctaaaaga accagtacat ggagtgtatt atgacccatc aaaagactta | 1440 |
| atagcagaaa tacagaagca ggggcaaggc caatggacat atcaaattta tcaagagcca | 1500 |
| tttaaaaatc tgaaaacagg aaagtatgca agaatgaggg gtgcccacac taatgatgta | 1560 |
| aaacaattaa cagaggcagt gcaaaaaata gccacagaaa gcatagtaat atggggaaag | 1620 |
| actcctaaat ttaaactacc catacaaaag gaaacatggg aagcatgtgt gacagagtat | 1680 |
| tggcaagcca cctggattcc tgagtgggag tttgtcaata cccctccctt agtaaaatta | 1740 |

```
tggtaccagt tagagaaaga acccatagta ggagcagaaa ctttctatgt agatggggca   1800
gctaatagag agactaaatt aggaaaagca ggatatgtta ctgacagagg aagacaaaaa   1860
gttgtctccc taactgacac aacaaatcag aagactgagt tacaagcaat tcatctagct   1920
ttgcaggatt cgggattaga agtaaacata gtaacagact cacaatatgc attaggaatc   1980
attcaagcac aaccagataa gagtgaatca gagttagtca gtcaaataat agagcagtta   2040
ataaaaaagg aaaaggtcta cctggcatgg gtaccagcac acaaaggaat tggaggaaat   2100
gaacaagtag ataaattagt cagtactgga atcaggaaag tactatttt ggatggaata   2160 gataaggccc aagaagaaca tgagaaatat cacagtaatt ggagagcaat ggctagtgat   2220
tttaacctgc cacctgtagt agcaaaagaa atagtagcca gctgtgataa atgtcagcta   2280
aaaggagaag ccatgcatgg acaagtagac tgtagtccag gaatatgca actagattgt   2340 acacatttag aaggaaaagt tatcctggta gcagttcatg tagccagtgg ctatatagaa   2400
gcagaagtta ttccagcaga acagggcag gaaacagcat actttctctt aaaattagca   2460
ggaagatggc cagtaaaagt aatacataca gacaatggca gcaatttcac cagtactaca   2520
gttaaggccg cctgttggtg ggcagggatc aagcaggaat ttggcattcc ctacaatccc   2580
caaagtcaag gagtagtaga atctatgaat aaagaattaa agaaaattat aggacaggta   2640
agagatcagg ctgaacatct taagacagca gtacaaatgg cagtattcat ccacaatttt   2700
aaaagaaaag ggggggattgg ggggtacagt gcagggaaa gaatagtaga cataatagca   2760
acagacatac aaactaaaga actacaaaaa caaattacaa aaattcaaaa ttttcgggtt   2820
tattacaggg acagcagaga tccactttgg aaaggaccag caaagcttct ctggaaaggt   2880
gaaggggcag tagtaataca agataatagt gacataaaag tagtgccaag aagaaaagca   2940
aagatcatta gggattatgg aaaacagatg gcaggtgatg attgtgtggc aagtagacag   3000
gatgaggatt ag                                                      3012
```

<210> SEQ ID NO 33
<211> LENGTH: 3012
<212> TYPE: DNA
<213> ORGANISM: Artificial Sequence
<220> FEATURE:
<223> OTHER INFORMATION: Least squares center of tree reconstruction of clade B pol gene sequence

<400> SEQUENCE: 33

```
ttttttaggg aagatctggc cttcccacaa gggaaggcca gggaatttc ttcagagcag     60 accagagcca acagccccac cagaagagag cttcaggttt ggggaagaga caacaactcc    120
ctctcagaag caggagccga tagacaagga actgtatcct ttagcttccc tcagatcact    180
ctttggcaac gacccctcgt cacaataaag atagggggc aactaaagga agctctatta    240
gatacaggag cagatgatac agtattagaa gaaatgaatt tgccaggaag atggaaacca    300
aaaatgatag ggggaattgg aggttttatc aaagtaagac agtatgatca gatacccata    360
gaaatctgtg gacataaagc tataggtaca gtattagtag gacctacacc tgtcaacata    420
attggaagaa atctgttgac tcagattggt tgcacttaa attttcccat tagtcctatt    480
gaaactgtac cagtaaaatt aaagccagga atggatggcc caaaagttaa acaatggcca    540
ttgacagaag aaaaaataaa agcattagta gaaatttgta cagaaatgga aaggaaggg    600 aaaatttcaa aaattgggcc tgaaaatcca tacaatactc cagtatttgc cataaagaaa    660
aaagacagta ctaaatggag aaaattagta gatttcagag aacttaataa gagaactcaa    720
```

-continued

```
gacttctggg aagttcaatt aggaatacca catcccgcag ggttaaaaaa gaaaaaatca    780
gtaacagtac tggatgtggg tgatgcatat ttttcagttc ccttagatga agacttcagg    840
aagtatactg catttaccat acctagtata acaatgaga caccagggat tagatatcag     900
tacaatgtgc ttccacaggg atggaaagga tcaccagcaa tattccaaag tagcatgaca    960
aaaatcttag agccttttag aaaacaaaat ccagacatag ttatctatca atacatggat   1020
gatttgtatg taggatctga cttagaaata gggcagcata gaacaaaaat agaggaactg   1080
agacaacatc tgttgaggtg gggatttacc acaccagaca aaaacatca gaaagaacct    1140
ccattccttt ggatgggtta tgaactccat cctgataaat ggacagtaca gcctatagtg   1200
ctgccagaaa aagacagctg gactgtcaat gacatacaga agttagtggg aaaattgaat   1260
tgggcaagtc agatttatgc agggattaaa gtaaagcaat tatgtaaact ccttagggga   1320
accaaagcac taacagaagt aataccacta acagaagaag cagagctaga actggcagaa   1380
aacagggaga ttctaaaaga accagtacat ggagtgtatt atgacccatc aaaagactta   1440
atagcagaaa tacagaagca ggggcaaggc caatggacat atcaaattta tcaagagcca   1500
tttaaaaatc tgaaaacagg aaagtatgca agaatgaggg gtgcccacac taatgatgta   1560
aaacaattaa cagaggcagt gcaaaaaata gccacagaaa gcatagtaat atggggaaag   1620
actcctaaat ttaaactacc catacaaaaa gaaacatggg aagcatggtg gacagagtat   1680
tggcaagcca cctggattcc tgagtgggag tttgtcaata cccctccctt agtgaaatta   1740
tggtaccagt tagagaaaga acccatagta ggagcagaaa cttctatgt agatggggca    1800
gctaataggg agactaaatt aggaaaagca ggatatgtta ctgacagagg aagacaaaaa   1860
gttgtctccc taactgacac aacaaatcag aagactgagt tacaagcaat tcatctagct   1920
ttgcaggatt cgggattaga agtaaacata gtaacagact cacaatatgc attaggaatc   1980
attcaagcac aaccagataa gagtgaatca gagttagtca gtcaaataat agagcagtta   2040
ataaaaaagg aaaaggtcta cctggcatgg gtaccagcac acaaaggaat tggaggaaat   2100
gaacaagtag ataaattagt cagtgctgga atcaggaaag tactattttt ggatggaata   2160
gataaggccc aagaagaaca tgagaaatat cacagtaatt ggagagcaat ggctagtgat   2220
tttaacctgc cacctgtagt agcaaaagaa atagtagcca gctgtgataa atgtcagcta   2280
aaaggagaag ccatgcatgg acaagtagac tgtagtccag gaatatggca actagattgt   2340
acacatttag aaggaaaagt tatcctggta gcagttcatg tagccagtgg atatatagaa   2400
gcagaagtta ttccagcaga gacagggcag gaaacagcat actttctctt aaaattagca   2460
ggaagatggc cagtaaaaac aatacataca gacaatggca gcaatttcac cagtactacg   2520
gttaaggccg cctgttggtg gcagggatc aagcaggaat ttggcattcc ctacaatccc    2580
caaagtcaag gagtagtaga atctatgaat aaagaattaa agaaaattat aggacaggta   2640
agagatcagg ctgaacatct taagacagca gtacaaatgg cagtattcat ccacaatttt   2700
aaaagaaaag ggggattggg gggtacagt gcagggaaa gaatagtaga cataatagca    2760
acagacatac aaactaaaga attacaaaaa caaattacaa aaattcaaaa ttttcgggtt   2820
tattacaggg acagcagaga tccactttgg aaaggaccag caaagcttct ctggaaaggt   2880
gaaggggcag tagtaataca agataatagt gacataaaag tagtgccaag aagaaaagca   2940
aagatcatta gggattatgg aaaacagatg gcaggtgatg attgtgtggc aagtagacag   3000
gatgaggatt ag                                                       3012
```

-continued

```
<210> SEQ ID NO 34
<211> LENGTH: 3012
<212> TYPE: DNA
<213> ORGANISM: Artificial sequence
<220> FEATURE:
<223> OTHER INFORMATION: Minimum of means center of tree reconstruction
      of clade B pol gene sequence

<400> SEQUENCE: 34 tttttaggg aagatctggc cttcccacaa gggaaggcca gggaattttc ttcagagcag      60
accagagcca acagccccac cagaagagag cttcaggttt ggggaagaga caacaactcc    120
ctctcagaag caggagccga tagacaagga actgtatcct ttagcttccc tcagatcact    180
ctttggcaac gacccctcgt cacaataaag ataggggggc aactaaagga agctctatta    240
gatacaggag cagatgatac agtattagaa gaaatgaatt tgccaggaag atggaaacca    300
aaaatgatag ggggaattgg aggttttatc aaagtaagac agtatgatca gatactcata    360
gaaatctgtg gacataaagc tataggtaca gtattagtag gacctacacc tgtcaacata    420
attggaagaa atctgttgac tcagattggt tgcactttaa attttcccat tagtcctatt    480
gaaactgtac cagtaaaatt aaagccagga atggatggcc caaaagttaa acaatggcca    540
ttgacagaag aaaaaataaa agcattagta gaaatttgta cagaaatgga aaaggaaggg    600
aaaatttcaa aaattgggcc tgaaaatcca tacaatactc cagtatttgc cataaagaaa    660
aaagacagta ctaaatggag aaaattagta gatttcagag aacttaataa gagaactcaa    720
gacttctggg aagttcaatt aggaatacca catcccgcag ggttaaaaaa gaaaaaatca    780
gtaacagtac tggatgtggg tgatgcatat ttttcagttc ccttagatga agacttcagg    840
aagtatactg catttaccat acctagtata aacaatgaga caccagggat tagatatcag    900
tacaatgtgc ttccacaggg atggaaagga tcaccagcaa tattccaaag tagcatgaca    960
aaaatcttag agccttttag aaaacaaaat ccagacatag ttatctatca atacatggat   1020
gatttgtatg taggatctga cttagaaata gggcagcata gaacaaaaat agaggaactg   1080
agacaacatc tgttgaggtg gggatttacc acaccagaca aaaaacatca gaaagaacct   1140
ccattccttt ggatgggtta tgaactccat cctgataaat ggacagtaca gcctatagtg   1200
ctgccagaaa aagacagctg gactgtcaat gacatacaga agttagtggg aaaattgaat   1260
tgggcaagtc agatttaccc agggattaaa gtaaagcaat tatgtaaact ccttagggga   1320
accaaagcac taacagaagt aataccacta acagaagaag cagagctaga actggcagaa   1380
aacagggaaa ttctaaaaga accagtacat ggagtgtatt atgacccatc aaaagactta   1440
atagcagaaa tacagaagca ggggcaaggc caatggacat atcaaattta tcaagagcca   1500
tttaaaaatc tgaaaacagg aaaatatgca agaatgaggg gtgcccacac taatgatgta   1560
aaacaattaa cagaggcagt gcaaaaaata gccacagaaa gcatagtaat atggggaaag   1620
actcctaaat ttaaactacc catacaaaaa gaaacatggg aaacatggtg gacagagtat   1680
tggcaagcca cctggattcc tgagtgggag tttgtcaata cccctccctt agtgaaatta   1740
tggtaccagt tagagaaaga acccatagta ggagcagaaa ctttctatgt agatggggca   1800
gctaacaggg agactaaatt aggaaaagca ggatatgtta ctaacagagg aagacaaaaa   1860
gttgtctccc taactgacac aacaaatcag aagactgagt tacaagcaat tcatctagct   1920
ttgcaggatt cgggattaga agtaaacata gtaacagact cacaatatgc attaggaatc   1980
attcaagcac aaccagataa aagtgaatca gagttagtca gtcaaataat agagcagtta   2040
ataaaaaagg aaaaggtcta cctggcatgg gtaccagcac acaaaggaat tggaggaaat   2100
```

-continued gaacaagtag ataaattagt cagtgctgga atcaggaaag tactattttt agatggaata 2160
gataaggccc aagaagaaca tgagaaatat cacagtaatt ggagagcaat ggctagtgat 2220
tttaacctgc cacctgtagt agcaaaagaa atagtagcca gctgtgataa atgtcagcta 2280
aaaggagaag ccatgcatgg acaagtagac tgtagtccag gaatatggca actagattgt 2340
acacatttag aaggaaaagt tatcctggta gcagttcatg tagccagtgg atatatagaa 2400
gcagaagtta ttccagcaga gacagggcag gaaacagcat actttctctt aaaattagca 2460
ggaagatggc cagtaaaaac aatacataca gacaatggca gcaatttcac cagtactacg 2520
gttaaggccg cctgttggtg ggcggggatc aagcaggaat ttggcattcc ctacaatccc 2580
caaagtcaag gagtagtaga atctatgaat aaagaattaa agaaaattat aggacaggta 2640
agagatcagg ctgaacatct taagacagca gtacaaatgg cagtattcat ccacaatttt 2700
aaaagaaaag gggggattgg ggggtacagt gcaggggaaa gaatagtaga cataatagca 2760
acagacatac aaactaaaga attacaaaaa caaattacaa aaattcaaaa ttttcgggtt 2820
tattacaggg acagcagaga tccactttgg aaaggaccag caaagcttct ctggaaaggt 2880
gaaggggcag tagtaataca agataatagt gacataaaag tagtgccaag aagaaaagca 2940
aagatcatta gggattatgg aaaacagatg gcaggtgatg attgtgtggc aagtagacag 3000
gatgaggatt ag 3012

<210> SEQ ID NO 35
<211> LENGTH: 360
<212> TYPE: DNA
<213> ORGANISM: Artificial sequence
<220> FEATURE:
<223> OTHER INFORMATION: Most recent common ancestor reconstruction of clade B rev gene sequence

<400> SEQUENCE: 35
atggcaggaa gaagcggaga cagcgacgaa gagctcctca agacagtcag actcatcaag 60
tttctctatc aaagcaaccc gcctcccagc cccgagggga cccgacaggc ccgaaggaat 120
agaagaagaa ggtggagaga gagacagaga cagatccgtt cgattagtga acggattctt 180
agcacttatc tgggacgatc tgcggagcct gtgcctcttc agctaccacc gcttgagaga 240
cttactcttg attgtagcga ggattgtgga acttctggga cgcagggggt gggaagtcct 300
caaatattgg tggaatctcc tgcagtattg gagtcaggaa ctaaagaata gtgctgttag 360

<210> SEQ ID NO 36
<211> LENGTH: 360
<212> TYPE: DNA
<213> ORGANISM: Artificial sequence
<220> FEATURE:
<223> OTHER INFORMATION: Least squares center of tree reconstruction of clade B rev gene sequence

<400> SEQUENCE: 36
atggcaggaa gaagcggaga cagcgacgaa gagctcctca agacagtcag actcatcaag 60
tttctctatc aaagcaaccc gcctcccagc cccgagggga cccgacaggc ccgaaggaat 120
cgaagaagaa ggtggagaga gagacagaga cagatccggt cgattagtga atggattctt 180
agcacttatc tgggtcgacc tgcggagcct gtgcctcttc agctaccacc gcttgagaga 240
cttactcttg attgtaacga ggattgtgga acttctggga cgcagggggt gggaagtcct 300
caaatattgg tggaatctcc tacagtattg gagtcaggaa ctaaagaata gtgctgttag 360

```
<210> SEQ ID NO 37
<211> LENGTH: 360
<212> TYPE: DNA
<213> ORGANISM: Artificial sequence
<220> FEATURE:
<223> OTHER INFORMATION: Minimum of means center of tree reconstruction
      of clade B rev gene sequence

<400> SEQUENCE: 37
atggcaggaa gaagcggaga cagcgacgaa gagctcctca agacagtcag actcatcaag      60
tttctctatc aaagcaaccc gcctcccagc cccgagggga cccgacaggc ccgaaggaat     120
cgaagaagaa ggtggagaga gagacagaga cagatccggt cgattagtga atggattctt     180
agcacttatc tgggacgacc tgcggagcct gtgcctcttc agctaccacc gcttgagaga     240
cttactcttg attgtagcga ggattgtgga acttctggga cgcaggggt gggaagtcct      300 caaatattgg tggaatctcc tgcagtattg gagtcaggaa ctaaagaata gtgctgttag     360

<210> SEQ ID NO 38
<211> LENGTH: 321
<212> TYPE: DNA
<213> ORGANISM: Artificial sequence
<220> FEATURE:
<223> OTHER INFORMATION: Most recent common ancestor reconstruction of
      clade B tat gene sequence

<400> SEQUENCE: 38
atggagccag tagatcctag actagagccc tggaagcatc caggaagtca gcctaagact      60
gcttgtacca attgctattg taaaaagtgt tgctatcatt gccaagtttg cttcataaca     120
aaaggcttag gcatctccta tggcaggaag aagcggagac

```
atggagccag tagatcctag actagagccc tggaagcatc caggaagtca gcctaagact    60
gcttgtacca attgctattg taaaaagtgt tgctttcatt gccaagtttg tttcataaca   120
aaaggcttag gcatctccta tggcaggaag aagcggagac agcgacgaag agctcctcaa   180
gacagtcaga ctcatcaagt ttctctatca aagcaacccg cctcccagcc ccgaggggac   240
ccgacaggcc cgaaggaatc gaagaagaag gtggagagag acagagagac agatccggtc   300
gattagtgga tggattctta t                                             321
```

<210> SEQ ID NO 41
<211> LENGTH: 579
<212> TYPE: DNA
<213> ORGANISM: Artificial sequence
<220> FEATURE:
<223> OTHER INFORMATION: Most recent common ancestor reconstruction of
      clade B vif gene sequence

<400> SEQUENCE: 41

```
atggaaaaca gatggcaggt gatgattgtg tggcaagtag acaggatgag gattagaaca    60
tggaaaagtt tagtaaaaca ccatatgtat atttcaaaga aagctaaggg atggttttat   120
agacatcact atgaaagcac tcatccaaga ataagttcag aagtacacat cccactagga   180
gatgctagat tggtaataaa aacatattgg ggtctgcata caggagaaag agaatggcat   240 tgggtcagg gagtctccat agaatggagg aaaaggagat atagcacaca gtagaccct    300 ggcctagcag accaactaat tcatctgtat tatttgatt gttttcaga atctgctata   360 agaaatgcca tattaggaca tatagttagt cctaggtgtg aatatcaagc aggacataac   420
aaggtaggat ctctacagta cttggcacta acagcattaa taacaccaaa aaagataaag   480
ccacctttgc ctagtgttag gaaactgaca gaggatagat ggaacaagcc ccagaagacc   540
aagggccaca gagggagcca tacaatgaat ggacactag                          579
```

<210> SEQ ID NO 42
<211> LENGTH: 579
<212> TYPE: DNA
<213> ORGANISM: Artificial sequence
<220> FEATURE:
<223> OTHER INFORMATION: Least squares and minimum of means center of
      tree reconstructions of clade B vif gene sequence

<400> SEQUENCE: 42

```
atggaaaaca gatggcaggt gatgattgtg tggcaagtag acaggatgag gattagaaca    60
tggaaaagtt tagtaaaaca ccatatgtat atttcaagga aagctaaggg atggttttat   120
agacatcact atgaaagcac tcatccaaga ataagttcag aagtacacat cccactaggg   180
gatgctagat tggtaataac aacatattgg ggtctgcata caggagaaag agactggcat   240
ttgggtcagg gagtctccat agaatggagg aaaagagat atagcacaca gtagaccct    300 gacctagcag accaactaat tcatctgtat tactttgatt gttttcaga atctgctata   360 agaaatgcca tattaggaca tatagttagt cctaggtgtg aatatcaagc aggacataac   420
aaggtaggat ctctacagta cttggcacta gcagcattaa taacaccaaa aaagataaag   480
ccacctttgc ctagtgttac gaaactgaca gaggatagat ggaacaagcc ccagaagacc   540
aagggccaca gagggagcca tacaatgaat ggacactag                          579
```

<210> SEQ ID NO 43
<211> LENGTH: 291
<212> TYPE: DNA

```
<213> ORGANISM: Artificial sequence
<220> FEATURE:
<223> OTHER INFORMATION: Most recent common ancestor reconstruction of
      clade b vpr gene sequence

<400> SEQUENCE: 43
atggaacaag ccccagaaga ccaagggcca cagagggagc catacaatga atggacacta      60
gagcttttag aggagcttaa gagtgaagct gttagacatt ttcctaggct atggctccat    120
agcttaggac aacatatcta tgaaacttat ggggatacct gggcaggagt ggaagctata    180
ataagaattc tgcaacaact gctgtttatt catttcagaa ttgggtgtca acatagcaga    240
ataggcatta ctcgacagag aagagcaaga aatggagcca gtagatccta g             291

<210> SEQ ID NO 44
<211> LENGTH: 291
<212> TYPE: DNA
<213> ORGANISM: Artificial sequence
<220> FEATURE:
<223> OTHER INFORMATION: Least squares and minimum of means center of
      tree reconstruction of clade B vpr gene sequence

<400> SEQUENCE: 44
atggaacaag ccccagaaga ccaagggcca cagagggagc catacaatga atggacacta      60
gagcttttag aggagcttaa gagtgaagct gttagacatt ttcctaggat atggctccat    120
agcttaggac aacatatcta tgaaacttat ggggatactt gggcaggagt ggaagccata    180
ataagaattc tgcaacaact gctgtttatt catttcagaa ttgggtgtcg acatagcaga    240
ataggcatta ctcgacagag gagagcaaga aatggagcca gtagatccta g             291

<210> SEQ ID NO 45
<211> LENGTH: 246
<212> TYPE: DNA
<213> ORGANISM: Artificial sequence
<220> FEATURE:
<223> OTHER INFORMATION: Most recent common ancestor reconstruction of
      clade B vpu gene sequence

<400> SEQUENCE: 45
atgcaacctt tagaaatatt agcaatagta gcattagtag tagcagcaat actagcaata     60
gttgtgtgga ccatagtatt catagaatat aggaaaatat taaggcaaag aaaaatagac    120
aggttaattg atagaataag agaaagagca gaagacagtg gcaatgagag tgaaggggat    180
caggaagaat tatcagcact tgtggaaatg gggcaccatg ctccttggga tgttgatgat    240
ctgtag                                                               246

<210> SEQ ID NO 46
<211> LENGTH: 246
<212> TYPE: DNA
<213> ORGANISM: Artificial sequence
<220> FEATURE:
<223> OTHER INFORMATION: Least squares and minimum of means center of
      tree reconstructions of clade B vpu gene sequence

<400> SEQUENCE: 46
atgcaacctt tacaaatatt agcaatagta gcattagtag tagcagcaat aatagcaata     60
gttgtgtgga ccatagtatt catagaatat aggaaaatat taagacaaag aaaaatagac    120
aggttaattg atagaataag agaaagagca gaagacagtg gcaatgagag tgaaggggat    180
caggaagaat tatcagcact tgtggagatg gggcaccatg ctccttggga tgttgatgat    240
ctgtag                                                               246
```

<210> SEQ ID NO 47
<211> LENGTH: 500
<212> TYPE: PRT
<213> ORGANISM: Artificial sequence
<220> FEATURE:
<223> OTHER INFORMATION: Most recent common ancestor reconstruction of clade B gag protein sequence

<400> SEQUENCE: 47

```
Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Val Leu Tyr Cys Val His Gln Lys Ile Glu Val Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Leu Gln Gly Gln Met Val His
    130                 135                 140

Gln Ala Leu Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Ala Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
```

-continued

```
                  355                 360                 365
Gln Val Thr Asn Ser Ala Thr Ile Met Met Gln Arg Gly Asn Phe Arg
    370                 375                 380

Asn Pro Arg Lys Thr Val Lys Cys Phe Asn Cys Gly Lys Glu Gly His
385                 390                 395                 400

Ile Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
                420                 425                 430

Phe Leu Gly Lys Ile Trp Pro Ser His Lys Gly Arg Pro Gly Asn Phe
            435                 440                 445

Leu Gln Ser Arg Pro Glu Pro Thr Ala Pro Glu Glu Ser Phe Arg
    450                 455                 460

Phe Gly Glu Glu Thr Thr Thr Pro Ser Gln Lys Gln Glu Gln Lys Asp
465                 470                 475                 480

Lys Glu Leu Tyr Pro Leu Ala Ser Leu Lys Ser Leu Phe Gly Asn Asp
                485                 490                 495

Pro Ser Ser Gln
            500

<210> SEQ ID NO 48
<211> LENGTH: 500
<212> TYPE: PRT
<213> ORGANISM: Artificial sequence
<220> FEATURE:
<223> OTHER INFORMATION: Least squares center of tree reconstruction of
      clade B gag protein sequence

<400> SEQUENCE: 48

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val

Ala Ala Glu Trp Asp Arg Leu His Pro Val His Ala Gly Pro Ile Ala
            210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
            245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
            275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
            405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
            435                 440                 445

Leu Gln Ser Arg Pro Glu Pro Thr Ala Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Asn Asp
            485                 490                 495

Pro Ser Ser Gln
            500

<210> SEQ ID NO 49
<211> LENGTH: 500
<212> TYPE: PRT
<213> ORGANISM: Artificial sequence
<220> FEATURE:
<223> OTHER INFORMATION: Minimum of means center of tree reconstruction
      of clade B gag protein sequence

<400

```
His Pro Ser Leu Gln Thr Gly Ser Glu Glu Leu Lys Ser Leu Tyr Asn
 65                  70                  75                  80

Thr Val Ala Thr Leu Tyr Cys Val His Gln Asn Ile Glu Val Arg Asp
                 85                  90                  95

Thr Lys Asp Ala Leu Glu Lys Ile Glu Glu Gln Asn Lys Ile Lys
            100                 105                 110

Lys Arg Ala Gln Gln Ala Ala Ala Asp Thr Gly Asn Ser Asn Pro Val
            115                 120                 125

Ser Gln Asn Tyr Pro Ile Val Gln Asn Met Gln Gly Gln Met Val His
130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
            195                 200                 205

Ala Ala Glu Trp Asp Arg Leu His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr His Asn Pro Pro Ile
                245                 250                 255

Pro Val Gly Glu Ile Tyr Lys Arg Trp Ile Ile Met Gly Leu Asn Lys
            260                 265                 270

Ile Val Arg Met Tyr Ser Pro Thr Ser Ile Leu Asp Ile Arg Gln Gly
            275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Ser His Lys Ala Arg Val Leu Ala Glu Ala Met Ser
            355                 360                 365

Gln Ala Thr Asn Ser Ala Thr Ile Met Met Gln Arg Gly Asn Phe Lys
370                 375                 380

Gly Gln Arg Lys Thr Val Lys Cys Phe Asn Cys Gly Lys Glu Gly His
385                 390                 395                 400

Ile Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
            435                 440                 445

Leu Gln Ser Arg Pro Glu Pro Thr Ala Pro Glu Glu Ser Phe Arg
450                 455                 460

Phe Gly Glu Glu Thr Thr Thr Pro Pro Gln Lys Gln Glu Pro Arg Asp
465                 470                 475                 480
```

```
Lys Glu Gln Tyr Pro Leu Thr Ser Leu Arg Ser Leu Phe Gly Asn Asp
                485                 490                 495

Pro Ser Ser Gln
            500

<210> SEQ ID NO 50
<211> LENGTH: 862
<212> TYPE: PRT
<213> ORGANISM: Artificial sequence
<220> FEATURE:
<223> OTHER INFORMATION: Most recent common ancestor reconstruction of
      clade B gp 160 protein sequence

<400> SEQUENCE: 50

Met Arg Val Lys Gly Ile Arg Lys Asn Cys Gln His Leu Trp Lys Trp
1               5                   10                  15

Gly Thr Met Leu Leu Gly Met Leu Met Ile Cys Ser Ala Ala Glu Asn
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Lys Thr Glu Val
        50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asp Ala Asn Lys Asn Ala Thr Asn Thr Asn Ser Ser Ser
        130                 135                 140

Gly Gly Thr Met Glu Lys Gly Glu Met Lys Asn Cys Ser Phe Asn Ile
145                 150                 155                 160

Thr Thr Ser Ile Arg Asp Lys Met Gln Lys Glu Tyr Ala Leu Phe Tyr
                165                 170                 175

Lys Leu Asp Val Val Pro Ile Asp Asn Asp Asn Ser Asn Asn Asn Asn
                180                 185                 190

Thr Asn Tyr Arg Leu Ile Asn Cys Asn Thr Ser Val Ile Thr Gln Ala
            195                 200                 205

Cys Pro Lys Val Ser Phe Glu Pro Ile Pro Ile His Tyr Cys Thr Pro
        210                 215                 220

Ala Gly Phe Ala Ile Leu Lys Cys Asn Asp Lys Lys Phe Asn Gly Thr
225                 230                 235                 240

Gly Pro Cys Lys Asn Val Ser Thr Val Gln Cys Thr His Gly Ile Arg
                245                 250                 255

Pro Val Val Ser Thr Gln Leu Leu Leu Asn Gly Ser Leu Ala Glu Glu
                260                 265                 270

Glu Val Val Ile Arg Ser Glu Asn Phe Thr Asp Asn Ala Lys Thr Ile
            275                 280                 285

Ile Val Gln Leu Asn Glu Ser Val Glu Ile Asn Cys Thr Arg Pro Asn
        290                 295                 300

Asn Asn Thr Arg Lys Ser Ile Pro Ile Gly Pro Gly Arg Ala Leu Tyr
305                 310                 315                 320

Thr Thr Gly Glu Ile Ile Gly Asp Ile Arg Gln Ala His Cys Asn Ile
                325                 330                 335
```

```
Ser Arg Ala Lys Trp Asn Asn Thr Leu Lys Gln Val Val Thr Lys Leu
            340                 345                 350

Arg Glu Gln Phe Gly Asn Asn Lys Thr Ile Val Phe Asn Pro Ser Ser
        355                 360                 365

Gly Gly Asp Pro Glu Ile Val Met His Ser Phe Asn Cys Gly Gly Glu
    370                 375                 380

Phe Phe Tyr Cys Asn Thr Thr Gln Leu Phe Asn Ser Thr Trp Asn Ser
385                 390                 395                 400

Thr Glu Gly Ser Asn Lys Thr Thr Gly Ser Asn Asn Thr Gly Gly Glu
            405                 410                 415

Thr Ile Thr Leu Pro Cys Arg Ile Lys Gln Ile Ile Asn Met Trp Gln
            420                 425                 430

Glu Val Gly Lys Ala Met Tyr Ala Pro Pro Ile Arg Gly Gln Ile Lys
            435                 440                 445

Cys Ser Ser Asn Ile Thr Gly Leu Leu Leu Thr Arg Asp Gly Gly Glu
    450                 455                 460

Asn Ser Thr Asn Glu Thr Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
            485                 490                 495

Glu Pro Leu Gly Val Ala Pro Thr Lys Ala Lys Arg Arg Val Val Gln
            500                 505                 510

Arg Glu Lys Arg Ala Val Gly Ile Ile Gly Ala Met Phe Leu Gly Phe
        515                 520                 525

Leu Gly Ala Ala Gly Ser Thr Met Gly Ala Ala Ser Met Thr Leu Thr
    530                 535                 540

Val Gln Ala Arg Gln Leu Leu Ser Gly Ile Val Gln Gln Gln Asn Asn
545                 550                 555                 560

Leu Leu Arg Ala Ile Glu Ala Gln Gln His Leu Leu Gln Leu Thr Val
            565                 570                 575

Trp Gly Ile Lys Gln Leu Gln Ala Arg Val Leu Ala Val Glu Arg Tyr
            580                 585                 590

Leu Arg Asp Gln Gln Leu Leu Gly Ile Trp Gly Cys Ser Gly Lys Leu
        595                 600                 605

Ile Cys Thr Thr Thr Val Pro Trp Asn Ala Ser Trp Ser Asn Lys Ser
    610                 615                 620

Leu Asp Lys Ile Trp Asn Asn Met Thr Trp Met Glu Trp Glu Arg Glu
625                 630                 635                 640

Ile Asp Asn Tyr Thr Gly Leu Ile Tyr Asn Leu Ile Glu Glu Ser Gln
            645                 650                 655

Asn Gln Gln Glu Lys Asn Glu Gln Glu Leu Leu Glu Leu Asp Lys Trp
            660                 665                 670

Ala Ser Leu Trp Asn Trp Phe Asp Ile Thr Gln Trp Leu Trp Tyr Ile
        675                 680                 685

Lys Ile Phe Ile Met Ile Val Gly Gly Leu Val Gly Leu Arg Ile Val
    690                 695                 700

Phe Ala Val Leu Ser Ile Val Asn Arg Val Arg Gln Gly Tyr Ser Pro
705                 710                 715                 720

Leu Ser Phe Gln Thr Arg Leu Pro Ala Pro Arg Gly Pro Asp Arg Pro
            725                 730                 735

Glu Gly Ile Glu Glu Glu Gly Gly Glu Arg Asp Arg Asp Arg Ser Gly
            740                 745                 750
```

```
Arg Leu Val Asn Gly Phe Leu Ala Leu Ile Trp Asp Asp Leu Arg Ser
            755                 760                 765

Leu Cys Leu Phe Ser Tyr His Arg Leu Arg Asp Leu Leu Leu Ile Val
        770                 775                 780

Ala Arg Ile Val Glu Leu Leu Gly Arg Arg Gly Trp Glu Ala Leu Lys
785                 790                 795                 800

Tyr Trp Trp Asn Leu Leu Gln Tyr Trp Ser Gln Glu Leu Lys Asn Ser
                805                 810                 815

Ala Val Ser Leu Leu Asn Ala Thr Ala Ile Ala Val Ala Glu Gly Thr
            820                 825                 830

Asp Arg Val Ile Glu Val Val Gln Arg Ala Cys Arg Ala Ile Leu His
            835                 840                 845

Ile Pro Arg Arg Ile Arg Gln Gly Leu Glu Arg Ala Leu Leu
            850                 855                 860

<210> SEQ ID NO 51
<211> LENGTH: 862
<212> TYPE: PRT
<213> ORGANISM: Artificial sequence
<220> FEATURE:
<223> OTHER INFORMATION: Least squares and minimum of means center of
      tree reconstruction of clade B gp 160 protein sequence

<400> SEQUENCE: 51

Met Arg Val Lys Gly Ile Arg Lys Asn Tyr Gln His Leu Trp Arg Trp
1               5                   10                  15

Gly Thr Met Leu Leu Gly Met Leu Met Ile Cys Ser Ala Ala Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Asn Lys Asn Ala Thr Asn Thr Asn Ser Ser Ser
    130                 135                 140

Gly Glu Met Met Glu Lys Gly Glu Ile Lys Asn Cys Ser Phe Asn Ile
145                 150                 155                 160

Thr Thr Ser Ile Arg Asp Lys Val Gln Lys Glu Tyr Ala Leu Phe Tyr
                165                 170                 175

Lys Leu Asp Val Val Pro Ile Asp Asp Asn Asn Thr Asn Asn Thr
            180                 185                 190

Thr Ser Tyr Arg Leu Ile Ser Cys Asn Thr Ser Val Ile Thr Gln Ala
        195                 200                 205

Cys Pro Lys Val Ser Phe Glu Pro Ile Pro Ile His Tyr Cys Ala Pro
    210                 215                 220

Ala Gly Phe Ala Ile Leu Lys Cys Asn Asp Lys Lys Phe Asn Gly Thr
225                 230                 235                 240

Gly Pro Cys Thr Asn Val Ser Thr Val Gln Cys Thr His Gly Ile Arg
                245                 250                 255
```

-continued

```
Pro Val Val Ser Thr Gln Leu Leu Asn Gly Ser Leu Ala Glu Glu
        260                 265                 270

Glu Val Val Ile Arg Ser Asp Asn Phe Thr Asp Asn Ala Lys Thr Ile
            275                 280                 285

Ile Val Gln Leu Asn Glu Ser Val Glu Ile Asn Cys Thr Arg Pro Asn
        290                 295                 300

Asn Asn Thr Arg Lys Ser Ile His Ile Gly Pro Gly Arg Ala Phe Tyr
305                 310                 315                 320

Thr Thr Gly Glu Ile Ile Gly Asp Ile Arg Gln Ala His Cys Asn Ile
                325                 330                 335

Ser Arg Ala Lys Trp Asn Asn Thr Leu Lys Gln Ile Val Lys Lys Leu
            340                 345                 350

Arg Glu Gln Phe Gly Asn Asn Lys Thr Ile Val Phe Asn Gln Ser Ser
        355                 360                 365

Gly Gly Asp Pro Glu Ile Val Met His Ser Phe Asn Cys Gly Gly Glu
    370                 375                 380

Phe Phe Tyr Cys Asn Ser Thr Gln Leu Phe Asn Ser Thr Trp Asn Gly
385                 390                 395                 400

Thr Trp Thr Trp Asn Thr Thr Glu Gly Ser Asn Asp Thr Glu Gly Asp
                405                 410                 415

Thr Ile Thr Leu Pro Cys Arg Ile Lys Gln Ile Ile Asn Met Trp Gln
            420                 425                 430

Glu Val Gly Lys Ala Met Tyr Ala Pro Pro Ile Arg Gly Gln Ile Arg
        435                 440                 445

Cys Ser Ser Asn Ile Thr Gly Leu Leu Leu Thr Arg Asp Gly Gly Asn
    450                 455                 460

Asn Asn Thr Asn Glu Thr Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Gln
            500                 505                 510

Arg Glu Lys Arg Ala Val Gly Ile Ile Gly Ala Val Phe Leu Gly Phe
        515                 520                 525

Leu Gly Ala Ala Gly Ser Thr Met Gly Ala Ala Ser Met Thr Leu Thr
    530                 535                 540

Val Gln Ala Arg Gln Leu Leu Ser Gly Ile Val Gln Gln Asn Asn
545                 550                 555                 560

Leu Leu Arg Ala Ile Glu Ala Gln Gln His Leu Leu Gln Leu Thr Val
                565                 570                 575

Trp Gly Ile Lys Gln Leu Gln Ala Arg Val Leu Ala Val Glu Arg Tyr
            580                 585                 590

Leu Arg Asp Gln Gln Leu Leu Gly Ile Trp Gly Cys Ser Gly Lys Leu
        595                 600                 605

Ile Cys Thr Thr Ala Val Pro Trp Asn Ala Ser Trp Ser Asn Lys Ser
    610                 615                 620

Leu Asp Glu Ile Trp Asn Asn Met Thr Trp Met Glu Trp Glu Arg Glu
625                 630                 635                 640

Ile Asp Asn Tyr Thr Ser Leu Ile Tyr Thr Leu Ile Glu Glu Ser Gln
                645                 650                 655

Asn Gln Gln Glu Lys Asn Glu Gln Glu Leu Leu Glu Leu Asp Lys Trp
        660                 665                 670
```

-continued

```
Ala Ser Leu Trp Asn Trp Phe Asp Ile Thr Asn Trp Leu Trp Tyr Ile
            675                 680                 685

Lys Ile Phe Ile Met Ile Val Gly Gly Leu Val Gly Leu Arg Ile Val
            690                 695                 700

Phe Ala Val Leu Ser Ile Val Asn Arg Val Arg Gln Gly Tyr Ser Pro
705                 710                 715                 720

Leu Ser Phe Gln Thr Arg Leu Pro Ala Pro Arg Gly Pro Asp Arg Pro
                725                 730                 735

Glu Gly Ile Glu Glu Glu Gly Gly Glu Arg Asp Arg Asp Arg Ser Gly
            740                 745                 750

Arg Leu Val Asn Gly Phe Leu Ala Leu Ile Trp Asp Asp Leu Arg Ser
                755                 760                 765

Leu Cys Leu Phe Ser Tyr His Arg Leu Arg Asp Leu Leu Leu Ile Val
            770                 775                 780

Thr Arg Ile Val Glu Leu Leu Gly Arg Arg Gly Trp Glu Ala Leu Lys
785                 790                 795                 800

Tyr Trp Trp Asn Leu Leu Gln Tyr Trp Ser Gln Glu Leu Lys Asn Ser
                805                 810                 815

Ala Val Ser Leu Leu Asn Ala Thr Ala Ile Ala Val Ala Glu Gly Thr
            820                 825                 830

Asp Arg Val Ile Glu Val Val Gln Arg Ala Cys Arg Ala Ile Leu His
                835                 840                 845

Ile Pro Thr Arg Ile Arg Gln Gly Leu Glu Arg Ala Leu Leu
            850                 855                 860

<210> SEQ ID NO 52
<211> LENGTH: 206
<212> TYPE: PRT
<213> ORGANISM: Artificial sequence
<220> FEATURE:
<223> OTHER INFORMATION: Most recent common ancestor reconstruction of
      clade B nef protein sequence

<400> SEQUENCE: 52

Met Gly Gly Lys Trp Ser Lys Arg Ser Val Val Gly Trp Pro Ala Val
1               5                   10                  15

Arg Glu Arg Met Arg Arg Ala Glu Pro Ala Ala Asp Gly Val Gly Ala
                20                  25                  30

Val Ser Arg Asp Leu Glu Lys His Gly Ala Ile Thr Ser Ser Asn Thr
            35                  40                  45

Ala Ala Thr Asn Ala Ala Cys Ala Trp Leu Glu Ala Gln Glu Glu Glu
        50                  55                  60

Glu Val Gly Phe Pro Val Arg Pro Gln Val Pro Leu Arg Pro Met Thr
65                  70                  75                  80

Tyr Lys Ala Ala Val Asp Leu Ser His Phe Leu Lys Glu Lys Gly Gly
                85                  90                  95

Leu Glu Gly Leu Val Tyr Ser Gln Lys Arg Gln Asp Ile Leu Asp Leu
            100                 105                 110

Trp Val Tyr His Thr Gln Gly Tyr Phe Pro Asp Trp Gln Asn Tyr Thr
        115                 120                 125

Pro Gly Pro Gly Thr Arg Tyr Pro Leu Thr Phe Gly Trp Cys Phe Lys
    130                 135                 140

Leu Val Pro Val Glu Pro Glu Lys Val Glu Glu Ala Thr Glu Gly Glu
145                 150                 155                 160

Asn Asn Ser Leu Leu His Pro Met Ser Leu His Gly Met Asp Asp Pro
                165                 170                 175
```

-continued

Glu Arg Glu Val Leu Val Trp Arg Phe Asp Ser Arg Leu Ala Phe His
             180                 185                 190

His Met Ala Arg Glu Lys His Pro Glu Tyr Tyr Lys Asp Cys
        195                 200                 205

<210> SEQ ID NO 53
<211> LENGTH: 206
<212> TYPE: PRT
<213> ORGANISM: Artificial sequence
<220> FEATURE:
<223> OTHER INFORMATION: Least squares center of tree reconstruction of
      clade B nef protein sequence

<400> SEQUENCE: 53

Met Gly Gly Lys Trp Ser Lys Arg Ser Val Val Gly Trp Pro Ala Val
1               5                   10                  15

Arg Glu Arg Met Arg Arg Ala Glu Pro Ala Ala Asp Gly Val Gly Ala
            20                  25                  30

Val Ser Arg Asp Leu Glu Lys His Gly Ala Ile Thr Ser Ser Asn Thr
        35                  40                  45

Ala Ala Thr Asn Ala Asp Cys Ala Trp Leu Glu Ala Gln Glu Glu Glu
    50                  55                  60

Glu Val Gly Phe Pro Val Arg Pro Gln Val Pro Leu Arg Pro Met Thr
65                  70                  75                  80

Tyr Lys Ala Ala Leu Asp Leu Ser His Phe Leu Lys Glu Lys Gly Gly
                85                  90                  95

Leu Glu Gly Leu Ile Tyr Ser Gln Lys Arg Gln Asp Ile Leu Asp Leu
            100                 105                 110

Trp Val Tyr His Thr Gln Gly Tyr Phe Pro Asp Trp Gln Asn Tyr Thr
        115                 120                 125

Pro Gly Pro Gly Ile Arg Tyr Pro Leu Thr Phe Gly Trp Cys Phe Lys
    130                 135                 140

Leu Val Pro Val Glu Pro Glu Lys Val Glu Glu Ala Asn Glu Gly Glu
145                 150                 155                 160

Asn Asn Ser Leu Leu His Pro Met Ser Leu His Gly Met Asp Asp Pro
                165                 170                 175

Glu Lys Glu Val Leu Val Trp Lys Phe Asp Ser Arg Leu Ala Phe His
            180                 185                 190

His Met Ala Arg Glu Leu His Pro Glu Tyr Tyr Lys Asp Cys
        195                 200                 205

<210> SEQ ID NO 54
<211> LENGTH: 206
<212> TYPE: PRT
<213> ORGANISM: Artificial sequence
<220> FEATURE:
<223> OTHER INFORMATION: Minimum of means center of tree reconstruction
      of clade B nef protein sequence

<400> SEQUENCE: 54

Met Gly Gly Lys Trp Ser Lys Arg Ser Val Val Gly Trp Pro Ala Val
1               5                   10                  15

Arg Glu Arg Met Arg Arg Ala Glu Pro Ala Ala Asp Gly Val Gly Ala
            20                  25                  30

Val Ser Arg Asp Leu Glu Lys His Gly Ala Ile Thr Ser Ser Asn Thr
        35                  40                  45

Ala Ala Thr Asn Ala Asp Cys Ala Trp Leu Glu Ala Gln Glu Glu Glu
    50                  55                  60

-continued

Glu Val Gly Phe Pro Val Arg Pro Gln Val Pro Leu Arg Pro Met Thr
65                  70                  75                  80

Tyr Lys Ala Ala Leu Asp Leu Ser His Phe Leu Lys Glu Lys Gly Gly
                85                  90                  95

Leu Glu Gly Leu Ile Tyr Ser Gln Lys Arg Gln Asp Ile Leu Asp Leu
            100                 105                 110

Trp Val Tyr His Thr Gln Gly Tyr Phe Pro Asp Trp Gln Asn Tyr Thr
                115                 120                 125

Pro Gly Pro Gly Ile Arg Tyr Pro Leu Thr Phe Gly Trp Cys Phe Lys
            130                 135                 140

Leu Val Pro Val Glu Pro Glu Lys Val Glu Glu Ala Asn Glu Gly Glu
145                 150                 155                 160

Asn Asn Cys Leu Leu His Pro Met Ser Gln His Gly Met Asp Asp Pro
                165                 170                 175

Glu Lys Glu Val Leu Val Trp Lys Phe Asp Ser Arg Leu Ala Phe His
            180                 185                 190

His Met Ala Arg Glu Leu His Pro Glu Tyr Tyr Lys Asp Cys
        195                 200                 205

<210> SEQ ID NO 55
<211> LENGTH: 1003
<212> TYPE: PRT
<213> ORGANISM: Artificial sequence
<220> FEATURE:
<223> OTHER INFORMATION: Most recent common ancestor reconstruction of
      clade B pol protein sequence

<400> SEQUENCE: 55

Phe Phe Arg Glu Asn Leu Ala Phe Pro Gln Gly Lys Ala Arg Glu Leu
1               5                   10                  15

Ser Ser Glu Gln Thr Arg Ala Asn Ser Pro Thr Arg Arg Glu Leu Gln
20 25 30

Val Trp Gly Arg Asp Asn Asn Ser Leu Ser Glu Ala Gly Ala Asp Arg
35 40 45

Gln Gly Thr Val Ser Phe Ser Phe Pro Gln Ile Thr Leu Trp Gln Arg
50 55 60

Pro Leu Val Thr Ile Lys Ile Gly Gly Gln Leu Lys Glu Ala Leu Leu
65 70 75 80

Asp Thr Gly Ala Asp Asp Thr Val Leu Glu Glu Met Asn Leu Pro Gly
85 90 95

Lys Trp Lys Pro Lys Met Ile Gly Gly Ile Gly Gly Phe Ile Lys Val
100 105 110

Arg Gln Tyr Asp Gln Ile Pro Ile Glu Ile Cys Gly His Lys Ala Ile
115 120 125

Gly Thr Val Leu Val Gly Pro Thr Pro Val Asn Ile Ile Gly Arg Asn
130 135 140

Leu Leu Thr Gln Ile Gly Cys Thr Leu Asn Phe Pro Ile Ser Pro Ile
145 150 155 160

Glu Thr Val Pro Val Lys Leu Lys Pro Gly Met Asp Gly Pro Lys Val
165 170 175

Lys Gln Trp Pro Leu Thr Glu Glu Lys Ile Lys Ala Leu Val Glu Ile
180 185 190

Cys Thr Glu Met Glu Lys Glu Gly Lys Ile Ser Lys Ile Gly Pro Glu
195 200 205

Asn Pro Tyr Asn Thr Pro Val Phe Ala Ile Lys Lys Lys Asp Ser Thr

-continued

```
                210                 215                 220
Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Lys Lys Lys Ser Val Thr Val Leu Asp Val Gly Asp Ala Tyr Phe Ser
                260                 265                 270

Val Pro Leu Asp Glu Asp Phe Arg Lys Tyr Thr Ala Phe Thr Ile Pro
                275                 280                 285

Ser Ile Asn Asn Glu Thr Pro Gly Ile Arg Tyr Gln Tyr Asn Val Leu
290                 295                 300

Pro Gln Gly Trp Lys Gly Ser Pro Ala Ile Phe Gln Ser Ser Met Thr
305                 310                 315                 320

Lys Ile Leu Glu Pro Phe Arg Lys Gln Asn Pro Glu Ile Val Ile Tyr
                325                 330                 335

Gln Tyr Met Asp Asp Leu Tyr Val Gly Ser Asp Leu Glu Ile Gly Gln
                340                 345                 350

His Arg Thr Lys Ile Glu Glu Leu Arg Glu His Leu Leu Arg Trp Gly
                355                 360                 365

Phe Thr Thr Pro Asp Lys Lys His Gln Lys Glu Pro Pro Phe Leu Trp
370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415

Gly Lys Leu Asn Trp Ala Ser Gln Ile Tyr Ala Gly Ile Lys Val Lys
                420                 425                 430

Gln Leu Cys Lys Leu Leu Arg Gly Thr Lys Ala Leu Thr Glu Val Val
                435                 440                 445

Pro Leu Thr Glu Glu Ala Glu Leu Glu Leu Ala Glu Asn Arg Glu Ile
                450                 455                 460

Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
                485                 490                 495

Tyr Gln Glu Pro Phe Lys Asn Leu Lys Thr Gly Lys Tyr Ala Arg Met
                500                 505                 510

Arg Gly Ala His Thr Asn Asp Val Lys Gln Leu Thr Glu Ala Val Gln
                515                 520                 525

Lys Ile Ala Thr Glu Ser Ile Val Ile Trp Gly Lys Thr Pro Lys Phe
                530                 535                 540

Lys Leu Pro Ile Gln Lys Glu Thr Trp Glu Ala Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Val Gly Ala
                580                 585                 590

Glu Thr Phe Tyr Val Asp Gly Ala Ala Asn Arg Glu Thr Lys Leu Gly
                595                 600                 605

Lys Ala Gly Tyr Val Thr Asp Arg Gly Arg Gln Lys Val Val Ser Leu
                610                 615                 620

Thr Asp Thr Thr Asn Gln Lys Thr Glu Leu Gln Ala Ile His Leu Ala
625                 630                 635                 640
```

```
Leu Gln Asp Ser Gly Leu Glu Val Asn Ile Val Thr Asp Ser Gln Tyr
            645                 650                 655
Ala Leu Gly Ile Ile Gln Ala Gln Pro Asp Lys Ser Glu Ser Glu Leu
            660                 665                 670
Val Ser Gln Ile Ile Glu Gln Leu Ile Lys Lys Glu Lys Val Tyr Leu
            675                 680                 685
Ala Trp Val Pro Ala His Lys Gly Ile Gly Gly Asn Glu Gln Val Asp
        690                 695                 700
Lys Leu Val Ser Thr Gly Ile Arg Lys Val Leu Phe Leu Asp Gly Ile
705                 710                 715                 720
Asp Lys Ala Gln Glu Glu His Glu Lys Tyr His Ser Asn Trp Arg Ala
                725                 730                 735
Met Ala Ser Asp Phe Asn Leu Pro Pro Val Val Ala Lys Glu Ile Val
            740                 745                 750
Ala Ser Cys Asp Lys Cys Gln Leu Lys Gly Glu Ala Met His Gly Gln
            755                 760                 765
Val Asp Cys Ser Pro Gly Ile Trp Gln Leu Asp Cys Thr His Leu Glu
        770                 775                 780
Gly Lys Val Ile Leu Val Ala Val His Val Ala Ser Gly Tyr Ile Glu
785                 790                 795                 800
Ala Glu Val Ile Pro Ala Glu Thr Gly Gln Thr Ala Tyr Phe Leu
            805                 810                 815
Leu Lys Leu Ala Gly Arg Trp Pro Val Lys Val Ile His Thr Asp Asn
            820                 825                 830
Gly Ser Asn Phe Thr Ser Thr Thr Val Lys Ala Ala Cys Trp Trp Ala
            835                 840                 845
Gly Ile Lys Gln Glu Phe Gly Ile Pro Tyr Asn Pro Gln Ser Gln Gly
        850                 855                 860
Val Val Glu Ser Met Asn Lys Glu Leu Lys Lys Ile Ile Gly Gln Val
865                 870                 875                 880
Arg Asp Gln Ala Glu His Leu Lys Thr Ala Val Gln Met Ala Val Phe
                885                 890                 895
Ile His Asn Phe Lys Arg Lys Gly Gly Ile Gly Gly Tyr Ser Ala Gly
            900                 905                 910
Glu Arg Ile Val Asp Ile Ile Ala Thr Asp Ile Gln Thr Lys Glu Leu
            915                 920                 925
Gln Lys Gln Ile Thr Lys Ile Gln Asn Phe Arg Val Tyr Tyr Arg Asp
        930                 935                 940
Ser Arg Asp Pro Leu Trp Lys Gly Pro Ala Lys Leu Leu Trp Lys Gly
945                 950                 955                 960
Glu Gly Ala Val Val Ile Gln Asp Asn Ser Asp Ile Lys Val Val Pro
                965                 970                 975
Arg Arg Lys Ala Lys Ile Ile Arg Asp Tyr Gly Lys Gln Met Ala Gly
            980                 985                 990
Asp Asp Cys Val Ala Ser Arg Gln Asp Glu Asp
        995                 1000
```

<210> SEQ ID NO 56
<211> LENGTH: 1003
<212> TYPE: PRT
<213> ORGANISM: Artificial sequence
<220> FEATURE:
<223> OTHER INFORMATION: Least squares center of tree reconstruction of clade B pol protein sequence

<400> SEQUENCE: 56

```
Phe Phe Arg Glu Asp Leu Ala Phe Pro Gln Gly Lys Ala Arg Glu Phe
1               5                   10                  15

Ser Ser Glu Gln Thr Arg Ala Asn Ser Pro Thr Arg Arg Glu Leu Gln
            20                  25                  30

Val Trp Gly Arg Asp Asn Asn Ser Leu Ser Glu Ala Gly Ala Asp Arg
        35                  40                  45

Gln Gly Thr Val Ser Phe Ser Phe Pro Gln Ile Thr Leu Trp Gln Arg
    50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Asn Leu Pro Gly
                85                  90                  95

Arg Trp Lys Pro Lys Met Ile Gly Gly Ile Gly Gly Phe Ile Lys Val
            100                 105                 110

Arg Gln Tyr Asp Gln Ile Pro Ile Glu Ile Cys Gly His Lys Ala Ile
        115                 120                 125

Gly Thr Val Leu Val Gly Pro Thr Pro Val Asn Ile Ile Gly Arg Asn
    130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Val Phe Ala Ile Lys Lys Lys Asp Ser Thr
    210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Lys Lys Lys Ser Val Thr Val Leu Asp Val Gly Asp Ala Tyr Phe Ser
            260                 265                 270

Val Pro Leu Asp Glu Asp Phe Arg Lys Tyr Thr Ala Phe Thr Ile Pro
        275                 280                 285

Ser Ile Asn Asn Glu Thr Pro Gly Ile Arg Tyr Gln Tyr Asn Val Leu
    290                 295                 300

Pro Gln Gly Trp Lys Gly Ser Pro Ala Ile Phe Gln Ser Ser Met Thr
305                 310                 315                 320

Lys Ile Leu Glu Pro Phe Arg Lys Gln Asn Pro Asp Ile Val Ile Tyr
                325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
        355                 360                 365

Phe Thr Thr Pro Asp Lys Lys His Gln Lys Glu Pro Pro Phe Leu Trp
    370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415
```

-continued

```
Gly Lys Leu Asn Trp Ala Ser Gln Ile Tyr Ala Gly Ile Lys Val Lys
            420                 425                 430
Gln Leu Cys Lys Leu Leu Arg Gly Thr Lys Ala Leu Thr Glu Val Ile
        435                 440                 445
Pro Leu Thr Glu Glu Ala Glu Leu Glu Leu Ala Glu Asn Arg Glu Ile
    450                 455                 460
Leu Lys Glu Pro Val His Gly Val Tyr Tyr Asp Pro Ser Lys Asp Leu
465                 470                 475                 480
Ile Ala Glu Ile Gln Lys Gln Gly Gln Gly Gln Trp Thr Tyr Gln Ile
                485                 490                 495
Tyr Gln Glu Pro Phe Lys Asn Leu Lys Thr Gly Lys Tyr Ala Arg Met
            500                 505                 510
Arg Gly Ala His Thr Asn Asp Val Lys Gln Leu Thr Glu Ala Val Gln
        515                 520                 525
Lys Ile Ala Thr Glu Ser Ile Val Ile Trp Gly Lys Thr Pro Lys Phe
    530                 535                 540
Lys Leu Pro Ile Gln Lys Glu Thr Trp Glu Ala Trp Trp Thr Glu Tyr
545                 550                 555                 560
Trp Gln Ala Thr Trp Ile Pro Glu Trp Glu Phe Val Asn Thr Pro Pro
                565                 570                 575
Leu Val Lys Leu Trp Tyr Gln Leu Glu Lys Glu Pro Ile Val Gly Ala
            580                 585                 590
Glu Thr Phe Tyr Val Asp Gly Ala Ala Asn Arg Glu Thr Lys Leu Gly
        595                 600                 605
Lys Ala Gly Tyr Val Thr Asp Arg Gly Arg Gln Lys Val Val Ser Leu
    610                 615                 620
Thr Asp Thr Thr Asn Gln Lys Thr Glu Leu Gln Ala Ile His Leu Ala
625                 630                 635                 640
Leu Gln Asp Ser Gly Leu Glu Val Asn Ile Val Thr Asp Ser Gln Tyr
                645                 650                 655
Ala Leu Gly Ile Ile Gln Ala Gln Pro Asp Lys Ser Glu Ser Glu Leu
            660                 665                 670
Val Ser Gln Ile Ile Glu Gln Leu Ile Lys Lys Glu Lys Val Tyr Leu
        675                 680                 685
Ala Trp Val Pro Ala His Lys Gly Ile Gly Gly Asn Glu Gln Val Asp
    690                 695                 700
Lys Leu Val Ser Ala Gly Ile Arg Lys Val Leu Phe Leu Asp Gly Ile
705                 710                 715                 720
Asp Lys Ala Gln Glu Glu His Glu Lys Tyr His Ser Asn Trp Arg Ala
                725                 730                 735
Met Ala Ser Asp Phe Asn Leu Pro Pro Val Val Ala Lys Glu Ile Val
            740                 745                 750
Ala Ser Cys Asp Lys Cys Gln Leu Lys Gly Glu Ala Met His Gly Gln
        755                 760                 765
Val Asp Cys Ser Pro Gly Ile Trp Gln Leu Asp Cys Thr His Leu Glu
    770                 775                 780
Gly Lys Val Ile Leu Val Ala Val His Val Ala Ser Gly Tyr Ile Glu
785                 790                 795                 800
Ala Glu Val Ile Pro Ala Glu Thr Gly Gln Glu Thr Ala Tyr Phe Leu
                805                 810                 815
Leu Lys Leu Ala Gly Arg Trp Pro Val Lys Thr Ile His Thr Asp Asn
            820                 825                 830
```

```
Gly Ser Asn Phe Thr Ser Thr Thr Val Lys Ala Ala Cys Trp Trp Ala
            835                 840                 845
Gly Ile Lys Gln Glu Phe Gly Ile Pro Tyr Asn Pro Gln Ser Gln Gly
        850                 855                 860
Val Val Glu Ser Met Asn Lys Glu Leu Lys Lys Ile Ile Gly Gln Val
865                 870                 875                 880
Arg Asp Gln Ala Glu His Leu Lys Thr Ala Val Gln Met Ala Val Phe
                885                 890                 895
Ile His Asn Phe Lys Arg Lys Gly Gly Ile Gly Gly Tyr Ser Ala Gly
            900                 905                 910
Glu Arg Ile Val Asp Ile Ile Ala Thr Asp Ile Gln Thr Lys Glu Leu
        915                 920                 925
Gln Lys Gln Ile Thr Lys Ile Gln Asn Phe Arg Val Tyr Tyr Arg Asp
        930                 935                 940
Ser Arg Asp Pro Leu Trp Lys Gly Pro Ala Lys Leu Leu Trp Lys Gly
945                 950                 955                 960
Glu Gly Ala Val Val Ile Gln Asp Asn Ser Asp Ile Lys Val Val Pro
                965                 970                 975
Arg Arg Lys Ala Lys Ile Ile Arg Asp Tyr Gly Lys Gln Met Ala Gly
            980                 985                 990
Asp Asp Cys Val Ala Ser Arg Gln  Asp Glu Asp
            995                  1000

<210> SEQ ID NO 57
<211> LENGTH: 1003
<212> TYPE: PRT
<213> ORGANISM: Artificial sequence
<220> FEATURE:
<223> OTHER INFORMATION: Minimum of means center of tree reconstruction
      of clade B pol protein sequence

<400> SEQUENCE: 57

Phe Phe Arg Glu Asp Leu Ala Phe Pro Gln Gly Lys Ala Arg Glu Phe
1               5                   10                  15
Ser Ser Glu Gln Thr Arg Ala Asn Ser Pro Thr Arg Arg Glu Leu Gln
            20                  25                  30
Val Trp Gly Arg Asp Asn Asn Ser Leu Ser Glu Ala Gly Ala Asp Arg
        35                  40                  45
Gln Gly Thr Val Ser Phe Ser Phe Pro Gln Ile Thr Leu Trp Gln Arg
    50                  55                  60
Pro Leu Val Thr Ile Lys Ile Gly Gly Gln Leu Lys Glu Ala Leu Leu
65                  70                  75                  80
Asp Thr Gly Ala Asp Asp Thr Val Leu Glu Glu Met Asn Leu Pro Gly
                85                  90                  95
Arg Trp Lys Pro Lys Met Ile Gly Gly Ile Gly Gly Phe Ile Lys Val
            100                 105                 110
Arg Gln Tyr Asp Gln Ile Leu Ile Glu Ile Cys Gly His Lys Ala Ile
        115                 120                 125
Gly Thr Val Leu Val Gly Pro Thr Pro Val Asn Ile Ile Gly Arg Asn
    130                 135                 140
Leu Leu Thr Gln Ile Gly Cys Thr Leu Asn Phe Pro Ile Ser Pro Ile
145                 150                 155                 160
Glu Thr Val Pro Val Lys Leu Lys Pro Gly Met Asp Gly Pro Lys Val
                165                 170                 175
Lys Gln Trp Pro Leu Thr Glu Glu Lys Ile Lys Ala Leu Val Glu Ile
            180                 185                 190
```

```
Cys Thr Glu Met Glu Lys Glu Gly Lys Ile Ser Lys Ile Gly Pro Glu
            195                 200                 205

Asn Pro Tyr Asn Thr Pro Val Phe Ala Ile Lys Lys Lys Asp Ser Thr
            210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
            245                 250                 255

Lys Lys Lys Ser Val Thr Val Leu Asp Val Gly Asp Ala Tyr Phe Ser
            260                 265                 270

Val Pro Leu Asp Glu Asp Phe Arg Lys Tyr Thr Ala Phe Thr Ile Pro
            275                 280                 285

Ser Ile Asn Asn Glu Thr Pro Gly Ile Arg Tyr Gln Tyr Asn Val Leu
            290                 295                 300

Pro Gln Gly Trp Lys Gly Ser Pro Ala Ile Phe Gln Ser Ser Met Thr
305                 310                 315                 320

Lys Ile Leu Glu Pro Phe Arg Lys Gln Asn Pro Asp Ile Val Ile Tyr
            325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
            355                 360                 365

Phe Thr Thr Pro Asp Lys Lys His Gln Lys Glu Pro Pro Phe Leu Trp
            370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
            405                 410                 415

Gly Lys Leu Asn Trp Ala Ser Gln Ile Tyr Pro Gly Ile Lys Val Lys
            420                 425                 430

Gln Leu Cys Lys Leu Leu Arg Gly Thr Lys Ala Leu Thr Glu Val Ile
            435                 440                 445

Pro Leu Thr Glu Glu Ala Glu Leu Glu Leu Ala Glu Asn Arg Glu Ile
450                 455                 460

Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
            485                 490                 495

Tyr Gln Glu Pro Phe Lys Asn Leu Lys Thr Gly Lys Tyr Ala Arg Met
            500                 505                 510

Arg Gly Ala His Thr Asn Asp Val Lys Gln Leu Thr Glu Ala Val Gln
            515                 520                 525

Lys Ile Ala Thr Glu Ser Ile Val Ile Trp Gly Lys Thr Pro Lys Phe
            530                 535                 540

Lys Leu Pro Ile Gln Lys Glu Thr Trp Glu Thr Trp Thr Glu Tyr
545                 550                 555                 560

Trp Gln Ala Thr Trp Ile Pro Glu Trp Glu Phe Val Asn Thr Pro Pro
            565                 570                 575

Leu Val Lys Leu Trp Tyr Gln Leu Glu Lys Glu Pro Ile Val Gly Ala
            580                 585                 590

Glu Thr Phe Tyr Val Asp Gly Ala Ala Asn Arg Glu Thr Lys Leu Gly
            595                 600                 605
```

```
Lys Ala Gly Tyr Val Thr Asn Arg Gly Arg Gln Lys Val Val Ser Leu
610                 615                 620

Thr Asp Thr Thr Asn Gln Lys Thr Glu Leu Gln Ala Ile His Leu Ala
625                 630                 635                 640

Leu Gln Asp Ser Gly Leu Glu Val Asn Ile Val Thr Asp Ser Gln Tyr
            645                 650                 655

Ala Leu Gly Ile Ile Gln Ala Gln Pro Asp Lys Ser Glu Ser Glu Leu
            660                 665                 670

Val Ser Gln Ile Ile Glu Gln Leu Ile Lys Lys Glu Lys Val Tyr Leu
            675                 680                 685

Ala Trp Val Pro Ala His Lys Gly Ile Gly Gly Asn Glu Gln Val Asp
            690                 695                 700

Lys Leu Val Ser Ala Gly Ile Arg Lys Val Leu Phe Leu Asp Gly Ile
705                 710                 715                 720

Asp Lys Ala Gln Glu Glu His Glu Lys Tyr His Ser Asn Trp Arg Ala
            725                 730                 735

Met Ala Ser Asp Phe Asn Leu Pro Pro Val Val Ala Lys Glu Ile Val
            740                 745                 750

Ala Ser Cys Asp Lys Cys Gln Leu Lys Gly Glu Ala Met His Gly Gln
            755                 760                 765

Val Asp Cys Ser Pro Gly Ile Trp Gln Leu Asp Cys Thr His Leu Glu
            770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
            805                 810                 815

Leu Lys Leu Ala Gly Arg Trp Pro Val Lys Thr Ile His Thr Asp Asn
            820                 825                 830

Gly Ser Asn Phe Thr Ser Thr Thr Val Lys Ala Ala Cys Trp Trp Ala
            835                 840                 845

Gly Ile Lys Gln Glu Phe Gly Ile Pro Tyr Asn Pro Gln Ser Gln Gly
            850                 855                 860

Val Val Glu Ser Met Asn Lys Glu Leu Lys Lys Ile Ile Gly Gln Val
865                 870                 875                 880

Arg Asp Gln Ala Glu His Leu Lys Thr Ala Val Gln Met Ala Val Phe
            885                 890                 895

Ile His Asn Phe Lys Arg Lys Gly Gly Ile Gly Gly Tyr Ser Ala Gly
            900                 905                 910

Glu Arg Ile Val Asp Ile Ile Ala Thr Asp Ile Gln Thr Lys Glu Leu
            915                 920                 925

Gln Lys Gln Ile Thr Lys Ile Gln Asn Phe Arg Val Tyr Tyr Arg Asp
            930                 935                 940

Ser Arg Asp Pro Leu Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
            965                 970                 975

Arg Arg Lys Ala Lys Ile Ile Arg Asp Tyr Gly Lys Gln Met Ala Gly
            980                 985                 990

Asp Asp Cys Val Ala Ser Arg Gln Asp Glu Asp
            995                 1000

<210> SEQ ID NO 58
<211> LENGTH: 116
<212> TYPE: PRT
```

```
<213> ORGANISM: Artificial sequence
<220> FEATURE:
<223> OTHER INFORMATION: Most recent common ancestor reconstruction of
      clade B rev protein sequence

<400> SEQUENCE: 58

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Pro Glu
            20                  25                  30

Gly Thr Arg Gln Ala Arg Arg Asn Arg Arg Arg Trp Arg Glu Arg
            35                  40                  45

Gln Arg Gln Ile Arg Ser Ile Ser Glu Arg Ile Leu Ser Thr Tyr Leu
    50                  55                  60

Gly Arg Ser

```
Gly Thr Arg Gln Ala Arg Arg Asn Arg Arg Arg Trp Arg Glu Arg
            35                  40                  45

Gln Arg Gln Ile Arg Ser Ile Ser Glu Trp Ile Leu Ser Thr Tyr Leu
 50                  55                  60

Gly Arg Pro Ala Glu Pro Val Pro Leu Gln Leu Pro Pro Leu Glu Arg
 65                  70                  75                  80

Leu Thr Leu Asp Cys Ser Glu Asp Cys Gly Thr Ser Gly Thr Gln Gly
                 85                  90                  95

Val Gly Ser Pro Gln Ile Leu Val Glu Ser Pro Ala Val Leu Glu Ser
            100                 105                 110

Gly Thr Lys Glu
        115

<210> SEQ ID NO 61
<211> LENGTH: 101
<212> TYPE: PRT
<213> ORGANISM: Artificial sequence
<220> FEATURE:
<223> OTHER INFORMATION: Most common recent ancestor reconstruction of
      clade B tat protein sequence

<400> SEQUENCE: 61

Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Tyr
                20                  25                  30

His Cys Gln Val Cys Phe Ile Thr Lys Gly Leu Gly Ile Ser Tyr Gly
            35                  40                  45

Arg Lys Lys Arg Arg Gln Arg Arg Pro Pro Gln Gly Ser Gln Thr
 50                  55                  60

His Gln Val Ser Leu Ser Lys Gln Pro Ala Ser Gln Pro Arg Gly Asp
 65                  70                  75                  80

Pro Thr Gly Pro Lys Glu Ser Lys Lys Val Glu Arg Glu Thr Glu
                 85                  90                  95

Thr Asp Pro Val Asp
            100

<210> SEQ ID NO 62
<211> LENGTH: 101
<212> TYPE: PRT
<213> ORGANISM: Artificial sequence
<220> FEATURE:
<223> OTHER INFORMATION: Least squares and minimum of means
      reconstruction of clade B tat protein sequence

<400> SEQUENCE: 62

Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
                20                  25                  30

His Cys Gln Val Cys Phe Ile Thr Lys Gly Leu Gly Ile Ser Tyr Gly
            35                  40                  45

Arg Lys Lys Arg Arg Gln Arg Arg Ala Pro Gln Asp Ser Gln Thr
 50                  55                  60

His Gln Val Ser Leu Ser Lys Gln Pro Ala Ser Gln Pro Arg Gly Asp
 65                  70                  75                  80

Pro Thr Gly Pro Lys Glu Ser Lys Lys Val Glu Arg Glu Thr Glu
                 85                  90                  95
```

```
-continued

Thr Asp Pro Val Asp
            100

<210> SEQ ID NO 63
<211> LENGTH: 192
<212> TYPE: PRT
<213> ORGANISM: Artificial sequence
<220> FEATURE:
<223> OTHER INFORMATION: Most recent common ancestor reconstruction of
      clade B vif protein sequence

<400> SEQUENCE: 63

Met Glu Asn Arg Trp Gln Val Met Ile Val Trp Gln Val Asp Arg Met
1               5                  10                  15

Arg Ile Arg Thr Trp Lys Ser Leu Val Lys His His Met Tyr Ile Ser
            20                  25                  30

Lys Lys Ala Lys Gly Trp Phe Tyr Arg His His Tyr Glu Ser Thr His
        35                  40                  45

Pro Arg Ile Ser Ser Glu Val His Ile Pro Leu Gly Asp Ala Arg Leu
    50                  55                  60

Val Ile Lys Thr Tyr Trp Gly Leu His Thr Gly Glu Arg Glu Trp His
65                  70                  75                  80

Leu Gly Gln Gly Val Ser Ile Glu Trp Arg Lys Arg Arg Tyr Ser Thr
                85                  90                  95

Gln Val Asp Pro Gly Leu Ala Asp Gln Leu Ile His Leu Tyr Tyr Phe
            100                 105                 110

Asp Cys Phe Ser Glu Ser Ala Ile Arg Asn Ala Ile Leu Gly His Ile
        115                 120                 125

Val Ser Pro Arg Cys Glu Tyr Gln Ala Gly His Asn Lys Val Gly Ser
    130                 135                 140

Leu Gln Tyr Leu Ala Leu Thr Ala Leu Ile Thr Pro Lys Lys Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
            180                 185                 190

<210> SEQ ID NO 64
<211> LENGTH: 192
<212> TYPE: PRT
<213> ORGANISM: Artificial sequence
<220> FEATURE:
<223> OTHER INFORMATION: Least squares and minimum of means
      reconstruction of clade B vif protein sequence

<400> SEQUENCE: 64

Met Glu Asn Arg Trp Gln Val Met Ile Val Trp Gln Val Asp Arg Met
1               5                  10                  15

Arg Ile Arg Thr Trp Lys Ser Leu Val Lys His His Met Tyr Ile Ser
            20                  25                  30

Arg Lys Ala Lys Gly Trp Phe Tyr Arg His His Tyr Glu Ser Thr His
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95
```

```
Gln Val Asp Pro Asp Leu Ala Asp Gln Leu Ile His Leu Tyr Tyr Phe
            100                 105                 110

Asp Cys Phe Ser Glu Ser Ala Ile Arg Asn Ala Ile Leu Gly His Ile
            115                 120                 125

Val Ser Pro Arg Cys Glu Tyr Gln Ala Gly His Asn Lys Val Gly Ser
            130                 135                 140

Leu Gln Tyr Leu Ala Leu Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Gly Ser His Thr Met Asn Gly His
                180                 185                 190

<210> SEQ ID NO 65
<211> LENGTH: 96
<212> TYPE: PRT
<213> ORGANISM: Artificial sequence
<220> FEATURE:
<223> OTHER INFORMATION: Most recent common ancestor reconstruction of
      clade B vpr protein sequence

<400> SEQUENCE: 65

Met Glu Gln Ala Pro Glu Asp Gln Gly Pro Gln Arg Glu Pro Tyr Asn
1               5                   10                  15

Glu Trp Thr Leu Glu Leu Leu Glu Glu Leu Lys Ser Glu Ala Val Arg
                20                  25                  30

His Phe Pro Arg Leu Trp Leu His Ser Leu Gly Gln His Ile T

```
<211> LENGTH: 96
<212> TYPE: PRT
<213> ORGANISM: Artificial sequence
<220> FEATURE:
<223> OTHER INFORMATION: Minimum of means reconstructions for the clade
      B of vpr protein sequence

<400> SEQUENCE: 67
```

Met Glu Gln Ala Pro Glu Asp Gln Gly Pro Gln Arg Glu Pro Tyr Asn
1               5                   10                  15

Glu Trp Thr Leu Glu Leu Leu Glu Glu Leu Lys Ser Glu Ala Val Arg
            20                  25                  30

His Phe Pro Arg Ile Trp Leu His Ser Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe Arg Ile Gly Cys Gln His Ser Arg
65                  70                  75                  80

Ile Gly Ile Thr Arg Gln Arg Arg Ala Arg Asn Gly Ala Ser Arg Ser
                85                  90                  95

```
<210> SEQ ID NO 68
<211> LENGTH: 81
<212> TYPE: PRT
<213> ORGANISM: Artificial sequence
<220> FEATURE:
<223> OTHER INFORMATION: Most recent common ancestor reconstruction of
      clade B rev protein sequence

<400> SEQUENCE: 68
```

Met Gln Pro Leu Glu Ile Leu Ala Ile Val Ala Leu Val Val Ala Ala
1               5                   10                  15

Ile Leu Ala Ile Val Val Trp Thr Ile Val Phe Ile Glu Tyr Arg Lys
            20                  25                  30

Ile Leu Arg Gln Arg Lys Ile Asp Arg Leu Ile Asp Arg Ile Arg Glu
        35                  40                  45

Arg Ala Glu Asp Ser Gly Asn Glu Ser Glu Gly Asp Gln Glu Glu Leu
    50                  55                  60

Ser Ala Leu Val Glu Met Gly His His Ala Pro Trp Asp Val Asp Asp
65                  70                  75                  80

Leu

```
<210> SEQ ID NO 69
<211> LENGTH: 81
<212> TYPE: PRT
<213> ORGANISM: Artificial sequence
<220> FEATURE:
<223> OTHER INFORMATION: Least squares and minimum of means
      reconstructions for the clade B vpu protein sequences

<400> SEQUENCE: 69
```

Met Gln Pro Leu Gln Ile Leu Ala Ile Val Ala Leu Val Val Ala Ala
1               5                   10                  15

Ile Ile Ala Ile Val Val Trp Thr Ile Val Phe Ile Glu Tyr Arg Lys
            20                  25                  30

Ile Leu Arg Gln Arg Lys Ile Asp Arg Leu Ile Asp Arg Ile Arg Glu
        35                  40                  45

Arg Ala Glu Asp Ser Gly Asn Glu Ser Glu Gly Asp Gln Glu Glu Leu
    50                  55                  60

Ser Ala Leu Val Glu Met Gly His His Ala Pro Trp Asp Val Asp Asp 65                70                75                80

Leu

<210> SEQ ID NO 70
<211> LENGTH: 1479
<212> TYPE: DNA
<213> ORGANISM: Artificial sequence
<220> FEATURE:
<223> OTHER INFORMATION: Most recent common ancestor reconstruction of clade C gag protein sequence

<400> SEQUENCE: 70

```
atgggtgcga gagcgtcaat attaagaggg ggaaaattag atacatggga aaaaattagg      60
ttaaggccag ggggaaagaa acattatatg ataaaacacc tagtatgggc aagcagggag     120
ctggaaagat ttgcacttaa ccctggcctt ttagagacat cagaaggctg taaacaaata     180
ataaaacagc tacaaccagc tcttcagaca ggaacagagg aacttaaatc attatataac     240
acagtagcaa ctctctattg tgtacatcaa aggatagagg tacgagacac caaggaagcc     300
ttagacaaga tagaggaaga acaaaacaaa agtcagcaaa aaacacagca ggcagaagcg     360
gctgacggaa aggtcagtca aaattatcct atagtgcaga atctccaagg gcaaatggta     420
caccaggcca tatcacctag aactttgaat gcatgggtaa agtaataga ggagaaggct     480
ttcagcccag aggtaatacc catgtttaca gcattatcag aaggagccac cccacaagat     540
ttaaacacca tgttaaatac agtggggggga catcaagcag ccatgcaaat gttaaaagat     600
accatcaatg aggaggctgc agaatgggat aggttacatc cagtgcatgc agggcctgtt     660
gcaccaggcc aaatgagaga accaagggga agtgacatag caggaactac tagtacccctt     720
caggaacaaa tagcatggat gacaagtaac ccacctatcc cagtgggaga catctataaa     780
agatggataa ttctggggtt aaataaaata gtaagaatgt atagccctgt cagcattttg     840
gacataaaac aaggcccaaa ggaaccctttt agagactatg tagaccggtt ctttaaaact     900
ttaagagctg aacaagctac acaagatgta aaaaattgga tgacagacac cttgttggtc     960
caaaatgcga acccagattg taagaccatt ttaagagcat taggaccagg ggctacacta    1020
gaagaaatga tgacagcatg tcagggagtg ggaggaccta gccataaagc aagagttttg    1080
gctgaggcaa tgagccaagc aaacaataca aacataatga tgcagagagg caattttaag    1140
ggccctagaa gaattgttaa atgtttcaac tgtggcaagg aaggacacat agccagaaat    1200
tgcagggccc ctaggaaaaa gggctgttgg aaatgtggaa aggaaggaca ccaaatgaaa    1260
gactgtactg agaggcaggc taattttta ggaaaatttt ggccttccca caggggagg    1320
ccagggaatt tccttcagag cagaccagag ccaacagccc caccagcaga gagcttcagg    1380
ttcgaggaga caacccccgc tccgaagcag gagccgaaag acagggaacc cttaacttcc    1440
ctcaaatcac tctttggcag cgaccccttg tctcaataa                           1479
```

<210> SEQ ID NO 71
<211> LENGTH: 1479
<212> TYPE: DNA
<213> ORGANISM: Artificial sequence
<220> FEATURE:
<223> OTHER INFORMATION: Least squares center minumum of means reconstructions for clade C gag gene

<400> SEQUENCE: 71

```
atgggtgcga gagcgtcaat attaagaggc ggaaaattag atacatggga aaaaattagg      60
ttaaggccag ggggaaagaa acattatatg ctaaaacacc tagtatgggc aagcagggag     120
```

| | |
|---|---|
| ctggaaagat ttgcacttaa ccctggcctt ttagagacat cagaaggctg taaacaaata | 180 |
| atgaaacagc tacaaccagc tcttcagaca ggaacagagg aacttagatc attatataac | 240 |
| acagtagcaa ctctctattg tgtacatgaa aagatagagg tacgagacac caaggaagcc | 300 |
| ttagacaaga tagaggaaga acaaaacaaa agtcagcaaa aaacacagca ggcagaagcg | 360 |
| gctgacggaa aggtcagtca aaattatcct atagtgcaga atctccaagg gcaaatggta | 420 |
| caccaggcca tatcacctag aactttgaat gcatgggtaa aagtaataga ggagaaggct | 480 |
| ttcagcccag aggtaatacc catgtttaca gcattatcag aaggagccac cccacaagat | 540 |
| ttaaacacca tgttaaatac agtgggggga catcaagcag ccatgcaaat gttaaaagat | 600 |
| accatcaatg aggaggctgc agaatgggat aggttacatc cagtacatgc agggcctgtt | 660 |
| gcaccaggcc aaatgagaga accaagggga agtgacatag caggaactac tagtacccct | 720 |
| caggaacaaa tagcatggat gacaagtaac ccacctgttc cagtgggaga catctataaa | 780 |
| agatggataa ttctggggtt aaataaaata gtaagaatgt atagccctgt cagcattttg | 840 |
| gacataaaac aagggccaaa ggaacccttt agagactatg tagaccggtt ctttaaaact | 900 |
| ttaagagctg aacaagctac acaagatgta aaaaattgga tgacagacac cttgttggtc | 960 |
| caaaatgcga acccagattg taagaccatt ttaagagcat taggaccagg ggctacatta | 1020 |
| gaagaaatga tgacagcatg tcaggagtg ggaggacctg ccacaaagc aagagtgttg | 1080 |
| gctgaggcaa tgagccaagc aaacaataca aacataatga tgcagagaag caattttaaa | 1140 |
| ggccctaaaa gaattgttaa atgtttcaac tgtggcaagg aagggcacat agccagaaat | 1200 |
| tgcagggccc ctaggaaaaa aggctgttgg aaatgtggaa aggaaggaca ccaaatgaaa | 1260 |
| gactgtactg agaggcaggc taattttta gggaaaattt ggccttccca caaggggagg | 1320 |
| ccagggaatt tccttcagag cagaccagag ccaacagccc caccagcaga gagcttcagg | 1380 |
| ttcgaggaga caaccccgc tccgaagcag gagccgaaag acaggggaacc cttaacttcc | 1440 |
| ctcaaatcac tctttggcag cgacccctg tctcaataa | 1479 |

<210> SEQ ID NO 72
<211> LENGTH: 1482
<212> TYPE: DNA
<213> ORGANISM: Artificial sequence
<220> FEATURE:
<223> OTHER INFORMATION: Minimum of means reconstructions for clade C
      gag gene

<400> SEQUENCE: 72

| | |
|---|---|
| atgggtgcga gagcgtcaat attaagaggc ggaaaattag atacatggga aaaaattagg | 60 |
| ttaaggccag ggggaaagaa acattatatg ctaaaacacc tagtatggc aagcagggag | 120 |
| ctggaaagat ttgcacttaa ccctggcctt ttagagacat cagaaggctg taaacaaata | 180 |
| atgaaacagc tacaaccagc tcttcagaca ggaacagagg aacttagatc attatataac | 240 |
| acagtagcaa ctctctattg tgtacatgaa aagatagagg tacgagacac caaggaagcc | 300 |
| ttagacaaga tagaggaaga acaaaacaaa agtcagcaaa aaacacagca ggcagaagcg | 360 |
| gctgctgacg gaaaggtcag tcaaaattat cctatagtgc agaatctcca agggcaaatg | 420 |
| gtacaccagg ccatatcacc tagaactttg aatgcatggg taaagtaat agaggagaag | 480 |
| gctttcagcc cagaggtaat acccatgttt acagcattat cagaaggagc caccccacaa | 540 |
| gatttaaaca ccatgttaaa tacagtgggg ggacatcaag cagccatgca atgttaaaa | 600 |
| gataccatca atgaggaggc tgcagaatgg gataggttac atccagtaca tgcagggcct | 660 |

```
gttgcaccag gccaaatgag agaaccaagg ggaagtgaca tagcaggaac tactagtacc    720
cttcaggaac aaatagcatg gatgacaagt aacccacctg ttccagtggg agacatctat    780
aaaagatgga taattctggg gttaaataaa atagtaagaa tgtatagccc tgtcagcatt    840
ttggacataa acaagggcc aaaggaaccc tttagagact atgtagaccg gttctttaaa    900
actttaagag ctgaacaagc tacacaagat gtaaaaaatt ggatgacaga cacctgttg    960 gtccaaaatg cgaacccaga ttgtaagacc attttaagag cattaggacc aggggctaca    1020
ttagaagaaa tgatgacagc atgtcaggga gtgggaggac ctggccacaa agcaagagtg    1080
ttggctgagg caatgagcca agcaaacaat acaaacataa tgatgcagag aagcaattt    1140 aaaggccta aaagaattgt taatgttc aactgtggca aggaagggca catagccaga    1200
aattgcaggg cccctaggaa aaaggctgt tggaaatgtg gaaggaagg acaccaaatg    1260 aaagactgta ctgagaggca ggctaatttt ttagggaaaa tttggccttc ccacaagggg    1320
aggccaggga atttccttca gagcagacca gagccaacag ccccaccagc agagagcttc    1380
aggttcgagg agacaacccc cgctccgaag caggagccga aagacaggga acccttaact    1440
tccctcaaat cactctttgg cagcgacccc ttgtctcaat aa                       1482
```

<210> SEQ ID NO 73
<211> LENGTH: 2547
<212> TYPE: DNA
<213> ORGANISM: Artificial sequence
<220> FEATURE:
<223> OTHER INFORMATION: Most recent common ancestor reconstructions of clade C env gene

<400> SEQUENCE: 73

```
atgagagtga tggggataca gaggaattgt caacaatggt ggatatgggg catcttaggc    60
ttttggatgt taatgatttg tagtgtggtg gggaacttgt gggtcacagt ctattatggg    120
gtacctgtgt ggaaagaagc aaaaactact ctattttgtg catcagatgc taaagcatat    180
gagagagaag tgcataatgt ctgggctaca catgcctgtg tacccacaga ccccaaccca    240
caagaaatgg ttttggaaaa tgtaacagaa aattttaaca tgtggaaaaa tgacatggtg    300
gatcagatgc atgaggatat aatcagttta tgggatcaaa gcctaaagcc atgtgtaaag    360
ttgaccccca tctgtgtcac tttaaactgt actaatgtta ataatactaa taataccaat    420
agtaccatga tggagaaat gaaaaattgc tctttcaata taaccacaga ataagagat    480 aagaagaaga aagaatatgc actttttat agacttgata tagtaccact taatgaaaat    540
aataacaata ctagtgaata tagattaata aattgtaata cctcagccat aacacaagcc    600
tgtccaaagg tctctttga cccaattcct atacattatt gtgctccagc tggttatgcg    660
attctaaagt gtaataataa gacattcaat ggaacaggac catgcaaaaa tgtcagcaca    720
gtacaatgta cacatggaat taagccagtg gtatcaactc aactactgtt aaatggtagt    780
ctagcagaag aagagataat aattagatct gaaaatctga caacaatgc caaaacaata    840 atagtacagc ttaatgaatc tgtagaaatt gtgtgtacaa gacccaacaa taatacaaga    900
aaaagtatga ggataggacc aggacaaaca ttctatgcaa caggagacat aataggagat    960
ataagacaag cacattgtaa cattagtgga agggaatgga ataacacttt acaacaggta    1020
gctgaaaaat taagaaaaca cttccctaat aaaacaataa atttgcacc atcctcagga    1080 ggggacctag aaattacaac acatagcttt aattgtagag gagaattttt ctattgcaat    1140
acatcaaaac tgtttaatag tacatacaat agtacaaata gtacaaattc aaccatcaca    1200
```

| | |
|---|---|
| ctcccatgca gaataaaaca aattataaac atgtggcagg gggtaggaca agcaatgtat | 1260 |
| gcccctccca ttgcaggaaa cataacatgt aaatcaaata tcacaggact actattgaca | 1320 |
| cgtgatggag gaaaaaatga aactaatgaa actgagacat tcagacctgg aggaggagat | 1380 |
| atgagggaca attggagaag tgaattatat aaatataaag tagtagaaat taaaccatta | 1440 |
| ggagtagcac ccactaaggc aaaaaggaga gtggtggaga gagaaaaaag agcagtggga | 1500 |
| ctaggagctg tgttccttgg gttcttggga gcagcaggaa gcactatggg cgcagcgtca | 1560 |
| ataacgctga cggtacaggc cagacaatta ttgtctggta tagtgcaaca gcaaagcaat | 1620 |
| ttgctgaggg ctatagaggc gcaacagcat atgttgcaac tcacagtctg gggcattaag | 1680 |
| cagctccagg caagagtcct ggctatgaaa agatacctaa aggatcaaca gctcctaggg | 1740 |
| atttggggct gctctggaaa actcatctgc accactgctg tgccttggaa ctctagttgg | 1800 |
| agtaataaat ctcaagatga tatttgggat aacatgacct ggatggagtg ggatagagaa | 1860 |
| attaacaatt acacagacac aatatacagg ttgcttgaag aatcgcaaaa ccagcaggaa | 1920 |
| aaaaatgaac aagatttatt ggcattggac agttgggaaa atctgtggaa ttggtttgac | 1980 |
| atatcaaatt ggctgtggta tataaaaata ttcataatga tagtaggagg cttgataggt | 2040 |
| ttaagaataa ttttttgctgt gctttctata gtaaatagag ttaggcaggg atactcacct | 2100 |
| ttgtcgtttc agacccttac cccaaacccg aggggacccg acaggctcga agaatcgaa | 2160 |
| gaagaaggtg gagagcaaga cagagacaga tccattcgat tagtgagcgg attcttagca | 2220 |
| cttgcctggg acgacctgcg gagcctgtgc ctcttcagct accaccgctt gagagacttc | 2280 |
| atcttgattg cagcgaggac tgtggaactt ctgggacgca gcagtctcag gggactacag | 2340 |
| aggggggtggg aagcccttaa atatctggga agtcttgtgc agtattgggg tcaggagcta | 2400 |
| aaaaagagtg ctattagtct gcttgatacc atagcaatag cagtagctga agggacagat | 2460 |
| aggattatag aagtagtaca aagagcttgt agagctatcc tcaacatacc tagaagaata | 2520 |
| agacagggct ttgaagcagc tttgcaa | 2547 |

<210> SEQ ID NO 74
<211> LENGTH: 2547
<212> TYPE: DNA
<213> ORGANISM: Artificial sequence
<220> FEATURE:
<223> OTHER INFORMATION: Least squares and minimum of means
reconstructions for clade C env gene

<400> SEQUENCE: 74

| | |
|---|---|
| atgagagtga gggggatact gaggaattgt caacaatggt ggatatgggg catcttaggc | 60 |
| ttttggatgt taatgatttg taatgtggtg gggaacttgt gggtcacagt ctattatggg | 120 |
| gtacctgtgt ggaaagaagc aaaaactact ctattctgtg catcagatgc taaagcatat | 180 |
| gagaaagaag tgcataatgt ctgggctaca catgcctgtg tacccacaga ccccaaccca | 240 |
| caagaaatgg ttttggaaaa tgtaacagaa aattttaaca tgtggaaaaa tgacatggtg | 300 |
| gatcagatgc atgaggatat aatcagttta tgggatcaaa gcctaaagcc atgtgtaaag | 360 |
| ttgaccccac tctgtgtcac tttaaattgt agtaatgtta atgctaccaa tactaccaat | 420 |
| aataccatga gggagaaat aaaaaattgc tctttcaatg caaccacaga ataagagat | 480 |
| aagaaacaga agtgtatgc acttttttat agacttgata tagtaccact taatgagaat | 540 |
| aatagcaatt ctagtgagta tagattaata aattgtaata cctcagccat aacacaagcc | 600 |
| tgtccaaagg tctcttttga cccaattcct atacattatt gtgctccagc tggttatgcg | 660 |

| | |
|---|---|
| attctaaagt gtaataataa gacattcaat ggaacaggac catgcaataa tgtcagcaca | 720 |
| gtacaatgta cacatggaat taagccagtg gtatcaactc aactactgtt aaatggtagc | 780 |
| ctagcagaag aagagataat aattagatct gaaaatctga caaacaatgt caaaacaata | 840 |
| atagtacatc ttaatgaatc tgtagaaatt gtgtgtacaa gacccaacaa taatacaaga | 900 |
| aaaagtataa ggataggacc aggacaaaca ttctatgcaa caggagacat aataggagac | 960 |
| ataagacaag cacattgtaa cattagtgaa gaggaatgga ataaaacttt acaaagggta | 1020 |
| ggtaaaaaat tagaagaaca cttccctaat aaaacaataa aatttgaacc atcctcagga | 1080 |
| ggggacctag aaattacaac acatagcttt aattgtagag gagaattttt ctattgcaat | 1140 |
| acatcaaaac tgtttaatag tacatacaat ggtacaaata gtacaaatac aaccatcaca | 1200 |
| ctcccatgca gaataaaaca aattataaac atgtggcagg aggtaggacg agcaatgtat | 1260 |
| gcccctccca ttgcaggaaa cataacatgt aaatcaaata tcacaggact actattggta | 1320 |
| cgtgatggag gaaaaaataa cacaaataac acagagatat tcagacctgg aggaggagat | 1380 |
| atgagggaca attggagaag tgaattatat aaatataaag tggtagaaat taagccattg | 1440 |
| ggaatagcac ccactaaggc aaaaaggaga gtggtggaga gagaaaaaag agcagtggga | 1500 |
| ataggagctg tgttccttgg gttcttggga gcagcaggaa gcactatggg cgcggcgtca | 1560 |
| ataacgctga cggtacaggc cagacaattg ttgtctggta tagtgcaaca gcaaagcaat | 1620 |
| ttgctgaggg ctatagaggc gcaacagcat atgttgcaac tcacggtctg gggcattaag | 1680 |
| cagctccaga caagagtcct ggctatagaa agatacctaa aggatcaaca gctcctaggg | 1740 |
| atttggggct gctctggaaa actcatctgc accactgctg tgccttggaa ctctagttgg | 1800 |
| agtaataaat ctcaagaaga tatttgggat aacatgacct ggatgcagtg ggatagaaaa | 1860 |
| attagtaatt acacagacac aatatacagg ttgcttgaag actcgcaaaa ccagcaggaa | 1920 |
| caaaatgaaa aagatttact agcattggac agttggaaaa atctgtggaa ttggtttgac | 1980 |
| ataacaaatt ggctgtggta tataaaaata ttcataatga tagtaggagg cttgataggt | 2040 |
| ttaagaataa tttttgctgt gctttctata gtgaatagag ttaggcaggg atactcacct | 2100 |
| ttgtcgtttc agacccttac cccaaacccg aggggacccg acaggctcgg aagaatcgaa | 2160 |
| gaagaaggtg gagagcaaga cagagacaga tccattcgat tagtgagcgg attcttagca | 2220 |
| cttgcctggg acgacctgcg gagcctgtgc ctcttcagct accaccgatt gagagacttc | 2280 |
| atattggtgg cagcgagagc ggtggaactt ctgggacgca gcagtctcag gggactacag | 2340 |
| aggggggtggg aagcccttaa gtatctggga agtcttgtgc agtattgggg tctggagcta | 2400 |
| aaaaagagtg ctattagtct gcttgatacc atagcaatag cagtagctga aggaacagat | 2460 |
| aggattatag aattaataca aagaatttgt agagctatcc gcaacatacc tagaagaata | 2520 |
| agacagggct ttgaagcagc tttgcaa | 2547 |

<210> SEQ ID NO 75
<211> LENGTH: 2550
<212> TYPE: DNA
<213> ORGANISM: Artificial sequence
<220> FEATURE:
<223> OTHER INFORMATION: Minimum of means reconstructions for clade C
      env gene

<400> SEQUENCE: 75

| | |
|---|---|
| atgagagtga gggggatact gaggaattgt caacaatggt ggatatgggg catcttaggc | 60 |
| ttttggatgt taatgatttg taatgtggtg gggaacttgt gggtcacagt ctattatggg | 120 |

```
gtacctgtgt ggaaagaagc aaaaactact ctattctgtg catcagatgc taaagcatat    180
gagaaagaag tgcataatgt ctgggctaca catgcctgtg tacccacaga ccccaaccca    240
caagaaatgt ttttggaaaa tgtaacagaa aattttaaca tgtggaaaaa tgacatggtg    300
gatcagatgc atgaggatat aatcagttta tgggatcaaa gcctaaagcc atgtgtaaag    360
ttgaccccac tctgtgtcac tttaaattgt agtaatgtta atactaccaa tactaccaat    420
aataccatga aggagaaat aaaaaattgc tctttcaatg taaccacaga actaagagat    480 aagaaaaga aagagtatgc actttttat agacttgata tagtaccact taatgagaat    540
aataacaatt ctagtgagta tagattaata aattgtaata cctcagccat aacacaagcc    600
tgtccaaagg tctcttttga cccaattcct atacattatt gtgctccagc tggttatgcg    660
attctaaagt gtaataataa gacattcaat ggaacaggac catgcaataa tgtcagcaca    720
gtacaatgta cacatggaat taagccagtg gtatcaactc aactactgtt aaatggtagc    780
ctagcagaag aagagataat aattagatct gaaaatctga caaacaatgc caaaacaata    840
atagtacatc ttaatgaatc tgtagaaatt gtgtgtacaa gacccaacaa taatacaaga    900
aaaagtataa ggataggacc aggacaaaca ttctatgcaa caggagacat aataggagac    960
ataagacaag cacattgtaa cattagtgaa gaggaatgga ataaaacttt acaagggta    1020 ggtaaaaaat tagaagaaca cttccctaat aaaacaataa aatttgaacc atcctcagga    1080
ggggacctag aaattacaac acatagcttt aattgtagag gagaattttt ctattgcaat    1140
acatcaaaac tgtttaatag tacatacaat ggtacaaata gtacaaattc aaccatcaca    1200
ctccaatgca gaataaaaca aattataaac atgtggcagg aggtaggacg agcaatgtat    1260
gcccctccca ttgcaggaaa cataacatgt aaatcaaata tcacaggact actattggta    1320
cgtgatggag gaaaaaatga cacaaatgac acagagatat tcagacctgg aggaggagat    1380
atgagggaca attggagaag tgaattatat aaatataaag tggtagaaat taagccattg    1440
ggaatagcac ccactaaggc aaaaaggaga gtggtggaga gagaaaaaag agcagtggga    1500
ataggagctg tgttccttgg gttcttggga gcagcaggaa gcactatggg cgcagcgtca    1560
ataacgctga cggtacaggc cagacaattg ttgtctggta tagtgcaaca gcaaagcaat    1620
ttgctgaggg ctatagaggc gcaacagcat atgttgcaac tcacggtctg ggcattaag    1680 cagctccaga caagagtcct ggctatagaa agatacctaa aggatcaaca gctcctaggg    1740
atttggggct gctctggaaa actcatctgc accactgctg tgccttggaa ctctagttgg    1800
agtaataaat ctcaagagga tatttgggat aacatgacct ggatgcagtg ggatagagaa    1860
attagtaatt acacagacac aatatacagg ttgcttgaag actcgcaaaa ccagcaggaa    1920
caaaatgaaa aagatttact agcattggac agttggaaaa atctgtggaa ttggtttgac    1980
ataacaaatt ggctgtggta tataaaaata ttcataatga tagtaggagg cttgataggt    2040
ttaagaataa ttttgctgt gctttctata gtgaatagag ttaggcaggg atactcacct    2100
ttgtcgtttc agacccttac cccaaacccg aggggacccg acaggctcgg aagaatcgaa    2160
gaagaaggtg gagagcaaga cagagacaga tccattcgat tagtgagcgg attcttagca    2220
cttgcctggg acgacctgcg gagcctgtgc ctcttcagct accaccgatt gagagacttc    2280
atattggtgg cagcgagagc ggtggaactt ctgggacgca gcagtctcag ggactacag    2340 agggggtggg aagcccttaa gtatctggga agtcttgtgc agtattgggg tctggagcta    2400
aaaaagagtg ctattagtct gcttgatacc atagcaatag cagtagctga aggaacagat    2460
```

<210> SEQ ID NO 76
<211> LENGTH: 618
<212> TYPE: DNA
<213> ORGANISM: Artificial sequence
<220> FEATURE:
<223> OTHER INFORMATION: Most recent common ancestor reconstructions of
      clade C nef gene

<400> SEQUENCE: 76

```
atgggggggca agtggtcaaa agcagtata gttggatggc ctgctgtaag agaaagaata    60
agacgaactg ctccagcagc agaaggagta ggagcagcgt ctcaagactt agataaacat   120
ggagcactta caagcagcaa cacagccgcc actaatgctg attgtgcctg gctggaagca   180
caagaggagg aagaagtagg ctttccagtc agacctcagg tgcctttaag accaatgact   240
tataagggag cagtcgatct cagcttcttt ttaaaagaaa agggggggact ggaagggtta   300
attactcta agaaaaggca agagatcctt gatttgtggg tctatcacac acaaggctac   360
ttccctgatt ggcaaaacta cacaccggga ccagggatca gatttccact gacctttgga   420
tggtgcttca agctagtgcc agttgaccca agggaagtag aagaggccaa tgaaggagag   480
aacaactgct tgctacaccc tatgagccag catggaatgg aggatgaaga cagagaagta   540
ttaaagtgga gtttgacag tcacctagca cgcagacaca tggcccgcga gctacatccg   600
gagtattaca aagactgc                                                 618
```

<210> SEQ ID NO 77
<211> LENGTH: 624
<212> TYPE: DNA
<213> ORGANISM: Artificial sequence
<220> FEATURE:
<223> OTHER INFORMATION: Least squares and minimum of means
      reconstructions of clade C nef gene

<400> SEQUENCE: 77

```
atgggggggca agtggtcaaa agcagtata gttggatggc ctgctgtaag agaaagaata    60
agacgaactg agccagcagc agagggagta ggagcagcgt ctcaagactt agataaacat   120
ggagcactta caagcagcaa cacagccgcc aataatgctg attgtgcctg gctggaagca   180
caagaggagg aagaagaagt aggctttcca gtcagacctc aggtgccttt aagaccaatg   240
acttataagg gagcattcga tctcagcttc tttttaaaag aaaaggggggg actggaaggg   300
ttaatttact ctaagaaaag gcaagagatc cttgatttgt gggtctatca cacacaaggc   360
tacttccctg attggcaaaa ctacacaccg ggaccagggg tcagatatcc actgaccttt   420
ggatggtgct tcaagctagt gccagttgac ccaagggaag tagaagaggc caacgaagga   480
gagaacaact gtttgctaca ccctatgagc cagcatggaa tggaggatga agacagagaa   540
gtattaaagt ggaagtttga cagtcaccta gcacgcagac acatggcccg cgagctacat   600
ccggagtatt acaaagactg ctga                                          624
```

<210> SEQ ID NO 78
<211> LENGTH: 3000
<212> TYPE: DNA
<213> ORGANISM: Artificial sequence
<220> FEATURE:
<223> OTHER INFORMATION: Most recent common ancestor reconstructions of
      clade C pol gene

<400> SEQUENCE: 78

```
tttttttaggg aaaatttggc cttcccacaa ggggaggcca gggaatttcc ttcagagcag      60
accagagcca acagccccac cagcagagag cttcaggttc gaggagacaa ccccgctcc      120
gaagcaggag ccgaaagaca gggaaccctt aacttccctc aaatcactct ttggcagcga     180
ccccttgtct caataaaagt aggggccag ataaaggaag ctctattaga tacaggagca      240
gatgatacag tattagaaga cataaatttg ccaggaaaat ggaaaccaaa aatgataggg      300
ggaattggag gttttatcaa gtaagacag tatgatcaaa tacttataga aatttgtgga      360
aaaaaggcta taggtacagt attagtagga cctacacctg tcaacataat tggaagaaat      420
atgttgactc agcttggttg cactctaaat tttccaatta gtcctattga aactgtacca      480
gtaaaattaa agccaggaat ggatggccca aaggttaaac aatggccatt gacagaagag      540
aaaataaaag cattaacagc aatttgtgaa gaaatggaaa aggaaggaaa aattacaaaa      600
attgggcctg aaaatccata taacactcca gtatttgcca taaaaaagaa ggacagtact      660
aagtggagaa aattagtaga tttcagagaa ctcaataaaa gaactcaaga cttctgggaa      720
gttcaattag gaataccaca cccagcaggg ttaaaaaaga aaaaatcagt aacagtactg      780
gatgtggggg atgcatattt ttcagttcct ttagatgaag acttcaggaa atatactgca      840
ttcaccatac ctagtataaa caatgaaaca ccagggatta gatatcaata taatgtgctt      900
ccacagggat ggaaaggatc accagcaata ttccagagta gcatgacaaa aatcttagag      960
ccctttaggg cacaaaaccc agaaatagtt atctatcaat acatggatga cttgtatgta     1020
ggatctgact tagaaatagg gcaacataga gcaaaaatag aggagttaag agaacatcta     1080
ttgaaatggg gatttaccac accagacaag aaacatcaga agaaccccc atttctttgg     1140
atggggtatg aactccatcc tgacaaatgg acagtacagc ctatacagct gccagaaaag     1200
gatagctgga ctgtcaatga tatacagaag ttagtgggaa aattaaactg gcaagtcag     1260
atttacccag ggattaaagt aaggcaactg tgtaaactcc ttaggggagc caaagcacta     1320
acagacatag taccactgac tgaagaagca gaattagaat tggcagagaa cagggaaatt     1380
ctaaaagaac cagtacatgg agtatattat gacccatcaa aagacttaat agctgaaata     1440
cagaaacagg ggcatgacca atggacatat caaatttacc aagaaccatt caaaaatctg     1500
aaaacaggaa agtatgcaaa aatgaggtct gcccacacta atgatgtaaa acaattaaca     1560
gaagcagtgc aaaaaatagc catggaaagc atagtaatat ggggaaagac tcctaaattt     1620
agactaccca tccaaaaaga aacatgggag acatggtgga cagactattg gcaagccacc     1680
tggattcctg agtgggagtt tgttaatacc cctcccctag taaaattatg gtaccagcta     1740
gaaaaagaac ccatagcagg agcagaaact ttctatgtag atggggcagc taatagggaa     1800
actaaactag gaaaagcagg gtatgttact gacaaaggaa gacagaaagt tgtttctcta     1860
actgaaacaa caaatcagaa gactgaatta caagcaattc agctagcttt gcaggattca     1920
ggatcagaag taaacatagt aacagactca caatatgcat taggaatcat tcaagcacaa     1980
ccagataaga gtgaatcaga gttagtcaat caaataatag agcagttaat aaaaaaggaa     2040
aaggtctacc tgtcatgggt accagcacat aaaggaattg gaggaaatga caagtagat      2100
aaattagtaa gttctggaat caggaaagtg ctgtttctag atggaataga taaagctcaa     2160
gaagaacatg aaaaatatca cagcaattgg agagcaatgg ctagtgagtt taatctgcca     2220
cccatagtag caaagaaat agtagctagc tgtgataaat gtcagctaaa aggggaagcc     2280
atgcatggac aagtagactg tagtccaggg atatggcaat tagattgtac acatttagaa     2340
```

| | |
|---|---|
| ggaaaagtta tcctggtagc agtccatgta gccagtggct acatagaagc agaagttatc | 2400 |
| ccagcagaaa caggacagga aacagcatac tttatattaa aattagcagg aagatggcca | 2460 |
| gtaaaagtaa tacatacaga caatggcagc aatttcacca gtgctgcagt taaggcagcc | 2520 |
| tgttggtggg caggtatcca acaggaattt ggaattccct acaatcccca aagtcaggga | 2580 |
| gtagtagaat ccatgaataa agaattaaag aaaatcatag gcaggtaag agatcaagct | 2640 |
| gagcacctta agacagcagt acaaatggca gtattcattc acaattttaa agaaaaggg | 2700 |
| gggattgggg ggtacagtgc aggggaaaga ataatagaca taatagcaac agacatacaa | 2760 |
| actaaagaat tacaaaaaca aattataaaa attcaaaatt ttcgggttta ttacagagac | 2820 |
| agcagagacc ctgtttggaa aggaccagcc aaactactct ggaaaggtga aggggcagta | 2880 |
| gtaatacaag acaatagtga cataaaggta gtaccaagga ggaaagcaaa gatcattagg | 2940 |
| gattatggaa aacagatggc aggtgctgat tgtgtggcag gtagacagga tgaagattag | 3000 |

<210> SEQ ID NO 79
<211> LENGTH: 2999
<212> TYPE: DNA
<213> ORGANISM: Artificial sequence
<220> FEATURE:
<223> OTHER INFORMATION: Least squares reconstruction for clade c pol
      gene

<400> SEQUENCE: 79

| | |
|---|---|
| tttttaggg aaaatttggc cttcccacaa ggggaggcca gggaatttcc ttcagagcag | 60 |
| accagagcca acagccccac cagcagagag cttcaggttc gaggagacaa ccccgctcc | 120 |
| gaagcaggag ccgaaagaca gggaacccctt aacttccctc aaatcactct ttggcagcga | 180 |
| cccccttgtct caataaaagt aggggccag ataaaggagg ctctcttaga cacaggagca | 240 |
| gatgatacag tattagaaga aataaatttg ccaggaaaat ggaaaccaaa atgatagga | 300 |
| ggaattggag gttttatcaa agtaagacag tatgatcaaa tacttataga aatttgtgga | 360 |
| aaaaaggcta taggtacagt attagtagga cctacacctg tcaacataat tggaagaaat | 420 |
| atgttgactc agcttggatg cacactaaat tttccaatta gtcccattga aactgtacca | 480 |
| gtaaaattaa agccaggaat ggatggccca aaggttaaac aatggccatt gacagaagag | 540 |
| aaaataaaac attaacagca atttgtgaag aaatggagaa ggaaggaaaa attacaaaaa | 600 |
| ttgggcctga aaatccatat aacactccag tatttgccat aaaaaagaag gacagtacta | 660 |
| agtggagaaa attagtagat ttcagggaac tcaataaaag aactcaagac ttttgggaag | 720 |
| ttcaattagg aataccacac ccagcagggt taaaaagaa aaaatcagtg acagtactgg | 780 |
| atgtggggga tgcatatttt tcagttcctt tagatgaagg cttcaggaaa tatactgcat | 840 |
| tcaccatacc tagtataaac aatgaaacac cagggattag atatcaatat aatgtgcttc | 900 |
| cacagggatg gaaaggatca ccagcaatat tccagagtag catgacaaaa atcttagagc | 960 |
| ccttaggc acaaaatcca gaaatagtca tctatcaata tatggatgac ttgtatgtag | 1020 |
| gatctgactt agaaataggg caacatagag caaaaataga ggagttaaga gaacatctat | 1080 |
| taaagtgggg atttaccaca ccagacaaga acatcagaa agaaccccca tttctttgga | 1140 |
| tggggtatga actccatcct gacaaatgga cagtacagcc tatacagctg ccagaaaagg | 1200 |
| atagctggac tgtcaatgat atacagaagt tagtgggaaa attaaactgg gcaagtcaga | 1260 |
| tttacccagg gattaaagta aggcaacttt gtaaactcct tagggggggcc aaagcactaa | 1320 |
| cagacatagt accactaact gaagaagcag aattagaatt ggcagagaac agggaaattc | 1380 | taaaagaacc agtacatgga gtatattatg acccatcaaa agacttgata gctgaaatac 1440
agaaacaggg gcatgaccaa tggacatatc aaatttacca agaaccattc aaaaatctga 1500
aaacagggaa gtatgcaaaa atgaggactg cccacactaa tgatgtaaaa cagttaacag 1560
aggcagtgca aaaaatagcc atggaaagca tagtaatatg ggaaagact cctaaattta 1620
gactacccat ccaaaaagaa acatgggaga catggtggac agactattgg caagccacct 1680
ggattcctga gtgggagttt gttaataccc ctcccctagt aaaattatgg taccagctgg 1740
agaaagaacc catagcagga gcagaaactt tctatgtaga tggagcagct aatagggaaa 1800
ctaaaatagg aaaagcaggg tatgttactg acagaggaag gcagaaaatt gtttctctaa 1860
ctgaaacaac aaatcagaag actgaattac aagcaattca gctagctttg caagattcag 1920
gatcagaagt aaacatagta acagactcac agtatgcatt aggaatcatt caagcacaac 1980
cagataagag tgaatcagag ttagtcaacc aaataataga acaattaata aaaaaggaaa 2040
gggtctacct gtcatgggta ccagcacata aaggaattgg aggaaatgaa caagtagata 2100
aattagtaag tagtggaatc aggaaagtgc tgtttctaga tggaatagat aaggctcaag 2160
aagagcatga aaagtatcac agcaattgga gagcaatggc tagtgagttt aatctgccac 2220
ccatagtagc aaaagaaata gtagctagct gtgataaatg tcagctaaaa ggggaagcca 2280
tacatggaca agtagactgt agtccaggga tatggcaatt agattgtaca catttagaag 2340
gaaaaatcat cctggtagca gtccatgtag ccagtggcta catagaagca gaggttatcc 2400
cagcagaaac aggacaagaa acagcatact ttatactaaa attagcagga agatggccag 2460
tcaaagtaat acatacagac aatggcagta atttcaccag tgctgcagtt aaggcagcct 2520
gttggtgggc aggtatccaa caggaatttg gaattcccta caatccccaa agtcagggag 2580
tagtagaatc catgaataaa gaattaaaga aaatcatagg gcaggtaaga gatcaagctg 2640
agcaccttaa gacagcagta caaatggcag tattcattca caattttaaa agaaaagggg 2700
ggattggggg gtacagtgca ggggaaagaa taatagacat aatagcaaca gacatacaaa 2760
ctaaagaatt acaaaaacaa attataaaaa ttcaaaattt tcgggtttat tacagagaca 2820
gcagagaccc tatttggaaa ggaccagcca aactactctg gaaaggtgaa ggggcagtag 2880
taatacaaga taatagtgac ataaaggtag taccaaggag gaaagcaaaa atcattaagg 2940
actatggaaa acagatggca ggtgctgatt gtgtggcagg tagacaggat gaagattag 2999


<210> SEQ ID NO 80
<211> LENGTH: 3000
<212> TYPE: DNA
<213> ORGANISM: Artificial sequence
<220> FEATURE:
<223> OTHER INFORMATION: Minimum of means reconstructions of clade c pol gene

<400> SEQUENCE: 80
tttttaggg aaaatttggc cttcccacaa ggggaggcca gggaatttcc ttcagagcag 60
accagagcca acagccccac cagcagagag cttcaggttc gaggagacaa ccccctctcc 120
gaagcaggag ccgaaagaca gggaaccctt aacttccctc aaatcactct ttggcagcga 180
ccccttgtca caataaaagt agggggacag ctaaaggagg ctctcttaga cacaggagca 240
gatgatacag tattagaaga aataaatttg ccaggaaaat ggaaaccaaa aatgatagga 300
ggaattggag gttttatcaa agtaagacag tatgatcaaa tacttataga aatttgtgga 360
aaaaaggcta taggtacagt actagtagga cctacacctg tcaacataat tggaagaaat 420

-continued

```
atgttgactc agcttggatg cacactaaat tttccaatta gtcccattga aactgtacca      480
gtaaaattaa agccaggaat ggatggccca aaggtcaaac aatggccatt gacagaagag      540
aaaataaaag cattaacagc aatttgtgaa gaaatggaga aggaaggaaa aattacaaaa      600
attgggcctg aaaatccata taacactcca gtatttgcca taaaaaagaa ggacagtact      660
aagtggagaa aattagtaga tttcagggaa ctcaataaaa gaactcaaga cttttgggaa      720
gttcaattag ggataccaca cccagcaggg ttaaaaaaga aaaaatcagt gacagtactg      780
gatgtggggg atgcatattt ttcagttcct ttagatgaag cttcaggaa atatactgca       840 ttcaccatac ctagtataaa caatgaaaca ccagggatta gatatcaata taatgtgctt      900
ccacagggat ggaaaggatc accagcaata ttccagagta gcatgacaaa aatcttagag      960
ccctttaggg cacaaaatcc agaaatagtt atctatcaat atatggatga cttgtatgta     1020
ggatctgact tagaaatagg gcaacataga gcaaaaatag aggagttaag agaacatcta     1080
ttgaagtggg gatttaccac accagacaag aaacatcaga agaaccccc atttctttgg      1140 atggggtatg aactccatcc tgacaaatgg acagtacagc ctatacagct gccagaaaag     1200
gatagctgga ctgtcaatga tatacagaag ttagtgggaa aattaaactg ggcaagtcag     1260
atttacccag ggattaaagt aaggcaactg tgtaaactcc ttaggggagc caaagcacta     1320
acagacatag taccactaac tgaagaagca gaattagaat tggcagagaa cagggaaatt     1380
ctaaaagaac cagtacatgg agtatattat gacccatcaa aagacttaat agctgaaata     1440
cagaaacagg ggcatgacca atggacatat caaatttacc aagaaccatt caaaaatctg     1500
aaaacaggga gtatgcaaa atgaggact gcccacacta atgatgtaaa acagttaaca       1560
gaggcagtgc aaaaaatagc catggaaagc atagtaatat ggggaaagac tcctaaattt     1620
agattaccca tccagaaaga acatgggag gcatggtgga cagactattg caagccacc      1680 tggattcctg agtgggagtt tgttaatacc cctccctag taaaattatg gtaccagctg      1740
gagaaagaac ccatagcagg agcagaaact ttctatgtag atggagcagc taatagggaa     1800
actaaaatag gaaaagcagg gtatgttact gacagaggaa ggcagaaaat tgtttctcta     1860
actgaaacaa caaatcagaa gactgaatta caagcaattc agctagcttt gcaggattca     1920
ggatcagaag taaacatagt aacagactca cagtatgcat taggaatcat tcaagcacaa     1980
ccagataaga gtgaatcaga gttagtcaat caaataatag aacagttaat aaaaaaggaa     2040
agggtctacc tgtcatgggt accagcacat aaaggaattg gaggaaatga acaagtagat     2100
aaattagtaa gtagtggaat caggaaagtg ctgtttctag atggaataga taaggctcaa     2160
gaagagcatg aaaaatatca cagcaattgg agagcaatgg ctagtgagtt taatctgcca     2220
cccatagtag caaaagaaat agtagctagc tgtgataaat gtcagctaaa aggggaagcc     2280
atacatggac aagtagactg tagtccaggg atatggcaat tagattgtac acatttagaa     2340
ggaaaaatca tcctggtagc agtccatgta gccagtggct acatagaagc agaggttatc     2400
ccagcagaaa caggacaaga aacagcatac tttatactaa aattagcagg aagatggcca     2460
gtcaaagtaa tacatacaga caatggcagt aatttcacca gtgctgcagt taaagcagcc     2520
tgttggtggg caggtatcca acaggaattt ggaattccct acaatcccca aagtcaggga     2580
gtagtagaat ccatgaataa agaattaaag aaaatcatag gcaggtaag agatcaagct      2640 gagcacctta agacagcagt acaaatggca gtattcattc acaattttaa aagaaaaggg     2700
gggattgggg ggtacagtgc aggggaaaga ataatagaca taatagcaac agacatacaa     2760
```

```
actaaagaat tacaaaaaca aattataaaa attcaaaatt ttcgggttta ttacagagac    2820
agcagagacc ctatttggaa aggaccagcc aaactactct ggaaaggtga aggggcagta    2880
gtaatacaag ataacagtga cataaaggta gtaccaagga ggaaagcaaa aatcattaag    2940
gactatggaa aacagatggc aggtgctgat tgtgtggcag gtagacagga tgaagattag    3000
```

<210> SEQ ID NO 81
<211> LENGTH: 381
<212> TYPE: DNA
<213> ORGANISM: Artificial sequence
<220> FEATURE:
<223> OTHER INFORMATION: Most common recent ancestor reconstructions of
    clade c rev gene

<400> SEQUENCE: 81

```
atggcaggaa gaagcggaga cagcgacgaa gcgctcctcc aagcagtgag gatcatcaaa     60
atcctatatc aaagcaaccc ttaccccaaa cccgagggga cccgacaggc tcgaaggaat    120
cgaagaagaa ggtggagagc aagacagaga cagatccatt cgattagtga gcggattctt    180
agcacttgcc tgggacgacc tgcggagcct gtgcctcttc agctaccacc gcttgagaga    240
cttcatcttg attgcagcga ggactgtgga acttctggga cgcagcagtc tcaggggact    300
acagaggggg tgggaagccc ttaaatatct gggaagcctt gtgcagtatt ggggtcagga    360
gctaaaaaag agtgctatta g                                             381
```

<210> SEQ ID NO 82
<211> LENGTH: 381
<212> TYPE: DNA
<213> ORGANISM: Artificial sequence
<220> FEATURE:
<223> OTHER INFORMATION: Least squares of reconstructions of clade c rev
    gene

<400> SEQUENCE: 82

```
atggcaggaa gaagcggaga cagcgacgaa gcgctcctcc aagcagtgag gatcatcaaa     60
atcttatatc aaagcaaccc ttaccccaaa cccgagggga cccgacaggc tcggaagaat    120
cgaagaagaa ggtggagagc aagacagaga cagatccatt cgattagtga gcggattctt    180
agcacttgcc tgggacgacc tgcggagcct gtgcctcttc agctaccacc gattgagaga    240
cttcatattg gtgacagcga gagcagtgga acttctggga cgcagcagtc tcaggggact    300
acagaggggg tgggaagccc ttaagtatct gggaagtctt gtgcagtatt gggtctgga     360 actaaaaaag agtgctatta g                                             381
```

<210> SEQ ID NO 83
<211> LENGTH: 381
<212> TYPE: DNA
<213> ORGANISM: Artificial sequence
<220> FEATURE:
<223> OTHER INFORMATION: Minimum of means reconstruction of clade C rev
    gene

<400> SEQUENCE: 83

```
atggcaggaa gaagcggaga cagcgacgaa gcgctcctcc aagcagtgag gatcatcaaa     60
atcctatatc aaagcaaccc ttaccccaaa cccgagggga cccgacaggc tcggaagaat    120
cgaagaagaa ggtggagagc aagacagaga cagatccatt cgattagtga gcggattctt    180
agcacttgcc tgggacgacc tgcggagcct gtgcctttc  agctaccacc gattgagaga    240
cttcatattg gtgacagcga gagcagtgga acttctggga cgcagcagtc tcaggggact    300
```

<210> SEQ ID NO 84
<211> LENGTH: 306
<212> TYPE: DNA
<213> ORGANISM: Artificial sequence
<220> FEATURE:
<223> OTHER INFORMATION: Most recent common ancestor reconstruction of clade C tat gene sequence

<400> SEQUENCE: 84

```
acagaggggg tgggaagccc ttaagtatct gggaagtctt gtgcagtatt ggggtctgga    360
actaaaaaag agtgctatta g                                              381
```

<210> SEQ ID NO 84
<211> LENGTH: 306
<212> TYPE: DNA
<213> ORGANISM: Artificial sequence
<220> FEATURE:
<223> OTHER INFORMATION: Most recent common ancestor reconstruction of
      clade C tat gene sequence

<400> SEQUENCE: 84

```
atggagccag tagatcctaa cctagagccc tggaaccatc caggaagtca gcctaaaact     60
gcttgtaata atgttattg taaaaaatgt agctatcatt gtctagtttg ctttctgaca     120
aaaggcttag gcatttccta tggcaggaag aagcggagac agcgacgaag agctcctcca   180
agcagtgagg atcatcaaaa tcctatatca aagcaaccct tatcccaaac ccgaggggac   240
ccgacaggct cggaggaatc gaagaagaag gtggagagca agacagagac agatccgtgc   300
gattag                                                              306
```

<210> SEQ ID NO 85
<211> LENGTH: 306
<212> TYPE: DNA
<213> ORGANISM: Artificial sequence
<220> FEATURE:
<223> OTHER INFORMATION: Least squares of reconstruction of clade C tat
      gene sequence

<400> SEQUENCE: 85

```
atggagccag tagatcctaa cctagagccc tggaaccatc caggaagtca gcctaaaact     60
ccttgtaata agtgttattg taaacactgt agctatcatt gtctagtttg ctttcagaca    120
aaaggcttag gcatttccta tggcaggaag aagcggagac agcgacgaag cgctcctcca   180
agcagtgagg atcatcaaaa tcctatatca aagcaaccct taccccaaac ccgaggggac   240
ccgacaggct cggaagaatc gaagaagaag gtggagagca agacagagac agatccattc   300
gattag                                                              306
```

<210> SEQ ID NO 86
<211> LENGTH: 306
<212> TYPE: DNA
<213> ORGANISM: Artificial sequence
<220> FEATURE:
<223> OTHER INFORMATION: Minimum of means reconstructions of clade C tat
      gene sequence

<400> SEQUENCE: 86

```
atggagccag tagatcctaa cctagagccc tggaaccatc caggaagtca gcctaaaact     60
ccttgtaata agtgttattg taaacactgt agctatcatt gtctagtttg ctttcagaca    120
aaaggcttag gcatttccta tggcaggaag aagcggagac agcgacgaag cgctcctcca   180
agcagtgagg atcatcaaaa tcctatatca aagcaaccct taccccaaac ccgaggggac   240
ccgacaggct cggaggaatc gaagaagaag gtggagagca agacagagac agatccattc   300
gattag                                                              306
```

<210> SEQ ID NO 87
<211> LENGTH: 579
<212> TYPE: DNA
<213> ORGANISM: Artificial sequence
<220> FEATURE:

```
<223> OTHER INFORMATION: Most recent common ancestor reconstructions of
      clade C vif gene sequence

<400> SEQUENCE: 87
atggaaaaca gatggcaggt gctgattgtg tggcaggtag acaggatgaa gattagaaca      60
tggaatagtt tagtaaaaca ccatatgtat gtttcaagga gagctaaagg atggtttat     120 agacatcact atgaaagcag acatccaaaa ataagttcag aagtacacat cccattaggg     180
gatgctagat tagtaataaa aacatattgg ggtttgcata caggagaaag agattggcat     240
ttgggtcatg gagtctccat agaatggaga ctgagaagat atagcacaca agtagaccct     300
ggcctggcag accaactaat tcatatgcat tattttgatt gttttgcaga ctctgccata     360
aggaaagcca tattaggaca tatagttagc cctaggtgtg actatcaagc aggacataac     420
aaggtaggat ctctacaata cttggcactg acagcattaa taaaaccaaa aaagataaag     480
ccacctctgc ctagtgttaa gaaattagta gaggatagat ggaacaagcc ccagaagacc     540
aggggccaca gagggagcca taatgaat ggacactag                              579

<210> SEQ ID NO 88
<211> LENGTH: 579
<212> TYPE: DNA
<213> ORGANISM: Artificial sequence
<220> FEATURE:
<223> OTHER INFORMATION: Least squares of reconstruction of clade C vif
      gene sequence

<400> SEQUENCE: 88
atggaaaaca gatggcaggt gctgattgtg tggcaggtag acaggatgaa gattagaaca      60
tggaatagtt tagtaaagca ccatatgtat gtttcaagga gagctaatgg atggttttac     120
agacatcatt atgaaagcag acatccaaaa gtaagttcag aagtacacat cccattaggg     180
gatgctagat tagtaataaa aacatattgg ggtttgcaaa caggagaaag agattggcat     240
ttgggtcatg gagtctccat agaatggaga ttgagaagat atagcacaca agtagaccct     300
ggcctggcag accagctaat tcatatgcat tattttgatt gttttgcaga ctctgccata     360
agaaaagcca tattaggaca catagttatt cctaggtgtg actatcaagc aggacataat     420
aaggtaggat ctctacaata cttggcactg acagcattga taaaaccaaa aaagataaag     480
ccacctctgc ctagtgttag gaaattagta gaggatagat ggaacaagcc ccagaagacc     540
aggggccgca gagggaacca tacaatgaat ggacactag                            579

<210> SEQ ID NO 89
<211> LENGTH: 579
<212> TYPE: DNA
<213> ORGANISM: Artificial sequence
<220> FEATURE:
<223> OTHER INFORMATION: Minimum of means center of tree reconstruction
      of clade C vif gene sequence

<400> SEQUENCE: 89
atggaaaaca gatggcaggt gctgattgtg tggcaggtag acaggatgaa gattagaaca      60
tggaatagtt tagtaaagca ccatatgtat gtttcaagga gagctaatgg atggttttac     120
agacatcatt atgaaagcag acatccaaaa gtaagttcag aagtacacat cccattaggg     180
gatgctagat tagtaataaa aacatattgg ggtttgcata caggagaaag agattggcat     240
ttgggtcatg gagtctccat agaatggaga ttgagaagat atagcacaca agtagaccct     300
ggcctggcag accagctaat tcatatgcat tattttgatt gttttgcaga ctctgccata     360
```

```
agaaaagcca tattaggaca catagttatt cctaggtgtg actatcaagc aggacataat    420
aaggtaggat ctctacaata cttggcactg acagcattga taaaaccaaa aaagataaag    480
ccacctctgc ctagtgttag gaaattagta gaggatagat ggaacaagcc ccagaagacc    540
aggggccgca gagggaacca tacaatgaat ggacactag                           579

<210> SEQ ID NO 90
<211> LENGTH: 291
<212> TYPE: DNA
<213> ORGANISM: Artificial sequence
<220> FEATURE:
<223> OTHER INFORMATION: Most recent common ancestor reconstructions for
      clade C vpr gene sequence

<400> SEQUENCE: 90
atggaacaag ccccagaaga ccaggggcca cagagggagc catacaatga atggacacta    60
gagcttttag aggaacttaa gcaggaagct gtcagacatt ttcctagacc atggctccat    120
agcttaggac aacatatcta tgaaacctat ggggatactt gggcgggagt tgaagctata    180
ataagaattc tgcaacaact actgtttatt catttcagaa ttgggtgcca acatagcaga    240
ataggcatta ttcgacagag aagagcaaga atggagcca gtagatccta a              291

<210> SEQ ID NO 91
<211> LENGTH: 291
<212> TYPE: DNA
<213> ORGANISM: Artificial sequence
<220> FEATURE:
<223> OTHER INFORMATION: Least squares center of tree reconstruction of
      clade C vpr gene sequence

<400> SEQUENCE: 91
atggaacaag ccccagaaga ccaggggccg cagagggaac catacaatga atggacacta    60
gagattttag aggaactcaa gcaggaagct gtcagacact ttcctagacc atggctccat    120
agcttaggac aatatatcta tgaaacctat ggggatactt ggacaggagt cgaagctcta    180
ataagaatac tgcaacaact actgtttatt catttcagaa ttgggtgcca gcatagcaga    240
ataggcattt tgcgacagag aagagcaaga atggagcca gtagatccta a              291

<210> SEQ ID NO 92
<211> LENGTH: 291
<212> TYPE: DNA
<213> ORGANISM: Artificial sequence
<220> FEATURE:
<223> OTHER INFORMATION: Minimum of means center of tree reconstruction
      of clade C vpr gene sequence

<400> SEQUENCE: 92
atggaacaag ccccagaaga ccaggggccg cagagggaac catacaatga atggacacta    60
gagcttttag aggaactcaa gcaggaagct gtcagacact ttcctagacc atggctccat    120
agcttaggac aacatatcta tgaaacctat ggggatactt ggacgggagt tgaagctcta    180
ataagaattc tgcaacaact actgtttatt catttcagaa ttgggtgcca gcatagcaga    240
ataggcatta tgcgacagag aagagcaaga atggagcca gtagatccta a              291

<210> SEQ ID NO 93
<211> LENGTH: 261
<212> TYPE: DNA
<213> ORGANISM: Artificial sequence
<220> FEATURE:
<223> OTHER INFORMATION: Most recent common ancestor reconstruction of
      clade C vpu gene sequence
```

<400> SEQUENCE: 93

```
atgttagatt taatagcaag agtagattat agattaggag taggagcatt gatagtagca    60
ctaatcatag caatagttgt gtggaccata gtatatatag aatataggaa attggtaaga   120
caaagaaaaa tagactggtt aattaaaaga attagggaaa gagcagaaga cagtggcaat   180
gagagtgatg gggatacaga ggaattgtca acactggtgg atatggggca tcttaggctt   240
ttggatgtta atgatttgta a                                             261
```

<210> SEQ ID NO 94
<211> LENGTH: 261
<212> TYPE: DNA
<213> ORGANISM: Artificial sequence
<220> FEATURE:
<223> OTHER INFORMATION: Least squares center of tree reconstruction of
       clade C vpu gene sequence

<400> SEQUENCE: 94

```
atgttagatt tactagcaag agtagattat agattaggag taggagcatt gatagtagca    60
ctaatcatag caatagttgt gtggaccata gtatatatag aatataggaa attgttaaga   120
caaagaaaaa tagactggtt aattaaaaga attagggaaa gagcagaaga cagtggcaat   180
gagagtgagg gggatactga ggaattgtca acaatggtgg atatggggca tcttaggctt   240
ttggatgtta atgatttgta a

-continued

```
                65                  70                  75                  80
            Thr Val Ala Thr Leu Tyr Cys Val His Gln Arg Ile Glu Val Arg Asp
                            85                  90                  95
            Thr Lys Glu Ala Leu Asp Lys Ile Glu Glu Gln Asn Lys Ser Gln
                            100                 105                 110
            Gln Lys Thr Gln Gln Ala Glu Ala Ala Asp Gly Lys Val Ser Gln Asn
                            115                 120                 125
            Tyr Pro Ile Val Gln Asn Leu Gln Gly Gln Met Val His Gln Ala Ile
                            130                 135                 140
            Ser Pro Arg Thr Leu Asn Ala Trp Val Lys Val Ile Glu Glu Lys Ala
            145                 150                 155                 160
            Phe Ser Pro Glu Val Ile Pro Met Phe Thr Ala Leu Ser Glu Gly Ala
                            165                 170                 175
            Thr Pro Gln Asp Leu Asn Thr Met Leu Asn Thr Val Gly Gly His Gln
                            180                 185                 190
            Ala Ala Met Gln Met Leu Lys Asp Thr Ile Asn Glu Glu Ala Ala Glu
                            195                 200                 205
            Trp Asp Arg Leu His Pro Val His Ala Gly Pro Val Ala Pro Gly Gln
                            210                 215                 220
            Met Arg Glu Pro Arg Gly Ser Asp Ile Ala Gly Thr Thr Ser Thr Leu
            225                 230                 235                 240
            Gln Glu Gln Ile Ala Trp Met Thr Ser Asn Pro Pro Ile Pro Val Gly
                            245                 250                 255
            Asp Ile Tyr Lys Arg Trp Ile Ile Leu Gly Leu Asn Lys Ile Val Arg
                            260                 265                 270
            Met Tyr Ser Pro Val Ser Ile Leu Asp Ile Lys Gln Gly Pro Lys Glu
                            275                 280                 285
            Pro Phe Arg Asp Tyr Val Asp Arg Phe Phe Lys Thr Leu Arg Ala Glu
                            290                 295                 300
            Gln Ala Thr Gln Asp Val Lys Asn Trp Met Thr Asp Thr Leu Leu Val
            305                 310                 315                 320
            Gln Asn Ala Asn Pro Asp Cys Lys Thr Ile Leu Arg Ala Leu Gly Pro
                            325                 330                 335
            Gly Ala Thr Leu Glu Glu Met Met Thr Ala Cys Gln Gly Val Gly Gly
                            340                 345                 350
            Pro Ser His Lys Ala Arg Val Leu Ala Glu Ala Met Ser Gln Ala Asn
                            355                 360                 365
            Asn Thr Asn Ile Met Met Gln Arg Gly Asn Phe Lys Gly Pro Arg Arg
                            370                 375                 380
            Ile Val Lys Cys Phe Asn Cys Gly Lys Glu Gly His Ile Ala Arg Asn
            385                 390                 395                 400
            Cys Arg Ala Pro Arg Lys Lys Gly Cys Trp Lys Cys Gly Lys Glu Gly
                            405                 410                 415
            His Gln Met Lys Asp Cys Thr Glu Arg Gln Ala Asn Phe Leu Gly Lys
                            420                 425                 430
            Ile Trp Pro Ser His Lys Gly Arg Pro Gly Asn Phe Leu Gln Ser Arg
                            435                 440                 445
            Pro Glu Pro Thr Ala Pro Ala Glu Ser Phe Arg Phe Glu Glu Thr
                            450                 455                 460
            Thr Pro Ala Pro Lys Gln Glu Pro Lys Asp Arg Glu Pro Leu Thr Ser
            465                 470                 475                 480
            Leu Lys Ser Leu Phe Gly Ser Asp Pro Leu Ser Gln
                            485                 490
```

<210> SEQ ID NO 97
<211> LENGTH: 492
<212> TYPE: PRT
<213> ORGANISM: Artificial sequence
<220> FEATURE:
<223> OTHER INFORMATION: Least squares center of tree reconstruction of clade C gag protein sequence

<400> SEQUENCE: 97

```
Met Gly Ala Arg Ala Ser Ile Leu Arg Gly Gly Lys Leu Asp Thr Trp
1               5                   10                  15

Glu Lys Ile Arg Leu Arg Pro Gly Gly Lys Lys His Tyr Met Leu Lys

-continued

```
        355                 360                 365

Asn Thr Asn Ile Met Met Gln Arg Ser Asn Phe Lys Gly Pro Lys Arg
    370                 375                 380

Ile Val Lys Cys Phe Asn Cys Gly Lys Glu Gly His Ile Ala Arg Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430

Ile Trp Pro Ser His Lys Gly Arg Pro Gly Asn Phe Leu Gln Ser Arg
        435                 440                 445

Pro Glu Pro Thr Ala Pro Pro Ala Glu Ser Phe Arg Phe Glu Glu Thr
    450                 455                 460

Thr Pro Ala Pro Lys Gln Glu Pro Lys Asp Arg Glu Pro Leu Thr Ser
465                 470                 475                 480

Leu Lys Ser Leu Phe Gly Ser Asp Pro Leu Ser Gln
                485                 490

<210> SEQ ID NO 98
<211> LENGTH: 493
<212> TYPE: PRT
<213> ORGANISM: Artificial sequence
<220> FEATURE:
<223> OTHER INFORMATION: Minimum of means center of tree reconstruction
      of clade C gag protein sequence

<400> SEQUENCE: 98

Met Gly Ala Arg Ala Ser Ile Leu Arg Gly Gly Lys Leu Asp Thr Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Met Lys Gln Leu
    50                  55                  60

Gln Pro Ala Leu Gln Thr Gly Thr Glu Glu Leu Arg Ser Leu Tyr Asn
65                  70                  75                  80

Thr Val Ala Thr Leu Tyr Cys Val His Glu Lys Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Glu Ala Ala Ala Asp Gly Lys Val Ser Gln
        115                 120                 125

Asn Tyr Pro Ile Val Gln Asn Leu Gln Gly Gln Met Val His Gln Ala
    130                 135                 140

Ile Ser Pro Arg Thr Leu Asn Ala Trp Val Lys Val Ile Glu Glu Lys
145                 150                 155                 160

Ala Phe Ser Pro Glu Val Ile Pro Met Phe Thr Ala Leu Ser Glu Gly
                165                 170                 175

Ala Thr Pro Gln Asp Leu Asn Thr Met Leu Asn Thr Val Gly Gly His
            180                 185                 190

Gln Ala Ala Met Gln Met Leu Lys Asp Thr Ile Asn Glu Glu Ala Ala
        195                 200                 205

Glu Trp Asp Arg Leu His Pro Val His Ala Gly Pro Val Ala Pro Gly
    210                 215                 220
```

```
Gln Met Arg Glu Pro Arg Gly Ser Asp Ile Ala Gly Thr Thr Ser Thr
225                 230                 235                 240

Leu Gln Glu Gln Ile Ala Trp Met Thr Ser Asn Pro Val Pro Val
            245                 250                 255

Gly Asp Ile Tyr Lys Arg Trp Ile Ile Leu Gly Leu Asn Lys Ile Val
            260                 265                 270

Arg Met Tyr Ser Pro Val Ser Ile Leu Asp Ile Lys Gln Gly Pro Lys
        275                 280                 285

Glu Pro Phe Arg Asp Tyr Val Asp Arg Phe Phe Lys Thr Leu Arg Ala
    290                 295                 300

Glu Gln Ala Thr Gln Asp Val Lys Asn Trp Met Thr Asp Thr Leu Leu
305                 310                 315                 320

Val Gln Asn Ala Asn Pro Asp Cys Lys Thr Ile Leu Arg Ala Leu Gly
                325                 330                 335

Pro Gly Ala Thr Leu Glu Glu Met Met Thr Ala Cys Gln Gly Val Gly
            340                 345                 350

Gly Pro Gly His Lys Ala Arg Val Leu Ala Glu Ala Met Ser Gln Ala
        355                 360                 365

Asn Asn Thr Asn Ile Met Met Gln Arg Ser Asn Phe Lys Gly Pro Lys
    370                 375                 380

Arg Ile Val Lys Cys Phe Asn Cys Gly Lys Glu Gly His Ile Ala Arg
385                 390                 395                 400

Asn Cys Arg Ala Pro Arg Lys Lys Gly Cys Trp Lys Cys Gly Lys Glu
                405                 410                 415

Gly His Gln Met Lys Asp Cys Thr Glu Arg Gln Ala Asn Phe Leu Gly
            420                 425                 430

Lys Ile Trp Pro Ser His Lys Gly Arg Pro Gly Asn Phe Leu Gln Ser
        435                 440                 445

Arg Pro Glu Pro Thr Ala Pro Pro Ala Glu Ser Phe Arg Phe Glu Glu
    450                 455                 460

Thr Thr Pro Ala Pro Lys Gln Glu Pro Lys Asp Arg Glu Pro Leu Thr
465                 470                 475                 480

Ser Leu Lys Ser Leu Phe Gly Ser Asp Pro Leu Ser Gln
                485                 490

<210> SEQ ID NO 99
<211> LENGTH: 849
<212> TYPE: PRT
<213> ORGANISM: Artificial sequence
<220> FEATURE:
<223> OTHER INFORMATION: Most recent common ancestor reconstruction of
      clade C gp160 protein sequence

<400> SEQUENCE: 99

Met Arg Val Met Gly Ile Gln Arg Asn Cys Gln Gln Trp Trp Ile Trp
1               5                   10                  15

Gly Ile Leu Gly Phe Trp Met Leu Met Ile Cys Ser Val Val Gly Asn
            20                  25                  30

Leu Trp Val Thr Val T

```
Asn Asp Met Val Asp Gln Met His Glu Asp Ile Ile Ser Leu Trp Asp
            100                 105                 110
Gln Ser Leu Lys Pro Cys Val Lys Leu Thr Pro Leu Cys Val Thr Leu
        115                 120                 125
Asn Cys Thr Asn Val Asn Asn Thr Asn Asn Thr Asn Ser Thr Met Asn
    130                 135                 140
Gly Glu Met Lys Asn Cys Ser Phe Asn Ile Thr Thr Glu Ile Arg Asp
145                 150                 155                 160
Lys Lys Lys Lys Glu Tyr Ala Leu Phe Tyr Arg Leu Asp Ile Val Pro
                165                 170                 175
Leu Asn Glu Asn Asn Asn Thr Ser Glu Tyr Arg Leu Ile Asn Cys
            180                 185                 190
Asn Thr Ser Ala Ile Thr Gln Ala Cys Pro Lys Val Ser Phe Asp Pro
        195                 200                 205
Ile Pro Ile His Tyr Cys Ala Pro Ala Gly Tyr Ala Ile Leu Lys Cys
    210                 215                 220
Asn Asn Lys Thr Phe Asn Gly Thr Gly Pro Cys Lys Asn Val Ser Thr
225                 230                 235                 240
Val Gln Cys Thr His Gly Ile Lys Pro Val Val Ser Thr Gln Leu Leu
                245                 250                 255
Leu Asn Gly Ser Leu Ala Glu Glu Ile Ile Ile Arg Ser Glu Asn
            260                 265                 270
Leu Thr Asn Asn Ala Lys Thr Ile Ile Val Gln Leu Asn Glu Ser Val
        275                 280                 285
Glu Ile Val Cys Thr Arg Pro Asn Asn Asn Thr Arg Lys Ser Met Arg
    290                 295                 300
Ile Gly Pro Gly Gln Thr Phe Tyr Ala Thr Gly Asp Ile Ile Gly Asp
305                 310                 315                 320
Ile Arg Gln Ala His Cys Asn Ile Ser Gly Arg Glu Trp Asn Asn Thr
                325                 330                 335
Leu Gln Gln Val Ala Glu Lys Leu Arg Lys His Phe Pro Asn Lys Thr
            340                 345                 350
Ile Lys Phe Ala Pro Ser Ser Gly Gly Asp Leu Glu Ile Thr Thr His
        355                 360                 365
Ser Phe Asn Cys Arg Gly Glu Phe Phe Tyr Cys Asn Thr Ser Lys Leu
    370                 375                 380
Phe Asn Ser Thr Tyr Asn Ser Thr Asn Ser Thr Asn Ser Thr Ile Thr
385                 390                 395                 400
Leu Pro Cys Arg Ile Lys Gln Ile Ile Asn Met Trp Gln Gly Val Gly
                405                 410                 415
Gln Ala Met Tyr Ala Pro Pro Ile Ala Gly Asn Ile Thr Cys Lys Ser
            420                 425                 430
Asn Ile Thr Gly Leu Leu Leu Thr Arg Asp Gly Gly Lys Asn Glu Thr
        435                 440                 445
Asn Glu Thr Glu Thr Phe Arg Pro Gly Gly Gly Asp Met Arg Asp Asn
    450                 455                 460
Trp Arg Ser Glu Leu Tyr Lys Tyr Lys Val Val Glu Ile Lys Pro Leu
465                 470                 475                 480
Gly Val Ala Pro Thr Lys Ala Lys Arg Arg Val Val Glu Arg Glu Lys
                485                 490                 495
Arg Ala Val Gly Leu Gly Ala Val Phe Leu Gly Phe Leu Gly Ala Ala
            500                 505                 510
```

```
Gly Ser Thr Met Gly Ala Ala Ser Ile Thr Leu Thr Val Gln Ala Arg
            515                 520                 525

Gln Leu Leu Ser Gly Ile Val Gln Gln Gln Ser Asn Leu Leu Arg Ala
        530                 535                 540

Ile Glu Ala Gln Gln His Met Leu Gln Leu Thr Val Trp Gly Ile Lys
545                 550                 555                 560

Gln Leu Gln Ala Arg Val Leu Ala Met Glu Arg Tyr Leu Lys Asp Gln
                565                 570                 575

Gln Leu Leu Gly Ile Trp Gly Cys Ser Gly Lys Leu Ile Cys Thr Thr
            580                 585                 590

Ala Val Pro Trp Asn Ser Ser Trp Ser Asn Lys Ser Gln Asp Asp Ile
        595                 600                 605

Trp Asp Asn Met Thr Trp Met Glu Trp Asp Arg Glu Ile Asn Asn Tyr
610                 615                 620

Thr Asp Thr Ile Tyr Arg Leu Leu Glu Glu Ser Gln Asn Gln Gln Glu
625                 630                 635                 640

Lys Asn Glu Gln Asp Leu Leu Ala Leu Asp Ser Trp Glu Asn Leu Trp
                645                 650                 655

Asn Trp Phe Asp Ile Ser Asn Trp Leu Trp Tyr Ile Lys Ile Phe Ile
            660                 665                 670

Met Ile Val Gly Gly Leu Ile Gly Leu Arg Ile Ile Phe Ala Val Leu
        675                 680                 685

Ser Ile Val Asn Arg Val Arg Gln Gly Tyr Ser Pro Leu Ser Phe Gln
        690                 695                 700

Thr Leu Thr Pro Asn Pro Arg Gly Pro Asp Arg Leu Glu Arg Ile Glu
705                 710                 715                 720

Glu Glu Gly Gly Glu Gln Asp Arg Asp Arg Ser Ile Arg Leu Val Ser
                725                 730                 735

Gly Phe Leu Ala Leu Ala Trp Asp Asp Leu Arg Ser Leu Cys Leu Phe
            740                 745                 750

Ser Tyr His Arg Leu Arg Asp Phe Ile Leu Ile Ala Ala Arg Thr Val
        755                 760                 765

Glu Leu Leu Gly Arg Ser Ser Leu Arg Gly Leu Gln Arg Gly Trp Glu
        770                 775                 780

Ala Leu Lys Tyr Leu Gly Ser Leu Val Gln Tyr Trp Gly Gln Glu Leu
785                 790                 795                 800

Lys Lys Ser Ala Ile Ser Leu Leu Asp Thr Ile Ala Ile Ala Val Ala
                805                 810                 815

Glu Gly Thr Asp Arg Ile Ile Glu Val Val Gln Arg Ala Cys Arg Ala
            820                 825                 830

Ile Leu Asn Ile Pro Arg Arg Ile Arg Gln Gly Phe Glu Ala Ala Leu
        835                 840                 845

Gln

<210> SEQ ID NO 100
<211> LENGTH: 849
<212> TYPE: PRT
<213> ORGANISM: Artificial sequence
<220> FEATURE:
<223> OTHER INFORMATION: Least squares of center of tree reconstructions
      of clade C gp160 protein sequence

<400> SEQUENCE: 100

Met Arg Val Arg Gly Ile Leu Arg Asn Cys Gln Gln Trp Trp Ile Trp
1

-continued

```
Gly Ile Leu Gly Phe Trp Met Leu Met Ile Cys Asn Val Val Gly Asn
             20                  25                  30

Leu Trp Val Thr Val Tyr Tyr Gly Val Pro Val Trp Lys Glu Ala Lys
         35                  40                  45

Thr Thr Leu Phe Cys Ala Ser Asp Ala Lys Ala Tyr Glu Lys Glu Val
 50                  55                  60

His Asn Val Trp Ala Thr His Ala Cys Val Pro Thr Asp Pro Asn Pro
 65                  70                  75                  80

Gln Glu Met Val Leu Glu Asn Val Thr Glu Asn Phe Asn Met Trp Lys
                 85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Ser Asn Val Asn Ala Thr Asn Thr Thr Asn Asn Thr Met Lys
130                 135                 140

Gly Glu Ile Lys Asn Cys Ser Phe Asn Ala Thr Thr Glu Ile Arg Asp
145                 150                 155                 160

Lys Lys Gln Lys Val Tyr Ala Leu Phe Tyr Arg Leu Asp Ile Val Pro
                165                 170                 175

Leu Asn Glu Asn Asn Ser Asn Ser Ser Glu Tyr Arg Leu Ile Asn Cys
            180                 185                 190

Asn Thr Ser Ala Ile Thr Gln Ala Cys Pro Lys Val Ser Phe Asp Pro
        195                 200                 205

Ile Pro Ile His Tyr Cys Ala Pro Ala Gly Tyr Ala Ile Leu Lys Cys
210                 215                 220

Asn Asn Lys Thr Phe Asn Gly Thr Gly Pro Cys Asn Asn Val Ser Thr
225                 230                 235                 240

Val Gln Cys Thr His Gly Ile Lys Pro Val Val Ser Thr Gln Leu Leu
                245                 250                 255

Leu Asn Gly Ser Leu Ala Glu Glu Ile Ile Ile Arg Ser Glu Asn
            260                 265                 270

Leu Thr Asn Asn Val Lys Thr Ile Ile Val His Leu Asn Glu Ser Val
        275                 280                 285

Glu Ile Val Cys Thr Arg Pro Asn Asn Asn Thr Arg Lys Ser Ile Arg
290                 295                 300

Ile Gly Pro Gly Gln Thr Phe Tyr Ala Thr Gly Asp Ile Ile Gly Asp
305                 310                 315                 320

Ile Arg Gln Ala His Cys Asn Ile Ser Glu Glu Trp Asn Lys Thr
                325                 330                 335

Leu Gln Arg Val Gly Lys Lys Leu Glu Glu His Phe Pro Asn Lys Thr
            340                 345                 350

Ile Lys Phe Glu Pro Ser Ser Gly Gly Asp Leu Glu Ile Thr Thr His
        355                 360                 365

Ser Phe Asn Cys Arg Gly Glu Phe Phe Tyr Cys Asn Thr Ser Lys Leu
370                 375                 380

Phe Asn Ser Thr Tyr Asn Gly Thr Asn Ser Thr Asn Thr Thr Ile Thr
385                 390                 395                 400

Leu Pro Cys Arg Ile Lys Gln Ile Ile Asn Met Trp Gln Glu Val Gly
                405                 410                 415

Arg Ala Met Tyr Ala Pro Pro Ile Ala Gly Asn Ile Thr Cys Lys Ser
            420                 425                 430

Asn Ile Thr Gly Leu Leu Leu Val Arg Asp Gly Gly Lys Asn Asn Thr
```

```
                435                 440                 445
Asn Asn Thr Glu Ile Phe Arg Pro Gly Gly Asp Met Arg Asp Asn
450                 455                 460
Trp Arg Ser Glu Leu Tyr Lys Tyr Lys Val Val Glu Ile Lys Pro Leu
465                 470                 475                 480
Gly Ile Ala Pro Thr Lys Ala Lys Arg Arg Val Val Glu Arg Glu Lys
                485                 490                 495
Arg Ala Val Gly Ile Gly Ala Val Phe Leu Gly Phe Leu Gly Ala Ala
                500                 505                 510
Gly Ser Thr Met Gly Ala Ala Ser Ile Thr Leu Thr Val Gln Ala Arg
                515                 520                 525
Gln Leu Leu Ser Gly Ile Val Gln Gln Gln Ser Asn Leu Leu Arg Ala
530                 535                 540
Ile Glu Ala Gln Gln His Met Leu Gln Leu Thr Val Trp Gly Ile Lys
545                 550                 555                 560
Gln Leu Gln Thr Arg Val Leu Ala Ile Glu Arg Tyr Leu Lys Asp Gln
                565                 570                 575
Gln Leu Leu Gly Ile Trp Gly Cys Ser Gly Lys Leu Ile Cys Thr Thr
                580                 585                 590
Ala Val Pro Trp Asn Ser Ser Trp Ser Asn Lys Ser Gln Glu Asp Ile
                595                 600                 605
Trp Asp Asn Met Thr Trp Met Gln Trp Asp Arg Glu Ile Ser Asn Tyr
                610                 615                 620
Thr Asp Thr Ile Tyr Arg Leu Leu Glu Asp Ser Gln Asn Gln Gln Glu
625                 630                 635                 640
Gln Asn Glu Lys Asp Leu Leu Ala Leu Asp Ser Trp Lys Asn Leu Trp
                645                 650                 655
Asn Trp Phe Asp Ile Thr Asn Trp Leu Trp Tyr Ile Lys Ile Phe Ile
                660                 665                 670
Met Ile Val Gly Gly Leu Ile Gly Leu Arg Ile Ile Phe Ala Val Leu
                675                 680                 685
Ser Ile Val Asn Arg Val Arg Gln Gly Tyr Ser Pro Leu Ser Phe Gln
690                 695                 700
Thr Leu Thr Pro Asn Pro Arg Gly Pro Asp Arg Leu Gly Arg Ile Glu
705                 710                 715                 720
Glu Glu Gly Gly Glu Gln Asp Arg Asp Arg Ser Ile Arg Leu Val Ser
                725                 730                 735
Gly Phe Leu Ala Leu Ala Trp Asp Asp Leu Arg Ser Leu Cys Leu Phe
                740                 745                 750
Ser Tyr His Arg Leu Arg Asp Phe Ile Leu Val Ala Ala Arg Ala Val
                755                 760                 765
Glu Leu Leu Gly Arg Ser Ser Leu Arg Gly Leu Gln Arg Gly Trp Glu
                770                 775                 780
Ala Leu Lys Tyr Leu Gly Ser Leu Val Gln Tyr Trp Gly Leu Glu Leu
785                 790                 795                 800
Lys Lys Ser Ala Ile Ser Leu Leu Asp Thr Ile Ala Ile Ala Val Ala
                805                 810                 815
Glu Gly Thr Asp Arg Ile Ile Glu Leu Ile Gln Arg Ile Cys Arg Ala
                820                 825                 830
Ile Arg Asn Ile Pro Arg Arg Ile Arg Gln Gly Phe Glu Ala Ala Leu
                835                 840                 845
Gln
```

```
<210> SEQ ID NO 101
<211> LENGTH: 849
<212> TYPE: PRT
<213> ORGANISM: Artificial sequence
<220> FEATURE:
<223> OTHER INFORMATION: Minimum of means of center of tree
      reconstructions for clade C gp160 protein sequence

<400> SEQUENCE: 101
```

|

```
Ser Phe Asn Cys Arg Gly Glu Phe Phe Tyr Cys Asn Thr Ser Lys Leu
    370                 375                 380

Phe Asn Ser Thr Tyr Asn Gly Thr Asn Ser Thr Asn Ser Thr Ile Thr
385                 390                 395                 400

Leu Gln Cys Arg Ile Lys Gln Ile Ile Asn Met Trp Gln Glu Val Gly
                405                 410                 415

Arg Ala Met Tyr Ala Pro Pro Ile Ala Gly Asn Ile Thr Cys Lys Ser
            420                 425                 430

Asn Ile Thr Gly Leu Leu Leu Val Arg Asp Gly Gly Lys Asn Asp Thr
        435                 440                 445

Asn Asp Thr Glu Ile Phe Arg Pro Gly Gly Gly Asp Met Arg Asp Asn
    450                 455                 460

Trp Arg Ser Glu Leu Tyr Lys Tyr Lys Val Glu Ile Lys Pro Leu
465                 470                 475                 480

Gly Ile Ala Pro Thr Lys Ala Lys Arg Arg Val Val Glu Arg Glu Lys
                485                 490                 495

Arg Ala Val Gly Ile Gly Ala Val Phe Leu Gly Phe Leu Gly Ala Ala
            500                 505                 510

Gly Ser Thr Met Gly Ala Ala Ser Ile Thr Leu Thr Val Gln Ala Arg
        515                 520                 525

Gln Leu Leu Ser Gly Ile Val Gln Gln Gln Ser Asn Leu Leu Arg Ala
    530                 535                 540

Ile Glu Ala Gln Gln His Met Leu Gln Leu Thr Val Trp Gly Ile Lys
545                 550                 555                 560

Gln Leu Gln Thr Arg Val Leu Ala Ile Glu Arg Tyr Leu Lys Asp Gln
                565                 570                 575

Gln Leu Leu Gly Ile Trp Gly Cys Ser Gly Lys Leu Ile Cys Thr Thr
            580                 585                 590

Ala Val Pro Trp Asn Ser Ser Trp Ser Asn Lys Ser Gln Glu Asp Ile
        595                 600                 605

Trp Asp Asn Met Thr Trp Met Gln Trp Asp Arg Glu Ile Ser Asn Tyr
    610                 615                 620

Thr Asp Thr Ile Tyr Arg Leu Leu Glu Asp Ser Gln Asn Gln Gln Glu
625                 630                 635                 640

Gln Asn Glu Lys Asp Leu Leu Ala Leu Asp Ser Trp Lys Asn Leu Trp
                645                 650                 655

Asn Trp Phe Asp Ile Thr Asn Trp Leu Trp Tyr Ile Lys Ile Phe Ile
            660                 665                 670

Met Ile Val Gly Gly Leu Ile Gly Leu Arg Ile Ile Phe Ala Val Leu
        675                 680                 685

Ser Ile Val Asn Arg Val Arg Gln Gly Tyr Ser Pro Leu Ser Phe Gln
    690                 695                 700

Thr Leu Thr Pro Asn Pro Arg Gly Pro Asp Arg Leu Gly Arg Ile Glu
705                 710                 715                 720

Glu Glu Gly Gly Glu Gln Asp Arg Asp Arg Ser Ile Arg Leu Val Ser
                725                 730                 735

Gly Phe Leu Ala Leu Ala Trp Asp Asp Leu Arg Ser Leu Cys Leu Phe
            740                 745                 750

Ser Tyr His Arg Leu Arg Asp Phe Ile Leu Val Ala Ala Arg Ala Val
        755                 760                 765

Glu Leu Leu Gly Arg Ser Ser Leu Arg Gly Leu Gln Arg Gly Trp Glu
    770                 775                 780
```

-continued

```
Ala Leu Lys Tyr Leu Gly Ser Leu Val Gln Tyr Trp Gly Leu Glu Leu
785                 790                 795                 800

Lys Lys Ser Ala Ile Ser Leu Leu Asp Thr Ile Ala Ile Ala Val Ala
            805                 810                 815

Glu Gly Thr Asp Arg Ile Ile Glu Leu Ile Gln Arg Ile Cys Arg Ala
        820                 825                 830

Ile Arg Asn Ile Pro Arg Arg Ile Arg Gln Gly Phe Glu Ala Ala Leu
    835                 840                 845

Gln

<210> SEQ ID NO 102
<211> LENGTH: 206
<212> TYPE: PRT
<213> ORGANISM: Artificial sequence
<220> FEATURE:
<223> OTHER INFORMATION: Most recent common ancestor of
      reconstructions of clade C nef protein sequences

<400> SEQUENCE: 102

Met Gly Gly Lys Trp Ser Lys Ser Ser Ile Val Gly Trp Pro Ala Val
1               5                   10                  15

Arg Glu Arg Ile Arg Arg Thr Ala Pro Ala Ala Glu Gly Val Gly Ala
            20                  25                  30

Ala Ser Gln Asp Leu Asp Lys His Gly Ala Leu Thr Ser Ser Asn Thr
        35                  40                  45

Ala Ala Thr Asn Ala Asp Cys Ala Trp Leu Glu Ala Gln Glu Glu Glu
    50                  55                  60

Glu Val Gly Phe Pro Val Arg Pro Gln Val Pro Leu Arg Pro Met Thr
65                  70                  75                  80

Tyr Lys Gly Ala Val Asp Leu Ser Phe Phe Leu Lys Glu Lys Gly Gly
                85                  90                  95

Leu Glu Gly Leu Ile Tyr Ser Lys Lys Arg Gln Glu Ile Leu Asp Leu
            100                 105                 110

Trp Val Tyr His Thr Gln Gly Tyr Phe Pro Asp Trp Gln Asn Tyr Thr
        115                 120                 125

Pro Gly Pro Gly Ile Arg Phe Pro Leu Thr Phe Gly Trp Cys Phe Lys
    130                 135                 140

Leu Val Pro Val Asp Pro Arg Glu Val Glu Glu Ala Asn Glu Gly Glu
145                 150                 155                 160

Asn Asn Cys Leu Leu His Pro Met Ser Gln His Gly Met Glu Asp Glu
                165                 170                 175

Asp Arg Glu Val Leu Lys Trp Lys Phe Asp Ser His Leu Ala Arg Arg
            180                 185                 190

His Met Ala Arg Glu Leu His Pro Glu Tyr Tyr Lys Asp Cys
        195                 200                 205

<210> SEQ ID NO 103
<211> LENGTH: 207
<212> TYPE: PRT
<213> ORGANISM: Artificial sequence
<220> FEATURE:
<223> OTHER INFORMATION: Least squares and minimum of means of center of
      tree reconstructions of clade C nef protein sequence

<400> SEQUENCE: 103

Met Gly Gly Lys Trp Ser Lys Ser Ser Ile Val Gly Trp Pro Ala Val
1               5                   10                  15

Arg Glu Arg Ile Arg Arg Thr Glu Pro Ala Ala Glu Gly Val Gly Ala
```

-continued

```
            20                  25                  30

Ala Ser Gln Asp Leu Asp Lys His Gly Ala Leu Thr Ser Ser Asn Thr
        35                  40                  45

Ala Ala Asn Asn Ala Asp Cys Ala Trp Leu Glu Ala Gln Glu Glu Glu
    50                  55                  60

Glu Glu Val Gly Phe Pro Val Arg Pro Gln Val Pro Leu Arg Pro Met
65                  70                  75                  80

Thr Tyr Lys Gly Ala Phe Asp Leu Ser Phe Phe Leu Lys Glu Lys Gly
                85                  90                  95

Gly Leu Glu Gly Leu Ile Tyr Ser Lys Lys Arg Gln Glu Ile Leu Asp
            100                 105                 110

Leu Trp Val Tyr His Thr Gln Gly Tyr Phe Pro Asp Trp Gln Asn Tyr
        115                 120                 125

Thr Pro Gly Pro Gly Val Arg Tyr Pro Leu Thr Phe Gly Trp Cys Phe
    130                 135                 140

Lys Leu Val Pro Val Asp Pro Arg Glu Val Glu Glu Ala Asn Glu Gly
145                 150                 155                 160

Glu Asn Asn Cys Leu Leu His Pro Met Ser Gln His Gly Met Glu Asp
                165                 170                 175

Glu Asp Arg Glu Val Leu Lys Trp Lys Phe Asp Ser His Leu Ala Arg
            180                 185                 190

Arg His Met Ala Arg Glu Leu His Pro Glu Tyr Tyr Lys Asp Cys
        195                 200                 205
```

<210> SEQ ID NO 104
<211> LENGTH: 999
<212> TYPE: PRT
<213> ORGANISM: Artificial sequence
<220> FEATURE:
<223> OTHER INFORMATION: Most recent common ancestor for reconstruction of clade C pol protein sequences

<400> SEQUENCE: 104

```
Phe Phe Arg Glu Asn Leu Ala Phe Pro Gln Gly Glu Ala Arg Glu Phe
1               5                   10                  15

Pro Ser Glu Gln Thr Arg Ala Asn Ser Pro Thr Ser Arg Glu Leu Gln
            20                  25                  30

Val Arg Gly Asp Asn Pro Arg Ser Glu Ala Gly Ala Glu Arg Gln Gly
        35                  40                  45

Thr Leu Asn Phe Pro Gln Ile Thr Leu Trp Gln Arg Pro Leu Val Ser
    50                  55                  60

Ile Lys Val Gly Gly Gln Ile Lys Glu Ala Leu Leu Asp Thr Gly Ala
65                  70                  75                  80

Asp Asp Thr Val Leu Glu Asp Ile Asn Leu Pro Gly Lys Trp Lys Pro
                85                  90                  95

Lys Met Ile Gly Gly Ile Gly Gly Phe Ile Lys Val Arg Gln Tyr Asp
            100                 105                 110

Gln Ile Leu Ile Glu Ile Cys Gly Lys Lys Ala Ile Gly Thr Val Leu
        115                 120                 125

Val Gly Pro Thr Pro Val Asn Ile Ile Gly Arg Asn Met Leu Thr Gln
    130                 135                 140

Leu Gly Cys Thr Leu Asn Phe Pro Ile Ser Pro Ile Glu Thr Val Pro
145                 150                 155                 160

Val Lys Leu Lys Pro Gly Met Asp Gly Pro Lys Val Lys Gln Trp Pro
                165                 170                 175
```

-continued

```
Leu Thr Glu Glu Lys Ile Lys Ala Leu Thr Ala Ile Cys Glu Glu Met
            180                 185                 190

Glu Lys Glu Gly Lys Ile Thr Lys Ile Gly Pro Glu Asn Pro Tyr Asn
            195                 200                 205

Thr Pro Val Phe Ala Ile Lys Lys Lys Asp Ser Thr Lys Trp Arg Lys
            210                 215                 220

Leu Val Asp Phe Arg Glu Leu Asn Lys Arg Thr Gln Asp Phe Trp Glu
225                 230                 235                 240

Val Gln Leu Gly Ile Pro His Pro Ala Gly Leu Lys Lys Lys Ser
            245                 250                 255

Val Thr Val Leu Asp Val Gly Asp Ala Tyr Phe Ser Val Pro Leu Asp
            260                 265                 270

Glu Asp Phe Arg Lys Tyr Thr Ala Phe Thr Ile Pro Ser Ile Asn Asn
            275                 280                 285

Glu Thr Pro Gly Ile Arg Tyr Gln Tyr Asn Val Leu Pro Gln Gly Trp
            290                 295                 300

Lys Gly Ser Pro Ala Ile Phe Gln Ser Ser Met Thr Lys Ile Leu Glu
305                 310                 315                 320

Pro Phe Arg Ala Gln Asn Pro Glu Ile Val Ile Tyr Gln Tyr Met Asp
            325                 330                 335

Asp Leu Tyr Val Gly Ser Asp Leu Glu Ile Gly Gln His Arg Ala Lys
            340                 345                 350

Ile Glu Glu Leu Arg Glu His Leu Leu Lys Trp Gly Phe Thr Thr Pro
            355                 360                 365

Asp Lys Lys His Gln Lys Glu Pro Pro Phe Leu Trp Met Gly Tyr Glu
            370                 375                 380

Leu His Pro Asp Lys Trp Thr Val Gln Pro Ile Gln Leu Pro Glu Lys
385                 390                 395                 400

Asp Ser Trp Thr Val Asn Asp Ile Gln Lys Leu Val Gly Lys Leu Asn
            405                 410                 415

Trp Ala Ser Gln Ile Tyr Pro Gly Ile Lys Val Arg Gln Leu Cys Lys
            420                 425                 430

Leu Leu Arg Gly Ala Lys Ala Leu Thr Asp Ile Val Pro Leu Thr Glu
            435                 440                 445

Glu Ala Glu Leu Glu Leu Ala Glu Asn Arg Glu Ile Leu Lys Glu Pro
            450                 455                 460

Val His Gly Val Tyr Tyr Asp Pro Ser Lys Asp Leu Ile Ala Glu Ile
465                 470                 475                 480

Gln Lys Gln Gly His Asp Gln Trp Thr Tyr Gln Ile Tyr Gln Glu Pro
            485                 490                 495

Phe Lys Asn Leu Lys Thr Gly Lys Tyr Ala Lys Met Arg Ser Ala His
            500                 505                 510

Thr Asn Asp Val Lys Gln Leu Thr Glu Ala Val Gln Lys Ile Ala Met
            515                 520                 525

Glu Ser Ile Val Ile Trp Gly Lys Thr Pro Lys Phe Arg Leu Pro Ile
            530                 535                 540

Gln Lys Glu Thr Trp Glu Thr Trp Trp Thr Asp Tyr Trp Gln Ala Thr
545                 550                 555                 560

Trp Ile Pro Glu Trp Glu Phe Val Asn Thr Pro Pro Leu Val Lys Leu
            565                 570                 575

Trp Tyr Gln Leu Glu Lys Glu Pro Ile Ala Gly Ala Glu Thr Phe Tyr
            580                 585                 590

Val Asp Gly Ala Ala Asn Arg Glu Thr Lys Leu Gly Lys Ala Gly Tyr
```

```
                595                 600                 605
Val Thr Asp Lys Gly Arg Gln Lys Val Val Ser Leu Thr Glu Thr Thr
    610                 615                 620
Asn Gln Lys Thr Glu Leu Gln Ala Ile Gln Leu Ala Leu Gln Asp Ser
625                 630                 635                 640
Gly Ser Glu Val Asn Ile Val Thr Asp Ser Gln Tyr Ala Leu Gly Ile
                645                 650                 655
Ile Gln Ala Gln Pro Asp Lys Ser Glu Ser Glu Leu Val Asn Gln Ile
            660                 665                 670
Ile Glu Gln Leu Ile Lys Lys Glu Lys Val Tyr Leu Ser Trp Val Pro
            675                 680                 685
Ala His Lys Gly Ile Gly Gly Asn Glu Gln Val Asp Lys Leu Val Ser
        690                 695                 700
Ser Gly Ile Arg Lys Val Leu Phe Leu Asp Gly Ile Asp Lys Ala Gln
705                 710                 715                 720
Glu Glu His Glu Lys Tyr His Ser Asn Trp Arg Ala Met Ala Ser Glu
                725                 730                 735
Phe Asn Leu Pro Pro Ile Val Ala Lys Glu Ile Val Ala Ser Cys Asp
            740                 745                 750
Lys Cys Gln Leu Lys Gly Glu Ala Met His Gly Gln Val Asp Cys Ser
        755                 760                 765
Pro Gly Ile Trp Gln Leu Asp Cys Thr His Leu Glu Gly Lys Val Ile
    770                 775                 780
Leu Val Ala Val His Val Ala Ser Gly Tyr Ile Glu Ala Glu Val Ile
785                 790                 795                 800
Pro Ala Glu Thr Gly Gln Glu Thr Ala Tyr Phe Ile Leu Lys Leu Ala
                805                 810                 815
Gly Arg Trp Pro Val Lys Val Ile His Thr Asp Asn Gly Ser Asn Phe
            820                 825                 830
Thr Ser Ala Ala Val Lys Ala Ala Cys Trp Trp Ala Gly Ile Gln Gln
        835                 840                 845
Glu Phe Gly Ile Pro Tyr Asn Pro Gln Ser Gln Gly Val Val Glu Ser
    850                 855                 860
Met Asn Lys Glu Leu Lys Lys Ile Ile Gly Gln Val Arg Asp Gln Ala
865                 870                 875                 880
Glu His Leu Lys Thr Ala Val Gln Met Ala Val Phe Ile His Asn Phe
                885                 890                 895
Lys Arg Lys Gly Gly Ile Gly Gly Tyr Ser Ala Gly Glu Arg Ile Ile
            900                 905                 910
Asp Ile Ile Ala Thr Asp Ile Gln Thr Lys Glu Leu Gln Lys Gln Ile
        915                 920                 925
Ile Lys Ile Gln Asn Phe Arg Val Tyr Tyr Arg Asp Ser Arg Asp Pro
    930                 935                 940
Val Trp Lys Gly Pro Ala Lys Leu Leu Trp Lys Gly Glu Gly Ala Val
945                 950                 955                 960
Val Ile Gln Asp Asn Ser Asp Ile Lys Val Val Pro Arg Arg Lys Ala
                965                 970                 975
Lys Ile Ile Arg Asp Tyr Gly Lys Gln Met Ala Gly Ala Asp Cys Val
            980                 985                 990
Ala Gly Arg Gln Asp Glu Asp
        995

<210> SEQ ID NO 105
```

<211> LENGTH: 999
<212> TYPE: PRT
<213> ORGANISM: Artificial sequence
<220> FEATURE:
<223> OTHER INFORMATION: Least squares center of tree reconstruction of clade C pol protein sequence

<400> SEQUENCE: 105

```
Phe Phe Arg Glu Asn Leu Ala Phe Pro G

```
            370                 375                 380
Leu His Pro Asp Lys Trp Thr Val Gln Pro Ile Gln Leu Pro Glu Lys
385                 390                 395                 400

Asp Ser Trp Thr Val Asn Asp Ile Gln Lys Leu Val Gly Lys Leu Asn
                405                 410                 415

Trp Ala Ser Gln Ile Tyr Pro Gly Ile Lys Val Arg Gln Leu Cys Lys
            420                 425                 430

Leu Leu Arg Gly Ala Lys Ala Leu Thr Asp Ile Val Pro Leu Thr Glu
        435                 440                 445

Glu Ala Glu Leu Glu Leu Ala Glu Asn Arg Glu Ile Leu Lys Glu Pro
    450                 455                 460

Val His Gly Val Tyr Tyr Asp Pro Ser Lys Asp Leu Ile Ala Glu Ile
465                 470                 475                 480

Gln Lys Gln Gly His Asp Gln Trp Thr Tyr Gln Ile Tyr Gln Glu Pro
                485                 490                 495

Phe Lys Asn Leu Lys Thr Gly Lys Tyr Ala Lys Met Arg Thr Ala His
            500                 505                 510

Thr Asn Asp Val Lys Gln Leu Thr Glu Ala Val Gln Lys Ile Ala Met
        515                 520                 525

Glu Ser Ile Val Ile Trp Gly Lys Thr Pro Lys Phe Arg Leu Pro Ile
    530                 535                 540

Gln Lys Glu Thr Trp Glu Thr Trp Trp Thr Asp Tyr Trp Gln Ala Thr
545                 550                 555                 560

Trp Ile Pro Glu Trp Glu Phe Val Asn Thr Pro Pro Leu Val Lys Leu
                565                 570                 575

Trp Tyr Gln Leu Glu Lys Glu Pro Ile Ala Gly Ala Glu Thr Phe Tyr
            580                 585                 590

Val Asp Gly Ala Ala Asn Arg Glu Thr Lys Ile Gly Lys Ala Gly Tyr
        595                 600                 605

Val Thr Asp Arg Gly Arg Gln Lys Ile Val Ser Leu Thr Glu Thr Thr
    610                 615                 620

Asn Gln Lys Thr Glu Leu Gln Ala Ile Gln Leu Ala Leu Gln Asp Ser
625                 630                 635                 640

Gly Ser Glu Val Asn Ile Val Thr Asp Ser Gln Tyr Ala Leu Gly Ile
                645                 650                 655

Ile Gln Ala Gln Pro Asp Lys Ser Glu Ser Glu Leu Val Asn Gln Ile
            660                 665                 670

Ile Glu Gln Leu Ile Lys Lys Glu Arg Val Tyr Leu Ser Trp Val Pro
        675                 680                 685

Ala His Lys Gly Ile Gly Gly Asn Glu Gln Val Asp Lys Leu Val Ser
    690                 695                 700

Ser Gly Ile Arg Lys Val Leu Phe Leu Asp Gly Ile Asp Lys Ala Gln
705                 710                 715                 720

Glu Glu His Glu Lys Tyr His Ser Asn Trp Arg Ala Met Ala Ser Glu
                725                 730                 735

Phe Asn Leu Pro Pro Ile Val Ala Lys Glu Ile Val Ala Ser Cys Asp
            740                 745                 750

Lys Cys Gln Leu Lys Gly Glu Ala Ile His Gly Gln Val Asp Cys Ser
        755                 760                 765

Pro Gly Ile Trp Gln Leu Asp Cys Thr His Leu Glu Gly Lys Ile Ile
    770                 775                 780

Leu Val Ala Val His Val Ala Ser Gly Tyr Ile Glu Ala Glu Val Ile
785                 790                 795                 800
```

-continued

```
Pro Ala Glu Thr Gly Gln Glu Thr Ala Tyr Phe Ile Leu Lys Leu Ala
                805                 810                 815
Gly Arg Trp Pro Val Lys Val Ile His Thr Asp Asn Gly Ser Asn Phe
            820                 825                 830
Thr Ser Ala Ala Val Lys Ala Ala Cys Trp Trp Ala Gly Ile Gln Gln
        835                 840                 845
Glu Phe Gly Ile Pro Tyr Asn Pro Gln Ser Gln Gly Val Val Glu Ser
    850                 855                 860
Met Asn Lys Glu Leu Lys Lys Ile Ile Gly Gln Val Arg Asp Gln Ala
865                 870                 875                 880
Glu His Leu Lys Thr Ala Val Gln Met Ala Val Phe Ile His Asn Phe
                885                 890                 895
Lys Arg Lys Gly Gly Ile Gly Gly Tyr Ser Ala Gly Glu Arg Ile Ile
            900                 905                 910
Asp Ile Ile Ala Thr Asp Ile Gln Thr Lys Glu Leu Gln Lys Gln Ile
        915                 920                 925
Ile Lys Ile Gln Asn Phe Arg Val Tyr Tyr Arg Asp Ser Arg Asp Pro
    930                 935                 940
Ile Trp Lys Gly Pro Ala Lys Leu Leu Trp Lys Gly Glu Gly Ala Val
945                 950                 955                 960
Val Ile Gln Asp Asn Ser Asp Ile Lys Val Val Pro Arg Arg Lys Ala
                965                 970                 975
Lys Ile Ile Lys Asp Tyr Gly Lys Gln Met Ala Gly Ala Asp Cys Val
            980                 985                 990
Ala Gly Arg Gln Asp Glu Asp
        995
```

```
<210> SEQ ID NO 106
<211> LENGTH: 999
<212> TYPE: PRT
<213> ORGANISM: Artificial sequence
<220> FEATURE:
<223> OTHER INFORMATION: Minimum of means center of tree reconstruction
      of clade C pol protein sequence

<400> SEQUENCE: 106

Phe Phe Arg Glu Asn Leu Ala Phe Pro Gln Gly Glu Ala Arg Glu Phe
1               5                   10                  15

Pro Ser Glu Gln Thr Arg Ala Asn Ser Pro Thr Ser Arg Glu Leu Gln
            20                  25                  30

Val Arg Gly Asp Asn Pro Leu Ser Glu Ala Gly Ala Glu Arg Gln Gly
        35                  40                  45

Thr Leu Asn Phe Pro Gln Ile Thr Leu Trp Gln Arg Pro Leu Val Thr
    50                  55                  60

Ile Lys Val Gly Gly Gln Leu Lys Glu Ala Leu Leu Asp Thr Gly Ala
65                  70                  75                  80

Asp Asp Thr Val Leu Glu Glu Ile Asn Leu Pro Gly Lys Trp Lys Pro
                85                  90                  95

Lys Met Ile Gly Gly Ile Gly Gly Phe Ile Lys Val Arg Gln Tyr Asp
            100                 105                 110

Gln Ile Leu Ile Glu Ile Cys Gly Lys Lys Ala Ile Gly Thr Val Leu
        115                 120                 125

Val Gly Pro Thr Pro Val Asn Ile Ile Gly Arg Asn Met Leu Thr Gln
    130                 135                 140

Leu Gly Cys Thr Leu Asn Phe Pro Ile Ser Pro Ile Glu Thr Val Pro
```

-continued

```
            145                 150                 155                 160
Val Lys Leu Lys Pro Gly Met Asp Gly Pro Lys Val Lys Gln Trp Pro
                    165                 170                 175
Leu Thr Glu Glu Lys Ile Lys Ala Leu Thr Ala Ile Cys Glu Met
            180                 185                 190
Glu Lys Glu Gly Lys Ile Thr Lys Ile Gly Pro Glu Asn Pro Tyr Asn
            195                 200                 205
Thr Pro Val Phe Ala Ile Lys Lys Asp Ser Thr Lys Trp Arg Lys
        210                 215                 220
Leu Val Asp Phe Arg Glu Leu Asn Lys Arg Thr Gln Asp Phe Trp Glu
225                 230                 235                 240
Val Gln Leu Gly Ile Pro His Pro Ala Gly Leu Lys Lys Lys Ser
                245                 250                 255
Val Thr Val Leu Asp Val Gly Asp Ala Tyr Phe Ser Val Pro Leu Asp
                260                 265                 270
Glu Gly Phe Arg Lys Tyr Thr Ala Phe Thr Ile Pro Ser Ile Asn Asn
            275                 280                 285
Glu Thr Pro Gly Ile Arg Tyr Gln Tyr Asn Val Leu Pro Gln Gly Trp
            290                 295                 300
Lys Gly Ser Pro Ala Ile Phe Gln Ser Ser Met Thr Lys Ile Leu Glu
305                 310                 315                 320
Pro Phe Arg Ala Gln Asn Pro Glu Ile Val Ile Tyr Gln Tyr Met Asp
                325                 330                 335
Asp Leu Tyr Val Gly Ser Asp Leu Glu Ile Gly Gln His Arg Ala Lys
                340                 345                 350
Ile Glu Glu Leu Arg Glu His Leu Leu Lys Trp Gly Phe Thr Thr Pro
            355                 360                 365
Asp Lys Lys His Gln Lys Glu Pro Pro Phe Leu Trp Met Gly Tyr Glu
            370                 375                 380
Leu His Pro Asp Lys Trp Thr Val Gln Pro Ile Gln Leu Pro Glu Lys
385                 390                 395                 400
Asp Ser Trp Thr Val Asn Asp Ile Gln Lys Leu Val Gly Lys Leu Asn
                405                 410                 415
Trp Ala Ser Gln Ile Tyr Pro Gly Ile Lys Val Arg Gln Leu Cys Lys
                420                 425                 430
Leu Leu Arg Gly Ala Lys Ala Leu Thr Asp Ile Val Pro Leu Thr Glu
            435                 440                 445
Glu Ala Glu Leu Glu Leu Ala Glu Asn Arg Glu Ile Leu Lys Glu Pro
            450                 455                 460
Val His Gly Val Tyr Tyr Asp Pro Ser Lys Asp Leu Ile Ala Glu Ile
465                 470                 475                 480
Gln Lys Gln Gly His Asp Gln Trp Thr Tyr Gln Ile Tyr Gln Glu Pro
                485                 490                 495
Phe Lys Asn Leu Lys Thr Gly Lys Tyr Ala Lys Met Arg Thr Ala His
                500                 505                 510
Thr Asn Asp Val Lys Gln Leu Thr Glu Ala Val Gln Lys Ile Ala Met
            515                 520                 525
Glu Ser Ile Val Ile Trp Gly Lys Thr Pro Lys Phe Arg Leu Pro Ile
            530                 535                 540
Gln Lys Glu Thr Trp Glu Ala Trp Trp Thr Asp Tyr Trp Gln Ala Thr
545                 550                 555                 560
Trp Ile Pro Glu Trp Glu Phe Val Asn Thr Pro Pro Leu Val Lys Leu
                565                 570                 575
```

```
Trp Tyr Gln Leu Glu Lys Glu Pro Ile Ala Gly Ala Glu Thr Phe Tyr
            580                 585                 590

Val Asp Gly Ala Ala Asn Arg Glu Thr Lys Ile Gly Lys Ala Gly Tyr
        595                 600                 605

Val Thr Asp Arg Gly Arg Gln Lys Ile Val Ser Leu Thr Glu Thr Thr
    610                 615                 620

Asn Gln Lys Thr Glu Leu Gln Ala Ile Gln Leu Ala Leu Gln Asp Ser
625                 630                 635                 640

Gly Ser Glu Val Asn Ile Val Thr Asp Ser Gln Tyr Ala Leu Gly Ile
                645                 650                 655

Ile Gln Ala Gln Pro Asp Lys Ser Glu Ser Glu Leu Val Asn Gln Ile
            660                 665                 670

Ile Glu Gln Leu Ile Lys Lys Glu Arg Val Tyr Leu Ser Trp Val Pro
            675                 680                 685

Ala His Lys Gly Ile Gly Gly Asn Glu Gln Val Asp Lys Leu Val Ser
        690                 695                 700

Ser Gly Ile Arg Lys Val Leu Phe Leu Asp Gly Ile Asp Lys Ala Gln
705                 710                 715                 720

Glu Glu His Glu Lys Tyr His Ser Asn Trp Arg Ala Met Ala Ser Glu
                725                 730                 735

Phe Asn Leu Pro Pro Ile Val Ala Lys Glu Ile Val Ala Ser Cys Asp
            740                 745                 750

Lys Cys Gln Leu Lys Gly Glu Ala Ile His Gly Gln Val Asp Cys Ser
        755                 760                 765

Pro Gly Ile Trp Gln Leu Asp Cys Thr His Leu Glu Gly Lys Ile Ile
    770                 775                 780

Leu Val Ala Val His Val Ala Ser Gly Tyr Ile Glu Ala Glu Val Ile
785                 790                 795                 800

Pro Ala Glu Thr Gly Gln Glu Thr Ala Tyr Phe Ile Leu Lys Leu Ala
                805                 810                 815

Gly Arg Trp Pro Val Lys Val Ile His Thr Asp Asn Gly Ser Asn Phe
            820                 825                 830

Thr Ser Ala Ala Val Lys Ala Ala Cys Trp Trp Ala Gly Ile Gln Gln
        835                 840                 845

Glu Phe Gly Ile Pro Tyr Asn Pro Gln Ser Gln Gly Val Val Glu Ser
    850                 855                 860

Met Asn Lys Glu Leu Lys Lys Ile Ile Gly Gln Val Arg Asp Gln Ala
865                 870                 875                 880

Glu His Leu Lys Thr Ala Val Gln Met Ala Val Phe Ile His Asn Phe
                885                 890                 895

Lys Arg Lys Gly Gly Ile Gly Gly Tyr Ser Ala Gly Glu Arg Ile Ile
            900                 905                 910

Asp Ile Ile Ala Thr Asp Ile Gln Thr Lys Glu Leu Gln Lys Gln Ile
        915                 920                 925

Ile Lys Ile Gln Asn Phe Arg Val Tyr Tyr Arg Asp Ser Arg Asp Pro
    930                 935                 940

Ile Trp Lys Gly Pro Ala Lys Leu Leu Trp Lys Gly Glu Gly Ala Val
945                 950                 955                 960

Val Ile Gln Asp Asn Ser Asp Ile Lys Val Val Pro Arg Arg Lys Ala
                965                 970                 975

Lys Ile Ile Lys Asp Tyr Gly Lys Gln Met Ala Gly Ala Asp Cys Val
            980                 985                 990
```

-continued

```
Ala Gly Arg Gln Asp Glu Asp
        995

<210> SEQ ID NO 107
<211> LENGTH: 107
<212> TYPE: PRT
<213> ORGANISM: Artificial sequence
<220> FEATURE:
<223> OTHER INFORMATION: Most common recent ancestor reconstructions of
      clade C rev protein sequence

<400> SEQUENCE: 107

Met Ala Gly Arg Ser Gly Asp Ser Asp Glu Ala Leu Leu Gln Ala Val
1               5                   10                  15

Arg Ile Ile Lys Ile Leu Tyr Gln Ser Asn Pro Tyr Pro Lys Pro Glu
            20                  25                  30

Gly Thr Arg Gln Ala Arg Arg Asn Arg Arg Arg Trp Arg Ala Arg
        35                  40                  45

Gln Arg Gln Ile His Ser Ile Ser Glu Arg Ile Leu Ser Thr Cys Leu
    50                  55                  60

Gly Arg Pro Ala Glu Pro Val Pro Leu Gln Leu Pro Pro Leu Glu Arg
65                  70                  75                  80

Leu His Leu Asp Cys Ser Glu Asp Cys Gly Thr Ser Gly Thr Gln Gln
                85                  90                  95

Ser Gln Gly Thr Thr Glu Gly Val Gly Ser Pro
            100                 105

<210> SEQ ID NO 108
<211> LENGTH: 107
<212> TYPE: PRT
<213> ORGANISM: Artificial sequence
<220> FEATURE:
<223> OTHER INFORMATION: Least squares center of tree reconstructions of
      clade C rev protein sequence

<400> SEQUENCE: 108

Met Ala Gly Arg Ser Gly Asp Ser Asp Glu Ala Leu Leu Gln Ala Val
1               5                   10                  15

Arg Ile Ile Lys Ile Leu Tyr Gln Ser Asn Pro Tyr Pro Lys Pro Glu
            20                  25                  30

Gly Thr Arg Gln Ala Arg Lys Asn Arg Arg Arg Trp Arg Ala Arg
        35                  40                  45

Gln Arg Gln Ile His Ser Ile Ser Glu Arg Ile Leu Ser Thr Cys Leu
    50                  55                  60

Gly Arg Pro Ala Glu Pro Val Pro Leu Gln Leu Pro Pro Ile Glu Arg
65                  70                  75                  80

Leu His Ile Gly Asp Ser Glu Ser Ser Gly Thr Ser Gly Thr Gln Gln
                85                  90                  95

Ser Gln Gly Thr Thr Glu Gly Val Gly Ser Pro
            100                 105

<210> SEQ ID NO 109
<211> LENGTH: 107
<212> TYPE: PRT
<213> ORGANISM: Artificial sequence
<220> FEATURE:
<223> OTHER INFORMATION: Minimum of means center of tree reconstructions
      of clade C rev protein sequence

<400> SEQUENCE: 109

Met Ala Gly Arg Ser Gly Asp Ser Asp Glu Ala Leu Leu Gln Ala Val
```

```
                1               5                      10                     15
Arg Ile Ile Lys Ile Leu Tyr Gln Ser Asn Pro Tyr Pro Lys Pro Glu
                    20                      25                     30

Gly Thr Arg Gln Ala Arg Lys Asn Arg Arg Arg Trp Arg Ala Arg
                    35                      40                     45

Gln Arg Gln Ile His Ser Ile Ser Glu Arg Ile Leu Ser Thr Cys Leu
        50                      55                      60

Gly Arg Pro Ala Glu Pro Val Pro Phe Gln Leu Pro Pro Ile Glu Arg
65                      70                      75                      80

Leu His Ile Gly Asp Ser Glu Ser Ser Gly Thr Ser Gly Thr Gln Gln
                    85                      90                      95

Ser Gln Gly Thr Thr Glu Gly Val Gly Ser Pro
                100                     105

<210> SEQ ID NO 110
<211> LENGTH: 101
<212> TYPE: PRT
<213> ORGANISM: Artificial sequence
<220> FEATURE:
<223> OTHER INFORMATION: Most recent common ancestor reconstructions of
      clade C tat protein sequence

<400> SEQUENCE: 110

Met Glu Pro Val Asp Pro Asn Leu Glu Pro Trp Asn His Pro Gly Ser
1               5                       10                      15

Gln Pro Lys Thr Ala Cys Asn Lys Cys Tyr Cys Lys Lys Cys Ser Tyr
                    20                      25                      30

His Cys Leu Val Cys Phe Leu Thr Lys Gly Leu Gly Ile Ser Tyr Gly
            35                      40                      45

Arg Lys Lys Arg Arg Gln Arg Arg Ala Pro Pro Ser Ser Glu Asp
        50                      55                      60

His Gln Asn Pro Ile Ser Lys Gln Pro Leu Ser Gln Thr Arg Gly Asp
65                      70                      75                      80

Pro Thr Gly Ser Glu Glu Ser Lys Lys Lys Val Glu Ser Lys Thr Glu
                    85                      90                      95

Thr Asp Pro Cys Asp
                100

<210> SEQ ID NO 111
<211> LENGTH: 101
<212> TYPE: PRT
<213> ORGANISM: Artificial sequence
<220> FEATURE:
<223> OTHER INFORMATION: Least squares and minimum of means center of
      tree reconstruction of clade C tat protein sequence

<400> SEQUENCE: 111

Met Glu Pro Val Asp Pro Asn Leu Glu Pro Trp Asn His Pro Gly Ser
1               5                       10                      15

Gln Pro Lys Thr Pro Cys Asn Lys Cys Tyr Cys Lys His Cys Ser Tyr
                    20                      25                      30

His Cys Leu Val Cys Phe Gln Thr Lys Gly Leu Gly Ile Ser Tyr Gly
            35                      40                      45

Arg Lys Lys Arg Arg Gln Arg Arg Ser Ala Pro Pro Ser Ser Glu Asp
        50                      55                      60

His Gln Asn Pro Ile Ser Lys Gln Pro Leu Pro Gln Thr Arg Gly Asp
65                      70                      75                      80

Pro Thr Gly Ser Glu Glu Ser Lys Lys Lys Val Glu Ser Lys Thr Glu
```

-continued

```
                        85                  90                  95

Thr Asp Pro Phe Asp
            100

<210> SEQ ID NO 112
<211> LENGTH: 192
<212> TYPE: PRT
<213> ORGANISM: Artificial sequence
<220> FEATURE:
<223> OTHER INFORMATION: Most recent common ancestor reconstructions of
      clade C vif protein sequence

<400> SEQUENCE: 112

Met Glu Asn Arg Trp Gln Val Leu Ile Val Trp Gln Val Asp Arg Met
1               5                   10                  15

Lys Ile Arg Thr Trp Asn Ser Leu Val Lys His His Met Tyr Val Ser
            20                  25                  30

Arg Arg Ala Lys Gly Trp Phe Tyr Arg His His Tyr Glu Ser Arg His
        35                  40                  45

Pro Lys Ile Ser Ser Glu Val His Ile Pro Leu Gly Asp Ala Arg Leu
    50                  55                  60

Val Ile Lys Thr Tyr Trp Gly Leu His Thr Gly Glu Arg Asp Trp His
65                  70                  75                  80

Leu Gly His Gly Val Ser Ile Glu Trp Arg Leu Arg Arg Tyr Ser Thr
                85                  90                  95

Gln Val Asp Pro Gly Leu Ala Asp Gln Leu Ile His Met His Tyr Phe
            100                 105                 110

Asp Cys Phe Ala Asp Ser Ala Ile Arg Lys Ala Ile Leu Gly His Ile
        115                 120                 125

Val Ser Pro Arg Cys Asp Tyr Gln Ala Gly His Asn Lys Val Gly Ser
    130                 135                 140

Leu Gln Tyr Leu Ala Leu Thr Ala Leu Ile Lys Pro Lys Lys Ile Lys
145                 150                 155                 160

Pro Pro Leu Pro Ser Val Lys Lys Leu Val Glu Asp Arg Trp Asn Lys
                165                 170                 175

Pro Gln Lys Thr Arg Gly His Arg Gly Ser His Thr Met Asn Gly His
            180                 185                 190

<210> SEQ ID NO 113
<211> LENGTH: 192
<212> TYPE: PRT
<213> ORGANISM: Artificial sequence
<220> FEATURE:
<223> OTHER INFORMATION: Least squares center of tree reconstruction of
      clade C vif protein sequence

<400> SEQUENCE: 113

Met Glu Asn Arg Trp Gln Val Leu Ile Val Trp Gln Val Asp Arg Met
1               5                   10                  15

Lys Ile Arg Thr Trp Asn Ser Leu Val Lys His His Met Tyr Val Ser
            20                  25                  30

Arg Arg Ala Asn Gly Trp Phe Tyr Arg His His Tyr Glu Ser Arg His
        35                  40                  45

Pro Lys Val Ser Ser Glu Val His Ile Pro Leu Gly Asp Ala Arg Leu
    50                  55                  60

Val Ile Lys Thr Tyr Trp Gly Leu Gln Thr Gly Glu Arg Asp Trp His
65                  70                  75                  80

Leu Gly His Gly Val Ser Ile Glu Trp Arg Leu Arg Arg Tyr Ser Thr
```

```
                    85                  90                  95

Gln Val Asp Pro Gly Leu Ala Asp Gln Leu Ile His Met His Tyr Phe
                100                 105                 110

Asp Cys Phe Ala Asp Ser Ala Ile Arg Lys Ala Ile Leu Gly His Ile
            115                 120                 125

Val Ile Pro Arg Cys Asp Tyr Gln Ala Gly His Asn Lys Val Gly Ser
        130                 135                 140

Leu Gln Tyr Leu Ala Leu Thr Ala Leu Ile Lys Pro Lys Lys Ile Lys
145                 150                 155                 160

Pro Pro Leu Pro Ser Val Arg Lys Leu Val Glu Asp Arg Trp Asn Lys
                165                 170                 175

Pro Gln Lys Thr Arg Gly Arg Arg Gly Asn His Thr Met Asn Gly His
                180                 185                 190

<210> SEQ ID NO 114
<211> LENGTH: 192
<212> TYPE: PRT
<213> ORGANISM: Artificial sequence
<220> FEATURE:
<223> OTHER INFORMATION: Minimum of means center of tree reconstructions
      of clade C vif protein sequence

<400> SEQUENCE: 114

Met Glu Asn Arg Trp Gln Val Leu Ile Val Trp Gln Val Asp Arg Met
1               5                   10                  15

Lys Ile Arg Thr Trp Asn Ser Leu Val Lys His His Met Tyr Val Ser
                20                  25                  30

Arg Arg Ala Asn Gly Trp Phe Tyr Arg His His Tyr Glu Ser Arg His
            35                  40                  45

Pro Lys Val Ser Ser Glu Val His Ile Pro Leu Gly Asp Ala Arg Leu
        50                  55                  60

Val Ile Lys Thr Tyr Trp Gly Leu His Thr Gly Glu Arg Asp Trp His
65                  70                  75                  80

Leu Gly His Gly Val Ser Ile Glu Trp Arg Leu Arg Arg Tyr Ser Thr
                85                  90                  95

Gln Val Asp Pro Gly Leu Ala Asp Gln Leu Ile His Met His Tyr Phe
                100                 105                 110

Asp Cys Phe Ala Asp Ser Ala Ile Arg Lys Ala Ile Leu Gly His Ile
            115                 120                 125

Val Ile Pro Arg Cys Asp Tyr Gln Ala Gly His Asn Lys Val Gly Ser
        130                 135                 140

Leu Gln Tyr Leu Ala Leu Thr Ala Leu Ile Lys Pro Lys Lys Ile Lys
145                 150                 155                 160

Pro Pro Leu Pro Ser Val Arg Lys Leu Val Glu Asp Arg Trp Asn Lys
                165                 170                 175

Pro Gln Lys Thr Arg Gly Arg Arg Gly Asn His Thr Met Asn Gly His
                180                 185                 190

<210> SEQ ID NO 115
<211> LENGTH: 96
<212> TYPE: PRT
<213> ORGANISM: Artificial sequence
<220> FEATURE:
<223> OTHER INFORMATION: Most recent common ancestor reconstructions for
      clade C vpr protein sequence

<400> SEQUENCE: 115

Met Glu Gln Ala Pro Glu Asp Gln Gly Pro Gln Arg Glu Pro Tyr Asn
```

```
                 1               5                  10                 15
Glu Trp Thr Leu Glu Leu Leu Glu Glu Leu Lys Gln Glu Ala Val Arg
                    20                  25                 30

His Phe Pro Arg Pro Trp Leu His Ser Leu Gly Gln His Ile Tyr Glu
            35                  40                  45

Thr Tyr Gly Asp Thr Trp Ala Gly Val Glu Ala Ile Ile Arg Ile Leu
        50                  55                  60

Gln Gln Leu Leu Phe Ile His Phe Arg Ile Gly Cys Gln His Ser Arg
65                  70                  75                  80

Ile Gly Ile Ile Arg Gln Arg Arg Ala Arg Asn Gly Ala Ser Arg Ser
                85                  90                  95

<210> SEQ ID NO 116
<211> LENGTH: 96
<212> TYPE: PRT
<213> ORGANISM: Artificial sequence
<220> FEATURE:
<223> OTHER INFORMATION: Least squares center of tree reconstruction of
      clade C vpr protein sequence

<400> SEQUENCE: 116

Met Glu Gln Ala Pro Glu Asp Gln Gly Pro Gln Arg Glu Pro Tyr Asn
1               5                   10                  15

Glu Trp Thr Leu Glu Ile Leu Glu Glu Leu Lys Gln Glu Ala Val Arg
                    20                  25                  30

His Phe Pro Arg Pro Trp Leu His Ser Leu Gly Gln Tyr Ile Tyr Glu
            35                  40                  45

Thr Tyr Gly Asp Thr Trp Thr Gly Val Glu Ala Leu Ile Arg Ile Leu
        50                  55                  60

Gln Gln Leu Leu Phe Ile His Phe Arg Ile Gly Cys Gln His Ser Arg
65                  70                  75                  80

Ile Gly Ile Leu Arg Gln Arg Arg Ala Arg Asn Gly Ala Ser Arg Ser
                85                  90                  95

<210> SEQ ID NO 117
<211> LENGTH: 96
<212> TYPE: PRT
<213> ORGANISM: Artificial sequence
<220> FEATURE:
<223> OTHER INFORMATION: Minimum of means center of tree reconstruction
      of clade C vpr protein sequence

<400> SEQUENCE: 117

Met Glu Gln Ala Pro Glu Asp Gln Gly Pro Gln Arg Glu Pro Tyr Asn
1               5                   10                  15

<213> ORGANISM: Artificial sequence
<220> FEATURE:
<223> OTHER INFORMATION: Most recent common ancestor reconstructions for
     clade C vpu protein sequence

<400> SEQUENCE: 118

Met Leu Asp Leu Ile Ala Arg Val Asp Tyr Arg Leu Gly Val Gly Ala
1               5                   10                  15

Leu Ile Val Ala Leu Ile Ala Ile Val Val Trp Thr Ile Val Tyr
            20                  25                  30

Ile Glu Tyr Arg Lys Leu Val Arg Gln Arg Lys Ile Asp Trp Leu Ile
        35                  40                  45

Lys Arg Ile Arg Glu Arg Ala Glu Asp Ser Gly Asn Glu Ser Asp Gly
    50                  55                  60

Asp Thr Glu Glu Leu Ser Thr Leu Val Asp Met Gly His

```
Leu Val Cys Glu Gln Gly Asn Ser Thr Asp Asn Glu Ser Arg Cys Tyr
                85                  90                  95

Met Asn His Cys Asn Thr Ser Val Ile Gln Glu Ser Cys Asp Lys His
            100                 105                 110

Tyr Trp Asp Thr Ile Arg Phe Arg Tyr Cys Ala Pro Pro Gly Tyr Ala
        115                 120                 125

Leu Leu Arg Cys Asn Asp Thr Asn Tyr Ser Gly Phe Met Pro Lys Cys
    130                 135                 140

Ser Lys Val Val Ser Ser Cys Thr Arg Met Met Glu Thr Gln Thr
145                 150                 155                 160

Ser Thr Trp Phe Gly Phe Asn Gly Thr Arg Ala Glu Asn Arg Thr Tyr
                165                 170                 175

Ile Tyr Trp His Gly Arg Asp Asn Arg Thr Ile Ile Ser Leu Asn Lys
            180                 185                 190

Tyr Tyr Asn Leu Thr Met Lys Cys Arg Arg Pro Gly Asn Lys Thr Val
        195                 200                 205

Leu Pro Val Thr Ile Met Ser Gly Leu Val Phe His Ser Gln Pro Ile
    210                 215                 220

Asn Asp Arg Pro Lys Gln Ala Trp Cys Trp Phe Gly Gly Lys Trp Lys
225                 230                 235                 240

Asp Ala Ile Lys Glu Val Lys Gln Thr Ile Val Lys His Pro Arg Tyr
                245                 250                 255

Thr Gly Thr Asn Asn Thr Asp Lys Ile Asn Leu Thr Ala Pro Gly Gly
            260                 265                 270

Gly Asp Pro Glu Val Thr Phe Met Trp Thr Asn Cys Arg Gly Glu Phe
        275                 280                 285

Leu Tyr Cys Lys Met Asn Trp Phe Leu Asn Trp Val Glu Asp Arg Asp
    290                 295                 300

Val Thr Thr Gln Arg Pro Lys Glu Arg His Arg Arg Asn Tyr Val Pro
305                 310                 315                 320

Cys His Ile Arg Gln Ile Ile Asn Thr Trp His Lys Val Gly Lys Asn
                325                 330                 335

Val Tyr Leu Pro Pro Arg Glu Gly Asp Leu Thr Cys Asn Ser Thr Val
            340                 345                 350

Thr Ser Leu Ile Ala Asn Ile Asp Trp Thr Asp Gly Asn Gln Thr Asn
        355                 360                 365

Ile Thr Met Ser Ala Glu Val Ala
    370                 375

<210> SEQ ID NO 121
<211> LENGTH: 883
<212> TYPE: PRT
<213> ORGANISM: Artificial sequence
<220> FEATURE:
<223> OTHER INFORMATION: Deduced ancestor env protein sequence

<400> SEQUENCE: 121

Met Arg Val Lys Gly Ile Arg Lys Asn Tyr Gln His Leu Trp Arg Trp
1               5                   10                  15

Gly Thr Met Leu Leu Gly Met Leu Met Ile Cys Ser Ala Ala Glu Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
        50                  55                  60
```

-continued

```
His Asn Val Trp Ala Thr His Ala Cys Val Pro Thr Asp Pro Asn Pro
 65                  70                  75                  80

Gln Glu Val Val Leu Glu Asn Val Thr Glu Asn Phe Asn Met Trp Lys
                 85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Leu Arg Thr Asn Ala Thr Asn Thr Thr Asn Ser
    130                 135                 140

Ser Ala Thr Thr Asn Thr Thr Ser Ser Gly Gly Thr Met Glu Gly
145                 150                 155                 160

Glu Lys Gly Glu Ile Lys Asn Cys Ser Phe Asn Val Thr Thr Ser Ile
                165                 170                 175

Arg Asp Lys Met Gln Lys Glu Tyr Ala Leu Phe Tyr Lys Leu Asp Val
            180                 185                 190

Val Pro Ile Asp Asn Asp Asn Asn Thr Asn Asn Thr Ser Tyr
        195                 200                 205

Arg Leu Ile Asn Cys Asn Thr Ser Val Ile Thr Gln Ala Cys Pro Lys
210                 215                 220

Val Ser Phe Glu Pro Ile Pro Ile His Tyr Cys Thr Pro Ala Gly Phe
225                 230                 235                 240

Ala Ile Leu Lys Cys Asn Asp Lys Lys Phe Asn Gly Thr Gly Pro Cys
                245                 250                 255

Thr Asn Val Ser Thr Val Gln Cys Thr His Gly Ile Arg Pro Val Val
            260                 265                 270

Ser Thr Gln Leu Leu Leu Asn Gly Ser Leu Ala Glu Glu Val Val
        275                 280                 285

Ile Arg Ser Glu Asn Phe Thr Asp Asn Ala Lys Thr Ile Ile Val Gln
290                 295                 300

Leu Asn Glu Ser Val Glu Ile Asn Cys Thr Arg Pro Asn Asn Asn Thr
305                 310                 315                 320

Arg Lys Ser Ile Pro Ile Gly Pro Gly Arg Ala Leu Tyr Ala Thr Gly
                325                 330                 335

Lys Ile Ile Gly Asp Ile Arg Gln Ala His Cys Asn Leu Ser Arg Ala
            340                 345                 350

Lys Trp Asn Asn Thr Leu Lys Gln Ile Val Thr Lys Leu Arg Glu Gln
        355                 360                 365

Phe Gly Asn Asn Lys Thr Thr Ile Val Phe Asn Gln Ser Ser Gly Gly
    370                 375                 380

Asp Pro Glu Ile Val Met His Ser Phe Asn Cys Gly Gly Glu Phe Phe
385                 390                 395                 400

Tyr Cys Asn Ser Thr Gln Leu Phe Asn Ser Thr Trp His Phe Asn Gly
                405                 410                 415

Thr Trp Gly Asn Asn Thr Glu Arg Ser Asn Asn Ala Ala Asp Asp
            420                 425                 430

Asn Asp Thr Ile Thr Leu Pro Cys Arg Ile Lys Gln Ile Ile Asn Met
        435                 440                 445

Trp Gln Glu Val Gly Lys Ala Met Tyr Ala Pro Pro Ile Ser Gly Gln
    450                 455                 460

Ile Arg Cys Ser Ser Asn Ile Thr Gly Leu Leu Leu Thr Arg Asp Gly
465                 470                 475                 480

Gly Asn Asn Glu Asn Thr Asn Asn Thr Asp Thr Glu Ile Phe Arg Pro
```

```
                         485                 490                 495
Gly Gly Gly Asp Met Arg Asp Asn Trp Arg Ser Glu Leu Tyr Lys Tyr
                500                 505                 510

Lys Val Val Lys Ile Glu Pro Leu Gly Val Ala Pro Thr Lys Ala Lys
            515                 520                 525

Arg Arg Val Val Gln Arg Glu Lys Arg Ala Val Gly Met Leu Gly Ala
        530                 535                 540

Met Phe Leu Gly Phe Leu Gly Ala Ala Gly Ser Thr Met Gly Ala Ala
545                 550                 555                 560

Ser Met Thr Leu Thr Val Gln Ala Arg Gln Leu Leu Ser Gly Ile Val
                565                 570                 575

Gln Gln Gln Asn Asn Leu Leu Arg Ala Ile Glu Ala Gln Gln His Leu
            580                 585                 590

Leu Gln Leu Thr Val Trp Gly Ile Lys Gln Leu Gln Ala Arg Val Leu
        595                 600                 605

Ala Val Glu Arg Tyr Leu Lys Asp Gln Gln Leu Leu Gly Ile Trp Gly
610                 615                 620

Cys Ser Gly Lys Leu Ile Cys Thr Thr Ala Val Pro Trp Asn Ala Ser
625                 630                 635                 640

Trp Ser Asn Lys Ser Leu Asp Lys Ile Trp Asn Asn Met Thr Trp Met
                645                 650                 655

Glu Trp Glu Arg Glu Ile Asp Asn Tyr Thr Gly Leu Ile Tyr Thr Leu
            660                 665                 670

Ile Glu Glu Ser Gln Asn Gln Gln Glu Lys Asn Glu Gln Glu Leu Leu
        675                 680                 685

Glu Leu Asp Lys Trp Ala Ser Leu Trp Asn Trp Phe Asp Ile Thr Asn
690                 695                 700

Trp Leu Trp Tyr Ile Lys Ile Phe Ile Met Ile Val Gly Gly Leu Val
705                 710                 715                 720

Gly Leu Arg Ile Val Phe Ala Val Leu Ser Ile Val Asn Arg Val Arg
                725                 730                 735

Gln Gly Tyr Ser Pro Leu Ser Phe Gln Thr Arg Leu Pro Ala Pro Arg
            740                 745                 750

Gly Pro Asp Arg Pro Glu Gly Ile Glu Glu Gly Gly Glu Arg Asp
        755                 760                 765

Arg Asp Arg Ser Gly Arg Leu Val Asn Gly Phe Leu Ala Leu Ile Trp
        770                 775                 780

Asp Asp Leu Arg Ser Leu Cys Leu Phe Ser Tyr His Arg Leu Arg Asp
785                 790                 795                 800

Leu Leu Leu Ile Val Ala Arg Ile Val Glu Leu Leu Gly Arg Arg Gly
                805                 810                 815

Trp Glu Ala Leu Lys Tyr Trp Trp Asn Leu Leu Gln Tyr Trp Ser Gln
            820                 825                 830

Glu Leu Lys Asn Ser Ala Val Ser Leu Leu Asn Ala Thr Ala Ile Ala
        835                 840                 845

Val Ala Glu Gly Thr Asp Arg Val Ile Glu Val Val Gln Arg Ala Cys
850                 855                 860

Arg Ala Ile Leu His Ile Pro Arg Arg Ile Arg Gln Gly Leu Glu Arg
865                 870                 875                 880

Ala Leu Leu

<210> SEQ ID NO 122
<211> LENGTH: 25
```

```
<212> TYPE: DNA
<213> ORGANISM: Artificial sequence
<220> FEATURE:
<223> OTHER INFORMATION: First round primer UP-3

<400> SEQUENCE: 122
agactgcaga tgtgaagagg tacac                                   25

<210> SEQ ID NO 123
<211> LENGTH: 22
<212> TYPE: DNA
<213> ORGANISM: Artificial sequence
<220> FEATURE:
<223> OTHER INFORMATION: First round primer PEXTM6

<400> SEQUENCE: 123
ggatctggta tgctcatagc aa                                      22

<210> SEQ ID NO 124
<211> LENGTH: 25
<212> TYPE: DNA
<213> ORGANISM: Artificial sequence
<220> FEATURE:
<223> OTHER INFORMATION: Second round primers PEXTM7

<400> SEQUENCE: 124
gatactgcag caacagcaac agctg                                   25

<210> SEQ ID NO 125
<211> LENGTH: 24
<212> TYPE: DNA
<213> ORGANISM: Artificial sequence
<220> FEATURE:
<223> OTHER INFORMATION: Second round primer UP-5

<400> SEQUENCE: 125
gcaaagcttc tctggttggc agtg                                    24
```

ANCESTRAL AND COT VIRAL SEQUENCES, PROTEINS AND IMMUNOGENIC COMPOSITIONS

CROSS-REFERENCES TO RELATED APPLICATIONS

This application is a continuation-in-part and claims priority to U.S. patent application Ser. No. 10/204,204, filed Feb. 16, 2001, now abandoned which is a U.S. National Phase application of PCT/US01/05288, filed Feb. 16, 2001, which claims the benefit of U.S. Provisional Patent Application No. 60/183,659, filed Feb. 18, 2000. This application also claims the benefit of U.S. Provisional Application No. 60/447,586, filed Feb. 14, 2003. All of these applications are incorporated by reference herein. All of these patent applications are incorporated herein by reference, in their entirety.

STATEMENT AS TO RIGHTS TO INVENTIONS MADE UNDER FEDERALLY SPONSORED RESEARCH OR DEVELOPMENT

This work was supported by a grant from the US Public Health Service through a grant to the University of Washington Center for AIDS Research (AI-27757) and PHS T32A107509 and T32CA0922925. The Federal Government may have certain rights in this invention.

BACKGROUND OF THE INVENTION

HIV-1 has proved to be an extremely difficult target for vaccine development. Immune correlates of protective immunity against HIV-1 infection remain uncertain. The virus persistently replicates in the infected individual, leading inexorably to disease despite the generation of vigorous humoral and cellular immune responses. HIV-1 rapidly mutates during infection, resulting in the generation of viruses that can escape immune recognition. Unlike other highly diverse viruses (e.g., influenza), there does not appear to be a succession of variants where one prototypical strain is replaced by successive uniform strains. Rather, an evolutionary tree of viral sequences sampled from a large number of HIV-infected individuals form a star-burst pattern with most of the variants roughly equidistant from the center of the tree. HIV-1 viruses can also persist indefinitely as latent proviral DNA, capable of replicating in individuals at a later time.

Currently, several HIV-1 vaccine approaches are being developed, each with its own relative strengths and weaknesses. These approaches include the development of live attenuated vaccines, inactivated viruses with adjuvant peptides and subunit vaccines, live vector-based vaccines, and DNA vaccines. Envelope glycoproteins were considered as the prime antigen in the vaccine regimen due to their surface-exposure, until it became evident that they are not ideal immunogens. This is an expected consequence of the immunological selective forces that drive the evolution of these viruses: it appears that the same features of envelope glycoproteins that dictate poor immunogenicity in natural infections have hampered vaccine development. However, modification of the vaccine recipe may overcome these problems. For example, a recent report of successful neutralization (in mice) of primary isolates from infected individuals with a fusion-competent immunogen supports this idea.

Another approach could be to use natural isolates of HIV-1 in a vaccine recipe. Identification of early variants even from stored specimens near the start of the AIDS epidemic is very unlikely, however. Natural isolates are also unlikely to embody features (e.g., epitopes) that are ideal for a vaccine candidate. Furthermore, any given natural virus isolate will have features that reflect adaptations due to specific interactions within that particular human host. These individual-specific features are not expected to be found in all or most strains of the virus, and thus vaccines based on individual isolates are unlikely to be effective against a broad range of circulating virus.

Another approach could be to include as many diverse HIV-1 isolates as possible in the vaccine recipe in an effort to elicit broad protection against HIV-1 challenge. First, one or more strains are chosen from among the many circulating strains of HIV. The advantage of this approach is that such a strain is known to be an infectious form of a viable virus. However, such a strain will be genetically quite dissimilar to other strains in circulation, and thus can fail to elicit broad protection. A related approach is to build a consensus sequence based on circulating strains, or on strains in the database. The consensus sequence is likely to be less distant in a genetic sense from circulating strains, but is not an estimate of any real virus, however, and thus may not provide broad protection.

Accordingly, there is a need in the art for new effective methods of identifying candidate sequences for vaccine development to prevent and treat HIV infection. The present invention fulfills this and other needs.

BRIEF SUMMARY OF THE INVENTION

The present invention provides methods for determining founder sequences from highly diverse virus populations. Also provided are determined founder sequences for highly diverse virus populations.

In one aspect, computational methods are provided for determining an ancestral viral sequence for highly diverse viruses, such as HIV-1, HIV-2 or Hepatitis C. These computational methods use samples of circulating viruses to determine an ancestral viral sequence by maximum likelihood phylogeny analysis. The ancestral viral sequence can be, for example, an HIV-1 ancestral viral gene sequence, an HIV-2 ancestral viral gene sequence, or a Hepatitis C ancestral viral gene sequence. In other embodiments, the ancestral viral gene sequence is of HIV-1 subtype A, B, C, D, E, F, G, H, J, AG, or AGI; HIV-1 Group M, N, or O; or HIV-2 subtype A or B. The ancestral viral gene sequence can be derived from widely dispersed HIV-1 variants, geographically-restricted HIV-1 variants, widely dispersed HIV-2 variants, or geographically-restricted HIV-2 variants. Typically, the ancestor gene is an env gene or a gag gene.

The ancestral viral gene sequence is more closely related, on average, to a gene sequence of any given circulating virus than to any other variant. In some embodiments, the ancestral viral gene sequence has at least 70% identity with the sequence set forth in SEQ ID NO:1, SEQ ID NO:3, SEQ ID NO:5, SEQ ID NO:6, but does not have 100% identity with any circulating viral variant.

In another aspect, ancestral sequences for the env gene of HIV-1 subtype B are provided. HIV-1 subtype B gives rise to most infections in the Western Hemisphere and in Europe. The determined ancestral viral sequence is on average more closely related to any given circulating virus than to any other variant. The env ancestral gene sequence encodes an open reading frame for gp160, the gene product of env. In additional specific embodiments, the ancestral viral sequence has a gene sequence set forth in FIGS. 9 to 17 (designated "mrca").

In another aspect, ancestral sequences for the env gene of HIV-1 subtype C are provided. Subtype C is the most prevalent subtype worldwide. The determined founder sequence is, on average, more closely related to any given circulating virus than to any other variant. This sequence encodes an open reading frame for gp160, the gene product of env. In additional specific embodiments, the ancestral viral sequence has a gene sequence set forth in FIGS. 27 to 35 (designated "mrca").

Isolated HIV ancestor proteins or fragments thereof are also provided. The isolated ancestor protein can be, for example, the contiguous sequence of HIV-1, subtype B, env ancestor protein (SEQ ID NO:2) or HIV-1, subtype C, env ancestor protein (SEQ ID NO:4). The ancestor protein can also be of HIV-1 subtype A, B, C, D, E, F, G, H, J, AG, or AGI; HIV-1 Group M, N, or O; or HIV-2 subtype A or B. In additional specific embodiments, the ancestor protein can have a sequence set forth in FIGS. 18-26 or 36 to 44 (designated "mrca").

In another aspect, computational methods are provided for determining a COT viral sequence for highly diverse viruses, such as HIV-1, HIV-2 or Hepatitis C. These computational methods use samples of circulating viruses to determine a COT viral sequence by Least Squares or Minimum of Means methodologies. The COT viral sequence can be, for example, an HIV-1 COT viral gene sequence, an HIV-2 COT viral gene sequence, or a Hepatitis C COT viral gene sequence. In other embodiments, the COT viral gene sequence is of HIV-1 subtype A, B, C, D, E, F, G, H, J, AG, or AGI; HIV-1 Group M, N, or O; or HIV-2 subtype A or B. The COT viral gene sequence can be derived from widely dispersed HIV-1 variants, geographically-restricted HIV-1 variants, widely dispersed HIV-2 variants, or geographically-restricted HIV-2 variants. Typically, the COT viral gene is an env gene or a gag gene.

The COT viral gene sequence is more closely related, on average, to a gene sequence of any given circulating virus than to any other variant. In certain embodiments, the COT viral gene sequence has at least 70% identity with the LScot and MMcot sequences set forth in FIGS. 9 to 17 or 27 to 35, but does not have 100% identity with any circulating viral variant.

In another aspect, COT sequences for genes of HIV-1 subtype B are provided. HIV-1 subtype B gives rise to most infections in the Western Hemisphere and in Europe. The determined COT viral sequences are, on average, more closely related to any given circulating virus than to any other variant. In specific embodiments, the COT viral gene sequence is an LScot or MMcot sequence set forth in FIGS. 9 to 17, but does not have 100% identity with any circulating viral variant.

In another aspect, COT sequences for genes of HIV-1 subtype C are provided. Subtype C is the most prevalent subtype worldwide. The determined COT sequence is, on average, more closely related to any given circulating virus than to any other variant. In specific embodiments, the COT viral gene sequence is an LScot or MMcot sequence set forth in FIGS. 27 to 35, but does not have 100% identity with any circulating viral variant.

Isolated HIV COT proteins and or fragments thereof are also provided. The isolated ancestor protein can be, for example, an LScot or MMcot amino acid sequence set forth in FIGS. 27 to 25 and 36 to 44.

Also provided are computational methods for determining other ancestral or COT viral sequences. The computational methods can be extended, for example, to determine an ancestral or COT viral sequence for other HIV subtypes, such as, for example, HIV-1 subtype E, which is widely spread in developing countries. The computational methods can also be extended to determine an ancestral or COT viral sequence for all known and newly emerging highly diverse virus, such as, for example, HIV-1 strains, subtypes and groups. For example, ancestral or COT viral sequences can be determined for HIV-1-B in Thailand or Brazil, HIV-1-C in China, India, South Africa or Brazil, and the like. In other embodiments, the ancestral or COT viral sequence is determined for the HIV-1 nef gene or polypeptide, pol gene or polypeptide or other auxiliary genes or polypeptide (see infra).

The present invention also provides an expression construct including a transcriptional promoter; a nucleic acid encoding an ancestor protein; and a transcriptional terminator. The nucleic acid can encode, for example, an HIV-1 ancestor or COT protein (e.g., SEQ ID NO:2 or SEQ ID NO:4). The nucleic acid can be, for example, an HIV-1 subtype B or C env gene sequence (e.g., SEQ ID NO:1, SEQ ID NO:3, SEQ ID NO:5, or SEQ ID NO:6). In one embodiment, the nucleic acid sequence is optimized for expression in a host cell.

The promoter can be a heterologous promoter, such as the cytomegalovirus promoter. The expression construct can be expressed in prokaryotic or eukaryotic cells. Suitable cells include, for example, mammalian cells, human cells, *Escherichia coli* cells, and *Saccharomyces cerevisiae* cells. In one embodiment, the expression construct has the nucleic acid sequence operably linked to a Semliki Forest Virus replicon, wherein the resulting recombinant replicon is operably linked to a cytomegalovirus promoter.

In another aspect, compositions are provided for inducing an immune response in a mammal, the compositions include a viral ancestor protein or an immunogenic fragment of an ancestor or COT protein. The ancestor or COT protein can be derived from HIV-1 subtype B or C env ancestor or COT protein, or from other HIV-1, HIV-2 or Hepatitis C ancestor or COT proteins. In other aspects, the composition can be used as a vaccine, such as an AIDS vaccine to protect against infection by the highly diverse human immunodeficiency virus, type 1 (HIV-1), or for protection against HIV-2 or Hepatitis C infections. The ancestral or COT viral sequence can be an HIV-1 group determined founder (e.g., for Group M), for an HIV-1 subtype (e.g., B, C or E), for a widely spread variant, for a geographically-restricted variant, or for a newly emerging variant.

In another aspect, isolated antibodies are provided that bind specifically to a viral ancestor or COT protein and that bind specifically to a plurality of circulating descendant viral ancestor or COT proteins. The ancestor or COT protein can be from, for example, HIV-1, HIV-2, or Hepatitis C. The antibody can be a monoclonal antibody or antigen binding fragment thereof. In one embodiment, the antibody is a humanized monoclonal antibody. Other suitable antibodies or antigen binding fragments thereof can be a single chain antibody, a single heavy chain antibody, an antigen binding F(ab')$_2$ fragment, an antigen binding Fab' fragment, an antigen binding Fab fragment, or an antigen binding Fv fragment.

In addition to determining ancestral and COT viral sequences, the present invention also provides methods for preparing and testing immunogenic compositions based on an ancestral or COT viral sequence. In specific embodiments, immunogenic compositions (based on an ancestral or COT viral sequence) are prepared and administered to a mammal, employing an appropriate model, such as, for example, a mouse model or simian-human immunodeficiency virus (SHIV) macaque model. Immunogenic compositions can be prepared using an isolated ancestral or COT viral gene sequence, or polypeptide sequence, or a portion thereof.

In yet another aspect, diagnostic methods are provided to detect HIV and/or AIDS in a subject, using the nucleic acids, peptides or antibodies based on an ancestral or COT viral sequence.

BRIEF DESCRIPTION OF THE DRAWINGS

FIG. 1 shows a phylogenetic classification of HIV-1. The circled nodes approximate the ancestral state of the HIV-1 main group (Group M) and the main group clades A-G, J, AGI and AG.

FIG. 2 shows the phylogenetic relationship of HIV-1 subtype B and the placement of the determined subtype B ancestral node on that tree. The phylogenetic relationship of HIV-1 subtype D is shown as an outgroup.

FIG. 3 shows an ancestral viral sequence reconstruction of the most recent common ancestor using maximum likelihood reconstruction for an SIV inoculum up to three years after infection into macaques. The consensus sequence and the most recent common ancestor sequence were found to differ 1.5% in nucleotide sequence.

FIG. 4 provides an example of the development of a digital vaccine using an ancestral viral sequence.

FIG. 5 shows a comparison of a "most parsimonious reconstruction" methodology and a "maximum likelihood reconstruction methodology."

FIG. 6 shows another comparison of the "most parsimonious reconstruction" methodology and the "maximum likelihood reconstruction methodology." (SEQ ID NOS: 7-23).

FIG. 9 shows a comparison of the Most Recent Common Ancestor ("MRCA"), COT Least Squares ("LScot") and COT Minimum of Means ("MMcot") reconstructions for the Clade B gag gene (SEQ ID NOS: 24-26).

FIG. 10 shows a comparison of the Most Recent Common Ancestor ("MRCA"), COT Least Squares ("LScot") and COT Minimum of Means ("MMcot") reconstructions for the Clade B env (encoding gp160) (SEQ ID NOS: 27-28).

FIG. 11 shows a comparison of the Most Recent Common Ancestor ("MRCA"), COT Least Squares ("LScot") and COT Minimum of Means ("MMcot") reconstructions for the Clade B nef gene (SEQ ID NOS: 29-31).

FIG. 12 shows a comparison of the Most Recent Common Ancestor ("MRCA"), COT Least Squares ("LScot") and COT Minimum of Means ("MMcot") reconstructions for the Clade B pol gene (SEQ ID NOS: 32-34).

FIG. 13 shows a comparison of the Most Recent Common Ancestor ("MRCA"), COT Least Squares ("LScot") and COT Minimum of Means ("MMcot") reconstructions for the Clade B rev gene(SEQ ID NOS: 35-37).

FIG. 14 shows a comparison of the Most Recent Common Ancestor ("MRCA"), COT Least Squares ("LScot") and COT Minimum of Means ("MMcot") reconstructions for the Clade B tat gene (SEQ ID NOS: 38-40).

FIG. 15 shows a comparison of the Most Recent Common Ancestor ("MRCA"), COT Least Squares ("LScot") and COT Minimum of Means ("MMcot") reconstructions for the Clade B vif gene (SEQ ID NOS: 41-42).

FIG. 16 shows a comparison of the Most Recent Common Ancestor ("MRCA"), COT Least Squares ("LScot") and COT Minimum of Means ("MMcot") reconstructions for the Clade B vpr gene (SEQ ID NOS: 43-44).

FIG. 17 shows a comparison of the Most Recent Common Ancestor ("MRCA"), COT Least Squares ("LScot") and COT Minimum of Means ("MMcot") reconstructions for the Clade B vpu gene (SEQ ID NOS: 45-46).

FIG. 18 shows a comparison of the Most Recent Common Ancestor ("MRCA"), COT Least Squares ("LScot") and COT Minimum of Means ("MMcot") reconstructions for the Clade B gag protein (SEQ ID NOS: 47-49).

FIG. 19 shows a comparison of the Most Recent Common Ancestor ("MRCA"), COT Least Squares ("LScot") and COT Minimum of Means ("MMcot") reconstructions for the Clade B gp160 protein (SEQ ID NOS: 50-51).

FIG. 20 shows a comparison of the Most Recent Common Ancestor ("MRCA"), COT Least Squares ("LScot") and COT Minimum of Means ("MMcot") reconstructions for the Clade B nef protein (SEQ ID NOS: 52-54).

FIG. 21 shows a comparison of the Most Recent Common Ancestor ("MRCA"), COT Least Squares ("LScot") and COT Minimum of Means ("MMcot") reconstructions for the Clade B pol protein (SEQ ID NOS: 55-57).

FIG. 22 shows a comparison of the Most Recent Common Ancestor ("MRCA"), COT Least Squares ("LScot") and COT Minimum of Means ("MMcot") reconstructions for the Clade B rev protein (SEQ ID NOS: 58-60).

FIG. 23 shows a comparison of the Most Recent Common Ancestor ("MRCA"), COT Least Squares ("LScot") and COT Minimum of Means ("MMcot") reconstructions for the Clade B tat protein (SEQ ID NOS: 61-62).

FIG. 24 shows a comparison of the Most Recent Common Ancestor ("MRCA"),COT Least Squares ("LScot") and COT Minimum of Means ("MMcot") reconstructions for the Clade B vif protein (SEQ ID NOS: 63-64).

FIG. 25 shows a comparison of the Most Recent Common Ancestor ("MRCA"), COT Least Squares ("LScot") and COT Minimum of Means ("MMcot") reconstructions for the Clade B vpr protein (SEQ ID NOS: 65-67).

FIG. 26 shows a comparison of the Most Recent Common Ancestor ("MRCA"), COT Least Squares ("LScot") and COT Minimum of Means ("MMcot") reconstructions for the Clade B vpu protein (SEQ ID NOS: 68-69).

FIG. 27 shows a comparison of the Most Recent Common Ancestor ("MRCA"), COT Least Squares ("LScot") and COT Minimum of Means ("MMcot") reconstructions for the Clade C gag gene (SEQ ID NOS: 70-72).

FIG. 28 shows a comparison of the Most Recent Common Ancestor ("MRCA"), COT Least Squares ("LScot") and COT Minimum of Means ("MMcot") reconstructions for the Clade C env (encoding gp160) (SEQ ID NOS: 73-75).

FIG. 29 shows a comparison of the Most Recent Common Ancestor ("MRCA"), COT Least Squares ("LScot") and COT Minimum of Means ("MMcot") reconstructions for the Clade C nef gene (SEQ ID NOS: 76-77).

FIG. 30 shows a comparison of the Most Recent Common Ancestor ("MRCA"), COT Least Squares ("LScot") and COT Minimum of Means ("MMcot") reconstructions for the Clade C pol gene (SEQ ID NOS: 78-80).

FIG. 31 shows a comparison of the Most Recent Common Ancestor ("MRCA"), COT Least Squares ("LScot") and COT Minimum of Means ("MMcot") reconstructions for the Clade C rev gene (SEQ ID NOS: 81-83).

FIG. 32 shows a comparison of the Most Recent Common Ancestor ("MRCA"), COT Least Squares ("LScot") and COT Minimum of Means ("MMcot") reconstructions for the Clade C tat gene (SEQ ID NOS: 84-86).

FIG. 33 shows a comparison of the Most Recent Common Ancestor ("MRCA"), COT Least Squares ("LScot") and COT Minimum of Means ("MMcot") reconstructions for the Clade C vif gene (SEQ ID NOS: 87-89).

FIG. 34 shows a comparison of the Most Recent Common Ancestor ("MRCA"), COT Least Squares ("LScot") and COT Minimum of Means ("MMcot") reconstructions for the Clade C vpr gene (SEQ ID NOS: 90-92).

FIG. 35 shows a comparison of the Most Recent Common Ancestor ("MRCA"), COT Least Squares ("LScot") and COT Minimum of Means ("MMcot") reconstructions for the Clade C vpu gene (SEQ ID NOS: 93-95).

FIG. 36 shows a comparison of the Most Recent Common Ancestor ("MRCA"), COT Least Squares ("LScot") and COT Minimum of Means ("MMcot") reconstructions for the Clade C gag protein (SEQ ID NOS: 96-90).

FIG. 37 shows a comparison of the Most Recent Common Ancestor ("MRCA"), COT Least Squares ("LScot") and COT Minimum of Means ("MMcot") reconstructions for the Clade C gp160 protein (SEQ ID NOS: 99-101).

FIG. 38 shows a comparison of the Most Recent Common Ancestor ("MRCA"), COT Least Squares ("LScot") and COT Minimum of Means ("MMcot") reconstructions for the Clade C nef protein (SEQ ID NOS: 102-103).

FIG. 39 shows a comparison of the Most Recent Common Ancestor ("MRCA"), COT Least Squares ("LScot") and COT Minimum of Means ("MMcot") reconstructions for the Clade C pol protein (SEQ ID NOS: 104-106).

FIG. 40 shows a comparison of the Most Recent Common Ancestor ("MRCA"), COT Least Squares ("LScot") and COT Minimum of Means ("MMcot") reconstructions for the Clade C rev protein (SEQ ID NOS: 107-109).

FIG. 41 shows a comparison of the Most Recent Common Ancestor ("MRCA"), COT Least Squares ("LScot") and COT Minimum of Means ("MMcot") reconstructions for the Clade C tat protein (SEQ ID NOS: 110-111).

FIG. 42 shows a comparison of the Most Recent Common Ancestor ("MRCA"), COT Least Squares ("LScot") and COT Minimum of Means ("MMcot") reconstructions for the Clade C vif protein (SEQ ID NOS: 112-114).

FIG. 43 shows a comparison of the Most Recent Common Ancestor ("MRCA"), COT Least Squares ("LScot") and COT Minimum of Means ("MMcot") reconstructions for the Clade C vpr protein (SEQ ID NOS: 115-117).

FIG. 44 shows a comparison of the Most Recent Common Ancestor ("MRCA"), COT Least Squares ("LScot") and COT Minimum of Means ("MMcot") reconstructions for the Clade C vpu protein (SEQ ID NOS: 118-119).

Figure 1:
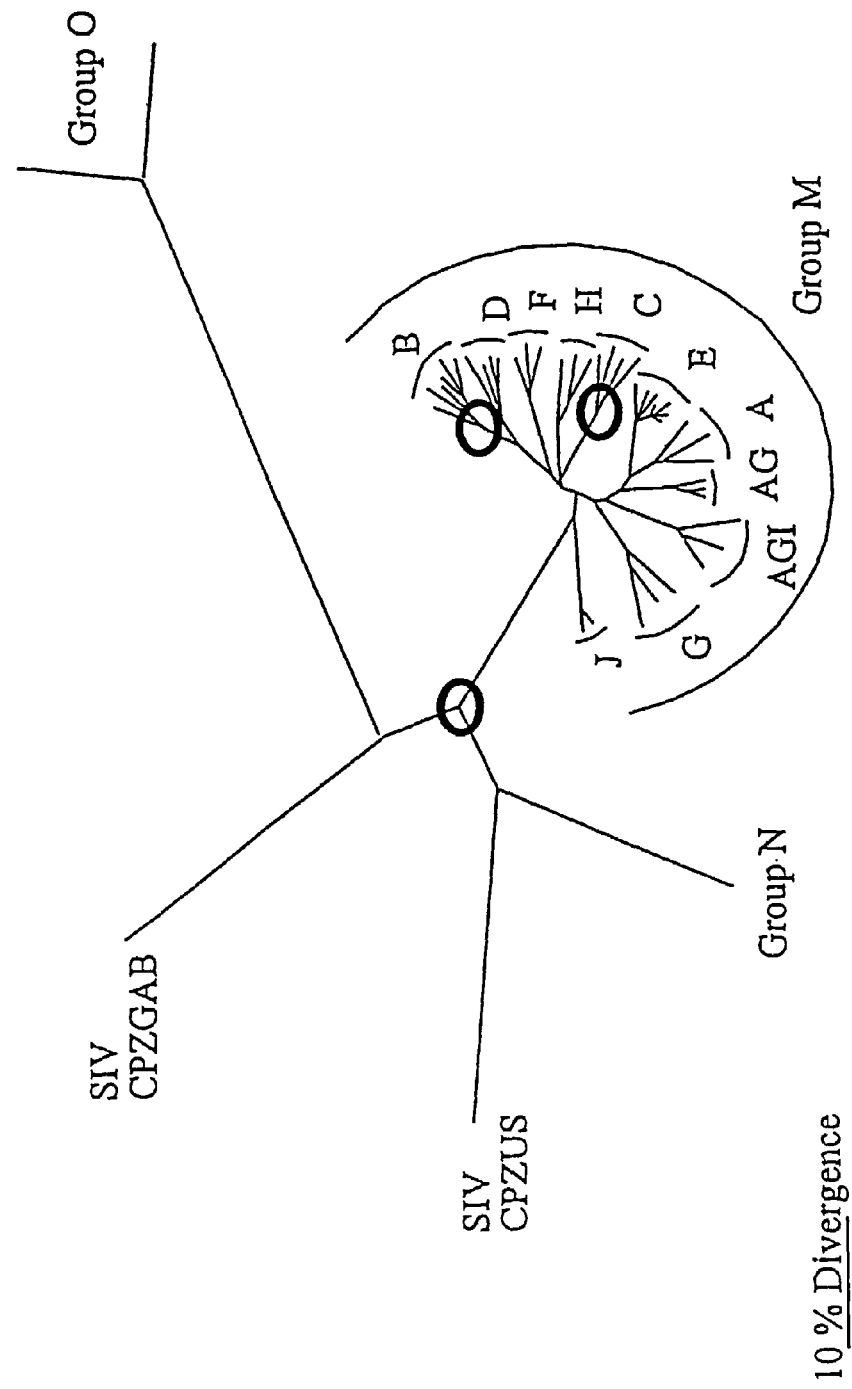

FIG. 45. Phylogenetic relationships of different phylogenetic structures and between HIV-1 group M, Subtype B gp160 sequences. A. thirty-eight Subtype B sequences and three Subtype D (outgroup) sequences used to root the Subtype B sequences (see Table 11). The Subtype B sequences were from nine countries, representing a broad sample of Subtype B diversity: Australia, 8; China, 1; France, 6; Gabon, 1; Germany, 2; Great Britain, 2; The Netherlands, 2; Spain, 1; USA, 15). B. Idealized phylogenetic trees with caterpillar (left) and star (right) shapes.

FIG. 46. Deduced ancestor protein sequences SIVBK28 ancestor (Env segment) and AN1-EnvB (SEQ ID NOS: 120-121).

DESCRIPTION OF THE SPECIFIC EMBODIMENTS

The present invention provides methods for determining founder sequences from highly diverse virus populations. Also provided are determined founder sequences for highly diverse virus populations.

Prior to setting forth the invention in more detail, it may be helpful to a further understanding thereof to set forth definitions of certain terms as used hereinafter.

Definitions

Unless defined otherwise, all technical and scientific terms used herein have the same meaning as commonly understood by one of ordinary skill in the art to which this invention pertains. Although any methods and materials similar to those described herein can be used in the practice or testing of the present invention, only exemplary methods and materials are described. For purposes of the present invention, the following terms are defined below.

An "ancestral sequence" refers to a determined founder sequence, determined through application of maximum likelihood phylogenetic analysis. An ancestral sequence is typically one that is more closely related, on average, to any given variant than to any other variant. An "ancestral viral sequence" refers to a determined founder sequence, typically one that is more closely related, on average, to any given circulating virus than to any other variant. An "ancestral viral sequence" is determined through application of maximum likelihood phylogenetic analysis using the nucleic acid and/or amino acid sequences of circulating viruses. An "ancestor virus" is a virus comprising the "ancestral viral sequence." An "ancestor protein" is a protein, polypeptide or peptide having an amino acid ancestral viral sequence.

A "COT sequence" refers to a determined founder sequence, determined through application of a COT Least Squares Method or a COT Minimum of Means Method. A "COT sequence" is a position at a node or on a branch of a phylogenetic tree having completely specified branch lengths. A "COT viral sequence" refers to a founder nucleic acid sequence determined by COT Least Squares Method or a COT Minimum of Means Method, using the nucleic acid and/or amino acid sequences of circulating viruses. An "COT virus" is a virus comprising the "COT viral sequence." A "COT viral protein" or "COT protein" is a protein, polypeptide or peptide having an amino acid COT viral sequence.

The term "circulating virus" refers to virus found in an infected individual.

The term "variant" refers to a virus, gene or gene product that differs in sequence from other viruses, genes or gene products by one or more nucleotide or amino acids.

The terms "immunological" or "immune response" refer to the development of a beneficial humoral (i.e., antibody mediated) and/or a cellular (i.e., mediated by antigen-specific T-cells or their secretion products) response directed against an HIV peptide in a recipient subject. Such a response can be, in particular, an active response induced by the administration of an immunogen. A cellular immune response is elicited by the presentation of epitopes in association with Class I or Class II MHC molecules to activate antigen-specific CD4$^+$T helper cells (i.e., Helper T lymphocytes) and/or CD8$^+$cytotoxic T cells. The presence of a cell-mediated immunological response can be determined by, for example, proliferation assays of CD4$^+$T cells (i.e., measuring the HTL (Helper T lymphocyte) response) or by CTL (cytotoxic T lymphocyte) assays (see, e.g., Burke et al., *J. Inf. Dis.* 170:1110-19 (1994); Tigges et al., *J. Immunol.* 156:3901-10 (1996)). The relative contributions of humoral and cellular responses to the protective or therapeutic effect of an immunogen can be distinguished by separately isolating IgG and T-cells from an immunized syngeneic animal and measuring protective or therapeutic effects in a second subject. For example, the effector cells can be deleted and the resulting response analyzed (see, e.g., Schmitz et al., *Science* 283:857-60 (1999); Jin et al., *J Exp. Med.* 189:991-98 (1999)).

"Antibody" refers to a polypeptide substantially encoded by an immunoglobulin gene or immunoglobulin genes, or fragments thereof, that specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain has a variable region of about 100 to 110 or more amino acids primarily responsible for antigen recognition. The terms variable light chain (VL) and variable heavy chain (VH) refer to these light and heavy chains, respectively.

Antibodies exist, for example, as intact immunoglobulins or as a number of well characterized antigen-binding fragments produced by digestion with various peptidases. For example, pepsin digests an antibody below the disulfide linkages in the hinge region to produce an F(ab')$_2$ fragment, a dimer of Fab which itself is a light chain joined to VH-CH1 by a disulfide bond. The F(ab')$_2$ fragment can be reduced under mild conditions to break the disulfide linkage in the hinge region, thereby converting the F(ab')$_2$ dimer into an Fab' monomer. The Fab' monomer is essentially an Fab with part of the hinge region (see, *Fundamental Immunology*, Third Edition, W. E. Paul (ed.), Raven Press, N.Y. (1993)). While various antibody fragments are defined in terms of the digestion of an intact antibody, one of skill will appreciate that such fragments can be synthesized de novo either chemically or by utilizing recombinant DNA methodology. Thus, the term antibody, as used herein, also includes antibody fragments, such as a single chain antibody, an antigen binding F(ab')$_2$ fragment, an antigen binding Fab' fragment, an antigen binding Fab fragment, an antigen binding Fv fragment, a single heavy chain or a chimeric antibody. Such antibodies can be produced by the modification of whole antibodies or synthesized de novo using recombinant DNA methodologies.

The term "biological sample" refers to any tissue or liquid sample having genomic or viral DNA or other nucleic acids (e.g., mRNA, viral RNA, or the like) or proteins. "Biological sample" further includes fluids, such as serum and plasma, that contain cell-free virus, and also includes both normal healthy cells and cells suspected of HIV infection.

The term "nucleic acid" refers to deoxyribonucleotides or ribonucleotides and polymers thereof in either single or double stranded form. Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions can be achieved by generating sequences in which the third position of one or more selected (or all) codons is substituted with mixed-base and/or deoxyinosine residues (see, e.g., Batzer et al., *Nucleic Acid Res*. 19:5081 (1991); Ohtsuka et al., *J. Biol. Chem*. 260:2605-08 (1985); Rossolini et al., *Mol. Cell. Probes* 8:91-98 (1994)). Nucleic acids also include fragments of at least 10 contiguous nucleotides (e.g., a hybridizable portion); in other embodiments, the nucleic acids comprise at least 25 nucleotides, 50 nucleotides, 100 nucleotides, 150 nucleotides, 200 nucleotides, or even up to 250 nucleotides or more. The term "nucleic acid" is used interchangeably with gene, cDNA, and mRNA encoded by a gene.

As used herein a "nucleic acid probe" is defined as a nucleic acid capable of binding to a target nucleic acid (e.g., an HIV-1 nucleic acid) of complementary sequence through one or more types of chemical bonds, usually through complementary base pairing, such as by hydrogen bond formation. As used herein, a probe may include natural (e.g., A, G, C, or T) or modified bases (e.g., 7-deazaguanosine, inosine, or the like). In addition, the bases in a probe can be joined by a linkage other than a phosphodiester bond, so long as it does not interfere with hybridization. Thus, for example, probes can be peptide nucleic acids in which the constituent bases are joined by peptide bonds rather than phosphodiester linkages. It will be understood by one of skill in the art that probes can bind target sequences lacking complete complementarity with the probe sequence, at levels that depend upon the stringency of the hybridization conditions.

Nucleic acid probes can be DNA or RNA fragments. DNA fragments can be prepared, for example, by digesting plasmid DNA, by use of PCR, or by chemical synthesis, such as by the phosphoramidite method described by Beaucage and Carruthers (*Tetrahedron Lett*. 22:1859-62 (1981)), or by the triester method according to Matteucci et al. (*J. Am. Chem. Soc*. 103:3185 (1981)). A double stranded fragment can then be obtained, if desired, by annealing the chemically synthesized single strands together under appropriate conditions, or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double stranded nucleic acid.

A "labeled nucleic acid probe" is a nucleic acid probe that is bound, either covalently, through a linker, or through ionic, van der Waals or hydrogen bonds, to a label such that the presence of the probe can be detected by detecting the presence of the label bound to the probe.

The term "operably linked" refers to functional linkage between a nucleic acid expression control sequence (such as a promoter, signal sequence, or any of an array of transcription factor binding sites) and a second nucleic acid sequence, wherein the expression control sequence affects transcription and/or translation of the nucleic acid corresponding to the second sequence.

"Amplification primers" are nucleic acids, typically oligonucleotides, comprising either natural or analog nucleotides that can serve as the basis for the amplification of a selected nucleic acid sequence. They include, for example, both polymerase chain reaction primers and ligase chain reaction oligonucleotides.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The terms "amino acid" or "amino acid residue", as used herein, refer to naturally occurring L-amino acids or to D-amino acids as described further below. The commonly used one- and three-letter abbreviations for amino acids are used herein (see, e.g., Alberts et al., *Molecular Biology of the Cell*, Garland Publishing, Inc., New York (3d ed. 1994); Creighton, *Proteins*, W.H. Freeman and Company (1984)).

A "conservative substitution," when describing a protein, refers to a change in the amino acid composition of the protein that is less likely to substantially alter the protein's activity.

Thus, "conservatively modified variations" of a particular amino acid sequence refers to amino acid substitutions of those amino acids that are less likely to be critical for protein activity or substitution of amino acids with other amino acids having similar properties (e.g., acidic, basic, positively or negatively charged, polar or non-polar, or the like) such that the substitutions of even critical amino acids do not substantially alter activity. Conservative substitution tables providing amino acids that are often functionally similar are well known in the art (see, e.g., Creighton, *Proteins*, W.H. Freeman and Company (1984)). In addition, individual substitutions, deletions or additions which alter, add or delete a single amino acid or a small percentage of amino acids in an encoded sequence are also "conservatively modified variations."

The terms "identical" or "percent identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region, as measured using one of the following sequence comparison algorithms or by manual alignment and visual inspection. Such sequences are then said to be "substantially identical." This definition also refers to the complement of a test sequence. Optionally, the identity exists over a region that is at least about 30 amino acids or nucleotides in length, typically over a region that is 50, 75 or 150 amino acids or nucleotides. In certain embodiments, the sequences are substantially identical over the entire length of the coding regions.

The terms "similarity," or "percent similarity," in the context of two or more polypeptide sequences, refer to two or more sequences or subsequences that have a specified percentage of amino acid residues that are either the same or similar as defined in the conservative amino acid substitutions defined above (i.e., at least 60%, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 25 amino acids in length, or more typically over a region that is at least about 50, 75 or 100 amino acids in length.

For sequence comparison, typically one sequence acts as a reference sequence to which test sequences are compared. When using a sequence comparison algorithm, test and reference sequences are typically input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (*Adv. Appl. Math.* 2:482 (1981)), by the homology alignment algorithm of Needleman and Wunsch (*J. Mol. Biol.* 48:443 (1970)), by the search for identity method of Pearson and Lipman (*Proc. Natl. Acad Sci. USA* 85:2444 (1988)), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see, generally Ausubel et al., *Current Protocols in Molecular Biology*, John Wiley and Sons, New York (1996)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (*J. Mol. Evol.* 35:351-60 (1987)). The method used is similar to the CLUSTAL method described by Higgins and Sharp (Gene 73:237-44 (1988); *CABIOS* 5:151-53 (1989)). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul et al. (*J. Mol. Biol.* 215:403-10 (1990)). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin and Altschul, *Proc. Natl. Acad. Sci. USA* 90:5873-87 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is typically between about 0.35 and about 0.1. Another indication that two nucleic acids are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization conditions" and "stringent hybridization wash conditions" in the context of nucleic acid hybridization experiments, such as Southern and northern hybridizations, are sequence-dependent, and are different under different environmental parameters. Longer sequences hybridize specifically at higher temperatures. An extensive guide to the hybridization of nucleic acids is found in Tijssen, *Laboratory Techniques in Biochemistry and Molecular Biology—Hybridization with Nucleic Acid Probes*, part I, chapter 2 "Overview of principles of hybridization and the strategy of nucleic acid probe assays," Elsevier, N.Y. (1993). Generally, highly stringent hybridization and wash conditions are selected to be about 5° C. lower than the thermal melting point ($T_m$) for the specific sequence at a defined ionic strength and pH. Typically, under "stringent conditions," a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide in 4-6×SSC or SSPE at 42° C., or 65-68° C. in aqueous solution containing 4-6×SSC or SSPE. An example of highly stringent wash conditions is 0.15 M NaCl at 72° C. for about 15 minutes. An example of stringent wash conditions is a 0.2×SSC wash at 65° C. for 15 minutes. (See generally Sambrook et al., *Molecular Cloning, A Laboratory Manual*, 2nd ed., Cold Spring Harbor Publish., Cold Spring Harbor, N.Y. (1989)). Often, a high stringency wash is preceded by a low stringency wash to remove background probe signal. An example of medium stringency wash for a duplex of, for example, more than 100 nucleotides, is 1×SSC at 45° C. for 15 minutes. An example of low stringency wash for a duplex of, for example, more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code.

A further indication that two nucleic acids or polypeptides are substantially identical is that the polypeptide encoded by the first nucleic acid is immunologically cross reactive with, or specifically binds to, antibodies raised against the polypeptide encoded by the second nucleic acid. Thus, a polypeptide is typically substantially identical to a second polypeptide, for example, where the two peptides differ only by conservative substitutions.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for the particular protein. For example, antibodies raised to the protein with the amino acid sequence encoded by any of the nucleic acids of the invention can be selected to obtain antibodies specifically immunoreactive with that protein and not with other proteins except for polymorphic variants. A variety of immunoassay formats can be used to select antibodies specifically immunoreactive with a particular protein. For example, solid-phase ELISA immunoassays, Western blots, or immunohistochemistry are routinely used to select monoclonal antibodies specifically immunoreactive with a protein (see, e.g., Harlow and Lane, *Antibodies, A Laboratory Manual*, Cold Spring Harbor Publications, N.Y. (1988), for a description of immunoassay formats and conditions that can be used to determine specific immunoreactivity). Typically, a specific or selective reaction will be at least twice background signal or noise and more typically more than 10 to 100 times background.

The term "immunogenic composition" refers to a composition that elicits an immune response which produces antibodies or cell-mediated immune responses against a specific immunogen. Immunogenic compositions can be prepared as injectables, as liquid solutions, suspensions, emulsions, and the like.

The term "vaccine" refers to an immunogenic composition for in vivo administration to a host, which may be a primate, particularly a human host, to confer protection against disease, particularly a viral disease.

The term "isolated" refers to a virus, nucleic acid or polypeptide that has been removed from its natural cellular environment. An isolated virus, nucleic acid or polypeptide is typically at least partially purified from cellular nucleic acids, polypeptides and other constituents.

In the context of the present invention, a "Coalescent Event" refers to the joining of two lineages on a genealogy at the point of their most recent common ancestor.

A "Coalescent Interval" describes the time between coalescent events. The expected time for each coalescent interval is exponentially distributed with mean $E[t_{nyn}-1]=2N/n(n-1)$ generations for n<<N.

Determination of Ancestral Sequences

In one aspect, computational methods are provided for determining ancestral sequences. Such methods can be used, for example, to determine ancestral sequences for viruses.

These computational methods are typically used to determine an ancestral sequence of a virus that exists as a highly diverse viral population. For example, some highly diverse viruses (including HIV-1, HIV-2, Hepatitis C, and the like) do not appear to evolve through a succession of variants, where one prototypical strain is replaced by successive uniform strains. Instead, an evolutionary tree of viral sequences can form a "star-burst pattern," with most of the variants approximately equidistant from the center of the star-burst. This star-burst pattern indicates that multiple, diverse circulating strains evolve from a common ancestor. The computational methods can be used to determine ancestral sequences for such highly diverse viruses, such as, for example, HIV-1, HIV-2, Hepatitis C, and other viruses.

Methods for determining ancestral sequences are typically based on the nucleic acid sequences of circulating viruses. As a viral nucleic acid sequence is replicated, it acquires base changes due to errors in the replication process. For example, as some nucleic acid sequences are replicated, thymine (T) might bind to a guanine (G) rather than its normal complement, cytosine (C). Most of these base changes (or mutations) are not reproduced in subsequent replication events, but a certain proportion of mutations are passed down to the descendant sequences. With more replication cycles, nucleic acid sequences acquire more mutations. If a nucleic acid sequence bearing one or more mutations gives rise to two separate lineages, then the resulting two lineages will share the same parental nucleic acid sequence, and have the same parental mutation(s). If the "histories" of these lineages are traced backwards, they will have a common branch point, at which the two lineages arose from a common ancestor. Similarly, if the histories of presently circulating viral nucleic acid sequences are traced backwards, the branching points in these histories also correspond to points, designated as nodes, at which a single ancestor gave rise to the descendant lineages.

Figure 2:
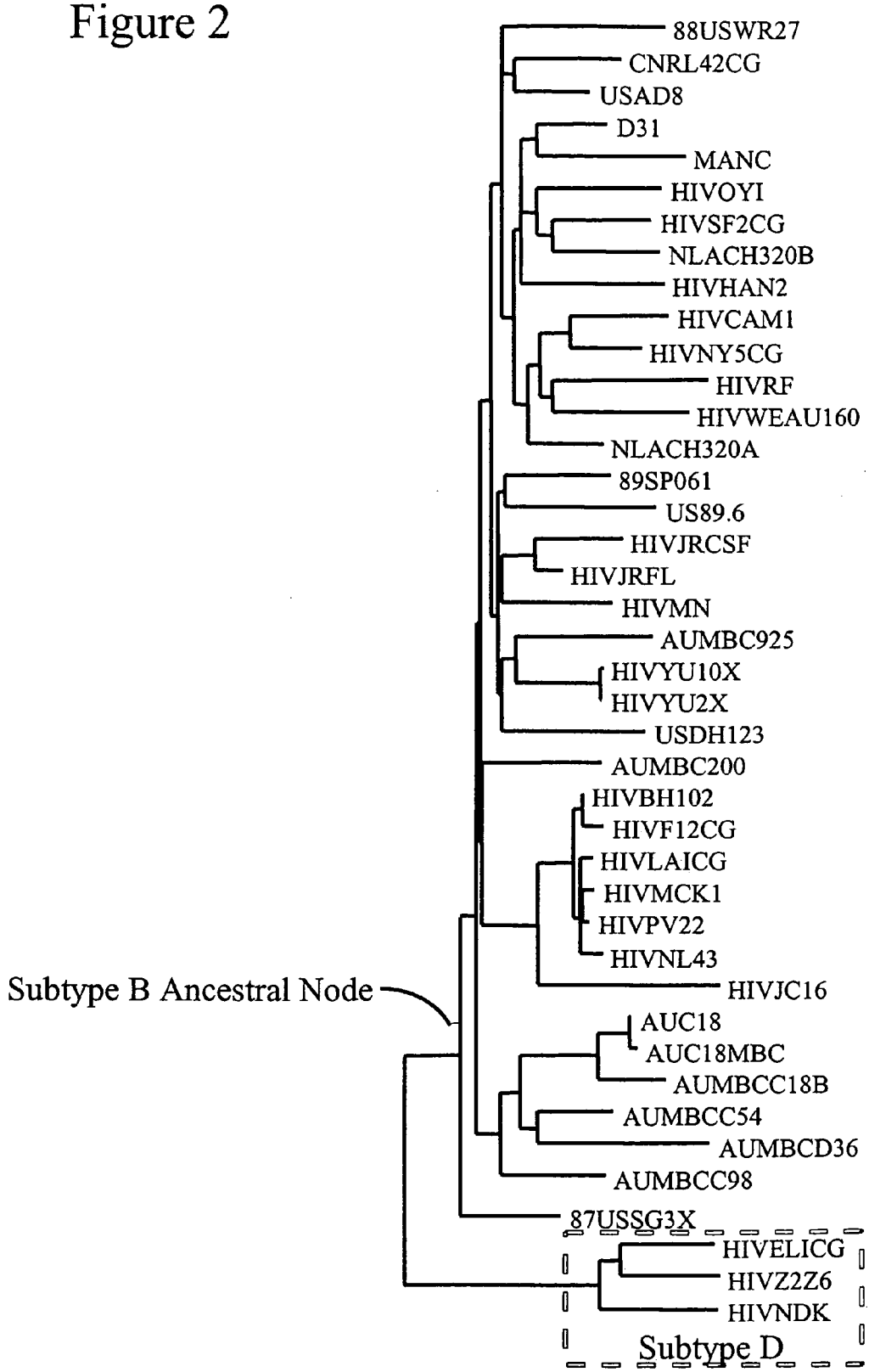

The present computational methods are based on the principle of maximum likelihood and use samples of nucleic acid sequences of circulating viruses. The sequences of the viruses in the samples typically share a common feature, such as being from the same viral strain, subtype or group. A phylogeny is constructed by using a model of evolution that specifies the probabilities of nucleotide substitutions in the replicating viral nucleic acids. At positions in the sequences where the nucleotides differ (i.e., at the site of a mutation), the methodology assigns one of the nucleotides to the node (i.e., the branch point of the lineages) such that the probability of obtaining the observed viral sequences is maximized. The assignment of nucleotides to the nodes is based on the predicted phylogeny or phylogenies. For each data set, several sequences from a different viral strain, subtype or group are used as an outgroup to root the sequences of interest. A model of sequence substitutions and then a maximum likelihood phylogeny are determined for each data set (e.g., subtype and outgroup). The maximum likelihood phylogeny the one that has the highest probability of giving the observed nucleic acid sequences in the samples. The sequence at the base node of the maximum likelihood phylogeny is referred to as the ancestral sequence (or most recent common ancestor). (See, e.g., FIGS. 1 and 2). This ancestral sequence is thus approximately equidistant from the different sequences within the samples.

Maximum likelihood phylogeny uses samples of the sequences of circulating virus. The sequences of circulating viruses can be determined, for example, by extracting nucleic acids from blood, tissues or other biological samples of virally infected persons and sequencing the viral nucleic acids. (See, e.g., Sambrook et al., *Molecular Cloning, A Laboratory Manual*, 2nd ed., Cold Spring Harbor Publish., Cold Spring Harbor, N.Y. (1989); Kriegler, *Gene Transfer and Expression: A Laboratory Manual*, W.H. Freeman, N.Y. (1990); Ausubel et al., supra.) In one embodiment, extracted viral nucleic acids can be amplified by polymerase chain reaction, and then DNA sequenced. Samples of circulating virus can be obtained from stored biological samples and/or prospectively from samples of circulating virus (e.g., sampling HIV-1 subtype C in India versus Ethiopia). Viral sequences can also be identified from databases (e.g., GenBank and Los Alamos sequence databases).

Once samples of circulating viruses are collected (typically about 20 to about 50 samples), the nucleic acid sequences for one or more genes are analyzed using the computational methods according to the present invention. In one method, for any given site in the sequence, the nucleotides at all nodes on a tree are assigned. The configuration of the nucleotides for all nodes that maximizes the probability of obtaining the observed sequences of circulating viruses is determined. With this method, the joint likelihood of the states across all nodes is maximized.

A second method is to choose, for a given nucleotide site and a given node on the tree, the nucleotide that maximizes the probability of obtaining the observed sequences of circulating viruses, allowing for all possible assignments of nucleotides at the other nodes on the tree. This second method maximizes the marginal likelihood of a particular assignment. For these methods, the reconstruction of the ancestral sequence (i.e., ancestral state) need not result in only a single determined sequence, however. It is possible to choose a number of ancestral sequences, ranked in order of their likelihood.

With HIV populations, a second layer of modeling can be added to the maximum likelihood phylogenetic analysis, in particular the layer is added to the model of evolution that is employed in the analysis. This second layer is based on coalescent likelihood analysis. The coalescent is a mathematical description of a genealogy of sequences, taking account of the processes that act on the population. If these processes are known with some certainty, the use of the coalescent can be used to assign prior probabilities to each type of tree. Taken together with the likelihood of the tree, the posterior probability can be determined that a determined phylogenetic tree is correct given the data. Once a tree is chosen, the ancestral states are determined, as described above. Thus, coalescent likelihood analysis can also be applied to determine the sequence of an ancestral viral sequence (e.g., a founder, or Most Recent Common Ancestor (MRCA), sequence).

In a typical embodiment, maximum likelihood phylogeny analysis is applied to determine an ancestor sequence (e.g., an ancestral viral sequence). Typically, between 20 and 50 nucleic acid sequence samples are used that have a common feature, such as a viral strain, subtype or group (e.g., samples encompassing a worldwide diversity of the same subtype). Additional sequences from other viruses (e.g., another strain, subtype, or group) are obtained and used as an outgroup to root the viral sequences being analyzed. The samples of viral sequences are determined from presently circulating viruses, identified from the database (e.g., GenBank and Los Alamos sequence databases), or from similar sources of sequence information. The sequences are aligned using CLUSTALW (Thompson et al., *Nucleic Acids Res.* 22:4673-80 (1994), the disclosure of which is incorporated by reference herein) and these alignments are refined using GDE (Smith et al., *CABIOS* 10:671-75 (1994) the disclosure of which is incorporated by reference herein). The amino acid sequences are also translated from the nucleic acid sequences. Gaps are manipulated so that they are inserted between codons. This alignment (alignment I) is modified for phylogenetic analysis so that regions that can not be unambiguously aligned are removed (Learn et al., *J. Virol.* 70:5720-30 (1996), the disclosure of which is incorporated by reference herein) resulting in alignment II.

An appropriate evolutionary model for phylogeny and ancestral state reconstructions for these sequences (alignment II) is selected using the Akaike Information Criterion (AIC) (Akaike, *IEEE Trans. Autom. Contr.* 19:716-23 (1974); which is incorporated by reference herein) as implemented in Modeltest 3.0 (Posada and Crandall, *Bioinformatics* 14:817-8 (1998), which is incorporated by reference herein). For example, for the analysis for the subtype C ancestral sequence the optimal model is equal rates for both classes of transitions and different rates for all four classes of transversions, with invariable sites and a X distribution of site-to-site rate variability of variable sites (referred to as a TVM+I+G model). The parameters of the model in this case can be, for example, equilibrium nucleotide frequencies: $f_A$=0.3576, $f_C$=0.1829, $f_G$=0.2314, $f_T$=0.2290; proportion of invariable sites=0.2447; shape parameter (α) of the X distribution=0.7623; rate matrix (R) matrix values: $R_{A\rightarrow C}$=1.7502, $R_{A\rightarrow G}$=$R_{C\rightarrow T}$=4.1332, $R_{A\rightarrow T}$=0.6825, $R_{C\rightarrow G}$=0.6549, $R_{G\rightarrow T}$=1.

Evolutionary trees for the sequences (alignment II) are inferred using maximum likelihood estimation (MLE) methods as implemented in PAUP* version 4.0b (Swofford, PAUP 4.0: Phylogenetic Analysis Using Parsimony (And Other Methods); Sinauer Associates, Inc. (2000) the disclosure of which is incorporated by reference herein). For example, for HIV-1 subtype C sequences, ten different subtree-pruning-regrafting (SPR) heuristic searches can be performed, each using a different random addition order. The ancestral viral nucleotide sequence is determined to be the sequence at the basal node using the phylogeny, the sequences from the databases (alignment II), and the TVM+I+G model above using marginal likelihood estimation (see infra).

In some cases, the determined sequence may not include ancestral sequence for portions of variable regions (e.g., variable regions V1, V2, V4 and V5 for HIV-1-C), and or some short regions may not be unambiguously aligned. The following procedure can optionally be used to predict amino acid sequences for the complete sequence, including the highly variable regions (such as those deleted from alignment I). The determined ancestral sequence is visually aligned to alignment I and translated using GDE (Smith et al., supra). Since the highly variable regions can be deleted as complete codons, the translational reading frame can be preserved and codons can be maintained. The ancestral amino acid sequence for the regions deleted from alignment II can be predicted visually and refined using a parsimony-based sequence reconstruction for these sites using the computer program MacClade, version 3.08a (Maddison and Maddison. MacClade—Analysis of Phylogeny and Character Evolution—Version 3. Sinauer Associates, Inc. (1992)).

The ancestral amino acid sequence is optionally optimized for expression in a particular cell type. Amino acid sequences can converted to a DNA sequence optimized for expression in certain cell types (e.g., human cells) using, for example, the BACKTRANSLATE program of the Wisconsin Sequence Analysis Package (GCG), version 10 and a human gene codon table from the Codon Usage Database (www.kazusa.or.jp/codon/cgi-bin/showcodon.cgi?species=Homo+sapiens+[gbpri]), both incorporated by reference herein.

The optimized sequences encode the same amino acid sequence for the gene of interest (e.g., the env gene) as the non-optimized ancestral sequence. A synthetic virus having the optimized sequence may not be fully functional due to the disruption of auxiliary genes in different reading frames the presence of RNA secondary structural feature (e.g., the Rev responsive element (RRE) of HIV-1), and the like. The optimization process may affect the coding region of the auxiliary genes (e.g., vpu, tat and rev genes of HIV-1), and may disrupt RNA secondary structure. Thus, the ancestral sequences can be semi-optimized. A semi-optimized sequence has the optimized sequence for portions of the sequence that do not span other features, where the non-optimized ancestral sequence is used instead. For example, for HIV-1 ancestral sequences, the optimized ancestral sequence is used for portions of the sequence that do not span the vpu, tat, rev and RRE regions, while the "non-optimized" ancestral sequence is used for the portions of the sequence that overlap the vpu, tat, rev and RRE regions.

Determination of HIV Ancestral Viral Sequences

Ancestral viral sequences can be determined for any gene or genes from HIV type 1 (HIV-1), HIV type 2 (HIV-2), or other HIV viruses, including, for example, for an HIV-1 subtype, for an HIV-2 subtype, for other HIV subtypes, for an emerging HIV subtype, and for HIV variants, such as widely dispersed or geographically isolated variants. For example, an ancestral viral gene sequence can be determined for env and gag genes of HIV-1, such as for HIV-1 subtypes A, B, C, D, E, F, G, H, J, AG, AGI, and for groups M, N, 0, or for HIV-2 viruses or HIV-2 subtypes A or B. In specific embodiments, ancestral viral sequences are determined for env genes of HIV-1 subtypes B and/or C, or for gag genes from subtypes B and/or C. In other embodiments, the ancestral viral sequence is determined for other HIV genes or polypeptides, such as nef, pol, or other auxiliary genes or polypeptides.

Nucleic acid sequences of a selected HIV-1 or HIV-2 gene from presently and/or formerly circulating viruses can be identified from existing databases (e.g., from GenBank or Los Alamos sequence databases). The sequence of circulating viruses can also be determined by recombinant DNA methodologies. (See, e.g., Sambrook et al., *Molecular Cloning, A Laboratory Manual*, 2nd ed., Cold Spring Harbor Publish., Cold Spring Harbor, N.Y. (1989); Kriegler, *Gene Transfer and Expression: A Laboratory Manual*, W.H. Freeman, N.Y. (1990); Ausubel et al., supra.) For each data set, several sequences from a different viral strain, subtype or group are used as an outgroup to root the sequences of interest. A model of sequence substitutions and then a maximum likelihood phylogeny is determined for each data set (e.g., subtype and outgroup). The ancestral viral sequence is determined as the sequence at the basal node of the variant sequences (see, e.g., FIGS. 1 and 2). This ancestral viral sequence is thus approximately equidistant from the different sequences within the subtype.

In one embodiment, an ancestral HIV-1 group M, subtype B, env sequence was determined using 41 distinct isolates. (The determined nucleic acid and amino acid sequences are depicted in Tables 1 and 2 (SEQ ID NO:1 and SEQ ID NO:2), respectively). Referring to FIG. 2, 38 subtype B sequences and 3 subtype D (outgroup) sequences were used to root the subtype B sequences. The subtype B sequences were from nine countries, representing a broad sample of subtype B diversity: Australia, 8 sequences; China, 1 sequence; France, 5 sequences; Gabon, 1 sequence; Germany, 2 sequences; Great Britain, 2 sequences; the Netherlands, 2 sequences; Spain, 1 sequence; U.S.A., 15 sequences. The determined ancestor protein is 884 amino acids in length. The distances between this ancestral viral sequence and circulating strains used to determine it were on average 12.3% (range: 8.0-

21.0%) while the available specimens were 17.3% different from each other (range: 13.3-23.2%). The ancestor sequence is therefore, on average, more closely related to any given circulating virus than to any other variant. When compared with other subtype B strains, the ancestral sequence is most similar to USAD8 (Theodore et al., *AIDS Res. Human Retrovir*. 12:191-94 (1996)), with an identity of 94.6% at the amino acid level.

Surprisingly, the determined ancestral viral sequence of the HIV-1 subtype B env gene encodes a wide variety of immunologically active peptides when processed for antigen presentation. Nearly all known subtype B CTL epitope consensus amino acids (387/390; 99.23%) are represented in the determined ancestral viral sequence for the subtype B, gp160 sequence. In contrast, most other variants of HIV-1 subtype B have below 95% epitope sequence conservation (although this is a not a necessary feature of ancestral viral sequences, but is a consequence of the rapid expansion of HIV-1). Thus, an immunogenic composition to this subtype B ancestor protein will elicit broad neutralizing antibody against HIV-1 isolates of the same subtype. An immunogenic composition to this subtype B ancestor protein will also elicit a broad cellular response mediated by antigen-specific T-cells.

Figure 8:
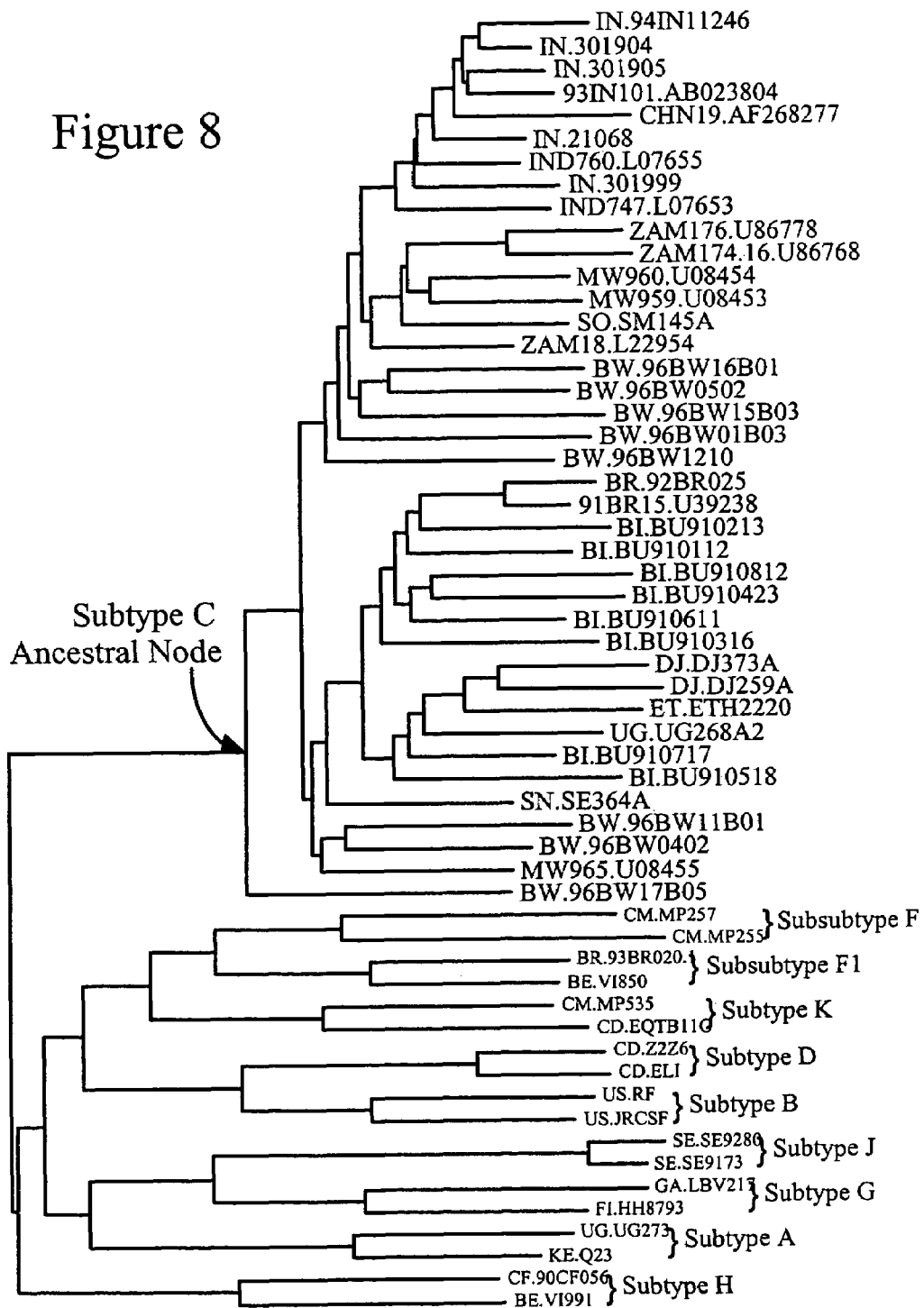

In another embodiment, similar computational methods were used to determine the ancestral viral sequence of the HIV-1 subtype C env gene sequence. HIV-1 subtype C is widespread in developing countries. Subtype C is the most common subtype worldwide, responsible for an estimated 30% of HIV-1 infections, and a major component of epidemics in Africa, India and China. The ancestral viral sequence for HIV-1 group M, subtype C, env gene was determined using 57 distinct isolates (39 subtype C sequences and 18 outgroup sequences (two from each of the other group M subtypes); FIG. 8). The determined amino acid sequence is depicted in Table 4 (SEQ ID NO:4). The determined nucleic acid sequence, optimized for expression in human cells, is depicted in Table 3 (SEQ ID NO:3).

The subtype C sequences were from twelve African and Asian countries, representing a broad sample of subtype C diversity worldwide: Botswana, 8 sequences; Brazil, 2 sequences; Burundi, 8 sequences; Peoples Republic of China, 1 sequence; Djibouti, 2 sequences; Ethiopia, 1 sequence; India, 8 sequences; Malawi, 3 sequences; Senegal, 1 sequence; Somalia, 1 sequence; Uganda, 1 sequence; and Zambia, 3 sequences. The determined ancestor protein is 853 amino acids in length. The distances between this ancestral viral sequence and circulating strains used to determine it were on average 11.7% (range: 9.3-14.3%) while the available specimens were on average 16.6% different from each other (range: 7.1-21.7%). The ancestor protein sequence is therefore, on average, more closely related to any given circulating virus than to any other variant. When compared with other subtype C strains, the ancestral sequence is most similar to MW965 (Gao et al., *J Virol*. 70:1651-67 (1996)), with an identity of 89.5% at the amino acid level.

Surprisingly, the determined ancestral viral sequence encodes a wide variety of immunologically active peptides when processed for antigen presentation. Nearly all known subtype C CTL epitope consensus sequences (389/396; 98.23%) are represented in the determined ancestral viral sequence for the subtype C, gp160 sequence. In contrast, typical variants of HIV-1 subtype C (those used to determine the ancestral sequence) have less than 95.19% epitope sequence conservation (average 90.36%, range 64.56-95.19%). Thus, a vaccine to this subtype C ancestral viral sequence will elicit broad neutralizing antibody against HIV-1 isolates of the same subtype. An immunogenic composition to this subtype C ancestor protein will also elicit a broad cellular response mediated by antigen-specific T-cells.

Optimized and semi-optimized sequences for an HIV ancestral sequence are also provided. Ancestral viral sequences can be optimized for expression in particular host cells. While the optimized ancestral sequence encodes the same amino acid sequence for a gene as the non-optimized sequence, the optimized sequence may not be fully functional in a synthetic virus due to the disruption of auxiliary genes in different reading frames, disruption of the RNA secondary structure, and the like. For example, optimization of the HIV-1 env sequence can disrupt the auxiliary genes for vpu, tat and/or rev, and/or the RNA secondary structure Rev responsive element (RRE). Semi-optimized sequences are prepared by using optimized sequences for portions of the sequence that do not span other genes, RNA secondary structure, and the like. For portions of the sequence that overlap such features, the "non-optimized" ancestral sequence is used (e.g., for regions overlapping vpu, tat, rev and/or RRE). In specific embodiments, semi-optimized ancestral viral sequences for HIV-1 subtypes B and C are provided. (See Tables 5 (SEQ ID NO: 5) and 6 (SEQ ID NO:6).)

In other embodiments, ancestral viral sequences are determined for widely circulating variants or geographically-restricted variants. For example, samples can be collected of an HIV-1 subtype which is widely spread (e.g. present in many countries or in regions without obvious geographic boundaries). Similarly, samples can be collected of an HIV-1 subtype which is geographically restricted (e.g., to a country, regions or other physically defined area). The sequences of the genes (e.g., gag or env) in the samples are determined by recombinant DNA methods (see, e.g., Sambrook et al., supra; Kriegler, supra; Ausubel et al., supra), or from information in databases. Typically, the number of samples will range from about 20 to about 50, depending on their current availability and the time the virus has been circulating in the region of interest (e.g., the longer the time the virus has been circulating, the greater the diversity and the greater the information to be gleaned from the samples). The ancestral viral sequence, either nucleic acid or amino acid, is then determined using the computational methods described herein.

Ancestor Proteins

The invention further relates to ancestor proteins based on a determined ancestral viral sequence. Such ancestor proteins include, for example, full-length protein, polypeptides, fragments, derivatives and analogs thereof. In one aspect, the invention provides amino acid sequences of ancestor proteins (see, e.g., Tables 2 and 4; SEQ ID NO:2; SEQ ID NO:4). In certain embodiments, the ancestor protein is functionally active. Ancestor proteins, fragments, derivatives and analogs typically have the desired immunogenicity or antigenicity and can be used, for example, in immunoassays, for immunization, in vaccines, and the like. A specific embodiment relates to an ancestor protein, fragment, derivative or analog that can be bound by an antibody. Such ancestor proteins, fragments, derivatives or analogs can be tested for the desired immunogenicity by procedures known in the art. (See e.g., Harlow and Lane, supra).

In another aspect, a polypeptide is provided which consists of or comprises a fragment that has at least 8-10 contiguous amino acids of the ancestor protein. In other embodiments, the fragment comprises at least 20 or 50 contiguous amino acids of the ancestor protein. In other embodiments, the fragments are not larger than 35, 100 or 200 amino acids.

Ancestor protein derivatives and analogs can be produced by various methods known in the art. The manipulations which result in their production can occur at the gene or protein level. For example, a nucleic acid encoding an ancestor protein can be modified by any of numerous strategies known in the art (see, e.g., Sambrook et al., supra), such as by making conservative substitutions, deletions, insertions, and the like. The nucleic acid sequence can be cleaved at appropriate sites with restriction endonuclease(s), followed by further enzymatic modification, if desired, isolated, and ligated in vitro. In the production of nucleic acids encoding a fragment, derivative or analog of an ancestor protein, the modified nucleic acid typically remains in the proper translational reading frame, so that the reading frame is not interrupted by translational stop signals or other signals that interfere with the synthesis of the fragment, derivative or analog. The ancestral viral sequence nucleic acid can also be mutated in vitro or in vivo to create and/or destroy translation, initiation and/or termination sequences. The ancestral viral sequence-encoding nucleic acid can also be mutated to create variations in coding regions and/or to form new restriction endonuclease sites or destroy preexisting ones and to facilitate further in vitro modification. Any technique for mutagenesis known in the art can be used, including but not limited to chemical mutagenesis, in vitro site-directed mutagenesis, and the like.

Manipulations of the ancestral viral sequence can also be made at the protein level. Included within the scope of the invention are ancestor protein fragments, derivatives or analogs that are differentially modified during or after synthesis (e.g., in vivo or in vitro translation). Such modifications include conservative substitution, glycosylation, acetylation, phosphorylation, phosphorylation, amidation, derivatization by known protecting/locking groups, proteolytic cleavage, linkage to an antibody molecule or other cellular ligand, and the like. Any of numerous chemical modifications can be carried out by known techniques, including, but not limited to, specific chemical cleavage (e.g., by cyanogen bromide); enzymatic cleavage (e.g., by trypsin, chymotrypsin, papain, V8 protease, and the like); modification by, for example, $NaBH_4$ acetylation, formylation, oxidation and reduction; metabolic synthesis in the presence of tunicamycin; and the like.

In addition, fragments, derivatives and analogs of ancestor proteins can be chemically synthesized. For example, a peptide corresponding to a portion, or fragment, of an ancestor protein, which comprises a desired domain, can be synthesized by use of chemical synthetic methods using, for example, an automated peptide synthesizer. (See also Hunkapiller et al., *Nature* 310:105-11 (1984); Stewart and Young, *Solid Phase Peptide Synthesis*, 2nd ed., Pierce Chemical Co., Rockford, Ill., (1984).) Furthermore, if desired, non-classical amino acids or chemical amino acid analogs can be introduced as a substitution or addition into the polypeptide sequence. Non-classical amino acids include, but are not limited to, the D-isomers of the common amino acids, α-amino isobutyric acid, 4-aminobutyric acid, 2-amino butyric acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and other amino acid analogs. Furthermore, the amino acid can be D (dextrorotary) or L (levorotary).

The ancestor protein, fragment, derivative or analog can also be a chimeric, or fusion, protein comprising an ancestor protein, fragment, derivative or analog thereof (typically consisting of at least a domain or motif of the ancestor protein, or at least 10 contiguous amino acids of the ancestor protein) joined at its amino- or carboxy-terminus via a peptide bond to an amino acid sequence of a different protein. In one embodiment, such a chimeric protein is produced by recombinant expression of nucleic acid encoding the chimeric protein. The chimeric nucleic acid can be made by ligating the appropriate nucleic acid sequences to each other in the proper reading frame and expressing the chimeric product by methods commonly known in the art. Alternatively, the chimeric protein can be made by protein synthetic techniques (e.g., by use of an automated peptide synthesizer).

Ancestor protein can be isolated and purified by standard methods including chromatography (e.g., ion exchange, affinity, sizing column chromatography, high pressure liquid chromatography), centrifugation, differential solubility, or by any other standard technique for the purification of proteins.

Determination of COT Sequences

The present invention also provides methods for determining a nucleic acid and protein sequences using Center of Tree (or COT) analysis.

COT provides a method for identifying a position at a node or on a branch of a phylogenetic tree having completely specified branch lengths. This position, called the "center of tree" or COT, is the point at which a specified function F of the lengths from any point to all tips of the tree is minimized. By way of explanation, suppose a tree T has n tips or leaves, labelled $a_1, a_2, \ldots, a_n$, and p is a point on a branch or is a node of the tree. Let $l_i$ be the distance along the tree branches from p to $a_i$. Then a COT of T for the function F, is a point $\hat{p}$ satisfying the following relationship:

$$F(\hat{p}:l_1,l_2,\ldots,l_n) \leq F(p:l_1,l_2,\ldots,l_n), \text{ for all points p,}$$

where the notation $F(p:l_1,l_2,\ldots,l_n)$ highlights the fact that the distances $l_1$ depend on the point p.

In this description, the form of F is general; specific choices for F can be made, based on the intended application. A general algorithm that is applicable for most useful continuous Fs is described (infra). For a given choice of F, an algorithm based on COT analysis can be selected. A COT-based algorithm can be selected, for example, to be more efficient. Such an algorithm is described to find COT when F is the mean of squares (MS) of the ls. Depending upon F, one or more COTs may exist for a given tree, but for many reasonable choices of F, the COT will be unique.

General Algorithm

First, for a certain large class of functions $F:R^n \rightarrow R$, namely those which are continuous and have finitely many extreme points (which includes those functions described infra), that there is a finite number of points along the tree which are possible COTs, that can be enumerated constructively, and determine which points are in fact COTs.

For an unrooted tree T of n tips, there are $u \leq 2n-2$ nodes, counting tips and internal branches, and $w \leq 2n-3$ branches, including internal and external branches. (u and w are less than their maxima when polytomies exist in the tree.) For each node $q_j$, $1 \leq j \leq u$, $C_j = F(q_j:l_1,l_2,\ldots,l_n)$ is calculated. Each $q_j$ is a candidate COT.

The branches are enumerated $b_k$, $1 \leq k \leq w$. Candidate COTs are determined for each branch. Note each branch, say branch k, is flanked by two nodes, call them $R_k$ and $L_k$ (suggesting right and left nodes). Let the branch length of $b_k$ be l. Now the tree is divided into two parts, call them right and left, so that if the tree had a root within branch k, the tips $a_1, a_2, \ldots, a_n$ would be divided into two groups, those descended from $R_k$ and those descended from $L_k$. Suppose there are s right tips and t left tips. Let the distances from the right tips to $R_k$ be written $\rho_1, \ldots \rho_s$, and the distances from the left tips to $L_k$ be written $\lambda_1, \ldots \lambda_r$. Now, let a point p lying on branch $b_k$ be a distance x from the right node $R_k$. Then the distance from p to $L_k$ is l−x.

Then for branch $b_k$ and p defined along it as described above, $$F(p:l_1, \ldots, l_n) = F(p:\rho_1+x, \ldots, \rho_s+x, \lambda_1+l-x, \ldots, \lambda_r+l-x) = \tilde{F}_{b_k}(x), 0 \leq x < l.$$

In other words, on any branch k of T, the function F of n distances can be expressed for every point p along that branch as a function of a single variable x. By this assumption that F has a finite number of extreme points, the functions $\tilde{F}_{b_k}(x)$ have a finite number of minima for x between 0 and l. Because F is continuous, those minima can be found by standard numerical methods, and each minimum $\hat{x}$ is associated with a point $p_x$ as described above. Suppose there are v such points over all w branches (v may be greater than, equal to, or less than w). Then the following equation can be written: $d_i = F(p_i : l_1, \ldots, l_n) = \tilde{F}_{b(p_i)}(\hat{x}_i)$, for $1 \leq i \leq v$, where $b(p_i)$ is the branch associated with point $p_i$ (not necessarily the ith branch). Then each $p_i$ is a candidate COT, since if $p_i$ is to minimize F among all points on the tree, it must at least minimize F on those points comprising the branch on which p resides. Since the nodes and branches contain all points on the tree, all possible COTs in the $q_j$ and the $p_i$ have been enumerated.

Therefore, according to the definition of a COT in the first paragraph, any point $p \in \{q_1, \ldots, q_u, p_1, \ldots, p_v\}$ is a COT that satisfies $$F(p:l_1, \ldots, l_n) = \min\{c_1, \ldots, c_u, d_1, \ldots, d_v\}$$

and all such points p are the only COTs for tree T given function F.

This decomposition of possible COTs into separate consideration of nodes and branches allows phylogenetic trees to be expressed in computer programs as data structures that can be efficiently traversed by recursive routines which isolate each node and branch individually and systematically. The above decomposition formally describes the tasks to be performed upon consideration of each node and branch. During the algorithm, the points and function values are stored, and the final determination of COTs is easily accomplished by identifying the minima of the list of values and their associated points after the tree data structure has been completely traversed.

Algorithm to Find Points Minimizing the Mean Squared Distance from the Points to Tips (Least-Squares or LS-COT)

In this special case, let $$F(p:l_1, \ldots, l_n) = \frac{1}{n}\sum_{i=1}^{n} l_i^2,$$

the mean of the squared distances from the tips to point p. The COT obtained by minimizing this function essentially balances the average length of the branches on either side of point p, and as such provides a point which will yield a single reconstructed sequence that has the greatest amount of sequence similarity to all the tips as possible, given the evolutionary constraints of nucleotide change along the tree branches. As in the general algorithm, the tree is decomposed into nodes and branches, all possible COTs are enumerated, and F is calculated for each possibility. The point with the minimum F is the COT. The function F can be expressed in terms of quantities that can be efficiently calculated as the tree is traversed recursively; this allows the algorithm to accumulate the quantities $c_i$ and $d_i$. First, the method of identifying possible COTs and calculating $c_i$ and $d_i$ based on these quantities is described; then the recursion equations for these quantities is described that can be using in the tree-traversal algorithm.

Nodes: Consider each node $q_i$ as a temporary root of the tree, and suppose $q_i$ has k descendant branches, each of which defines a subtree with $t_m$ tips, $1 \leq m \leq k$. Then F can be written $$c_i = \frac{1}{n}\sum_{j=1}^{n} l_j^2$$

$$= \gamma_1\left(\frac{1}{t_1}\sum_{j=1}^{t_1}(l_j^{(1)})^2\right) + \ldots + \gamma_k\left(\frac{1}{t_k}\sum_{j=1}^{t_k}(l_j^{(k)})^2\right)$$

$$= \gamma_1 MS_1 + \ldots + \gamma_k MS_k,$$

where $$\gamma_m = \frac{t_m}{n},$$

and $(l_j^{(m)})$, $1 \leq j \leq t_m$ are the distances from $q_i$ to each of the $t_m$ tips of the mth subtree.

Each $MS_m$ is therefore the mean of squared distances of the branches of subtree m, considering node $q_i$ as the root, and each $\gamma_m$ is the proportion of the n tips of the entire tree associated with subtree m.

Branches: With this function F, there exists at most one possible COT on any branch. Consider a branch of length l with left and right nodes as described in the general algorithm above, and consider a point p within the branch. Let $M_L$ be the simple average of distances from point p to the left tips, and $M_R$ be the average of distances from p to the right tips. Suppose there are t left tips and s right tips, and let $$\gamma = \frac{t}{n}.$$

Now, define α as follows:

$$\alpha = \frac{(1-\gamma)M_R - \gamma M_L}{l} + 1 - \gamma.$$

Then there is a possible COT within the branch if $0 < \alpha < 1$, and it is the distance αl from the left node along the branch. If there is such a point, then the value of F at that point, $d_i$, can be written as $$d_i = \gamma(1-\gamma)(M_L+M_R+l) - \gamma(M_L^2 - MS_L) - (1-\gamma)(M_R^2 - MS_R)$$

where MS is the mean of summed squared distances from the left or right nodes to their descendant tips as indicated.

Finally, the COT is the point which is associated with the smallest value among the $c_i$ and $d_i$.

Algorithm to Find Points Minimizing the Mean Distance from the Points to Tips ("Minimum of Means" or MM-COT)

Another useful and simpler function is $$F(p:l_1, \ldots, l_n) = \frac{1}{n}\sum_{i=1}^{n} l_i = \frac{M_L + M_R}{2}$$

for points within branches, and $M_q$ for nodes. For points within branches, the condition that must be met such that p is a possible COT is the inequality involving α above, with γ set equal to 0.5. The "minimum of means" COT is then min $\{c_1, \ldots, c_u, d_1, \ldots, d_v\}$, where now $c_i = M_{q(i)}$ for each node i, and $$d_i = \frac{M_{L(i)} + M_{R(i)}}{2}$$

for points on branches.

Recursions to Calculate M and MS for the Above Algorithms

Suppose node q has k descendant nodes. Each of the k nodes is connected to q by a branch of length $l_i$, and each is the root of a subtree having $s_i$ tips, $1 \leq i \leq k$. Suppose for each subtree, the mean distance $M_i$ and the mean squared distances $MS_i$ from node to tips have been calculated. Then the mean distance $M_q$ and mean squared distance $MS_q$ from q to all $s = s_1 + \ldots + S_k$ descendant tips are given by:

$M_q = \gamma_1(M_1+l_1) + \ldots + \gamma_k(M_k+l_k)$, and $MS_q = \gamma_1(MS_1+2l_1M_1+l_1^2) + \ldots + \gamma_k(MS_k+2l_kM_k+l_k^2)$, where $$\gamma_i = \frac{s_i}{s}$$

for $1 \leq i \leq k$.

These quantities can thus be built up as a tree is recursively traversed, and can be used in the calculations described above.

As will be appreciated by the skilled, the methodology for COT analysis can be applied to determine the nucleic acid sequences for a highly disperse viruses. In addition to the embodiments of the determination of HIV COT nucleic acid and protein sequences (infra), COT analysis can be used to determine nucleic acid and protein sequences for other highly disperse viruses.

HIV COT Sequences

COT viral sequences can be determined for any gene or genes from HIV type 1 (HIV-1), HIV type 2 (HIV-2), or other HIV viruses, including, for example, for an HIV-1 subtype, for an HIV-2 subtype, for other HIV subtypes, for an emerging HIV subtype, and for HIV variants, such as widely dispersed or geographically isolated variants. For example, an COT viral gene sequence can be determined for env and gag genes of HIV-1, such as for HIV-1 subtypes A, B, C, D, E, F, G, H, J, AG, AGI, and for groups M, N, 0, or for HIV-2 viruses or HIV-2 subtypes A or B. In specific embodiments, COT viral sequences are determined for env genes of HIV-1 subtypes B and/or C, or for gag genes from subtypes B and/or C. In other embodiments, the COT viral sequence is determined for other HIV genes or polypeptides, such as nef, pol, or other auxiliary genes or polypeptides.

Nucleic acid sequences of a selected HIV-1 or HIV-2 gene from presently and/or formerly circulating viruses can be identified from existing databases (e.g., from GenBank or Los Alamos sequence databases). The sequence of circulating viruses can also be determined by recombinant DNA methodologies. (See, e.g., Sambrook et al., *Molecular Cloning, A Laboratory Manual*, 2nd ed., Cold Spring Harbor Publish., Cold Spring Harbor, N.Y. (1989); Kriegler, *Gene Transfer and Expression: A Laboratory Manual*, W.H. Freeman, N.Y. (1990); Ausubel et al., supra.) For each data set, several sequences from a different viral strain, subtype or group are used as an outgroup to root the sequences of interest.

The determined COT viral gene sequence is more closely related, on average, to a gene sequence of any given circulating virus than to any other variant. In certain embodiments, the COT viral gene sequence has at least 70% identity with the LScot and MMcot sequences set forth in FIGS. 9 to 17 or 27-35, but does not have 100% identity with any circulating viral variant. In specific embodiments, the COT viral gene sequence is an LScot or MMcot sequence set forth in FIGS. 9 to 17, but does not have 100% identity with any circulating viral variant. In additional specific embodiments, the COT viral gene sequence is an LScot or MMcot sequence set forth in FIGS. 27 to 35, but does not have 100% identity with any circulating viral variant.

Optimized and semi-optimized sequences for an HIV COT sequence are also provided. COT viral sequences can be optimized for expression in particular host cells. While the optimized COT sequence encodes the same amino acid sequence for a gene as the non-optimized sequence, the optimized sequence may not be fully functional in a synthetic virus due to the disruption of auxiliary genes in different reading frames, disruption of the RNA secondary structure, and the like. For example, optimization of the HIV-1 env sequence can disrupt the auxiliary genes for vpu, tat and/or rev, and/or the RNA secondary structure Rev responsive element (RRE). Semi-optimized sequences are prepared by using optimized sequences for portions of the sequence that do not span other genes, RNA secondary structure, and the like. For portions of the sequence that overlap such features, the "non-optimized" COT sequence is used (e.g., for regions overlapping vpu, tat, rev and/or RRE). In specific embodiments, semi-optimized COT viral sequences for HIV-1 subtypes B and C are provided.

In other embodiments, COT viral sequences are determined for widely circulating variants or geographically-restricted variants. For example, samples can be collected of an HIV-1 subtype which is widely spread (e.g. present in many countries or in regions without obvious geographic boundaries). Similarly, samples can be collected of an HIV-1 subtype which is geographically restricted (e.g., to a country, regions or other physically defined area). The sequences of the genes (e.g., gag or env) in the samples are determined by recombinant DNA methods (see, e.g., Sambrook et al., supra; Kriegler, supra; Ausubel et al., supra), or from information in databases. Typically, the number of samples will range from about 20 to about 50, depending on their current availability and the time the virus has been circulating in the region of interest (e.g., the longer the time the virus has been circulating, the greater the diversity and the greater the information to be gleaned from the samples). The COT viral sequence, either nucleic acid or amino acid, is then determined using the computational methods described herein.

COT Proteins

The invention further relates to COT proteins based on a determined COT viral sequence. Such COT proteins include, for example, full-length protein, polypeptides, fragments, derivatives and analogs thereof. In one aspect, amino acid sequences of COT proteins are provided. In certain embodiments, the COT protein is functionally active. COT proteins, fragments, derivatives and analogs typically are immunogenic or antigenic and can be used, for example, in immunoassays, for immunization, in vaccines, and the like. A specific embodiment relates to an COT protein, fragment, derivative or analog that can be bound by an antibody. Such COT proteins, fragments, derivatives or analogs can be tested for the desired immunogenicity by procedures known in the art. (See e.g., Harlow and Lane, supra). In specific embodiments, an isolated COT protein has the sequence of an LScot or MMcot amino acid sequence set forth in FIGS. 27 to 25 and 36 to 44.

In another aspect, a polypeptide is provided which consists of or comprises a fragment that has at least 8-10 contiguous amino acids of the COT protein. In other embodiments, the fragment comprises at least 20 or 50 contiguous amino acids of the COT protein. In other embodiments, the fragments are not larger than 35, 100 or 200 amino acids. In specific embodiments, an isolated antigenic COT protein fragment is an antigenic fragment of an LScot or MMcot amino acid sequence set forth in FIGS. 27 to 25 and 36 to 44.

COT protein derivatives and analogs can be produced by various methods known in the art. The manipulations which result in their production can occur at the gene or protein level. For example, a nucleic acid encoding a COT protein can be modified by any of numerous strategies known in the art (see, e.g., Sambrook et al., supra), such as by making conservative substitutions, deletions, insertions, and the like. The nucleic acid sequence can be cleaved at appropriate sites with restriction endonuclease(s), followed by further enzymatic modification, if desired, isolated, and ligated in vitro. In the production of nucleic acids encoding a fragment, derivative or analog of a COT protein, the modified nucleic acid typically remains in the proper translational reading frame, so that the reading frame is not interrupted by translational stop signals or other signals that interfere with the synthesis of the fragment, derivative or analog. The COT viral sequence nucleic acid can also be mutated in vitro or in vivo to create and/or destroy translation, initiation and/or termination sequences. The COT viral sequence-encoding nucleic acid can also be mutated to create variations in coding regions and/or to form new restriction endonuclease sites or destroy preexisting ones and to facilitate further in vitro modification. Any technique for mutagenesis known in the art can be used, including but not limited to chemical mutagenesis, in vitro site-directed mutagenesis, and the like.

Manipulations of the COT viral sequence can also be made at the protein level. Included within the scope of the invention are COT protein fragments, derivatives or analogs that are differentially modified during or after synthesis (e.g., in vivo or in vitro translation). Such modifications include conservative substitution, glycosylation, acetylation, phosphorylation, amidation, derivatization by known protecting/blocking groups, proteolytic cleavage, linkage to an antibody molecule or other cellular ligand, and the like. Any of numerous chemical modifications can be carried out by known techniques, including, but not limited to, specific chemical cleavage (e.g., by cyanogen bromide); enzymatic cleavage (e.g., by trypsin, chymotrypsin, papain, V8 protease, and the like); modification by, for example, $NaBH_4$ acetylation, formylation, oxidation and reduction; metabolic synthesis in the presence of tunicamycin; and the like.

In addition, fragments, derivatives and analogs of COT proteins can be chemically synthesized. For example, a peptide corresponding to a portion, or fragment, of an COT protein, which comprises a desired domain, can be synthesized by use of chemical synthetic methods using, for example, an automated peptide synthesizer. (See also Hunkapiller et al., *Nature* 310:105-11 (1984); Stewart and Young, *Solid Phase Peptide Synthesis*, 2nd ed., Pierce Chemical Co., Rockford, Ill., (1984).) Furthermore, if desired, non-classical amino acids or chemical amino acid analogs can be introduced as a substitution or addition into the polypeptide sequence. Non-classical amino acids include, but are not limited to, the D-isomers of the common amino acids, α-amino isobutyric acid, 4-aminobutyric acid, 2-amino butyric acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and other amino acid analogs. Furthermore, the amino acid can be D (dextrorotary) or L (levorotary).

The COT protein, fragment, derivative or analog can also be a chimeric, or fusion, protein comprising an COT protein, fragment, derivative or analog thereof (typically consisting of at least a domain or motif of the COT protein, or at least 10 contiguous amino acids of the COT protein) joined at its amino- or carboxy-terminus via a peptide bond to an amino acid sequence of a different protein. In one embodiment, such a chimeric protein is produced by recombinant expression of nucleic acid encoding the chimeric protein. The chimeric nucleic acid can be made by ligating the appropriate nucleic acid sequences to each other in the proper reading frame and expressing the chimeric product by methods commonly known in the art. Alternatively, the chimeric protein can be made by protein synthetic techniques (e.g., by use of an automated peptide synthesizer).

COT protein can be isolated and purified by standard methods including chromatography (e.g., ion exchange, affinity, sizing column chromatography, high pressure liquid chromatography), centrifugation, differential solubility, or by any other standard technique for the purification of proteins.

Nucleic Acids Encoding Ancestral or COT Viral Sequences

Once an ancestral or COT viral sequence is determined by the methods described herein, recombinant DNA methods can be used to prepare nucleic acids encoding the ancestral or COT viral sequence of interest. Suitable methods include, but are not limited to: (1) modifying an existing viral strain most similar to the ancestor viral sequence; (2) synthesizing a nucleic acid encoding the ancestral or COT viral sequence by joining shorter oligonucleotides (e.g., 160-200 nucleotides in length); or (3) a combination of these methods (e.g., by modifying an existing sequence using fragments with very high similarity to the ancestral or COT viral sequence, while synthesizing de novo more divergent sequences).

The nucleic acid sequences can be produced and manipulated using routine techniques. (See, e.g., Sambrook et al., supra; Kriegler, supra; Ausubel et al., supra.)

TABLE 1

| | | | | | | |
|---|---|---|---|---|---|---|
| 1 | ATGCGCGTGA | AGGGCATCCG | CAAGAACTAC | CAGCACCTGT | GGCGCTGGGG | (SEQ ID NO: 1) |
| 51 | CACCATGCTG | CTGGGGATGC | TGATGATCTG | CTCCGCGGCC | GAGAAGCTGT | |
| 101 | GGGTGACCGT | GTACTACGGC | GTGCCCGTGT | GGAAGGAGGC | CACCACCACC | |

TABLE 1-continued

```
 151 CTGTTCTGCG CCAGCGACGC CAAGGCTTAC GACACCGAGG TCCACAACGT
 201 GTGGGCCACC CACGCCTGCG TGCCCACCGA CCCCAACCCC CAGGAGGTGG
 251 TGCTGGAGAA CGTGACCGAG AACTTCAACA TGTGGAAGAA CAACATGGTG
 301 GAGCAGATGC ACGAGGACAT CATCAGCCTG TGGGACCAGA GCCTGAAGCC
 351 CTGCGTGAAG TTAACCCCCC TGTGCGTGAC CCTGAACTGC ACCGACGACC
 401 TGCGCACCAA CGCCACCAAC ACCACCAACA GCAGCGCCAC CACCAACACC
 451 ACCAGCAGCG GCGGCGGCAC GATGGAGGGC GAGAAGGGCG AGATCAAGAA
 501 CTGCAGCTTC AACGTGACCA CCAGCATCCG CGACAAGATG CAGAAGGAGT
 551 ACGCCCTGTT CTACAAGCTG GACGTGGTGC CCATCGACAA CGACAACAAC
 601 AACACCAACA ACAACACCAG CTACCGCCTC ATCAACTGCA ACACCAGCGT
 651 GATCACCCAG GCCTGCCCCA AGGTGAGCTT CGAGCCCATC CCCATCCACT
 701 ACTGCACCCC CGCCGGCTTC GCCATCCTGA AGTGCAACGA CAAGAAGTTC
 751 AACGGCACCG GCCCCTGCAC CAACGTGAGC ACCGTGCAGT GCACCCACGG
 801 CATCCGCCCC GTGGTGAGCA CCCAGCTGCT GCTGAACGGC AGCCTGGCCG
 851 AGGAGGAGGT GGTGATCCGC AGCGAGAACT TCACCGACAA CGCCAAGACC
 901 ATCATCGTGC AGCTGAACGA GAGCGTGGAG ATCAACTGCA CGCGTCCCAA
 951 CAACAACACC CGCAAGAGCA TCCCCATCGG CCCTGGCCGC GCCCTGTACG
1001 CCACCGGCAA GATCATCGGC GACATCCGCC AGGCCCACTG CAACCTGTCG
1051 CGAGCCAAGT GGAACAACAC CCTGAAGCAG ATCGTGACCA AGCTGCGCGA
1101 GCAGTTCGGC AACAACAAGA CCACCATCGT GTTCAACCAG AGCAGCGGCG
1151 GCGACCCCGA GATCGTGATG CACAGCTTCA ACTGCGGCGG CGAATTCTTC
1201 TACTGCAACA GCACCCAGCT GTTCAACAGC ACCTGGCACT TCAACGGCAC
1251 CTGGGGCAAC AACAACACCG AGCGCAGCAA CAACGCCGCC GACGACAACG
1301 ACACCATCAC CCTGCCCTGC CGCATCAAGC AGATCATCAA CATGTGGCAG
1351 GAGGTGGGCA AGGCCATGTA CGCCCCCCCC ATCAGCGGCC AGATCCGCTG
1401 CAGCAGCAAC ATCACCGGCC TGCTGCTGAC TCGAGACGGC GGCAACAACG
1451 AGAACACCAA CAACACCGAC ACCGAGATCT TCCGCCCCGG GGGCGGCGAC
1501 ATGCGCGACA ACTGGCGCAG CGAGCTGTAC AAGTACAAGG TGGTGAAGAT
1551 CGAGCCCCTG GGCGTGGCCC CCACCAAGGC CAAGCGCCGC GTGGTGCAGC
1601 GCGAGAAGCG CGCCGTGGGC ATGCTGGGCG CCATGTTCCT GGGCTTCCTG
1651 GGCGCCGCCG GCAGCACCAT GGGCGCCGCC AGCATGACCC TGACCGTGCA
1701 GGCGCGCCAG CTGCTGAGCG GCATCGTGCA GCAGCAGAAC AACCTGCTGC
1751 GCGCCATCGA GGCCCAGCAG CACCTGCTGC AGCTGACCGT GTGGGGCATC
1801 AAGCAGCTGC AGGCCCGCGT GCTGGCCGTG GAGCGGTACC TGAAGGACGA
1851 GCAGCTGCTG GGCATCTGGG GCTGCAGCGG CAAGCTGATC TGCACCACCG
1901 CGGTGCCCTG GAACGCCAGC TGGAGCAACA AGAGCCTGGA CAAGATCTGG
1951 AACAACATGA CCTGGATGGA GTGGGAGCGC GAGATCGACA ACTACACCGG
2001 CCTGATCTAC ACCCTGATCG AGGAGAGCCA GAACCAGCAG GAGAAGAACG
2051 AGCAGGAGCT GCTGGAGCTG GACAAGTGGG CCAGGCTGTG GAACTGGTTC
```

TABLE 1-continued

```
2101 GATATCACCA ACTGGCTGTG GTACATCAAG ATCTTCATCA TGATCGTGGG

2151 CGGCCTGGTG GGCCTGCGCA TCGTGTTCGC CGTGCTGAGC ATCGTGAACC

2201 GCGTGCGCCA GGGCTACAGC CCCCTGAGCT TCCAGACCCG CCTGCCCGCC

2251 CCCCGCGGCC CCGACCGCCC CGAGGGCATC GAGGAGGAGG GCGGCGAGCG

2301 CGACCGCGAC CGCAGCGGGC GCCTGGTGAA CGGCTTCCTG GCCCTGATCT

2351 GGGACGACCT GCGCAGCCTG TGCCTGTTCA GCTACCACCG CCTGCGCGAC

2401 CTGCTGCTGA TCGTGGCCCG CATCGTGGAG CTGCTGGGCC GGCGCGGCTG

2451 GGAGGCCCTG AAGTATTGGT GGAACCTGCT GCAGTACTGG AGCCAGGAGC

2501 TGAAGAACAG CGCCGTGAGC CTGCTGAACG CCACCGCCAT CGCCGTGGCC

2551 GAGGGCACCG ACCGCGTGAT CGAGGTGGTG CAGCGCGCCT GCCGCGCCAT

2601 CCTGCACATC CCCCGCCGCA TCCGCCAGGG CCTGGAGCGC GCCCTGCTGT

2651 GA
```

TABLE 2

| | | | | | | |
|---|---|---|---|---|---|---|
| MRVKGIRKNY | QHLWRWGTML | LGMLMICSAA | EKLWVTVYYG | VPVWKEATTT | LFCASDAKAY | (SEQ ID NO: 2) |
| DTEVHNVWAT | HACVPTDPNP | QEVVLENVTE | NFNMWKNNMV | EQMHEDIISL | WDQSLKPCVK | |
| LTPLCVTLNC | TDDLRTNATN | TTNSSATTNT | TSSGGGTMEG | EKGEIKNCSF | NVTTSIRDKM | |
| QKEYALFYKL | DVVPIDNDNN | NTNNNTSYRL | INCNTSVITQ | ACPKVSFEPI | PIHYCTPAGF | |
| AILKCNDKKF | NGTGPCTNVS | TVQCTHGIRP | VVSTQLLLNG | SLAEEEVVIR | SENFTDNAKT | |
| IIVQLNESVE | INCTRPNNNT | RKSIPIGPGR | ALYATGKIIG | DIRQAHCNLS | RAKWNNTLKQ | |
| IVTKLREQFG | NNKTTIVFNQ | SSGGDPEIVM | HSFNCGGEFF | YCNSTQLFNS | TWHFNGTWGN | |
| NNTERSNNAA | DDNDTITLPC | RIKQIINMWQ | EVGKAMYAPP | ISGQIRCSSN | ITGLLLTRDG | |
| GNNENTNNTD | TEIFRPGGGD | MRDNWRSELY | KYKVVKIEPL | GVAPTKAKRR | VVQREKRAVG | |
| MLGAMFLGFL | GAAGSTMGAA | SMTLTVQARQ | LLSGIVQQQN | NLLRAIEAQQ | HLLQLTVWGI | |
| KQLQARVLAV | ERYLKDQQLL | GIWGCSGKLI | CTTAVPWNAS | WSNKSLDKIW | NNMTWMEWER | |
| EIDNYTGLIY | TLIEESQNQQ | EKNEQELLEL | DKWASLWNWF | DITNWLWYIK | IFIMIVGGLV | |
| GLRIVFAVLS | IVNRVRQGYS | PLSFQTRLPA | PRGPDRPEGI | EEEGGERDRD | RSGRLVNGFL | |
| ALIWDDLRSL | CLFSYHRLRD | LLLIVARIVE | LLGRRGWEAL | KYWWNLLQYW | SQELKNSAVS | |
| LLNATAIAVA | EGTDRVIEVV | QRACRAILHI | PRRIRQGLER | ALL | | |

TABLE 3

```
ATGCGGGTGATGGGCATCCTGCGGAACTGCCAGCAGTGCTGGATCTGGGGCATCCTGGGC  (SEQ ID NO: 3)

TTCTGGATGCTGATGATCTGCAGCGTGATGGGCAACCTGTGGGTGACCGTGTACTACGGC

GTGCCCGTGTGGAAGGAGGCCAAGACCACCCTGTTCTGCGCCAGCGACGCCAAGGCCTAC

GAGCGGGAGGTGCACAACGTGTGGGCCACCCACGCCTGCGTGCCCACCGACCCCAACCCC

CAGGAGATGGTGCTGGAGAACGTGACCGAGAACTTCAACATGTGGAAGAACGACATGGTG

GACCAGATGCACGAGGACATCATCAGCCTGTGGGACCAGAGCCTGAAGCCCTGCGTGAAG
```

TABLE 3-continued

```
CTGACCCCCCTGTGCGTGACCCTGAACTGCACCAAGGTGACCAACAGCAACAACAACAAC

AACACCAGCATGGGCGGGGAGATCAAGAACTGCAGCTTGAACATCACCAGCGAGCTGCGG

GACAAGAAGCAGAAGGTGTACGCCCTGTTCTACCGGCTGGACATCGTGCCCCTGAACGAG

AACAGCAACAGCAACAGCAGCGAGTACCGGCTGATCAACTGCAACACCAGCGCCATCACC

CAGGCCTGCCCCAAGGTGAGCTTCGACCCCATCCCCATCCACTACTGCGCCCCCGCCGGC

TACGCCATCCTGAAGTGCAACAACAAGACCTTCAACGGCACCGGCCCCTGCAACAACGTG

AGCACCGTGCAGTGCACCCACGGCATCAAGCCCGTGGTGAGCACCCAGCTGCTGCTGAAC

GGCAGCCTGGCCGAGGAGGAGATCATCATCCGGAGCGAGAACCTGACCAACAACGCCAAG

ACCATCATCGTGCACCTGAACGAGAGCGTGGAGATCGTGTGCACCCGGCCCAACAACAAC

ACCCGGAAGAGCATCCGGATCGGCCCCGGCCAGACCTTCTACGCGACCGGCGACATCATC

GGCGACATCCGGCAGGCCCACTGCAACATCAGCGAGAAGGAGTGGAACAAGACCCTGCAG

CGGGTGGGCAAGAAGCTGAAGGAGCACTTCCCCAACAAGACCATCAAGTTCGAGCCCAGC

AGCGGCGGCGACCTGGAGATCACCACCCACAGCTTCAACTGCCGGGGCGAGTTCTTCTAC

TGCAACACCAGCAAGCTGTTCAACAGCACCTACAACAGCACCAACAACGGCACCACCAGC

AACAGCACCATCACCCTGCCCTGCCGGATCAAGCAGATCATCAACATGTGGCAGGGCGTG

GGCCGGGCCATCTACGCCCCCCCCATCGCCGGCAACATCACCTGCAAGAGCAACATCACC

GGCCTGCTGCTGACCCGGGACGGCGGCAACACCAACAACACCACCGAGACCTTCCGGCCC

GGCGGCGGCGACATGCGGGACAACTGGCGGAGCGAGCTGTACAAGTACAAGGTGGTGGAG

ATCAAGCCCCTGGGCGTGGCCCCCACCGAGGCCAAGCGGCGGGTGGTGGAGCGGGAGAAG

CGGGCCGTGGGCATCGGCGCCGTGTTCCTGGGCTTCCTGGGCGCCGCCGGCAGCACCATG

GGCGCCGCCAGCATCACCCTGACCGTGCAGGCCCGGCAGCTGCTGAGCGGCATCGTGCAG

CAGCAGAGCAACCTGCTGCGGGCCATCGAGGCCCAGCAGCACATGCTGCAGCTGACCGTG

TGGGGCATCAAGCAGCTGCAGACCCGGGTGCTGGCCATCGAGCGGTACCTGAAGGACCAG

CAGCTGCTGGGCATCTGGGGCTGCAGCGGCAAGCTGATCTGCACCACCGCCGTGCCCTGG

AACAGCAGCTGGAGCAACAAGAGCCAGGACGACATCTGGGACAACATGACCTGGATGCAG

TGGGACCGGGAGATCAGCAACTACACCGACACCATCTACCGGCTGCTGGAGGACAGCCAG

AACCAGCAGGAGAAGAACGAGAAGGACCTGCTGGCCCTGGACAGCTGGAAGAACCTGTGG

AACTGGTTCGACATCACCAACTGGCTGTGGTACATCAAGATCTTCATCATGATCGTGGGC

GGCCTGATCGGCCTGCGGATCATCTTCGCCGTGCTGAGCATCGTGAACCGGGTGCGGCAG

GGCTACAGCCCCCTGAGCTTCCAGACCCTGACCCCCAACCCGCGGGGCCCCGACCGGCTG

GGCGGCATCGAGGAGGAGGGCGGCGAGCAGGACCGGGACCGGAGCATCCGGCTGGTGAGC

GGCTTCCTGGCCCTGGCCTGGGACGACCTGCGGAGCCTGTGCCTGTTCAGCTACCACCGG

CTGCGGGACTTCATCCTGATCGCCGCCCGGGGCGTGAACCTGCTGGGCCGGAGCAGCCTG

CGGGGCCTGCAGCGGGGTGGGAGGCCCTGAAGTACCTGGGCAGGCTGGTGCAGTACTGG

GGCCTGGAGCTGAAGAAGAGCGCCATCAGCCTGGTGGACACCATCGCGATCGCCGTGGCC

GAGGGCACCGACCGGATCATCGAGCTGGTGCAGCGGATCTGCCGGGCCATCCGGAACATC

CCCCGGCGGATCCGGCAGGGCTTCGAGGCCGCCCTGCAGTGA
```

TABLE 4

(SEQ ID NO: 4)

MRVMGILRNCQQWWIWGILGFWMLMICSVMGNLWVTVYYGVPVWKEAKTT
LFCASDAKAYEREVHNVWATHACVPTDPNPQEMVLENVTENFNMWKNDMV
DQMHEDIISLWDQSLKPCVKLTPLCVTLNCTNVTNTNNNNNTSMGGEIKN
CSFNITTELRDKKQKVYALFYRLDIVPLNENSNSNSSEYRLINCNTSAIT
QACPKVSFDPIPIHYCAPAGYAILKCNNKTFNGTGPCNNVSTVQCTHGIK
PVVSTQLLLNGSLAEEEIIRSENLTNNAKTIIVHLNESVEIVCTRPNNN
start* TRKSIRIGPGQTFYATGDIIGDIRQAHC-
NISEKEWNKTLQRVGKKLKEHF
PNKTIKFEPSSGGDLEITTHSFNCRGEFFYCNTSKLFNSTYNSTNNGTTS
NSTITLPCRIKQIINMWQGVGRAMYAPPIAGNITCKSNITGLLLTRDGGN
TNNTTETFRPGGGDMRDNWRSELYKYKVVEIKPLGVAPTEAKRRVVEREK
RAVGIGAVFLGFLGAAGSTMGAASITLTVQARQLLSGIVQQQSNLLRAIE
AQQHMLQLTVWGIKQLQTRVLAIERYLKDQQLLGIWGCSGKLICTTAVPW
NSSWSNKSQDDIWDNMTWMQWDREISNYTDTIYRLLEDSQNQQEKNEKDL
LALDSWKNLWNWFDITNWLWYIKIFIMIVGGLIGLRIIFAVLSIVNRVRQ
GYSPLSFQTLTPNPRGPDRLGGIEEEGGEQDRDRSIRLVSGFLALAWDDL
RSLCLFSYHRLRDFILIAARGVNLLGRSSLRGLQRGWEALKYLGSLVQYW
GLELKKSAISLLDTIAIAVAEGTDRIIELVQRICRAIRNIPRRIRQGFEA
ALQ

TABLE 5

(SEQ ID NO: 5)

ATGAGAGTGAAGGGGATCAGGAAGAACTATCAGCACTTGTGGAGATGGGG
CACCATGCTCCTTGGGATGTTGATGATCTGTAGCGCCGCCGAGAAGCTGT
GGGTGACCGTGTACTACGGCGTGCCCGTGTGGAAGGAGGCCACCACCACC
CTGTTCTGCGCCAGCGACGCCAAGGCTTACGACACCGAGGTCCACAACGT
GTGGGCCACCCACGCCTGCGTGCCCACCGACCCCAACCCCCAGGAGGTGG
TGCTGGAGAACGTGACCGAGAACTTCAACATGTGGAAGAACAACATGGTG
GAGCAGATGCACGAGGACATCATCAGCCTGTGGGACCAGAGCCTGAAGCC
CTGCGTGAAGTTAACCCCCCTGTGCGTGACCCTGAACTGCACCGACGACC
TGCGCACCAACGCCACCAACACCACCAACAGCAGCGCCACCACCAACACC
ACCAGCAGCGGCGGCGGCACGATGGAGGGCGAGAAGGGCGAGATCAAGAA
CTGCAGCTTCAACGTGACCACCAGCATCCGCGACAAGATGCAGAAGGAGT
ACGCCCTGTTCTACAAGCTGGACGTGGTGCCCATCGACAACGACAACAAC
AACACCAACAACAACACCAGCTACCGCCTCATCAACTGCAACACCAGCGT
GATCACCCAGGCCTGCCCCAAGGTGAGCTTCGAGCCCATCCCCATCCACT
ACTGCACCCCCGCCGGCTTCGCCATCCTGAAGTGCAACGACAAGAAGTTC
AACGGCACCGGCCCCTGCACCAACGTGAGCACCGTGCAGTGCACCCACGG
CATCCGCCCCGTGGTGAGCACCCAGCTGCTGCTGAACGGCAGCCTGGCCG
AGGAGGAGGTGGTGATCCGCAGCGAGAACTTCACCGACAACGCCAAGACC
ATCATCGTGCAGCTGAACGAGAGCGTGGAGATCAACTGCACGCGTCCCAA
CAACAACACCCGCAAGAGCATCCCCATCGGCCCTGGCCGCGCCCTGTACG
CCACCGGCAAGATCATCGGCGACATCCGCCAGGCCCACTGCAACCTGTCG
CGAGCCAAGTGGAACAACACCCTGAAGCAGATCGTGACCAAGCTGCGCGA
GCAGTTCGGCAACAACAAGACCACCATCGTGTTCAACCAGAGCAGCGGCG
GCGACCCCGAGATCGTGATGCACAGCTTCAACTGCGGCGGCGAATTCTTC
TACTGCAACAGCACCCAGCTGTTCAACAGCACCTGGCACTTCAACGGCAC
CTGGGGCAACAACAACACCGAGCGCAGCAACAACGCCGCCGACGACAACG
ACACCATCACCCTGCCCTGCCGCATCAAGCAGATCATCAACATGTGGCAG
GAGGTGGGCAAGGCCATGTACGCCCCCCCCATCAGCGGCCAGATCCGCTG
CAGCAGCAACATCACCGGCCTGCTGCTGACTCGAGACGGCGGCAACAACG
AGAACACCAACAACACCGACACCGAGATCTTCCGCCCCGGGGCGGCGAC
ATGCGCGACAACTGGCGCAGCGAGCTGTACAAGTACAAGGTGGTGAAGAT
CGAGCCCCTGGGCGTAGCACCCACCAAGGCAAAGAGAAGAGTGGTGCAGA
GAGAAAAAGCGCAGTGGGAATGCTAGGAGCTATGTTCCTTGGGTTCTTG
GGAGCAGCAGGAAGCACTATGGGCGCAGGGTCAATGACGCTGACCGTACA
GGCCAGACAATTATTGTCTGGTATAGTGCAGCAGCAGAACAATCTGCTGA
GGGCTATTGAGGCGCAACAGCATCTGTTGCAACTCACAGTCTGGGGCATC
AAGCAGCTCCAGGCAAGAGTCCTGGCTGTGGAAAGATACCTAAAGGATCA
GCAGCTCCTGGGGATTTGGGGTTGCTCTGGAAAACTCATCTGCACCACTG
CTGTGCCTTGGAATGCTAGCTGGAGCAACAAGAGCCTGGACAAGATCTGG
AACAACATGACCTGGATGGAGTGGGAGCGCGAGATCGACAACTACACCGG
CCTGATCTACACCCTGATCGAGGAGAGCCAGAACCAGCAGGAGAAGAACG
AGCAGGAGCTGCTGGAGCTGGACAAGTGGGCCAGCCTGTGGAACTGGTTC
GATATCACCAACTGGCTGTGGTACATCAAGATCTTCATCATGATCGTGGG
CGGCCTGGTGGGCCTGCGCATCGTGTTCGCCGTGCTGAGCATCGTGAACC
GCGTGCGCCAGGGCTACAGCCCCCTGAGCTTCCAGACCCACCTGCCAGCC
CCGAGGGGACCCGACAGGCCCGAAGGAATCGAAGAAGAAGGTGGAGAGAG
AGACAGAGACAGATCCGGTCGATTAGTGAATGGATTCTTAGCACTTATCT
GGGACGACGTGCGGAGCCTGTGCCTCTTCAGCTACCACCGCTTGAGCGAC
TTACTCTTGATTGTAGCGAGGATTGTGGAACTTCTGGGACGCAGGGGGTG
GGAGGCCCTCAAATATTGGTGGAATCTCCTGCAGTACTGGAGTCAGGAAC
TAAAGAATAGCGCCGTGAGCCTGCTGAACGCGACCGCCATCGCCGTGGCC
GAGGGCACCGACCGCGTGATCGAGGTGGTGCAGCGCGCCTGCCGCGCCAT
CCTGCACATCCCCCGCCGCATCCGCCAGGGCCTGGAGCGCGCCCTGCTGT
GA

TABLE 6

(SEQ ID NO: 6)

ATGAGAGTGATGGGGATACTGAGGAATTGTCAACAATGGTGGATATGGGG
CATCCTAGGCTTTTGGATGCTAATGATTTGTGACGTGATGGGCAACCTGT
GGGTGACCGTGTACTACGGCGTGCCCGTGTGGAAGGAGGCCAAGACCACC
CTGTTCTGCGCCAGCGACGCCAAGGCCTACGAGCGGGAGGTGCACAACGT
GTGGGCCACCCACGCCTGCGTGCCCACCGACCCCAACCCCCAGGAGATGG
TGCTGGAGAACGTGACCGAGAACTTCAACATGTGGAAGAACGACATGGTG
GACCAGATGCACGAGGACATCATCAGCCTGTGGGACCAGAGCCTGAAGCC
CTGCGTGAAGCTGACCCCCCTGTGCGTGACCCTGAACTGCACCAACGTGA
CCAACACCAACAACAACAACACCAGCATGGGCGGCGAGATCAAGAAC
TGCAGCTTCAACATCACCACCGAGCTGCGGGACAAGAAGCAGAAGGTGTA
CGCCCTGTTCTACCGGCTGGACATCGTGCCCCTGAACGAGAACAGCAACA
GCAACAGCAGCGAGTACCGGCTGATCAAGTGCAACACCAGCGCCATCACC
CAGGCCTGCCCCAAGGTGAGCTTCGACCCCATCCCCATCCACTACTGCGC
CCCCGCCGGCTACGCCATCCTGAAGTGCAACAACAAGACCTTCAACGGCA
CCGGCCCCTGCAACAACGTGAGCACCGTGCAGTGCACCCACGGCATCAAG
CCCGTGGTGAGCACCCAGCTGCTGCTGAACGGCAGCCTGGCCGAGGAGGA
GATCATCATCCGGAGCGAGAACCTGACCAACAACGCCAAGACCATCATCG
TGCACCTGAACGAGAGCGTGGAGATCGTGTGCACCCGGCCCAACAACAAC
ACCCGGAAGAGCATCCGGATCGGCCCCGGCCAGACCTTCTACGCCACCGG
CGACATCATCGGCGACATCCGGCAGGCCCACTGCAACATCAGCGAGAAGG
AGTGGAACAAGACCCTGCAGCGGGTGGGCAAGAAGCTGAAGGAGCACTTC
CCCAACAAGACCATCAAGTTCGAGCCCAGCAGCGGCGGCGACCTGGAGAT
CACCACCCACAGCTTCAACTGCCGGGGCGAGTTCTTCTACTGCAACACCA
GCAAGCTGTTCAACAGCACCTACAACAGCACCAACAACGGCACCACCAGC
AACAGCACCATCACCCTGCCCTGCCGGATCAAGCAGATCATCAACATGTG
GCAGGGCGTGGGCCGGGCCATGTACGCCCCCCCCATCGCCGGCAACATCA
CCTGCAAGAGCAACATCACCGGCCTGCTGCTGACCCGGGACGGCGGCAAC
ACCAACAACACCACCGAGACCTTCCGGCCCGGCGGCGGCGACATGCGGGA
CAACTGGCGGAGCGAGCTGTACAAGTACAAGGTGGTGGAGATCAAGCCCC
TGGGCGTAGCACCCACTGAGGCAAAAAGGAGAGTGGTGGAGAGAGAAAAA

AGAGCAGTGGGAATAGGAGCTGTGTTCCTTGGGTTCTTGGGAGCAGCAGG

AAGCACTATGGGCGCGGCGTCAATAACGCTGACGGTACAGGCCAGACAAT

TATTGTCTGGTATAGTGCAACAGCAAAGCAATTTGCTGAGGGCTATAGAG

GCGCAACAGCATATGTTGCAACTCACGGTCTGGGGCATTAAGCAGCTCCA

GACAAGAGTCCTGGCTATAGAAAGATACCTAAAGGATCAGCAGCTCCTGG

GCATTTGGGGCTGCTCTGGAAAACTCATCTGCACCACTGCTGTGCCTTGG

AACTCTAGCTGGAGCAACAAGAGCCAGGACGACATCTGGGACAACATGAC

CTGGATGCAGTGGGACCGGGAGATCAGCAACTACACCGACACCATCTACC

GGCTGCTGGAGGACAGCCAGAACCAGCAGGAGAAGAACGAGAAGGACCTG

TABLE 6-continued

CTGGCCCTGGACAGCTGGAAGAACCTGTGGAACTGGTTCGACATCACCAA

CTGGCTGTGGTACATCAAGATCTTCATCATGATCGTGGGCGGCCTGATCG

GCCTGCGGATCATCTTCGCCGTGCTGAGCATCGTGAACCGGGTGCGGCAG

GGCTACAGCCCCCTGAGCTTGCAGACCCTTACCCCAAACCCGAGGGGACC

CGACAGGCTCGGAGGAATCGAAGAAGAAGGTGGAGAGCAAGACAGAGACA

GATCCATTCGATTAGTGAGCGGATTCTTAGCACTGGCCTGGGACGACCTG

CGGAGCCTGTGCCTCTTCAGCTACCACCGATTGAGAGACTTCATATTGAT

TGCAGCCAGAGGGTGGGAACTTCTGGGACGCAGCAGTCTCAGGGGACTGC

AGAGGGGGTGGGAAGCCCTTAAGTATCTGGGAAGTCTTGTGCAGTATTGG

GGTCTGGAGCTAAAAAAGAGTGCTATTAGCCTGGTGGACACCATCGCCAT

CGCCGTGGCCGAGGGCACGGAGCGGATCATCGAGCTGGTGCAGCGGATCT

GCCGGGCCATCCGGAACATCCCCCGGCGGATCCGGCAGGGGTTCGAGGCC

GCCCTGCAGTGA

Unless otherwise stated, all enzymes are used in accordance with the manufacturer's instructions.

In a typical embodiment, a nucleic acid encoding the ancestral or COT viral sequence is synthesized by joining long oligonucleotides. By synthesizing a nucleic acid de novo, desired features are easily incorporated into the gene. Such features include, but are not limited to, the incorporation of convenient restriction sites to enable further manipulation of the nucleic acid sequence, optimization of the codon frequencies (e.g., human codon frequencies) to greatly enhance in vivo expression levels, which can favor the immunogenicity of the polypeptide sequence, and the like. Long oligonucleotides can be synthesized with a very low error rate using the solid-phase method. Long oligonucleotides designed with a 20-25 nucleotide complementary sequence at both 5' and 3' ends can be joined using DNA polymerase, DNA ligase, and the like. If necessary, the sequence of the synthesized nucleic acid can be verified by DNA sequence analysis.

Oligonucleotides that are not commercially available can be chemically synthesized. Suitable methods include, for example, the solid phase phosphoramidite triester method first described by Beaucage and Caruthers (*Tetrahedron Letts* 22(20):1859-62 (1981)), and the use of an automated synthesizer (see, e.g., Needham Van Devanter et al., *Nucleic Acids Res*. 12:6159-68 (1984)). Purification of oligonucleotides is, for example, by native acrylamide gel electrophoresis or by anion-exchange HPLC, as described in Pearson and Reanier (*J. Chrom*. 255:137-49 (1983)).

The sequence of the nucleic acids can be verified, for example, using the chemical degradation method of Maxam et al. (*Methods in Enzymology* 65:499-560 (1980)), or the chain termination method for sequencing double stranded templates (see, e.g., Wallace et al., *Gene* 16:21-26 (1981)). Southern blot hybridization techniques can be carried out according to Southern et al. (*J. Mol. Biol*. 98:503 (1975)), Sambrook et al. (supra), or Ausubel et al. (supra).

Expression of Ancestral or COT Viral Sequences

The nucleic acids encoding ancestral or COT viral sequences can be inserted into an appropriate expression vector (i.e., a vector which contains the necessary elements for the transcription and translation of the inserted polypeptide-coding sequence). A variety of host-vector systems can be utilized to express the polypeptide-coding sequence(s). These include, for example, mammalian cell systems infected with virus (e.g., vaccinia virus, adenovirus, sindbis virus, Venezuelan equine encephalitis (VEE) virus, and the like), insect cell systems infected with virus (e.g., baculovirus), microorganisms such as yeast containing yeast vectors, or bacteria transformed with bacteriophage DNA, plasmid DNA, or cosmid DNA. The expression elements of vectors vary in their strengths and specificities. Depending on the host-vector system utilized, any one of a number of suitable transcription and translation elements can be used. In specific embodiments, the ancestral or COT viral sequence is expressed in human cells, other mammalian cells, yeast or bacteria. In yet another embodiment, a fragment of an ancestral or COT viral sequence comprising an immunologically active region of the sequence is expressed.

Any suitable method can be used for insertion of nucleic acids encoding ancestral or COT viral sequences into an expression vector. Suitable expression vectors typically include appropriate transcriptional and translational control signals. Suitable methods include in vitro recombinant DNA and synthetic techniques and in vivo recombination techniques (genetic recombination). Expression of nucleic acid sequences can be regulated by a second nucleic acid sequence so that the encoded nucleic acid is expressed in a host transformed with the recombinant DNA molecule. For example, expression of an ancestral or COT viral sequence can be controlled by any suitable promoter/enhancer element known in the art. Suitable promoters include, for example, the SV40 early promoter region (Benoist and Chambon, *Nature* 290:304-10 (1981)), the promoter contained in the 3' long terminal repeat of Rous sarcoma virus (Yamamoto et al., *Cell* 22:787-97 (1980)), the herpes thymidine kinase promoter (Wagner et al., *Proc. Natl. Acad Sci. USA* 78:1441-45 (1981)), the Cytomegalovirus promoter, the translational elongation factor EF-1$\alpha$ promoter, the regulatory sequences of the metallothionein gene (Brinster et al., *Nature* 296:39-42 (1982)), prokaryotic promoters such as, for example, the $\beta$-lactamase promoter (Villa-Komaroff et al., *Proc. Natl. Acad Sci. USA* 75:3727-31 (1978)) or the tac promoter (deBoer et al., *Proc. Natl. Acad. Sci. USA* 80:21-25 (1983)), plant expression vectors including the cauliflower mosaic virus 35S RNA promoter (Gardner et al., *Nucl. Acids Res*. 9:2871-88 (1981)), and the promoter of the photosynthetic enzyme ribulose biphosphate carboxylase (Herrera-Estrella et al., *Nature* 310:115-20 (1984)), promoter elements from yeast or other fungi such as the GAL7 and GAL4 promoters, the ADH (alcohol dehydrogenase) promoter, the PGK (phosphoglycerol kinase) promoter, the alkaline phosphatase promoter, and the like.

Other exemplary mammalian promoters include, for example, the following animal transcriptional control regions, which exhibit tissue specificity: the elastase I gene control region which is active in pancreatic acinar cells (Swift et al., *Cell* 38:639-46 (1984); Ornitz et al., *Cold Spring Harbor Symp. Quant. Biol*. 50:399-409 (1986); MacDonald, *Hepatology* 7(1 Suppl.):42S-51S (1987); the insulin gene control region which is active in pancreatic beta cells (Hanahan, *Nature* 315:115-22 (1985)), the immunoglobulin gene control region which is active in lymphoid cells (Grosschedl et al., *Cell* 38:647-58 (1984); Adams et al., *Nature* 318:533-38 (1985); Alexander et al., *Mol. Cell. Biol*. 7:1436-44 (1987)), the mouse mammary tumor virus control region which is active in testicular, breast, lymphoid and mast cells (Leder et al., *Cell* 45:485-95 (1986)), the albumin gene control region which is active in liver (Pinkert et al., *Genes Dev*. 1:268-76 (1987)), the alpha-fetoprotein gene control region which is active in liver (Krumlauf et al., *Mol. Cell. Biol*. 5:1639-48 (1985); Hammer et al., *Science* 235:53-58 (1987); the alpha 1-antitrypsin gene control region which is active in the liver (Kelsey et al., *Genes and Devel*. 1:161-71 (1987)); the beta-globin gene control region which is active in myeloid cells (Magram et al., *Nature* 315:338-40 (1985); Kollias et al., *Cell* 46:89-94 (1986); the myelin basic protein gene control region which is active in oligodendrocyte cells in the brain (Readhead et al., *Cell* 48:703-12 (1987)); the myosin light chain-2 gene control region which is active in skeletal muscle (Shani, *Nature* 314:283-86 (1985)); and the gonadotropic releasing hormone gene control region which is active in the hypothalamus (Mason et al., *Science* 234:1372-78 (1986)).

In a specific embodiment, a vector is used that comprises a promoter operably linked to the ancestral or COT viral sequence encoding nucleic acid, one or more origins of replication, and, optionally, one or more selectable markers (e.g., an antibiotic resistance gene). Suitable selectable markers include, for example, those conferring resistance to ampicillin, tetracycline, neomycin, G418, and the like. An expression construct can be made, for example, by subcloning a nucleic acid encoding an ancestral or COT viral sequence into a restriction site of the pRSECT expression vector. Such a construct allows for the expression of the ancestral or COT viral sequence under the control of the T7 promoter with a histidine amino terminal flag sequence for affinity purification of the expressed polypeptide.

In an exemplary embodiment, a high efficiency expression system can be used which employs a high-efficiency DNA transfer vector (the pJW4304 SV40/EBV vector) with a very high efficiency RNA/protein expression component (e.g., from the Semliki Forest Virus) to achieve maximal protein expression, as further discussed infra. pJW4304 SV40/EBV was prepared from pJW4303, which is described by Robinson et al. (*Ann. New York Acad. Sci*. 27:209-11 (1995)) and Yasutomi et al. (*J. Virol*. 70:678-81 (1996)).

Expression vector/host systems expressing an ancestral or COT viral sequences can be identified by general approaches well known to the skilled artisan, including: (a) nucleic acid hybridization, (b) the presence or absence of "marker" gene function, (c) expression of inserted sequences; or (d) screening transformed cells by standard recombinant DNA methods. In the first approach, the presence of an ancestral or COT viral sequence nucleic acid inserted in host cells can be detected by nucleic acid hybridization using probes comprising sequences that are homologous to an inserted nucleic acid. In the second approach, the expression vector/host system can be identified and selected based upon the presence or absence of certain "marker" gene functions (e.g., thymidine kinase activity, resistance to antibiotics, transformation phenotype, occlusion body formation in baculovirus, and the like) caused by the insertion of a vector containing the desired nucleic acids. For example, if the nucleic acid is inserted within the marker gene sequence of the vector, recombinants containing the ancestral or COT viral sequence can be identified by the absence of the marker gene function.

In the third approach, expression vector/host systems can be identified by assaying for the ancestral or COT viral sequence polypeptide expressed by the recombinant host organism. Such assays can be based, for example, on the physical or functional properties of the ancestral or COT viral sequence polypeptide in in vitro assay systems (e.g., binding by antibody). In the fourth approach, expression vector/host cells can be identified by screening transformed host cells by known recombinant DNA methods.

Once a suitable expression vector host system and growth conditions are established, methods that are known in the art can be used to propagate it. In addition, host cells can be chosen that modulate the expression of the inserted nucleic acid sequences, or that modify or process the gene product in the specific fashion desired. Expression from certain promoters can be elevated in the presence of certain inducers; thus, expression of the ancestral or COT viral sequence can be controlled. Furthermore, different host cells having characteristic and specific mechanisms for the translational and post-translational processing and modification (e.g., glycosylation or phosphorylation) of polypeptides can be used. Appropriate cell lines or host systems can be chosen to ensure the desired modification and processing of the expressed polypeptide. For example, expression in a bacterial system can be used to produce an unglycosylated polypeptide.

Antibodies to Ancestor or COT Proteins, Fragments, Derivatives and Analogs:

Ancestor or COT proteins (including fragments, derivatives, and analogs thereof), can be used as an immunogen to generate antibodies which immunospecifically bind such ancestor or COT proteins and to circulating variants. Such antibodies include but are not limited to polyclonal antibodies, monoclonal antibodies, chimeric antibodies, single chain antibodies, antigen binding antibody fragments (e.g., Fab, Fab', F(ab')$_2$, Fv, or hypervariable regions), and an Fab expression library. In some embodiments, polyclonal and/or monoclonal antibodies to an ancestor or COT protein are produced. In other embodiments, antibodies to a domain of an ancestor or COT protein are produced. In yet other embodiments, fragments of an ancestor or COT protein that are identified as immunogenic (e.g., hydrophilic) are used as immunogens for antibody production.

Various procedures known in the art can be used for the production of polyclonal antibodies. For the production of such antibodies, various host animals (including, but not limited to, rabbits, mice, rats, sheep, goats, camels, and the like) can be immunized by injection with the ancestor or COT protein, fragment, derivative or analog. Various adjuvants can be used to increase the immunological response, depending on the host species including, but not limited to, Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward an ancestor or COT protein, fragment, derivative, or analog thereof, any technique that provides for the production of antibody molecules by continuous cell lines in culture can be used. Such techniques include, for example, the hybridoma technique originally developed by Kohler and Milstein (see, e.g., *Nature* 256:495-97 (1975)), the trioma technique (see, e.g., Hagiwara and Yuasa, *Hum. Antibodies Hybridomas.* 4:15-19 (1993); Hering et al., *Biomed. Biochim. Acta* 47:211-16 (1988)), the human B-cell hybridoma technique (see, e.g., Kozbor et al., *Immunology Today* 4:72 (1983)), and the EBV-hybridoma technique to produce human monoclonal antibodies (see, e.g., Cole et al., In: *Monoclonal Antibodies and Cancer Therapy*, Alan R. Liss, Inc., pp. 77-96 (1985)). Human antibodies can be used and can be obtained by using human hybridomas (see, e.g., Cote et al., *Proc. Natl. Acad. Sci. USA* 80:2026-30 (1983)) or by transforming human B cells with EBV virus in vitro (see, e.g., Cole et al., supra).

Further to the invention, "chimeric" or "humanized" antibodies (see, e.g., Morrison et al., *Proc. Natl. Acad Sci. USA* 81:6851-55 (1984); Neuberger et al., *Nature* 312:604-08 (1984); Takeda et al., *Nature* 314:452-54 (1985)) can be prepared. Such chimeric antibodies are typically prepared by splicing the non-human genes for an antibody molecule specific for ancestor or COT protein together with genes from a human antibody molecule of appropriate biological activity. It can be desirable to transfer the antigen binding regions (e.g., Fab', F(ab')$_2$, Fab, Fv, or hypervariable regions) of non-human antibodies into the framework of a human antibody by recombinant DNA techniques to produce a substantially human molecule. Methods for producing such "chimeric" molecules are generally well known and described in, for example, U.S. Pat. Nos. 4,816,567; 4,816,397; 5,693,762; and 5,712,120; International Patent Publications WO 87/02671 and WO 90/00616; and European Patent Publication EP 239 400 (the disclosures of which are incorporated by reference herein). Alternatively, a human monoclonal antibody or portions thereof can be identified by first screening a human B-cell cDNA library for DNA molecules that encode antibodies that specifically bind to an ancestor or COT protein according to the method generally set forth by Huse et al. (*Science* 246:1275-81 (1989)). The DNA molecule can then be cloned and amplified to obtain sequences that encode the antibody (or binding domain) of the desired specificity. Phage display technology offers another technique for selecting antibodies that bind to ancestor or COT proteins, fragments, derivatives or analogs thereof. (See, e.g., International Patent Publications WO 91/17271 and WO 92/01047; Huse et al., supra.)

According to another aspect of the invention, techniques described for the production of single chain antibodies (see, e.g., U.S. Pat. Nos. 4,946,778 and 5,969,108) can be adapted to produce single chain antibodies. An additional aspect of the invention utilizes the techniques described for the construction of a Fab expression library (see, e.g., Huse et al., supra) to allow rapid and easy identification of monoclonal Fab fragments with the desired specificity for ancestor or COT proteins, fragments, derivatives, or analogs thereof.

Antibody that contains the idiotype of the molecule can be generated by known techniques. For example, such fragments include but are not limited to, the F(ab')$_2$ fragment which can be produced by pepsin digestion of the antibody molecule, the Fab' fragments which can be generated by reducing the disulfide bridges of the F(ab')$_2$ fragment, the Fab fragments which can be generated by treating the antibody molecule with papain and a reducing agent, and Fv fragments. Recombinant Fv fragments can also be produced in eukaryotic cells using, for example, the methods described in U.S. Pat. No. 5,965,405.

In the production of antibodies, screening for the desired antibody can be accomplished by techniques known in the art (e.g., ELISA (enzyme-linked immunosorbent assay)). In one example, antibodies that recognize a specific domain of an ancestor or COT protein can be used to assay generated hybridomas for a product which binds to polypeptide containing that domain. Antibodies specific to a domain of an ancestor or COT protein are also provided.

Antibodies against ancestor or COT proteins (including fragments, derivatives and analogs) can be used for passive antibody treatment, according to methods known in the art. Antibodies can be introduced into an individual to prevent or treat viral infection. Typically, such antibody therapy is practiced as an adjuvant to the vaccination protocols. The antibodies can be produced as described supra and can be polyclonal or monoclonal antibodies and administered intravenously, enterally (e.g., as an enteric coated tablet form), by aerosol, orally, transdermally, transmucosally, intrapleurally, intrathecally, or by other suitable routes.

Immunogenic Compositions and Vaccines

The present invention also provides immunogenic compositions, such as vaccines. An example of the development of a vaccine ("digital vaccine") using the sequences of the invention is illustrated in FIG. 4. The present invention also provides a new way to produce vaccines, using HIV ancestral or COT viral sequences (e.g., HIV env or gag genes or polypeptides). Such ancestral or COT viral sequences typically correspond to the structure of a real biological entity—the founding virus (i.e., "the viral Eve").

Formulations

Immunogenic compositions and vaccines that contain an immunogenically effective amount of one or more ancestor or COT viral protein sequences, or fragments, derivatives, or analogs thereof, are provided. Immunogenic epitopes in an ancestral or COT protein sequence can be identified according to methods known in the art, and proteins, fragments, derivatives, or analogs containing those epitopes can be delivered by various means, in a vaccine composition. Suitable compositions can include, for example, lipopeptides (e.g., Vitiello et al., *J. Clin. Invest*. 95:341 (1995)), peptide compositions encapsulated in poly(DL-lactide-co-glycolide) ("PLG") microspheres (see, e.g., Eldridge et al., *Molec. Immunol.* 28:287-94 (1991); Alonso et al., *Vaccine* 12:299-306 (1994); Jones et al., *Vaccine* 13:675-81 (1995)), peptide compositions contained in immune stimulating complexes (ISCOMS) (see, e.g., Takahashi et al., *Nature* 344:873-75 (1990); Hu et al., *Clin. Exp. Immunol*. 113:235-43 (1998)), multiple antigen peptide systems (MAPs) (see, e.g., Tam, *Proc. Natl. Acad. Sci. U.S.A*. 85:5409-13 (1988); Tam, *J. Immunol. Methods* 196:17-32 (1996)), viral delivery vectors (see, e.g., Perkus et al., In: *Concepts in vaccine development*, Kaufmann (ed.), p. 379 (1996)), particles of viral or synthetic origin (see, e.g., Kofler et al., *J. Immunol. Methods.* 192:25-35 (1996); Eldridge et al., *Sem. Hematol*. 30:16 (1993); Falo et al., *Nature Med.* 7:649 (1995)), adjuvants (see, e.g., Warren et al., *Annu. Rev. Immunol*. 4:369 (1986); Gupta et al., *Vaccine* 11:293 (1993)), liposomes (see, e.g., Reddy et al., *J. Immunol*. 148:1585 (1992); Rock, *Immunol. Today* 17:131 (1996)), or naked or particle absorbed cDNA (see, e.g., Shiver et al., In: *Concepts in vaccine development*, Kaufmann (ed.), p. 423 (1996)). Toxin-targeted delivery technologies, also known as receptor-mediated targeting, such as those of Avant Immunotherapeutics, Inc. (Needham, Mass.) can also be used.

Furthermore, useful carriers that can be used with immunogenic compositions and vaccines of the invention are well known in the art, and include, for example, thyroglobulin, albumins such as human serum albumin, tetanus toxoid, polyamino acids such as poly L-lysine, poly L-glutamic acid, influenza, hepatitis B virus core protein, and the like. The compositions and vaccines can contain a physiologically tolerable (i.e., acceptable) diluent such as water, or saline, typically phosphate buffered saline. The compositions and vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating ancestor or COT proteins (or fragments, derivative or analogs thereof) to lipids, such as tripalmitoyl-S-glycerylcysteinyl-seryl-serine ($P_3CSS$).

As disclosed in greater detail herein, upon immunization with a composition or vaccine containing an ancestor or COT viral sequence protein composition in accordance with the invention, via injection, aerosol, oral, transdermal, transmucosal, intrapleural, intrathecal, or other suitable routes, the immune system of the host responds to the composition or vaccine by producing large amounts of CTL's, HTL's and/or antibodies specific for the desired antigen. Consequently, the host typically becomes at least partially immune to later infection, or at least partially resistant to developing an ongoing chronic infection, or derives at least some therapeutic benefit.

For therapeutic or prophylactic immunization, ancestor or COT proteins (including fragments, derivatives and analogs) can also be expressed by viral or bacterial vectors. Examples of expression vectors include attenuated viral hosts, such as vaccinia or fowlpox. In one embodiment, this approach involves the use of vaccinia virus, for example, as a vector to express nucleotide sequences that encode the polypeptide. Upon introduction into an acutely or chronically infected host, or into a non-infected host, the recombinant vaccinia virus expresses the immunogenic protein, and thereby elicits a host CTL, HTL and/or antibody response. Vaccinia vectors and methods useful in immunization protocols are described in, for example, U.S. Pat. No. 4,722,848, the disclosure of which is incorporated by reference herein. A wide variety of other vectors useful for therapeutic administration or immunization of the peptides of the invention, for example, adeno and adeno-associated virus vectors, retroviral vectors, *Salmonella typhimurium* vectors, detoxified anthrax toxin vectors, Alphavirus, and the like, can also be used, as will be apparent to those skilled in the art from the description herein. Alphavirus vectors that can be used include, for example, Sindbis and Venezuelan equine encephalitis (VEE) virus. (See, e.g., Coppola et al., *J. Gen. Virol*. 76:635-41 (1995); Caley et al., *Vaccine* 17:3124-35 (1999); Loktev et al., *J. Biotechnol*. 44:129-37 (1996).)

Polynucleotides (e.g, DNA or RNA) encoding one or more ancestral or COT proteins (including fragments, derivative or analogs) can also be administered to a patient. This approach is described in, for example, Wolff et al., (*Science* 247:1465 (1990)), in U.S. Pat. Nos. 5,580,859; 5,589,466; 5,804,566; 5,739,118; 5,736,524; 5,679,647; and WO 98/04720; and in more detail below. Examples of DNA-based delivery technologies include "naked DNA", facilitated (bupivicaine, polymer, or peptide-mediated) delivery, cationic lipid complexes, particle-mediated ("gene gun"), or pressure-mediated delivery (see, e.g., U.S. Pat. No. 5,922,687).

The direct injection of naked plasmid DNA encoding a protein antigen as a means of vaccination is, among several HIV delivery and expression systems that have been developed in the last decade, one that has attracted much attention. In mouse models, as well as in large animal models, both humoral and cellular immune responses are readily induced, resulting in protective immunity against challenge infections in some instances. A Semliki Forest Virus (SFV) replicon can also be used, for example, in the context of naked DNA immunization. SFV belongs to the Alphavirus family wherein the genome consists of a single stranded RNA of positive polarity encoding its own replicase. By replacing the SFV structural genes with the gene of interest, expression levels as high as 25% of the total cell protein are obtained. Another advantage of this alphavirus over plasmid vectors is its non-persistence: the antigen of interest is expressed at high levels but for a short period (typically <72 hours). In contrast, plasmid vectors generally induce synthesis of the antigen of interest over extended time periods, risking chromosomal integration of foreign DNA and cell transformation. Furthermore, antigen persistence or repeated inoculations of small amounts of antigen has been shown experimentally to induce tolerance. Prolonged antigen synthesis, therefore, can theoretically result in unresponsiveness rather than immunity.

Ancestor or COT proteins, fragments, derivative, and analogs can also be introduced into a subject in vivo or ex vivo. For example, ancestral or COT viral sequences can be transferred into defined cell populations. Suitable methods for gene transfer include, for example:

1) Direct gene transfer. (See, e.g., Wolff et al., *Science* 247:1465-68 (1990)).

2) Liposome-mediated DNA transfer. (See, e.g, Caplen et al., *Nature Med*. 3:39-46 (1995); Crystal, *Nature Med*. 1:15-17 (1995); Gao and Huang, *Biochem. Biophys. Res. Comm*. 179:280-85 (1991).)

3) Retrovirus-mediated DNA transfer. (See, e.g., Kay et al., *Science* 262:117-19 (1993); Anderson, *Science* 256:808-13 (1992).) Retroviruses from which the retroviral plasmid vectors can be derived include lentiviruses. They further include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, Myeloproliferative Sarcoma Virus, and mammary tumor virus. In one embodiment, the retroviral plasmid vector is derived from Moloney Murine Leukemia Virus. Examples illustrating the use of retroviral vectors in gene therapy further include the following: Clowes et al. (*J. Clin. Invest*. 93:644-51 (1994)); Kiem et al. (*Blood* 83:1467-73 (1994)); Salmons and Gunzberg (*Human Gene Therapy* 4:129-41 (1993)); and Grossman and Wilson (*Curr. Opin. in Genetics and Devel.* 3:110-14 (1993)).

4) DNA Virus-mediated DNA transfer. Such DNA viruses include adenoviruses (e.g., Ad-2 or Ad-5 based vectors), herpes viruses (typically herpes simplex virus based vectors), and parvoviruses (e.g., "defective" or non-autonomous parvovirus based vectors, or adeno-associated virus based vectors, such as AAV-2 based vectors). (See, e.g., Ali et al., *Gene Therapy* 1:367-84 (1994); U.S. Pat. Nos. 4,797,368 and 5,139,941, the disclosures of which are incorporated herein by reference.) Adenoviruses have the advantage that they have a broad host range, can infect quiescent or terminally differentiated cells, such as neurons or hepatocytes, and appear essentially non-oncogenic. Adenoviruses do not appear to integrate into the host genome. Because they exist extrachromosomally, the risk of insertional mutagenesis is greatly reduced. Adeno-associated viruses exhibit similar advantages as adenoviral-based vectors. However, AAVs exhibit site-specific integration on human chromosome 19.

Kozarsky and Wilson (*Current Opinion in Genetics and Development* 3:499-503 (1993)) present a review of adenovirus-based gene therapy. Bout et al. (*Human Gene Therapy* 5:3-10 (1994)) demonstrated the use of adenovirus vectors to transfer genes to the respiratory epithelia of rhesus monkeys. Herman et al. (*Human Gene Therapy* 10:1239-49 (1999)) describe the intraprostatic injection of a replication-deficient adenovirus containing the herpes simplex thymidine kinase gene into human prostate, followed by intravenous administration of the prodrug ganciclovir in a phase I clinical trial. Other instances of the use of adenoviruses in gene therapy can be found in Rosenfeld et al. (*Science* 252:431-34 (1991)); Rosenfeld et al. (*Cell* 68:143-55 (1992)); Mastrangeli et al. (*J. Clin. Invest*. 91:225-34 (1993)); Thompson (*Oncol. Res*. 11:1-8 (1999)).

The choice of a particular vector system for transferring the ancestral or COT viral sequence of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity. However, recent developments in the field of lentiviral vectors may circumvent some of these limitations. (See Naldini et al., *Science* 272:263-67 (1996).)

The skilled artisan will appreciate that any suitable expression vector containing nucleic acid encoding an ancestor or COT protein, or fragment, derivative or analog thereof can be used in accordance with the present invention. Techniques for constructing such a vector are known. (See, e.g., Anderson, *Nature* 392:25-30 (1998); Verma, *Nature* 389:239-42 (1998).) Introduction of the vector to the target site can be accomplished using known techniques.

Figure 7:
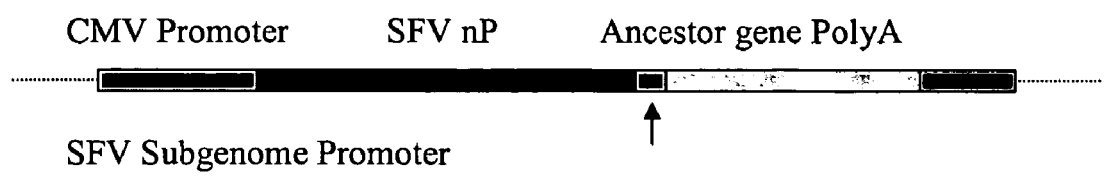

In another one embodiment, a novel expression system employing a high-efficiency DNA transfer vector (the pJW4304 SV40/EBV vector (pJW4304 SV40/EBV was prepared from pJW4303, which is described by Robinson et al., *Ann. New York Acad. Sci.* 27:209-11 (1995) and Yasutomi et al., *J. Virol*. 70:678-81 (1996)) with a very high efficiency RNA/protein expression system (the Semliki Forest Virus) is used to achieve maximal protein expression in vaccinated hosts with a safe and inexpensive vaccine. SFV cDNA is placed, for example, under the control of a cytomegalovirus (CMV) promoter (see FIG. 7). Unlike conventional DNA vectors, the CMV promoter does not directly drive the expression of the antigen encoding nucleic acids. Instead, it directs the synthesis of recombinant SFV replicon RNA transcript. Translation of this RNA molecule produces the SFV replicase complex, which catalyzes cytoplasmic self-amplification of the recombinant RNA, and eventual high-level production of the actual antigen-encoding mRNA. Following vector delivery, the transfected host cell dies within a few days. In the context of the present invention, env and/or gag genes are typically cloned into this vector. In vitro experiments using Northern blot, Western blot, SDS-PAGE, immunoprecipitation assay, and CD4 binding assays can be performed, as described infra, to determine the efficiency of this system by assessing protein expression level, protein characteristics, duration of expression, and cytopathic effects of the vector.

In some embodiments, ancestor or COT protein (or a fragment, derivative or analog thereof) is administered to a subject in need thereof. The dosage for an initial therapeutic immunization generally occurs in a unit dosage range where the lower value is about 1, 5, 50, 500, or 1,000 μg and the higher value is about 10,000; 20,000; 30,000; or 50,000 μg. Dosage values for a human typically range from about 500 μg to about 50,000 μg per 70 kilogram patient. Boosting dosages of between about 1.0 μg to about 50,000 μg of polypeptide pursuant to a boosting regimen over weeks to months can be administered depending upon the patient's response and condition as determined by measuring the antibody levels or specific activity of CTL and HTL obtained from the patient's blood.

A human unit dose form of the protein or nucleic acid composition is typically included in a pharmaceutical composition that comprises a human unit dose of an acceptable carrier, typically an aqueous carrier, and is administered in a volume of fluid that is known by those of skill in the art to be used for administration of such compositions to humans (see, e.g., Remington "*Pharmaceutical Sciences*", 17 Ed., Gennaro (ed.), Mack Publishing Co., Easton, Pa. (1985)).

The ancestor or COT proteins and nucleic acids can also be administered via liposomes, which serve to target the peptides to a particular tissue, such as lymphoid tissue, or to target selectively to infected cells, as well as to increase the half-life of the composition. Liposomes include emulsions, foams, micelles, insoluble monolayers, liquid crystals, phospholipid dispersions, lamellar layers and the like. In these preparations, the protein or nucleic acid to be delivered is incorporated as part of a liposome, alone or in conjunction with a molecule that binds to a receptor prevalent among lymphoid cells, such as monoclonal antibodies that bind to the CD45 antigen, or with other therapeutic or immunogenic compositions. Thus, liposomes either filled or decorated with a desired protein or nucleic acid can be directed to the site of lymphoid cells, where the liposomes then deliver the protein compositions to the cells. Liposomes for use in accordance with the invention are formed from standard vesicle-forming lipids, which generally include neutral and negatively charged phospholipids and a sterol, such as cholesterol. The selection of lipids is generally guided by consideration of, for example, liposome size, acid lability and stability of the liposomes in the blood stream. A variety of methods are available for preparing liposomes, as described in, for example, Szoka et al., *Ann. Rev. Biophys. Bioeng.* 9:467 (1980), and U.S. Pat. Nos. 4,235,871; 4,501,728; 4,837,028; and 5,019,369.

For targeting cells of the immune system, a ligand to be incorporated into the liposome can include, for example, antibodies or fragments thereof specific for cell surface determinants of the desired immune system cells. A liposome suspension containing a protein or nucleic acid can be administered, for example, intravenously, locally, topically, etc., in a dose which varies according to, inter alia, the manner of administration, the protein or nucleic acid being delivered, and the like.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, the ancestor or COT proteins or nucleic acids, and typically at a concentration of 25%-75%.

For aerosol administration, the immunogenic proteins or nucleic acids are typically in finely divided form along with a surfactant and propellant. Suitable percentages of peptides are about 0.01% to about 20% by weight, typically about 1% to about 10%. The surfactant is, of course, nontoxic, and typically soluble in the propellant. Representative of such agents are the esters or partial esters of fatty acids containing from 6 to 22 carbon atoms, such as caproic, octanoic, lauric, palmitic, stearic, linoleic, linolenic, stearic and oleic acids with an aliphatic polyhydric alcohol or its cyclic anhydride. Mixed esters, such as mixed or natural glycerides can be employed. The surfactant can constitute about 0.1% to about 20% by weight of the composition, typically 0.25-5%. The balance of the composition is ordinarily propellant. A carrier can also be included, as desired, as with, for example, lecithin for intranasal delivery.

Immune Responses Elicited by the Ancestral or COT Viral Sequences

Ancestor or COT proteins (including fragments, derivative and analogs) can be used as a vaccine, as described supra. Such vaccines, referred to as a "digital vaccine", are typically screened for those that elicit neutralizing antibody and/or viral (e.g., HIV) specific CTLs against a larger fraction of circulating strains than a vaccine comprising a protein antigen encoded by any sequences of existing viruses or by consensus sequences. Such a digital vaccine will typically provide protection when challenged by the same subtype of virus (e.g., HIV-1 virus) as the subtype from which the ancestral or COT viral sequence was derived.

The invention also provides methods to analyze the function of ancestral or COT viral gene sequences. For example, in one embodiment, the gp160 ancestor or COT viral gene sequence is analyzed by assays for functions, such as, for example, CD4 binding, co-receptor binding, receptor specificity (e.g., binding to the CCR5 receptor), protein structure, and the ability to cause cell fusion. Although the ancestor or COT sequences can result in a viable virus, such a viable virus is not necessary for obtaining a successful vaccine. For example, a gp160 ancestor or COT not correctly folded can be more immunogenic by exposing epitopes that are normally buried to the immune system. Further, although the ancestor or COT viral sequence can be successfully used as a vaccine, such a sequence need not include alternate open reading frames that encode proteins such a tat or rev, when used as an immunogen (e.g., a vaccine).

Accordingly, in one aspect, mice are immunized with an ancestor or COT protein and tested for humoral and cellular immune responses. Typically, 5-10 mice are intradermally or intramuscularly injected with a plasmid containing a gag and/or env gene encoding an ancestral or COT viral sequence in, for example, 50 µl volume. Two control groups are typically used to interpret the results. One control group is injected with the same vector containing the gag or env gene from a standard laboratory strain (e.g., HIV-1-IIIB). A second control group is injected with same vector without any insert. Antibody titration against gag or env protein is performed using standard immunoassays (e.g., ELISA), as described infra. The neutralizing antibody is analyzed by subtype-specific laboratory HIV-1 strains, such as for example pNL4-3 (HIV-1-IIIB), as well as primary isolates from HIV-1 infected individuals. The ability of an ancestor or COT viral sequence protein-elicited neutralizing antibody to neutralize a broad primary isolates is one factor indicative of an immunogenic or vaccine composition. Similar studies can be performed in large animals, such as non-human animals (e.g, macques) or in humans.

Immunoassays for Titrating the Ancestor or COT Protein-Elicited Antibodies

There are a variety of assays known to those of ordinary skill in the art for detecting antibodies in a sample (see, e.g., Harlow and Lane, supra). In general, the presence or absence of antibodies in a subject immunized with an ancestor or COT protein vaccine can be determined by (a) contacting a biological sample obtained from the immunized subject with one or more ancestor or COT proteins (including fragments, derivatives or analogs thereof); (b) detecting in the sample a level of antibody that binds to the ancestor or COT protein(s); and (c) comparing the level of antibody with a predetermined cut-off value.

In a typical embodiment, the assay involves the use of an ancestor or COT protein (including fragment, derivative or analog) immobilized on a solid support to bind to and remove the antibody from the sample. The bound antibody can then be detected using a detection reagent that contains a reporter group. Suitable detection reagents include antibodies that bind to the antibody/ancestor or COT protein complex and free protein labeled with a reporter group (e.g., in a semi-competitive assay). Alternatively, a competitive assay can be utilized, in which an antibody that binds to the ancestor or COT protein of interest is labeled with a reporter group and allowed to bind to the immobilized antigen after incubation of the antigen with the sample. The extent to which components of the sample inhibit the binding of the labeled antibody to the ancestor or COT protein of interest is indicative of the reactivity of the sample with the immobilized ancestor or COT protein.

The solid support can be any solid material known to those of ordinary skill in the art to which the antigen may be attached. For example, the solid support can be a test well in a microtiter plate or a nitrocellulose or other suitable membrane. Alternatively, the support can be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681, the disclosure of which is incorporated by reference herein.

The ancestor or COT proteins can be bound to the solid support using a variety of techniques known to those of ordinary skill in the art, which are amply described in the patent and scientific literature. In the context of the present invention, the term "bound" refers to both non-covalent association, such as adsorption, and covalent attachment (see, e.g., Pierce *Immunotechnology Catalog and Handbook*, at A12-A13 (1991)).

In certain embodiments, the assay is an enzyme-linked immunosorbent assay (ELISA). This assay can be performed by first contacting an ancestor or COT protein that has been immobilized on a solid support, commonly the well of a microtiter plate, with the sample, such that antibodies present within the sample that recognize the ancestor or COT protein of interest are allowed to bind to the immobilized protein. Unbound sample is then removed from the immobilized ancestor or COT protein and a detection reagent capable of binding to the immobilized antibody-protein complex is added. The amount of detection reagent that remains bound to the solid support is then determined using a method appropriate for the specific detection reagent.

More specifically, once the ancestor or COT protein is immobilized on the support as described above, the remaining protein binding sites on the support are typically blocked. Any suitable blocking agent known to those of ordinary skill in the art, such as bovine serum albumin or Tween 2O (Sigma Chemical Co., St. Louis, Mo.), can be employed. The immobilized ancestor or COT protein is then incubated with the sample, and the antibody is allowed to bind to the protein. The sample can be diluted with a suitable diluent, such as phosphate-buffered saline (PBS) prior to incubation. In general, an appropriate contact time (i.e., incubation time) is a period of time that is sufficient to detect the presence of antibody within a biological sample of an immunized subject. Those of ordinary skill in the art will recognize that the time necessary to achieve equilibrium can be readily determined by assaying the level of binding that occurs over a period of time. At room temperature, an incubation time of about 30 minutes is generally sufficient.

Unbound sample can then be removed by washing the solid support with an appropriate buffer, such as PBS containing 0.1% Tween 20. Detection reagent can then be added to the solid support. An appropriate detection reagent is any compound that binds to the immobilized antibody-protein complex and that can be detected by any of a variety of means known to those in the art. Typically, the detection reagent contains a binding agent (such as, for example, Protein A, Protein G, immunoglobulin, lectin or free antigen) conjugated to a reporter group. Suitable reporter groups include enzymes (such as horseradish peroxidase or alkaline phosphatase), substrates, cofactors, inhibitors, dyes, radionuclides, luminescent groups, fluorescent groups, and biotin. The conjugation of a binding agent to the reporter group can be achieved using standard methods known to those of ordinary skill in the art. Common binding agents, pre-conjugated to a variety of reporter groups, can be purchased from many commercial sources (e.g., Zymed Laboratories, San Francisco, Calif., and Pierce, Rockford, Ill.).

The detection reagent is then incubated with the immobilized antibody-protein complex for an amount of time sufficient to detect the bound antibody. An appropriate amount of time can generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods can be used to detect dyes, luminescent groups and fluorescent groups. Biotin can be detected using avidin, coupled to a different reporter group (commonly a radioactive or fluorescent group or an enzyme). Enzyme reporter groups can generally be detected by the addition of substrate (generally for a specific period of time), followed by spectroscopic or other analysis of the reaction products.

To determine the presence or absence of anti-ancestor or COT protein antibodies in the sample, the signal detected from the reporter group that remains bound to the solid support is generally compared to a signal that corresponds to a predetermined cut-off value. In one embodiment, the cut-off value is the average mean signal obtained when the immobilized ancestor or COT protein is incubated with samples from non-immunized subject.

In a related embodiment, the assay is performed in a rapid flow-through or strip test format, wherein the ancestor or COT protein is immobilized on a membrane, such as, for example, nitrocellulose, nylon, PVDF, and the like. In the flow-through test, antibodies within the sample bind to the immobilized polypeptide as the sample passes through the membrane. A detection reagent (e.g., protein A-colloidal gold) then binds to the antibody-protein complex as the solution containing the detection reagent flows through the membrane. The detection of bound detection reagent can then be performed as described above. In the strip test format, one end of the membrane to which the ancestor or COT protein is bound is immersed in a solution containing the sample. The sample migrates along the membrane through a region containing the detection reagent and to the area of immobilized ancestor or COT protein. The concentration of the detection reagent at the protein indicates the presence of anti-ancestor or COT protein antibodies in the sample. Typically, the concentration of detection reagent at that site generates a pattern, such as a line, that can be read visually. The absence of such a pattern indicates a negative result. In general, the amount of protein immobilized on the membrane is selected to generate a visually discernible pattern when the biological sample contains a level of antibodies that would be sufficient to generate a positive signal (e.g., in an ELISA) as discussed supra. Typically, the amount of protein immobilized on the membrane ranges from about 25 ng to about 1 µg, and more typically from about 50 ng to about 500 ng. Such tests can typically be performed with a very small amount (e.g., one drop) of subject serum or blood.

Cytotoxic T-Lymphocyte Assay

Another factor in treating HIV-1 infection is the cellular immune response, in particular the cellular immune response involving the $CD8^+$ cytotoxic T lymphocytes (CTL's). A cytotoxic T lymphocyte assay can be used to monitor the cellular immune response following sub-genomic immunization with an ancestral or COT viral sequence against homologous and heterologous HIV strains, as above using standard methods (see, e.g., Burke et al., supra; Tigges et al., supra).

Conventional assays utilized to detect T cell responses include, for example, proliferation assays, lymphokine secretion assays, direct cytotoxicity assays, limiting dilution assays, and the like. For example, antigen-presenting cells that have been incubated with an ancestor or COT protein can be assayed for the ability to induce CTL responses in responder cell populations. Antigen-presenting cells can be cells such as peripheral blood mononuclear cells or dendritic cells. Alternatively, mutant non-human mammalian cell lines that are deficient in their ability to load class I molecules with internally processed peptides and that have been transfected with the appropriate human class I gene, can be used to test the capacity of an ancestor or COT peptide of interest to induce in vitro primary CTL responses.

Peripheral blood mononuclear cells (PBMCs) can be used as the responder cell source of CTL precursors. The appropriate antigen-presenting cells are incubated with the ancestor or COT protein, after which the protein-loaded antigen-presenting cells are incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

Another suitable method allows direct quantification of antigen-specific T cells by staining with Fluorescein-labeled HLA tetrameric complexes (Altman et al., *Proc. Natl. Acad. Sci. USA* 90:10330 (1993); Altman et al., *Science* 274:94 (1996)). Other relatively recent technical developments include staining for intracellular lymphokines, and interferon release assays or ELISPOT assays. Tetramer staining, intracellular lymphokine staining and ELISPOT assays are typically at least 10-fold more sensitive than more conventional assays (Lalvani et al., *J. Exp. Med.* 186:859 (1997); Dunbar et al., *Curr. Biol.* 8:413 (1998); Murali-Krishna et al., *Immunity* 8:177 (1998)).

Diagnosis

The present invention also provides methods for diagnosing viral (e.g., HIV) infection and/or AIDS, using the ancestor or COT viral sequences described herein. Diagnosing viral (e.g., HIV) infection and/or AIDS can be carried out using a variety of standard methods well known to those of skill in the art. Such methods include, but are not limited to, immunoassays, as described supra, and recombinant DNA methods to detect the presence of nucleic acid sequences. The presence of a viral gene sequence can be detected, for example, by Polymerase Chain Reaction (PCR) using specific primers designed using the sequence, or a portion thereof, set forth in Tables 1 or 3, using standard techniques (see, e.g. Innis et al., *PCR Protocols A Guide to Methods and Application* (1990); U.S. Pat. Nos. 4,683,202; 4,683,195; and 4,889,818; Gyllensten et al., *Proc. Natl. Acad. Sci. USA* 85:7652-56 (1988); Ochman et al., *Genetics* 120:621-23 (1988); Loh et al., *Science* 243:217-20 (1989)). Alternatively, a viral gene sequence can be detected in a biological sample using hybridization methods with a nucleic acid probe having at least 70% identity to the sequence set forth in Tables 1 or 3, according to methods well known to those of skill in the art (see, e.g., Sambrook et al., supra).

EXAMPLES

Example 1

Determination of Ancestral Viral Sequences

Sequences representing genes of a HIV-1 subtype C were selected from the GenBank and Los Alamos sequence databases. 39 subtype C sequences were used. 18 outgroup sequences (two from each of the other group M subtypes (FIG. 8) were used as an outgroup to root the subtype C sequences. The sequences were aligned using CLUSTALW (Thompson et al., *Nucleic Acids Res.* 22:4673-80 (1994)), the alignments were refined using GDE (Smith et al., *CABIOS* 10:671-5 (1994)), and amino acid sequences translated from them. Gaps were manipulated so that they were inserted between codons. This alignment (alignment I) was modified for phylogenetic analysis so that regions that could not be unambiguously aligned were removed (Learn et al., *J. Virol.* 70:5720-30 (1996)) resulting in alignment II.

An appropriate evolutionary model for phylogeny and ancestral state reconstructions for these sequences (alignment II) was selected using the Akaike Information Criterion (AIC) (Akaike, *IEEE Trans. Autom. Contr.* 19:716-23 (1974)) as implemented in Modeltest 3.0 (Posada and Crandall, Bioinformatics 14: 817-8 (1998)). For the analysis for the subtype C ancestral sequence the optimal model is equal rates for both classes of transitions and different rates for all four classes of transversions, with invariable sites and a X distribution of site-to-site rate variability of variable sites (referred to as a TVM+I+G model). The parameters of the model in this case were: equilibrium nucleotide frequencies: $f_A$=0.3576, $f_C$=0.1829, $f_G$=0.2314, $f_T$=0.2290; proportion of invariable sites=0.2447; shape parameter ($\alpha$) of the X distribution=0.7623; rate matrix (R) matrix values: $R_{A \rightarrow C}$=1.7502, $R_{A \rightarrow G}$=$R_{C \rightarrow T}$=4.1332, $R_{A \rightarrow T}$=0.6825, $R_{C \rightarrow G}$=0.6549, $R_{G \rightarrow T}$=1.

Evolutionary trees for the sequences (alignment II) were inferred using maximum likelihood estimation (MLE) methods as implemented in PAUP* version 4.0b (Swofford, PAUP 4.0: Phylogenetic Analysis Using Parsimony (And Other Methods). Sinauer Associates, Inc. (2000)). Specifically for the subtype C sequences, ten different subtree-pruning-regrafting (SPR) heuristic searches were performed each using a different random addition order. All ten searches found the same MLE phylogeny (LnL=−33585.74). The ancestral nucleotide sequence for subtype C was inferred to be the sequence at the basal node of this subtype using this phylogeny, the sequences from the databases (alignment II), and the TVM+I+G model above using marginal likelihood estimation (see below).

This inferred sequence does not include predicted ancestral sequence for portions of several variable regions (V1, V2, V4 and V5) and four additional short regions that could not be unambiguously aligned (these eight regions were removed from alignment I to produce alignment II). The following procedure was used to predict amino acid sequences for the complete gp160 including the highly variable regions. The inferred ancestral sequence was visually aligned to alignment I and translated using GDE (Smith et al., supra). Since the highly variable regions were deleted as complete codons, the translation was in the correct reading frame and codons were properly maintained. The ancestral amino acid sequence for the regions deleted from alignment II were predicted visually and refined using a parsimony-based sequence reconstruction for these sites using the computer program MacClade, version 3.08a (Maddison and Maddison. MacClade—Analysis of Phylogeny and Character Evolution—Version 3. Sinauer Associates, Inc. (1992)). This amino acid sequences was converted to DNA sequence optimized for expression in human cells using the BACKTRANSLATE program of the Wisconsin Sequence Analysis Package (GCG), version 10 and a human gene codon table from the Codon Usage Database (www.kazusa.or.jp/codon/cgi-bin/showcodon.cgi?species=Homo+sapiens+[gbpri]).

Example 2

Different methods are available to determine the maximum likelihood phylogeny for a given subtype. One such method is based on the coalescent theory, which is a mathematical description of the genealogy of a sample of gene sequences drawn from a large evolving population. Coalescence analysis takes into account the HIV population in vivo and in the larger epidemic and offers a way of understanding how sampled genealogies behave when different processes operate on the HIV population. This theory can be used to determine the sequence of the ancestral viral sequence, such as a founder, or MRCA. Exponentially growing populations have decreasing coalescent intervals going back in time, while the converse is true for a declining population.

Epidemics in the USA and Thailand are growing exponentially. The coalescent dates for subtype B epidemics in the USA and Thailand are in accordance with the epidemiologic data. The coalescent date for subtype E epidemic in Thailand is earlier than predicted from the epidemiologic data. Potential reasons that can account for this discrepancy include, for example, the existence of multiple introductions of HIV-1 (there is no evidence from phylogenetics on this point), the absence of HIV-1 detection in Thailand for about 7 years, and the difference in the mutation rates for env gene in the HIV-1 subtypes E and B.

The Unit of Reconstruction

This unit of reconstruction relates to the ancestral viral sequence (i.e., state) state that is reconstructed. There are three possible units of reconstruction: nucleotides, amino acids or codons. In one embodiment, the states of the individual nucleotides are reconstructed and the amino acid sequences are then determined on the basis of this reconstruction. In another embodiment, the amino acid ancestral states are directly reconstructed. In a typical embodiment, the codons are reconstructed using a likelihood-based procedure that uses a codon model of evolution. A codon model of evolution takes into account the frequencies of the codons and implicitly the probability of substituting one nucleotide for another—in other words, it incorporates both nucleotide and amino acid substitutions in a single model. Computer programs capable of doing this are available or can readily be developed, as will be appreciated by the skilled artisan.

Use of Marginal or Joint Likelihoods for Estimating the Ancestral States

The ancestral state can be estimated using either a marginal or a joint likelihood. The marginal and joint likelihoods differ on the basis of how ancestral states at other nodes in the phylogenetic tree estimated. For any particular tree, the probability that the ancestral state of a given site on a sequence alignment at the root is, for example, an A can be determined in different ways.

The likelihood that the nucleotide is an adenine (A) can be determined regardless of whether higher nodes (i.e., those nodes closer to the ancestral viral sequence, founder or MRCA) have an adenine, cytosine (C), guanine(G), or thymine (T). This is the marginal likelihood of the ancestral state being A.

Alternatively, the likelihood that the nucleotide is an A can be determined depending on whether the nodes above are A, C, G, or T. This estimation is the joint likelihood of A with all the other ancestral reconstructions for that site.

The joint likelihood is a preferred method when all the ancestral states along the entire tree need to be determined. To establish the most likely states at one given node, the marginal likelihood is preferably used. In case of uncertainty at a particular site, a likelihood estimate of the ancestral state allows testing whether one state is statistically better than another. If two possible ancestral states do not have statistically different likelihoods, or if one ends up with multiple states over a number of sites building all possible sequences is not desirable. The likelihoods of all combinations can however be computed and ranked, and only those above a certain critical value are used. For example, when two sites on a sequence, each with different likelihoods for A, C, G, T, are considered:

L(A) L(C) L(G) L(T)* * L represents the -lnL (the negative log-likelihood); therefore, the smaller the more likely.

Site 1 3 2 1.5 1
Site 2 10 7 5 1 there are 16 possible sequence configurations, each with its own log-likelihood, that is simply the sum of the log-likelihoods for each base, which are:

| AA 13 | CA 12 | GA 11.5 | TA 11 |
|---|---|---|---|
| AC 10 | CC 9 | GC 8.5 | TC 8 |
| AG 8 | CG 7 | GG 6.5 | TG 6 |
| AT 4 | CT 3 | GT 2.5 | TT 2 |

In order of likelihood the ranking is:

TT, GT, CT, AT, TG, GG, CG, AG,

TC, GC, CC, AC, TA, GA, CA, AA

The first four sequences have T at the second site. This results from the likelihood at that site being spread over a large range, resulting into a very low probability of having any nucleotide other than T at this site. At Site 1, however, any nucleotide tends to give quite similar likelihoods. This kind of ranking is one way of whittling down the number of possible sequences to look at if variation is to be taken into account.

The above variation in reconstructed ancestral states deals with variation that comes about because of the stochastic nature of the evolutionary process, and because of the probabilistic models of that process that are typically used. Another source of variation results from the sampling of sequences. One way of testing how sampling affects ancestral state reconstruction is to perform jackknife re-sampling on an existing data set. This involves deleting randomly without replacement of some portion (e.g., half) of the sequences, and reconstructing the ancestral state. Alternatively, the ancestral state can be estimated for each of a set of bootstrap trees, and the number of times a particular nucleotide was estimated can be reported as the ancestral state for a given site. The bootstrap trees are generated using bootstrapped data, but the ancestral state reconstructions use the bootstrap trees on the original data.

Different models of evolution can be used to reconstruct the ancestral states for the root node. Examples of models are known and can be chosen on a multitude of levels. For example, a model of evolution can be chosen by some heuristic means or by picking one that gives the highest likelihood for the ancestral sequence (obtained by summing the likelihoods over all sites). Alternatively the ancestral states are reconstructed at each site over all models of evolution, all of the likelihoods obtained summed, and the ancestral state chosen that has the maximum likelihood.

Example 3

The conservation of HIV-1 subtype C CTL amino acid consensus epitopes was analyzed. The total number of epitopes was 395. The table below summarize the results of the similarly of each circulating viral sequence to the C subtype CTL consensus sequence. The determined ancestor viral sequence for the HIV-1 subtype C env protein (SEQ ID NO:4) has the highest score (98.48%). Note that the scores for several strains are below 65%, because truncated sequences were used.

| Sequence Name | Total AA number | Percentage CTL to Consensus |
|---|---|---|
| cCanc95-mod1 | 389 | 98.48% |
| cBR.92BR025 | 376 | 95.19% |
| cBI.BU910717 | 363 | 91.90% |
| cIN.21068 | 368 | 93.16% |
| cIN.301905 | 370 | 93.67% |
| cMW959.U08453 | 358 | 90.63% |
| cBW.96BW1210 | 365 | 92.41% |
| cBI.BU910316 | 367 | 92.91% |
| cZAM176.U86778 | 352 | 89.11% |
| cMW965.U08455 | 364 | 92.15% |
| cZAM174.16.U86768 | 351 | 88.86% |
| c84ZR085.U88822 | 322 | 81.52% |
| cSN.SE364A | 370 | 93.67% |
| cMW960.U08454 | 365 | 92.41% |
| cBI.BU910812 | 368 | 93.16% |
| cET.ETH2220 | 358 | 90.63% |
| cBI.BU910518 | 361 | 91.39% |
| cIN.94IN11246 | 361 | 91.39% |
| cBW.96BW15B03 | 359 | 90.89% |
| cDJ.DJ259A | 355 | 89.87% |
| cBI.BU910213 | 365 | 92.41% |
| cBW.96BW01B03 | 362 | 91.65% |
| cIND760.L07655 | 255 | 64.56% |
| cIN.301904 | 372 | 94.18% |
| cSO.SM145A | 354 | 89.62% |
| cCHN19.AF268277 | 356 | 90.13% |
| cIND747.L07653 | 255 | 64.56% |
| cBW.96BW0402 | 364 | 92.15% |
| cBI.BU910611 | 367 | 92.91% |
| cBI.BU910423 | 359 | 90.89% |
| cBW.96BW17B05 | 355 | 89.87% |
| cBW.96BW0502 | 367 | 92.91% |
| cUG.UG268A2 | 372 | 94.18% |
| cZAM18.L22954 | 365 | 92.41% |
| cIN.301999 | 368 | 93.16% |
| c91BR15.U39238 | 371 | 93.92% |
| cDJ.DJ373A | 361 | 91.39% |
| cBI.BU910112 | 369 | 93.42% |
| c93IN101.AB023804 | 365 | 92.41% |
| cBW.96BW16B01 | 361 | 91.39% |
| cBW.96BW11B01 | 361 | 91.39% |
| cINdiananc66 | 363 | 91.90% |

Example 4

Figure 3:
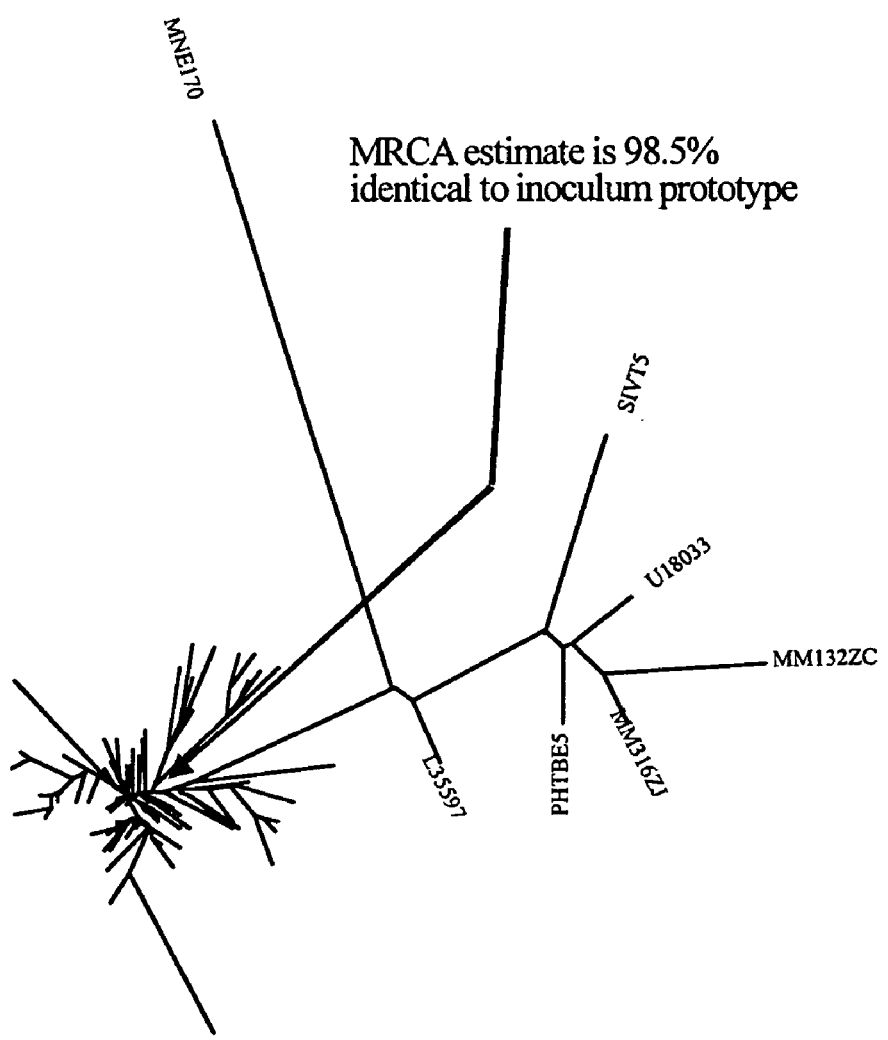

Ancestor sequence reconstruction was performed on simian immunodeficiency viruses grown in macaques. Macaques were infected and challenged with a relatively homogeneous SIV inoculum. Viral sequences were obtained up to three years following infection and were used to deduce an MRCA using maximum likelihood phylogeny analysis. The resulting sequence was compared to the consensus sequence of the inoculum. The MRCA sequence was found to be 97.4% identical to the virus inoculum. This figure improved to 98.2% when convergence at 5 glycosylation sites was removed—this convergence was due to readaptation of the virus from tissue culture to growth in the animal (Edmonson et al., J. Virol. 72:405-14 (1998)). The MRCA sequence and the consensus sequence were found to differ at 1.5% at the nucleotide level. FIG. 3 illustrates the determination of simian immunodeficiency virus MRCA phylogeny.

Example 5

An experiment to test the biological activity of the HIV-1 subtype B ancestral viral env gene sequence was performed. A nucleic acid sequence encoding the HIV-1 subtype B ancestral viral env gene sequence was assembled from long (160-200 base) oligonucleotides; the assembled gene was designated ANC1. The biological activity of ANC1 HIV-1-B Env was evaluated in co-receptor binding and syncytium formation assays. The plasmid pANC1, harboring the determined and chemically synthesized HIV-1 subtype B Ancestor gp160 Env sequence, or a positive control plasmid containing the HIV-1 subtype B 89.6 gp160 Env, was transfected into COS7 cells. These cells are capable of taking up and expressing foreign DNA at high efficiencies and thus are routinely used to produce viral proteins for presentation to other cells. The transfected COS7 cells were then mixed with GHOST cells expressing either one of the two major HIV-1 co-receptor proteins, CCR5 or CXCR4. CCR5 is the predominant receptor used by HIV early in infection. CXCR4 is used later in infection, and use of the latter receptor is temporally associated with the development of disease. The COS7-GHOST-co-receptor+ cells were then monitored for giant cell formation by light microscopy and for expression of viral Env protein by HIV-Env-specific antibody staining and fluorescence detection.

Cells expressing the ANC1 Env were shown to be expressed by virtue of binding to HIV-specific antibody and fluorescent detection, and to cause the formation of giant multinucleated cells in the presence of the CCR5 co-receptor, but not the CXCR4 co-receptor. The positive control 89.6 Env uses both CCR5 and CXCR4 and formed syncytia with cells expressing either co-receptor. Thus, the ANC1 Env protein was shown to be biologically active by co-receptor binding and syncytium formation.

Example 6

Maximum likelihood phylogeny reconstruction differs from traditional consensus sequence determinations because a consensus sequence represents a sequence of the most common nucleotide or amino acid residue at each site in the sequence. Thus, a consensus sequence is subject to biased sampling. In particular, the determination of a consensus sequence can be biased if many samples have the same sequence. In addition, the consensus sequence is a real viral sequence.

In contrast, maximum likelihood phylogeny analysis is less likely to be affected by biased sample because it does not determine the sequence of a most recent common ancestor based solely on the frequencies of the each nucleotide at each position. The determined ancestral viral sequence is an estimate of a real virus, the virus that is the common ancestor of the sampled circulating viruses.

In the simplest of methods for determining an ancestral sequence, for a single site on a sequence alignment nucleotides are assigned to ancestral nodes such that the total number of changes between nodes is minimized; this approach is called a "most parsimonious reconstruction." An alternative methodology, based on the principle of maximum likelihood, assigns nucleotides at the nodes such that the probability of obtaining the observed sequences, given a phylogeny, is maximized. The phylogeny is constructed by using a model of evolution that specifies the probabilities of nucleotide substitutions. The maximum likelihood phylogeny is the one that has the highest probability of giving the observed data.

Referring to FIG. 5, a comparison is presented of parsimony methodology and maximum likelihood methodology of determining an ancestral viral sequence (e.g., a founder sequence or a most recent common ancestor sequence (MRCA)). The most parsimonious reconstruction ("MP") can have the undesirable problem of creating an ambiguous state at the ancestral branch point (i.e., node). In this example, the two descendant sequences from this node have an adenine (A) or guanine (G) at a particular position in the sequence. The most parsimonious reconstruction ("MP Reconstruction") for the ancestral sequence at this site is ambiguous, because there can be either an A or G (symbolized by "R") at this position. In contrast, a maximum likelihood phylogeny analysis applies knowledge about sequence evolution. For example, likelihood analysis relies, in part, on the identity of nucleotides at the same position in other variants. Thus, in this example, a G to A mutation is more likely than an A to G change because variant at the adjacent node also has a G at the same position.

Figure 6:
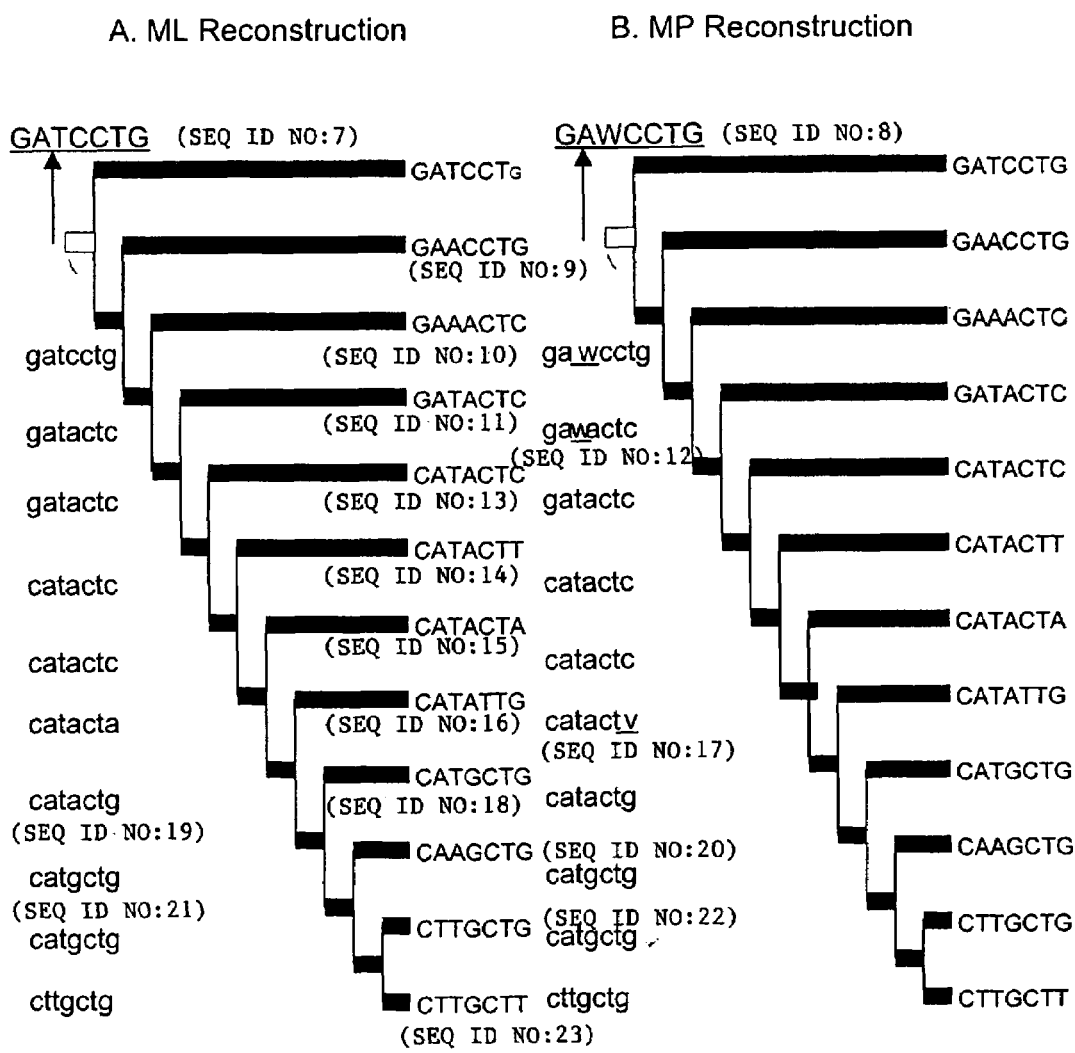

Referring to FIG. 6, another example illustrates the differences in these methodologies to determine a most recent common ancestor. In this example, twelve sequences of seven nucleotides are presented. These sequences share the illustrated evolutionary history. A consensus sequence calculated from these sequences is CATACTG (SEQ ID NO: 19). In panel A, the maximum likelihood reconstruction of the determined ancestral node is shown as GATCCTG (SEQ ID NO: 7). Other determined sequences are presented adjacent the other internal nodes. In panel B, the most parsimonious reconstruction at the same nodes is presented. As shown, the most parsimonious reconstruction predicts the consensus sequence GAWCCTG (SEQ ID NO: 8), where "W" symbolizes that either an A or T is equally possible to be at the third position. Similarly other most parsimonious reconstructions are shown at the various internal nodes. At the seventh internal node, the last nucleotide is indicated with the symbol "V" representing that an A, C or G might be present. Also note in this example, the consensus sequence differs in at least two sites (the $1^{st}$ and $4^{th}$ positions) from either the maximum likelihood- or parsimony-determined sequence for the MRCA.

Example 7

MRCA and COT state reconstructions were performed. Complete HIV-1 genome sequences were obtained from the Los Alamos National Laboratory HIV Sequence database or from research done in support of the HIV Vaccine Trials Network (HVTN) in the Mullins laboratory (HVTN1925c1.US98, HVTN3605c9.US98, HVTN8229c6.US98, and HVTN941c16.US98). Each sequence set, subtype B (Table 7) and subtype C (Table 9), was aligned using CLUSTALW (Thompson, 1994 #6159). Resulting alignments were examined and adjusted using amino acid alignments as guides with MacClade version 4 (Maddison, 2001 #13641). Alignment gaps were inserted between adjacent codons. Regions that could not be unambiguously aligned were omitted from the following phylogenetic analyses but included in the ancestral state reconstructions (see below). The complete genome alignments were partitioned into 9 gene coding regions (gag, env (encoding gp160), nef, pol, rev, tat, vif, vpr, and vpu); tat and rev exon sequences were spliced together after the intervening intron sequence was removed to produce a single continuous protein coding region.

Parameter values of optimal evolutionary models for each of these nucleotide alignments, except for subtype C env and gag, were estimated using MODELTEST (Posada, 1998 #10104) in conjunction with PAUP* (Swofford, 1999 #9501) based on the Akaike Information Criterion (Akaike, 1974 #10404). For subtype C env and gag, PAUP* was used to estimate HKY parameter values (Hasegawa, 1985 #9867) based on a neighbor-joining (Saitou, 1987 #5332) phylogenetic tree. Evolutionary model parameter values are presented for the subtype B genes (Table 8) and the subtype C genes (Table 10). These values were used for maximum-likelihood phylogenetic analyses using PAUP* (Swofford, 1999 #9501). For all genes except subtype C env and gag, 10 random-addition subtree-pruning-regrafting iterations were done. For subtype C env and gag, a single iteration based on a neighbor-joining starting trees were used.

After phylogenetic trees were obtained, the regions of ambiguous alignment that were removed (see above) were included in their original positions in the alignments. For the MRCA estimation, the sequence states at the ancestral node (the point at which the subtype D sequences attach to the portion of the tree that solely included subtype B sequences) were derived using marginal maximum-likelihood estimation with PAUP* {Swofford, 1999 #9501}. The MRCA protein sequence is the translation of the MRCA nucleotide sequence. For the COT state reconstructions, the outgroup sequences (subtype D sequences in Table 7; subtype other than C in Table 9) were pruned from the phylogenetic tree for each gene using PAUP* (Swofford, 1999 #9501). The remaining gene trees were analyzed using perl computer programs to determine the point at the center of the phylogenetic tree via the Minimum of Means, and Least-Squares Method. Evolutionary states at this point for each method for each gene tree were then estimated using marginal state estimation using PAUP* (Swofford, 1999 #9501).

TABLE 7

Sequence Names, GenBank Accession Numbers and Country of Isolation for the sequences used in the complete genome MRCA and COT estimation of subtype B.

| Sequence | Accession number | Country | Subtype[§] |
|---|---|---|---|
| 1WK.KR97 | AF224507 | Korea | B |
| 3202A21.NL86 | U34604 | Netherlands | B |
| 89SP061.ES89 | AJ006287 | Spain | B |
| AD8.US86 | AF004394 | U.S.A. | B |
| ARCH054.AR98 | AY037268 | Argentina | B |
| ARMA173.AR99 | AY037274 | Argentina | B |
| ARMS008.AR00 | AY037269 | Argentina | B |
| BK132.TH90 | AY173951 | Thailand | B |
| BOL122.BO99 | AY037270 | Bolivia | B |
| BZ167.BR89 | AY173956 | Brazil | B |
| CAM1.GB83 | D10112 | United Kingdom | B |
| D31.DE86 | U43096 | Germany | B |
| DH123.US91 | AF069140 | U.S.A. | B |
| HAN.DE86 | U43141 | Germany | B |
| HVTN1925c1.US98 | * | U.S.A. | B |
| HVTN3605c9.US98 | * | U.S.A. | B |
| HVTN8229c6.US98 | * | U.S.A. | B |
| HVTN941c16.US98 | * | U.S.A. | B |
| HXB2.FR83 | K03455 | France | B |
| JRCSF.US86 | M38429 | U.S.A. | B |
| MBC200.AU86 | AF042100 | Australia | B |
| MBC925.AU87 | AF042101 | Australia | B |
| MBCC18B.AU93 | AF042102 | Australia | B |
| MBCC98.AU96 | AF042104 | Australia | B |

TABLE 7-continued

Sequence Names, GenBank Accession Numbers and Country of Isolation for the sequences used in the complete genome MRCA and COT estimation of subtype B.

| Sequence | Accession number | Country | Subtype§ |
|---|---|---|---|
| MBCD36.AU96 | AF042105 | Australia | B |
| MN.US84 | M17449 | U.S.A. | B |
| NY5.US84 | M38431 | U.S.A. | B |
| OYI.GA88 | M26727 | Gabon | B |
| P896.US89 | U39362 | U.S.A. | B |
| RF.US83 | M17451 | U.S.A. | B |
| RL42.CN | U71182 | China | B |
| SF2.US83 | K02007 | U.S.A. | B |
| TWCYS.TW94 | AF086817 | Taiwan | B |
| WCIPR9018.US90 | U69591 | U.S.A. | B |
| WEAU160.US90 | U21135 | U.S.A. | B |
| WR27.US88 | U26546 | U.S.A. | B |
| YU2.US86 | M93258 | U.S.A. | B |
| D.ELI.CD83 | K03454 | D. R. Congo | D |
| D.UG1141.UG94 | U88824 | Uganda | D |
| D.ZR085.CD84 | U88822 | D. R. Congo | D |

§subtype D sequences included as an outgroup to root the clade B phylogeny;
*unpublished complete genome sequences from HVTN project.

TABLE 9

Sequence Names, GenBank Accession Numbers and Country of Isolation for the sequences used in the complete genome MRCA and COT estimation of subtype C.

| Sequence | Accession number | Country | SUBTYPE§ |
|---|---|---|---|
| 86ETH2220 | U46016 | Ethiopia | C |
| 92BR025 | U52953 | Brazil | C |
| 93IN904 | AF067157 | India | C |
| 94IN476 | AF286223 | India | C |
| 95IN21068 | AF067155 | India | C |
| 96BW0402 | AF110962 | Botswana | C |
| 96BW0408 | AF110964 | Botswana | C |
| 96BW0502 | AF110967 | Botswana | C |
| 96BW06J4 | AF290028 | Botswana | C |
| 96BW1106 | AF110970 | Botswana | C |
| 96BW1210 | AF110972 | Botswana | C |
| 96BW15B03 | AF110973 | Botswana | C |
| 96BW16B01 | AF110976 | Botswana | C |
| 96BW17A09 | AF110979 | Botswana | C |
| 96BW96BW01B03 | AF110959 | Botswana | C |
| 96BWM032 | AF443075 | Botswana | C |
| 96ZM651 | AF286224 | Zambia | C |
| 96ZM751 | AF286225 | Zambia | C |
| 97TZ04 | AF361874 | Tanzania | C |

TABLE 8

Evolutionary model parameters for phylogenetic analysis and ancestral and COT state reconstruction for subtype B gene sequences.

| gene | $R_{A<->C}$ | $R_{A<->G}$ | $R_{A<->T}$ | $R_{C<->G}$ | $R_{C<->T}$ | $R_{G<->T}$ | Shape parameter | Assumed proportion of invariable sites | freq(A) | freq(C) | freq(G) | freq(T) |
|---|---|---|---|---|---|---|---|---|---|---|---|---|
| gag | 1.787 | 4.4321 | 0.8198 | 0.9897 | 5.2536 | 1 | 0.5253 | 0.3028 | 0.3832 | 0.1751 | 0.2268 | 0.2149 |
| gp160 | 2.469 | 5.6546 | 1.1659 | 0.9752 | 5.6546 | 1 | 0.5833 | 0.2469 | 0.3575 | 0.1858 | 0.2236 | 0.2331 |
| nef | 1.2074 | 3.3345 | 1.193 | 0.5574 | 3.3345 | 1 | 0.5329 | none | 0.346 | 0.2094 | 0.2613 | 0.1833 |
| pol | 2.6829 | 11.9199 | 1.1681 | 1.342 | 11.9199 | 1 | 0.6476 | 0.369 | 0.3937 | 0.1717 | 0.2138 | 0.2208 |
| rev | 1 | 2.1615 | 0.3786 | 0.3786 | 2.1615 | 1 | 0.4075 | none | 0.3224 | 0.2751 | 0.2411 | 0.1614 |
| tat | 1.9279 | 3.0288 | 0.3625 | 1.2287 | 3.0288 | 1 | 0.5314 | 0.1979 | 0.3543 | 0.2489 | 0.2191 | 0.1777 |
| vif | 1.7739 | 3.7387 | 0.3906 | 0.5473 | 3.7387 | 1 | 0.5248 | 0.2459 | 0.3796 | 0.1809 | 0.2316 | 0.2079 |
| vpr | 3.657 | 7.8789 | 1.0026 | 1.3814 | 15.7753 | 1 | 0.6295 | 0.3193 | 0.3439 | 0.1894 | 0.2386 | 0.2281 |
| vpu | 2.3344 | 3.1513 | 1.4396 | 2.2202 | 8.3028 | 1 | 0.5218 | none | 0.368 | 0.1192 | 0.26 | 0.2528 |

TABLE 10

Evolutionary model parameters for phylogenetic analysis and ancestral and COT state reconstruction for subtype C gene sequences.

| gene | $R_{A<->C}$ | $R_{A<->G}$ | $R_{A<->T}$ | $R_{C<->G}$ | $R_{C<->T}$ | $R_{G<->T}$ | Shape parameter | Assumed proportion of invariable sites | freq(A) | freq(C) | freq(G) | freq(T) | Ti/Tv |
|---|---|---|---|---|---|---|---|---|---|---|---|---|---|
| gag | — | — | — | — | — | — | 0.3348 | none | 0.36904 | 0.18619 | 0.24234 | 0.20244 | 3.09542 |
| gp160 | — | — | — | — | — | — | 0.405447 | none | 0.34797 | 0.17109 | 0.23644 | 0.24449 | 2.3953 |
| nef | 2.0998 | 4.0826 | 1.4418 | 1.3501 | 5.7703 | 1 | 0.6877 | 0.1885 | 0.3426 | 0.2063 | 0.2579 | 0.1932 | — |
| pol | 1.9799 | 8.7785 | 1.078 | 0.7924 | 11.9393 | 1 | 0.7828 | 0.3661 | 0.3961 | 0.1705 | 0.2231 | 0.2103 | — |
| rev | 2.1477 | 5.7666 | 0.7273 | 0.3826 | 5.7666 | 1 | 0.71 | 0.1773 | 0.3116 | 0.2212 | 0.2668 | 0.2004 | — |
| tat | 4.1494 | 7.2595 | 1.082 | 1.0846 | 9.5448 | 1 | 0.6771 | 0.3018 | 0.3463 | 0.2367 | 0.2339 | 0.1831 | — |
| vif | 1.6981 | 4.1865 | 0.8836 | 0.7624 | 5.8585 | 1 | 0.525 | 0.2597 | 0.3842 | 0.1794 | 0.2363 | 0.2001 | — |
| vpr | 2.571 | 6.3751 | 0.9793 | 0.8462 | 9.8567 | 1 | 0.829 | 0.3024 | 0.3448 | 0.1814 | 0.2495 | 0.2243 | — |
| vpu | 1.5454 | 2.1322 | 0.5312 | 0.2609 | 5.7821 | 1 | 0.635 | 0.1585 | 0.4191 | 0.1036 | 0.2453 | 0.232 | — |

TABLE 9-continued

Sequence Names, GenBank Accession Numbers and Country of Isolation for the sequences used in the complete genome MRCA and COT estimation of subtype C.

| Sequence | Accession number | Country | SUBTYPE[§] |
|---|---|---|---|
| 97TZ05 | AF361875 | Tanzania | C |
| 97ZA012 | AF286227 | South Africa | C |
| 98BR004 | AF286228 | Brazil | C |
| 98BWMO1410 | AF443079 | Botswana | C |
| 98BWMO18D5 | AF443080 | Botswana | C |
| 98BWMO36A5 | AF443081 | Botswana | C |
| 98BWMO37D5 | AF443082 | Botswana | C |
| 98IN012 | AF286231 | India | C |
| 98IS002 | AF286233 | Israel | C |
| 98TZ013 | AF286234 | Tanzania | C |
| 98TZ017 | AF286235 | Tanzania | C |
| 99BW393212 | AF443083 | Botswana | C |
| 99BW46424 | AF443084 | Botswana | C |
| 99BW47458 | AF443085 | Botswana | C |
| 99BW47547 | AF443086 | Botswana | C |
| 00BW076820 | AF443089 | Botswana | C |
| 00BW087421 | AF443090 | Botswana | C |
| 00BW147127 | AF443091 | Botswana | C |
| 00BW16162 | AF443092 | Botswana | C |
| 00BW1686. | AF443093 | Botswana | C |
| 00BW17593 | AF443094 | Botswana | C |
| 00BW17835 | AF443096 | Botswana | C |
| 00BW17956 | AF443097 | Botswana | C |
| 00BW18113 | AF443098 | Botswana | C |
| 00BW18802 | AF443100 | Botswana | C |
| 00BW22767 | AF443107 | Botswana | C |
| 00BW38713 | AF443110 | Botswana | C |
| 00BW38769 | AF443111 | Botswana | C |
| 00BW38868 | AF443112 | Botswana | C |
| 00BW50311 | AF443115 | Botswana | C |
| ZA..CTSC2 | AY043176 | South Africa | C |
| ZA..DU151 | AY043173 | South Africa | C |
| ZA..DU179 | AY043174 | South Africa | C |
| A KE.Q2317 | AF004885 | Kenya | A |
| B US.JRFL | U63632 | U.S.A. | B |
| D UG.94UG1 | U88824 | Uganda | D |
| F BE.VI850 | AF077336 | Belgium | F |
| G SE.SE616 | AF061642 | Sweden | G |
| J SE.SE928 | AF082394 | Sweden | J |
| H CF.90CF0 | AF005496 | C.A.R. | H |

[§]sequences from subtypes other than D included as an outgroup to root the clade C phylogeny.

Comparisons of the MRCA, Least Squares Method ("LSCOT") and Minimum of Means COT ("MMCOT") reconstructions for the Clade B gag, env (encoding gp160), nef, pol, rev, tat, vif, vpr, and vpu genes are shown in FIGS. 9 to 17. Comparisons of the MRCA, Least Squares Method ("LSCOT") and Minimum of Means COT ("MMCOT") reconstructions for the Clade B gag, env (gp160), nef, pol, rev, tat, vif, vpr, and vpu proteins are shown in FIGS. 18 to 26.

Comparisons of the MRCA, Least Squares Method ("LSCOT") and Minimum of Means COT ("MMCOT") reconstructions for the Clade C gag, env (encoding gp160), nef, pol, rev, tat, vif, vpr, and vpu genes are shown in FIGS. 27 to 35. Comparisons of the MRCA, Least Squares Method ("LSCOT") and Minimum of Means COT ("MMCOT") reconstructions for the Clade C gag, env (gp160), nef, pol, rev, tat, vif, vpr, and vpu proteins are shown in FIGS. 36 to 44.

Example 8

HIV-1 has high replication and mutation rates that permit rapid generation of viruses that can escape immune recognition. Within an infected host, the HIV-1 population diversifies over time, producing mostly defective viruses but nonetheless persisting and accumulating mutations at a rate of up to 1% per year in its env gene. HIV sequences sampled from a population of infected individuals recapitulate a star-like phylogeny, i.e., most of the variants sampled at the same time are positioned roughly equidistant from the center of the tree. Thus, any given variant is approximately twice this distance from any other circulating strain. A primary concern in designing protective AIDS vaccines, then, is the choice of strains likely to best provide protection against the expanding population of HIV-1 variants.

Several methods for choosing a vaccine candidate on the basis of genetic or protein sequence data have been put forth recently. First, and the approach followed in current clinical trials, is to choose one or a small number of laboratory-grown or primary viral isolates, typically chosen to approximate a "circulating" strain or to simply match the HIV-1 subtype(s) in the targeted population. An advantage of this approach is that it typically employs viral genes derived from a viable virus and thus produces antigens likely to adopt "native" conformations. However, as a result of HIV-1 mutational radiation, any given "circulating" strain will be genetically, and presumably antigenically, dissimilar to other strains likely to be encountered by the vaccinee, with the degree of dissimilarity proportional to the length of time the virus has been circulating within the population. Thus, vaccines based on specific viral isolates are unlikely to be effective against a broad range of circulating viruses. The results of a first Phase III AIDS vaccine trial suggest that monomeric envelope proteins that are derived from such isolates are insufficient to provide protective immunity, although it remains an open question whether more native presentations of envelope protein might be an effective vaccine component.

To enhance the breadth of the elicited immune response, a second approach is to include as many diverse HIV-1 isolates as possible in the vaccine recipe, with the intention of inducing multiple responses against different Env proteins. This approach has been explored to a limited degree, without clear success. A third approach is to build a consensus sequence based on either circulating strains or strains in the HIV database. The consensus sequence will be genetically closer to circulating strains than any given natural virus isolate, but its sequence may be biased by sampling and may link polymorphisms in combinations not found in any natural or viable virus, thus potentially resulting in inappropriate structural conformations. Consequently, there is a need for new, effective methods of identifying candidate sequences for vaccine development to treat and/or prevent HIV infection.

To this end, the use of an HIV population ancestral sequence can be used as a vaccine candidate. Such a vaccine might correspond to an ancestor of all known HIV strains, an HIV sequence subtype, or viruses circulating in a given geographic region or risk group. The ancestral viral sequence is reconstructed from a phylogenetic tree describing the historical relationships of sequences sampled from the population of interest, and is thus expected to correspond to the most recent common ancestor (MRCA) of the viral strains sampled from the targeted population. It is also likely that such an ancestral sequence will encompass elements conserved within the sampled virus population. To maximize the opportunity for native Envelope protein expression in vivo, DNA vaccines expressing full-length Env gp160 or TM-truncated Env gp140 have been used. These vaccines have been shown are effective in both priming and boosting in macaques. Here, a predicted ancestral env sequence for subtype B HIV-1 encodes a functional protein that elicits neutralizing antibodies to primary isolates in rabbits. Boosting with gp120 protein did not significantly enhance the neutralization capacity of the sera.

Methods

Ancestral state simulations. To assess the accuracy of the ancestral state reconstruction method, the following in silico study was performed. Using the program Seq-Gen (Rambaut and Grassly, *Comput. Appl. Biosci*. 13:235-8 (1997)), the evolution of sequences was simulated, given an ancestral sequence and following the phylogenetic histories depicted in the trees in FIG. 45A and the model of evolution shown in Table 11. One hundred replicate data sets were generated for both tree shapes. The PAUP* (Swofford, D. 1999. PAUP*, Sinauer Associates, Inc.) to generate a maximum-likelihood tree and an ancestral sequence for all 200 datasets (100 simulations on both the star- and caterpillar-shaped phylogenies). To be conservative, the simulations were performed on trees with very long external branches (having a genetic distance of 20%), and the caterpillar trees had internal branch lengths of 1% genetic distance.

Ancestral state reconstruction of the SIVmacBK28 env sequence: SIVmac sequences obtained from a series of experimental infections of rhesus macaques (Edmonson et al., *J. Virol.* 72:405-14 (1998)) were used to reconstruct an ancestral sequence to compare to the plasmid-derived SIV clone used to inoculate these monkeys. A region of env from position 8,265 to 8,827 of the SIVmacBK28 genome was amplified by nested-PCR from uncultured PBMC DNA from the SIV infected macaques. First round primers were UP-3, positions (8,117 to 8,130), AGACTGCAGATGTGAAGAGGTACAC (SEQ ID NO: 122) and PEXTM6 (8,977 to 8,953), GGATCTGGTATGCTCATAGCAA (SEQ ID NO: 123). Second round primers were PEXTM7 (8,265 to 8,286), GATACTGCAGCAACAGCAACAGCTG (SEQ ID NO: 124) and UP-5 (8,827 to 8,810), GCAAAGCTTCTCTGGTTGGCAGTG (SEQ ID NO: 125). Amplified products were then cloned and sequenced. The GenBank accession numbers for these sequences are AY169007-AY169163. Methods for SIVmacBK28 ancestor reconstruction were identical to those outlined below. The model of evolution is given in Table 12 and the reconstructed sequence is provided in FIG. 46.

Ancestral state reconstruction of an HIV-1-B env sequence: Thirty-eight sequences representing env genes of HIV-1 subtype B were selected from GenBank and the Los Alamos sequence databases, with three additional sequences from clade D used as an outgroup for rooting (Kuiken et al., *HIV Sequence Compendium* 2001, Theoretical Biology and Biophysics Group, Los Alamos National Laboratory, Los Alamos, N.Mex.) (Table 11 and FIG. 45B). Sequences were aligned using CLUSTALW (Thompson et al., *Nucleic Acids Res*. 22:4673-80 (1994) and the alignment was refined using GDE (Smith et al., *Comput Appl. Biosci*. 10:671-5 (1994)). Inferred amino acid sequences were used to guide the introduction of alignment gaps such that they were inserted between codons. These alignments were then modified for phylogenetic analysis such that regions that could not be unambiguously aligned were removed (Learn et al., *J. Virol*. 70:5720-30 (1996)).

An appropriate evolutionary model for phylogeny and ancestral state reconstructions was selected using the Akaike Information Criterion (AIC) as implemented in Modeltest 3.0 (Posada and Crandall, *Bioinformatics* 14:817-8 (1998)). (See Table 12). Evolutionary trees for the sequences (B alignments) were inferred using maximum-likelihood estimation methods as implemented in PAUP* version 4.0b10 (Swofford, D. 1999. PAUP*, Sinauer Associates, Inc.). Ten different subtree-pruning-regrafting (SPR) heuristic searches were performed using a different random-addition order each time and using a neighbor-joining tree of the subtype B sequences as a backbone constraint. The ancestral nucleotide sequence was inferred as the sequence at the basal node of the clade using the inferred phylogenies. The nucleotide at each site of the ancestral sequence had the highest likelihood, integrated over all state assignments at other nodes. This derived sequence is provided in FIG. 46.

To predict the amino acid sequences for the complete gp160, including the highly variable regions, the inferred ancestral sequences were visually aligned to the alignments prior to gap-stripping and translated using GDE (Smith et al., *Comput. Appl. Biosci*. 10:671-5 (1994)). Since the highly variable regions were deleted as complete codon triplets, the translations into amino acids were in the correct reading frame and codons were properly maintained. The ancestral amino acid sequences for the regions deleted from the gap-striped alignment were predicted visually and refined using parsimony-based sequence reconstruction for these sites using the program MacClade (Maddison and Maddison, MacClade—Analysis of Phylogeny and Character Evolution, 3rd ed., Sinauer Associates, Inc, Sunderland, Mass. (1992)). The complete gp160 amino acid sequences were converted to DNA sequences optimized for expression in human cells using the BACKTRANSLATE program of the Wisconsin Sequence Analysis Package (GCG), version 10 and a human gene codon table from a Codon Usage Database (Nakamura et al., *Nucleic Acids Res*. 28:292 (2000)). The gene was then chemically synthesized, sequence-verified, and inserted into a mammalian expression vector to produce the plasmid pVR1012-AN1env (Vical, Inc). To generate a gp140 expression plasmid, pVR112-AN1env was subjected to site-directed mutagenesis (Quik-change kit, Stratagene) to introduce two stop codons after the codon for amino acid 711 (nucleotides 2134-9)

Fusion assay. GHOST-CCR5 or GHOST-CXCR4 cells were seeded in two-chamber culture slides (Falcon, Franklin Lakes, N.J.) at $5\times10^4$ cells/well, and transfected the next day with 0.5 μg env plasmid using Fugene-6 (Roche, Indianapolis, Ind.). Transfected cells were allowed to fuse for two days and then were fixed and stained for immunofluorescence using the monoclonal antibody b12 (gift of Dr. Dennis Burton) and 1:2500 FITC-conjugated goat anti-human IgG (Cappel). The presence of large multinucleated cells indicated that cell-cell fusion had occurred.

Western blot analysis. 293T cells were transfected in 6-well dishes with 1 μg env plasmid and Fugene-6, and medium and cell lysates were collected 48 hours later. Twenty one μl of each sample were used for SDS-PAGE, transferred to a PVDF membrane, probed with heat-inactivated pooled human $HIV^+$ serum (gift of Dr. Lisa M. Frenkel) and horseradish peroxidase-conjugated goat anti-human IgG (Sigma, St Louis, Mo.), and then developed with the color substrate 3-amino-9-ethylcarbazole (AEC).

Recombinant protein production. Recombinant gp120 from HIV-1 SF162 was provided by Chiron Corp and prepared as described in (Barnett et al., *Vaccine* 15:869-73 (1997)).

Rabbit immunizations. New Zealand White rabbits were vaccinated by Gene Gun (Bio-Rad, Hercules, Calif.). Eighteen shots of 2 μg DNA each were given for each dose. Animals were vaccinated at weeks 1, 5, 10, 19, 23, and 46. Protein boosts were given at weeks 68 and 78; these consisted of 44 μg recombinant gp120 mixed with an equal volume of Incomplete Freund's adjuvant, injected intramuscularly. Blood was collected the day before and 2 weeks after each immunization. Animals were housed at R+R Rabbitry, Marysville, Wash. and procedures followed IACUC-approved protocols.

Neutralization assays. cMAGI assay. Assays were performed as described by (Doria-Rose et al., *J. Virol.* 77:11563-77 (2003). Briefly, serial dilutions of sera were incubated with virus for one hour, then added to duplicate wells of cMAGI cells. After two days, cells were fixed and stained for β-galactosidase expression (indicating infection). The percent neutralization at a given titer is calculated by the equation (Vo−Vn)/Vo×100, where Vn is the number of infected cells in the virus+antibody wells and Vo is the number of positive cells in virus-alone wells. Titers were normalized to the titer of a standard HIV+ human serum pool that was included on each assay plate.

Luciferase reduction assay (M7-luc assay). 500 TCID$_{50}$ of virus was mixed and incubated with serial dilutions of serum in triplicate for 1 hr at 37° C. in 96-well microculture plates. 5.25.EGFP.Luc.M7 cells (kindly provided by Dr. Nathaniel Landau (Brandt et al., *J. Biol. Chem.* 277:17291-9 (2002)) suspended in RPMI with 12% fetal bovine serum and 25 µg/ml DEAE-dextran at 7.5×10$^4$ cells per well were then added and incubated for 3-4 days. These cells express luciferase and GFP upon HIV infection. Luciferase was measured using a commercial kit (Bright-Glo, Promega, Madison, Wis.) and a Fluoroskan luminometer. The titer was calculated as the dilution at which relative light units (RLU) were 50% that of virus-only wells. For the large panel of viruses, sera were assayed at a 1:10 dilution and the percent reduction in relative light units (RLU) was calculated in relation to a pre-immunization serum sample for each rabbit. A reduction of 50% is considered significant in this assay.

Results

Figure 45A:
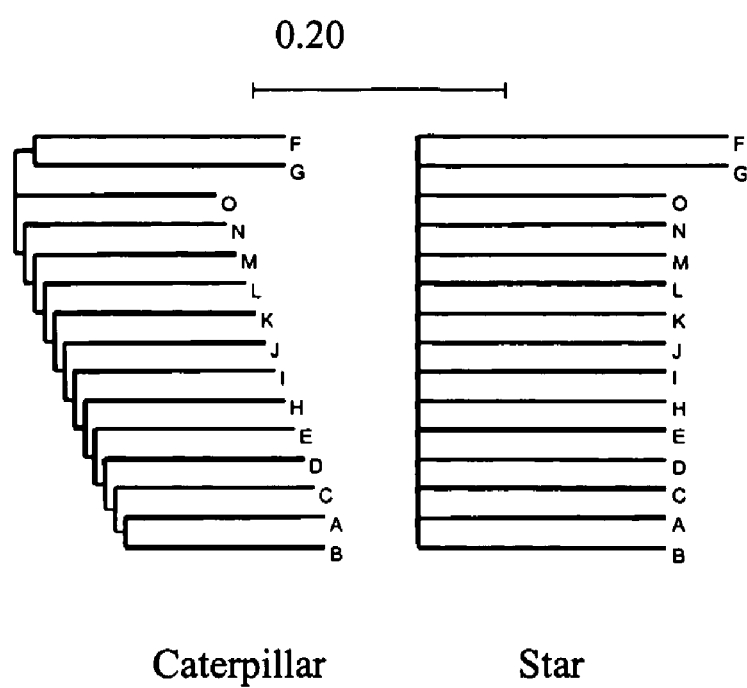
Figure 45B:
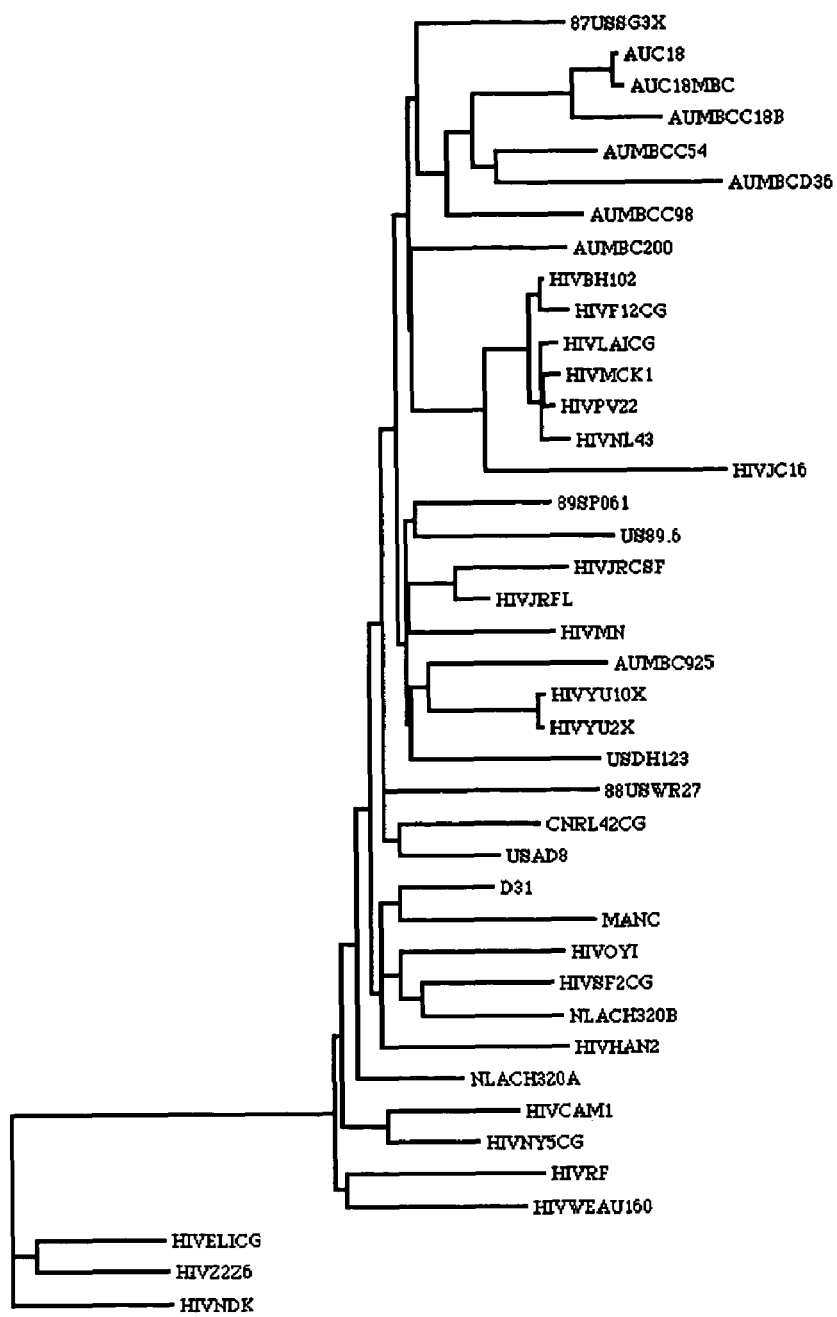

Method validation: First, the ability of likelihood-based phylogenetic methods to accurately predict ancestral sequences was evaluated using both a simulation and an experimental approach. HIV-1 is widely considered to have a star-like phylogeny with all external branches radiating from the same central point on the tree. However, there is at least some level of substructure in the phylogeny (i.e., some short internal branches at the base of the tree). In terms of tree space, the realized HIV-1 tree (see FIG. 45B) is somewhere between a true star and what can be called a caterpillar tree (i.e., long external branches with short internal branches) (FIG. 45*a*). To estimate the accuracy of ancestral state reconstruction, 100 simulations were performed with a known ancestor at each of the two extremes of the star-caterpillar continuum. For the caterpillar tree, the MRCA was estimated with 95.4% accuracy. For the star phylogeny, the MRCA was estimated with 98.2% accuracy. Since the true HIV phylogeny falls somewhere between the caterpillar and star structures, the MRCA reconstruction accuracy was estimated to be in the range of 95-98%.

Viral gene sequences taken from 4 rhesus macaques infected with a molecularly defined strain of SIV, SIV-mac251-BK28 (Kornfeld et al., *Nature* 326:610-3 (1987) were used in an effort to assess the reconstruction of the infecting viral sequence. From a phylogenetic tree of 1.1 kb env gene fragments taken between 1-3 years post infection, 99.8% of the infecting viral sequence (373 of 376 amino acids), including 98.2% of the 170 variable sites, were accurately predicted.

Derivation of subtype B ancestor: Using the same procedures, an ancestral nucleotide sequence of the envelope gene of HIV-1 subtype B, the most extensively evaluated HIV-1 subtype to date, was derived using the phylogeny shown in FIG. 45*b*. This ancestral sequence (AN1-EnvB) produced an open reading frame encoding a complete, 884-amino acid gp160 gene product. The amino acid distances between the ancestral sequence and the natural subtype B strains used to estimate it were 12.3% on average (range: 8.0-21.0%) while these sequences were 17.3% different from each other (range: 13.3-23.2%). At 884 amino acids, the encoded protein is long relative to most sequences; much of the additional length is in the variable loops. Also unusual is the number of putative sites for N-linked glycosylation, also called sequins: the average is 25, while AN1-EnvB has 35. Based on features V3 sequence features, AN1-EnvB is predicted to use CCR5 as a coreceptor In vitro validation of ancestor protein expression. The functional characteristics of the ancestral env sequence were evaluated. The deduced sequence was re-engineered to reflect the dominant patterns of human codon usage, without changing any of the encoded amino acids, and then chemically synthesized the gene and cloned it into a mammalian expression vector pVR1012. Transfection of this plasmid into COS-7 or 293T cells resulted in the production of high levels of viral protein gp160 and its cleavage products, gp120 and gp41—comparable to levels detected following transfection of the widely employed, humanized Env-gp160 gene of SHIV89.6P (Barouch et al., *Science* 290:486-92 (2000)). Control of viremia and prevention of clinical AIDS in rhesus monkey and higher than that of non-optimized HIV-1 89.6 Env. A truncated gp140 form, which is expected to retain the oligomeric properties of gp160 but is secreted, was also generated and expressed and shown to bind soluble CD4 in an ELISA assay. Western blot analysis of 293T cells transfected with either the gp160 or gp140 form showed that the expressed proteins were of the predicted sizes and were recognized by anti-HIV antibodies. Cell lysates contained both gp140 and gp160, while only the gp140 form appeared in the medium, showing that it was secreted as expected. Lysates of cells transfected with gp160 showed bands for gp41 and gp120, indicating that Env was cleaved to its mature form intracellularly. The cleavage was not complete, as full-length gp160 was also visible. The apparent molecular weight and somewhat diffuse nature of the bands suggested that the AN1-EnvB proteins were highly glycosylated.

Expression of gp160 in transfected cells was confirmed by an immunofluorescence assay. Cell-cell fusion occurred when GHOST-CCR5 cells (Cecilia et al., *J. Virol.* 72:6988-96 (1998)) expressing the HIV-1 receptors CD4 and CCR5 were transfected with AN1-EnvB gp160. In contrast, no fusion occurred when GHOST-CXCR4 cells expressing CD4 plus CXCR4 were transfected, although Env was expressed in these cells. These results indicated that AN1-EnvB used only CCR5, as predicted by its sequence, and that it was folded properly and fully functional for directing membrane fusion. To confirm the functionality of AN1-EnvB, pVR1012AN1env (encoding full-length gp160) was used to complement the env-defective genome Q23Δenv(Long et al., *AIDS Res. Hum. Retroviruses* 18:567-76 (2002)). The resulting pseudotyped virus particles were able to infect permissive cMAGI cells. Concentrated virions had a titer of $1.1\times10^4$ infectious particles/ml on cMAGI cells.

Immunogenicity of AN1-EnvB: To assess the humoral immune response potentially elicited by An1-EnvB, rabbits were immunized with DNA encoding gp160 and gp140 versions of the protein via Gene Gun followed by boosting with recombinant AN1-EnvB gp120 protein made in CHO cells. As controls, additional groups were immunized with a codon-optimized Env gp140 from a primary HIV-1 isolate, HIV-SF162 and recombinant SF162 gp120, or with the empty vector and adjuvant. All Envelope plasmids elicited Envelope-specific antibody binding titers in rabbits up to 1:1,000,000. Titers increased with protein boosting.

Virus neutralization: Antibody neutralization was measured using the cMAGI assay (Chackerian et al., *J. Virol.* 71:3932-9 (1997); Kimpton et al., *J. Virol.* 66:2232-9 (1992)) with five heterologous subtype B, primary R5 HIV-1 isolates SF162, 92US657, 92TH014, 91US056, and 92HT593, and one subtype C primary isolate, 93IN101 (Table 13). As a positive control, HIV+ sera pooled from several local subtype B-infected patients was included. All isolates tested were neutralized by this pool, but with differing sensitivities. After four DNA immunizations, all gp140-SF162-immunized rabbit sera had neutralizing activity against the homologous virus. Six of eight AN1-EnvB immunized rabbit sera also neutralized HIV-1 SF162, which in this case was heterologous. Seven of these eight rabbits had 50% neutralization titers of at least 1:8 against 92US657; all eight achieved 90% neutralization against 92TH014 after five immunizations (geometric mean titer=16). In contrast, sera against SF162 protein were less broadly reactive, with neutralization titers of at least 1:8 detected against two of five heterologous viruses (in one of four animals against 93IN101 and in two of four animals against 92US657). Furthermore, HIV 92TH014 and 92US657 were more effectively neutralized by the AN-1-EnvB-immunized rabbit sera compared with Env SF162 sera, with high titers at the 90% cutoff against 92TH014. Two of the six HIV-1 isolates tested were only very weakly or not neutralized by sera from any of the Env-immunized rabbits (92HT593 and 91US056), although the human HIV-positive serum control neutralized both. Subtype C 93IN101 was weakly neutralized by sera from at most one animal in each group.

These data were extended in a second neutralization assay using 5.25.EGFP.Luc.M7 cells. Strong neutralizing activity against HIV-1 SF162 was found in all Env-immunized rabbits, confirming the results in the cMAGI assay. This activity increased over the course of vaccinations. Titers increased with each of the first two immunizations and then declined, as has been seen with vaccinations in primates, while subsequent boosts resulted in sustained titers at a threshold level that was not additionally boosted. Levels of neutralizing antibody against HIV-SF162 were similar in each of the groups receiving homologous Env-SF162, or heterologous AN1-Env-B gp140 or AN1-Env-B-gp160. Inhibition of primary isolate Bx08 was found in four of eight AN1-EnvB- and in one of four SF162-immunized rabbits. However, none of the AN1-Env B-immunized rabbit sera neutralized Bal and JR-FL, whereas sera raised against Env-SF162 neutralized Bal and in one case, JR-FL. In summary, at least five of the eight primary (all heterologous) clade B viruses tested were neutralized by AN1-Env B sera (Table 14).

Discussion

Artificial HIV gene sequences, such as ancestors and consensus can be more effective vaccines and reagents than natural isolates. Such sequences can be engineered to contain more of the conserved features and epitopes found in primary isolates than any one isolate would have. This concept has been put into practice by predicting, synthesizing, and evaluating an ancestor of the HIV-1 clade B env gene. The AN1-EnvB protein can be stably expressed in mammalian cell lines, was glycosylated, bound CD4, directed cell-cell fusion, used CCR5 but not CXCR4, and complemented env-defective genomes. This functional protein elicited high titers of Env-binding antibodies in vaccinated mice and rabbits. After DNA priming and protein boosting, immunized rabbit sera neutralized a variety of primary isolates at a low level. gp140 constructs gave slightly higher titers (binding and neutralizing) than gp160, but this difference was not statistically significant.

The neutralization profile of AN1-EnvB-vaccinated rabbit sera supports the use of ancestral viral sequences as immunogenic compositions. In an effort to examine breadth of neutralization in an impartial manner, coded sera were tested using two different assays, performed in two different laboratories, using panels of laboratory and primary viruses with a single isolate in common, HIV-SF162. (No standard panel of HIV-1 primary isolates has been established for comparisons between laboratories to date.) Results in both laboratories indicated that sera from the AN1-EnvB-immunized rabbits could neutralize heterologous HIV-1 strains to a significant degree. Three of five subtype B viruses were neutralized by a majority of sera using the cMAGI assay and three of five subtype B viruses were neutralized by at least some of the sera in the M7-luc assay. Several rabbits showed low-level responses against one virus from subtype C, but none neutralized another C or the E subtype viruses tested. This profile was similar to that of sera from rabbits immunized with Env from HIV-1 SF162. Indeed, the neutralization of HIV-1 SF162 itself was similar for sera from rabbits given either immunogen, even though this isolate is homologous to the SF162 immunogen but heterologous to the AN1-EnvB immunogen. These data imply that the artificial sequence was at least as immunogenic as this natural isolate.

Several recent vaccine experiments have shown that DNA expressing unmodified HIV-1 Envelopes can elicit low-level antibodies that neutralize the homologous primary isolate at the 50% level. Low titer cross-reactive neutralizing antibodies were elicited using modified Envelope DNA vaccines or recombinant proteins. The codon-optimized vectors used here elicited high titers of binding antibodies with DNA vaccination alone. Responses to DNA vaccines can be effectively boosted with recombinant viral vectors or recombinant glycoproteins. The results reported here support the use of DNA vaccines alone in demonstrating low-level cross-clade neutralizing antibodies. Immunization of the DNA-primed rabbits with homologous gp120 subunit protein in adjuvant resulted in boosting of binding antibody titers against HIV-SF162. However, gp120 failed to boost heterologous (i.e., from a different HIV subtype) neutralizing antibody responses significantly. The gp140 and gp160 DNA vaccines presented native envelope conformations in vivo that were boosted poorly or not at all by adjuvated gp120 monomer proteins, raising responses only to the most neutralization-sensitive primary virus, HIV-SF162. Although native gp120 can bind conformation-dependent broad neutralizing antibodies, elicit neutralizing antibodies and boost DNA priming, there is evidence that use of oligomeric envelope proteins may be more effective in boosting broader responses.

TABLE 11

Sequences used for phylogenetic reconstruction

| Sequence name | Accession number | Subtype |
|---|---|---|
| HIVELICG | K03454 | D |
| HIVNDK | M27323 | D |
| HIVZ2Z6 | M22639 | D |
| 87USSG3X | L02317 | B |
| 88USWR27 | U26546 | B |
| 89SP061 | AJ006287 | B |
| AUC18 | AF042102 | B |
| AUC18MBC | U37270 | B |
| AUMBC200 | AF042100 | B |
| AUMBC925 | AF042101 | B |
| AUMBCC18B | AF042106 | B |
| AUMBCC54 | AF042103 | B |
| AUMBCC98 | AF042104 | B |

TABLE 11-continued

Sequences used for phylogenetic reconstruction

| Sequence name | Accession number | Subtype |
|---|---|---|
| AUMBCD36 | AF042105 | B |
| CNRL42CG | U71182 | B |
| D31 | U43096 | B |
| HIVBH102 | M15654 | B |
| HIVCAM1 | D10112 | B |
| HIVF12CG | Z11530 | B |
| HIVHAN2 | U43141 | B |
| HIVJC16 | AF049494 | B |
| HIVJRCSF | M38429 | B |
| HIVJRFL | U63632 | B |
| HIVLAICG | K02013 | B |
| HIVMCK1 | D86068 | B |
| HIVMN | M17449 | B |
| HIVNL43 | M19921 | B |
| HIVNY5CG | M38431 | B |
| HIVOYI | M26727 | B |
| HIVPV22 | K02083 | B |
| HIVRF | M17451 | B |
| HIVSF2CG | K02007 | B |
| HIVWEAU160 | U21135 | B |
| HIVYU10X | M93259 | B |
| HIVYU2X | M93258 | B |
| MANC | U23487 | B |
| NLACH320A | U34603 | B |
| NLACH320B | U34604 | B |
| US89.6 | U39362 | B |
| USAD8 | U19647 | B |
| USDH123 | AF069140 | B |

TABLE 12

Parameters for evolutionary models used for phylogenetic reconstructions.

| Evolutionary Model Class[a] | HIV-1-B ENV GTR + I + G | SIV env GTR + I + G |
|---|---|---|
| RC ↔ A[b] | 1.971 | 1.8418 |
| RG ↔ A | 4.315 | 10.9127 |
| RT ↔ A | 0.8539 | 0.5803 |
| RC ↔ G | 1.021 | 0.9283 |
| RC ↔ T | 3.826 | 6.8499 |
| fA[c] | 0.34857 | 0.3516 |
| fC | 0.17125 | 0.1642 |
| fG | 0.23694 | 0.2296 |
| fT | 0.24324 | 0.2546 |
| Proportion of assumed invariant sites | 0.26035 | 0.471 |
| $\alpha$[d] | 0.50434 | 0.9477 |

[a]GTR + I + G: General time-reversible model with a proportion of invariant sites and gamma-distributed site-to-site rate variation.
[b]Rate parameters of the symmetric substitution rate matrix: RX ↔ Y is the rate of substitution of nucleotide X by nucleotide Y (or Y by X) scaled to RG ↔ T = 1.
[c]fX: Equilibrium frequency of nucleotide X.
[d]$\alpha$: Shape parameter of the gamma distribution.

TABLE 13

Neutralization of HIV-1 primary isolates in the cMA GI assay

| | | SF162 | | | | 92US657 | | 92TH014 | | 92HT593 | 91US056 | | 93IN101 |
|---|---|---|---|---|---|---|---|---|---|---|---|---|---|
| Immunization Group | No. | 4 50% | 4 75% | 5 50% | 5 75% | 5 50% | 5 75% | 5 50% | 5 90% | 5 50% | 5 50% | 5 75% | 5 50% |
| SF162 | 32N | 22 | 15 | 16 | <8 | <8 | <8 | <8 | <8 | <4 | <4 | <4 | <8 |
| Gp140 | 91N | 22 | 18 | <8 | <8 | <8 | <8 | *55 | <8 | <4 | <4 | <4 | <8 |
| | 9335L | 9 | 9 | <8 | 9 | <8 | <8 | <8 | <8 | <4 | <4 | <4 | <8 |
| | 9578L | 40 | 13 | 18 | 9 | 14 | <8 | nt | nt | <4 | <4 | <4 | 8 |
| Ancestral | 168N | <4 | <4 | <8 | <8 | 20 | 12 | 40 | 16 | <4 | 16 | <4 | <8 |
| Gp140 | 245N | 11 | <4 | <8 | <8 | 32 | 16 | 88 | 48 | <4 | <4 | <4 | <8 |
| | 247N | 5 | <4 | <8 | <8 | 10 | <8 | 32 | 20 | <4 | <4 | <4 | <8 |
| | 9331L | 6 | <4 | 8 | <8 | 28 | 13 | *52 | *32 | <4 | <4 | <4 | 8 |
| Ancestral | 93N | 6 | 4 | <8 | <8 | 18 | 8 | 40 | 16 | <4 | 4 | <4 | <8 |
| Gp160 | 175M | 6 | 4 | 8 | <8 | 12 | <8 | 24 | 10 | <4 | 4 | <4 | <8 |
| | 9599L | <4 | <4 | <8 | <8 | 9 | <8 | 44 | 24 | <4 | <4 | <4 | <8 |
| | 9896L | 8 | 4 | <8 | <8 | <8 | <8 | 40 | 16 | <4 | <4 | <4 | nt |
| Control | 9827L | <4 | <4 | <8 | <8 | 8 | <8 | 15 | <8 | <4 | <4 | <4 | <8 |
| pcDNA | 8848L | <4 | <4 | <8 | <8 | <8 | <8 | 8 | <8 | <4 | <4 | <4 | <8 |
| HIV + serum pool | | nt | nt | 2500 | 500 | 1100 | 300 | 300 | 100 | 200 | 500 | 300 | 400 |

Individual pre-immunization sera were tested for isolates SF162, 92US657, 92TH014, and 93IN101; pooled sera were tested for 92HT593 and 91US056. All were below 50% at the indicated dilution, except as noted; for samples marked * the pre-bleed titer was subtracted.
nt, not tested.

Individual pre-immunization sera were tested for isolates SF162, 92US657, 92TH014, and 93IN101; pooled sera were tested for 92HT593 and 91US056. All were below 50% at the Indicated dilution, except as noted; for samples marked * the pre-bleed titer was subtracted. nt, not tested.

TABLE 14

Neutralization of HIV-1 by sera from immunized rabbits - Week 80 (post-8th vaccination)

| Rabbit | Immunogen | % Reduction in RLU of: | | | | | | |
|---|---|---|---|---|---|---|---|---|
| | | Bal clade B | JR-FL clade B | Bx08 clade B | 6101 clade B | 0692 clade B | S080 clade C | CM244 clade E |
| 91N | SF162 | 62 | 32 | 68 | 43 | 53 | 24 | 0 |
| 9335L | SF162 | 66 | 38 | 66 | 25 | 32 | 0 | 13 |
| 32N | SF162 | 0 | 0 | 65 | 13 | 35 | 0 | 0 |
| 175N | AN-gp160 | 71 | 36 | 61 | 1 | 62 | 0 | 27 |
| 93N | AN-gp160 | 36 | 0 | 45 | 0 | 35 | 0 | 0 |
| 9599L | AN-gp160 | 35 | 0 | 59 | 0 | 44 | 0 | 0 |
| 9896L | AN-gp160 | 0 | 0 | 0 | 5 | 0 | 0 | 0 |
| 245N | AN-gp160 | 30 | 3 | 45 | 8 | 40 | 0 | 2 |
| 247N | AN-gp160 | 0 | 0 | 25 | 0 | 41 | 0 | 33 |
| 9331L | AN-gp160 | 0 | 0 | 14 | 0 | 1 | 0 | 0 |
| 168N | AN-gp160 | 69 | 34 | 73 | 0 | 65 | 0 | 0 |
| 8848L | Control | 0 | 16 | 29 | 26 | 0 | 0 | 0 |
| 9827L | Control | 51 | 0 | 19 | 10 | 0 | 0 | 0 |

[1]Samples were assayed at a 1:10 dilution in triplicate. Values are the % reduction in relative luciferase units compared to the corresponding week 5 sample (05-16-02). Values ≥50% neutralization are shown in boldface type.

From the foregoing, it will be appreciated that, although specific embodiments of the invention have been described herein for the purpose of illustration, various modifications may be made without deviating from the spirit and scope of the invention. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. An isolated expression construct comprising the following operably linked elements: a transcriptional promoter; a nucleic acid sequence that encodes the polypeptide encoded by SEQ ID NO:25; and a transcriptional terminator.

2. The expression construct of claim 1, wherein the transcriptional promoter is a heterologous promoter.

3. The expression construct of claim 2, wherein the promoter is a cytomegalovirus promoter.

4. An isolated prokaryotic or eukaryotic cell transformed or transfected with the expression construct of claim 1.

5. The eukaryotic cell of claim 4, which is a mammalian cell.

6. The prokaryotic cell of claim 4, which is an *E. coli* cell.

7. The eukaryotic cell of claim 4, which is an *S. cerevisiae* cell.

8. The eukaryotic cell of claim 4, which is a human cell.

9. A vector comprising the expression construct of claim 1.

10. The vector of claim 9, wherein the nucleic acid sequence is operably linked to a Semlike Forest Virus replicon, and wherein the resulting recombinant replicon is operably linked to a cytomegalovirus promoter.

11. An isolated host cell comprising the vector of claim 9.

* * * * *

UNITED STATES PATENT AND TRADEMARK OFFICE
CERTIFICATE OF CORRECTION

PATENT NO. : 7,655,774 B2  
APPLICATION NO. : 10/780507  
DATED : February 2, 2010  
INVENTOR(S) : James I. Mullins et al.

Page 1 of 1

It is certified that error appears in the above-identified patent and that said Letters Patent is hereby corrected as shown below:

In Column 1, Lines 23-27, in the section labeled STATEMENT AS TO RIGHTS TO INVENTIONS MADE UNDER FEDERALLY SPONSORED RESEARCH OR DEVELOPMENT, please delete "This work was supported by a grant from The US Public Health Service through a grant to the University of Washington Center for AIDS Research (AI-27757) and PHS T32A107509 and T32CA0922925. The Federal Government may have certain rights in this invention." and replace with -- This invention was made with government support under NIAID P30 AI27757, AI 26503, and AI 27757 awarded by National Institutes of Health. The government has certain rights in the invention. --

Signed and Sealed this  
Thirteenth Day of November, 2012

David J. Kappos  
*Director of the United States Patent and Trademark Office*